(12) United States Patent
Hughes et al.

(10) Patent No.: US 10,131,960 B2
(45) Date of Patent: *Nov. 20, 2018

(54) GENETICALLY ENCODED FLUORESCENT SENSORS FOR DETECTING INTRACELLULAR SIGNALLING THROUGH DIACYLGLYCEROL PATHWAYS

(71) Applicant: MONTANA MOLECULAR LLC, Bozeman, MT (US)

(72) Inventors: Thomas E. Hughes, Bozeman, MT (US); Paul H. Tewson, Bozeman, MT (US); Anne Marie Quinn, Bozeman, MT (US)

(73) Assignee: Montana Molecular LLC, Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,111

(22) Filed: Jan. 16, 2017

(65) Prior Publication Data

US 2017/0198364 A1    Jul. 13, 2017

Related U.S. Application Data

(63) Continuation of application No. 14/384,464, filed as application No. PCT/US2013/031889 on Mar. 15, 2013, now Pat. No. 9,547,017.

(60) Provisional application No. 61/611,406, filed on Mar. 15, 2012.

(51) Int. Cl.
| | |
|---|---|
| *C12N 9/12* | (2006.01) |
| *C07K 14/00* | (2006.01) |
| *G01N 33/58* | (2006.01) |
| *G01N 33/92* | (2006.01) |
| *C12Q 1/6897* | (2018.01) |
| *C07K 14/435* | (2006.01) |
| *G01N 33/50* | (2006.01) |

(52) U.S. Cl.
CPC .......... *C12Q 1/6897* (2013.01); *C07K 14/00* (2013.01); *C07K 14/43595* (2013.01); *C12N 9/12* (2013.01); *C12N 9/1205* (2013.01); *C12Y 207/11013* (2013.01); *G01N 33/502* (2013.01); *G01N 33/5041* (2013.01); *G01N 33/582* (2013.01); *G01N 33/92* (2013.01); *C07K 2319/60* (2013.01); *G01N 2333/43595* (2013.01); *G01N 2333/912* (2013.01); *G01N 2333/916* (2013.01)

(58) Field of Classification Search
CPC .... G01N 2548/00; G01N 31/22; G01N 33/92; G01N 33/582; C12N 9/1205; C12N 9/12
See application file for complete search history.

(56) References Cited

U.S. PATENT DOCUMENTS

| | | |
|---|---|---|
| 5,519,163 A | 5/1996 | Gibbs et al. |
| 6,469,154 B1 | 10/2002 | Tsien et al. |
| 7,060,793 B2 | 6/2006 | Tsien et al. |
| 2005/0026234 A1 | 2/2005 | Violin et al. |
| 2007/0111270 A1 | 5/2007 | Zhang et al. |
| 2007/0172850 A1 | 7/2007 | Lukyanov et al. |
| 2010/0015701 A1 | 1/2010 | Lukyanov et al. |
| 2012/0022092 A1 | 1/2012 | Holland et al. |
| 2012/0034691 A1 | 2/2012 | Looger et al. |
| 2016/0274109 A1 | 9/2016 | Hughes et al. |

FOREIGN PATENT DOCUMENTS

| | | |
|---|---|---|
| CA | 2286293 | 10/1998 |
| WO | WO 2006/054167 | 5/2006 |
| WO | WO 2009/142735 | 11/2009 |
| WO | WO 2013/138684 | 9/2013 |

OTHER PUBLICATIONS

Adachi et al., "A technique for monitoring multiple signals with a combination of prism-based total internal reflection fluorescence microscopy and epifluorescence microscopy," Pflugers Arch—Eur. J. Physiol., 2009, vol. 459, pp. 227-234.

Akerboom et al., "Crystal Structures of the GCaMP Calcium Sensor Reveal the Mechanism of Fluorescence Signal Change and Aid Rational Design," The Journal of Biological Chemistry, 2009, vol. 284(10), pp. 6455-6464.

Akerboom et al., "Optimization of a GCaMP calcium indicator for neural activity imaging," J. Neuroscience, 2012, vol. 32(40), 43 pages.

Alford et al., "A Fluorogenic Red Fluorescent Protein Heterodimer," Chemical Biology, 2012, vol. 19(3), 16 pages.

Alford et al. "Dimerization-Dependent Green and Yellow Fluorescent Proteins," ACS Synthetic Biology, Dec. 2012, vol. 1, No. 12, pp. 569-575 (Abstract Only).

Almholt et al. "Changes in intracellular cAMP reported by a Redistribution® assay using a cAMP-dependent protein kinase-green fluorescent protein chimera," Cellular Signalling, Aug. 2004, No. 16, No. 8, pp. 907-920 (Abstract Only).

Altschul et al., "Gapped BLAST and PSI-BLAST: a new generation of protein database search programs," Nucleic Acids Research, 1997, vol. 25(17), pp. 3389-3402.

Baird et al., "Circular permutation and receptor insertion within green fluorescent proteins," Proc. Natl. Acad. Sci. USA, 1999, vol. 96, pp. 11241-11246.

(Continued)

*Primary Examiner* — Maryam Monshipouri
(74) *Attorney, Agent, or Firm* — Sheridan Ross PC

(57) ABSTRACT

Described herein are novel fluorescent sensors for Diacyl Glycerol (DAG) and phosphatidylinositol 4,5-bisphosphate (PIP2) that are based on circularly permuted fluorescent proteins. These sensors use less visible spectrum than FRET-based sensors, produce robust changes in fluorescence, and can be combined with one another, or with other sensors, in a multiplex assay on standard fluorescent plate readers or live cell imaging systems.

18 Claims, 9 Drawing Sheets

Specification includes a Sequence Listing.

(56) References Cited

OTHER PUBLICATIONS

Barak et al. "Pharmacological Characterization of Membrane-Expressed Human Trace Amine-Associated Receptor 1 (TAAR1) by a Bioluminescence Resonance Energy Transfer cAMP Biosensor," Molecular Pharmacology, Sep. 2008, vol. 74, No. 3, pp. 585-594.
Barnett et al., "A Fluorescent, Genetically-Encoded Voltage Probe Capable of Resolving Action Potentials," PLOS ONE, 2012, vol. 7(9), 7 pages.
Berkner et al., "Abundant Expression of Polyomavirus Middle T Antigen and Dihydrofolate Reductase in an Adenovirus Recombinant," J. Virology, 1987, vol. 61(4), pp. 1213-1220.
Binkowski et al. "A Luminescent Biosensor with Increased Dynamic Range for Intracellular cAMP." ACS Chemical Biology, Nov. 2011, vol. 6, No. 11, pp. 1193-1197 (Abstract Only).
Carlson et al., "Circularly permuted monomeric red fluorescent proteins with new termini in the β-sheet," Protein Science, 2010, vol. 19, pp. 1490-1499.
Cifuentes et al., "Proteolytic fragments of phosphoinositide-specific phospholipase C-delta 1. Catalytic and membrane binding properties," Journal of Biological Chemistry, 1993, vol. 268(16), pp. 11586-11593.
Davidson et al., "Overproduction of Polyomavirus Middle T Antigen in Mammalian Cells through the Use of an Adenovirus Vector," Journal of Virology, 1987, vol. 61(4), pp. 1226-1239.
Depry et al., "Multiplexed visualization of dynamic signaling networks using genetically encoded fluorescent protein-based biosensors," Pflugers Arch., 2013, vol. 465(3), 15 pages.
Falkenburger et al., "Kinetics of M1 muscarinic receptor and G protein signaling to phospholipase C in living cells," J. General Physiology, 2010, vol. 135(2), pp. 81-97.
Giorgione et al., "Increased Membrane Affinity of the C1 Domain of Protein Kinase Cδ Compensates for the Lack of Involvement of Its C2 Domain in Membrane Recruitment," The Journal of Biological Chemistry, 2006, vol. 281(3), pp. 1660-1669.
Haj-Ahmad et al., "Development of a Helper-Independent Human Adenovirus Vector and Its Use in the Transfer of the Herpes Simplex Virus Thymidine Kinase Gene," J. Virology, 1986, vol. 57(1), pp. 267-274.
Held et al. "Live Cell Imaging of GPCR Dependent Second-Messenger Systems Using the CytationTM 3 Cell Imaging Multi-Mode Reader to Image Genetically Encoded GPCR Reactive Sensors in Real Time." BioTek Application note, 2014, 8 pages [retrieved from: www.biotek.com/assets/tech_resources/Montana%20Molecular_App_Note.pdf].
Hong et al. "Improved molecular toolkit for cAMP studies in live cells," BMC Research Notes, Jul. 2011, vol. 4, 241, 5 pages.
Jensen et al., "Fluorescence changes reveal kinetic steps of muscarinic receptor-mediated modulation of phosphoinositides and Kv7.2/7.3 K+ channels," J. General Physiology, 2009, vol. 133(4), pp. 347-359.
Jiang et al. "Use of a cAMP BRET sensor to characterize a novel regulation of cAMP by the sphingosine 1-phosphate/G13 pathway." The Journal of Biological Chemistry, Apr. 2007, vol. 282, No. 14, 10576-10584.
Kavran et al., "Specificity and Promiscuity in Phosphoinositide Binding by Pleckstrin Homology Domains," J. Biol. Chem., 1998, vol. 273(46), pp. 30497-30508.
Kenakin et al. "Signalling bias in new drug discovery: detection, quantification and therapeutic impact," Nature Reviews Drug Discovery, Mar. 2013, vol. 12, No. 3, pp. 205-216 (Abstract Only).
Kitaguchi et al. "Extracellular calcium influx activates adenylate cyclase 1 and potentiates insulin secretion in MIN6 cells," Biochemical Journal, Mar. 2013, vol. 450, No. 2, pp. 365-373.
Klarenbeek et al. "A mTurquoise-Based cAMP Sensor for Both FLIM and Ratiometric Read-Out Has Improved Dynamic Range," PloS One, Apr. 2011, vol. 6, No. 4, e19170, 6 pages.
Kost et al. "Baculovirus as versatile vectors for protein expression in insect and mammalian cells," Nature Biotechnology, May 2005, vol. 23, No. 5, 567-575 (Abstract Only).
Kredel et al. "Optimized and Far-Red-Emitting Variants of Fluorescent Protein eqFP611," Cell Chemical Biology, Mar. 2008, vol. 15, No. 3, pp. 224-233.
Kyte et al. "A simple method for displaying the hydropathic character of a protein," Journal of Molecular Biology, May 1982, vol. 157, No. 1, pp. 105-132 (Abstract Only).
Lam et al., "Improving FRET dynamic range with bright green and red fluorescent proteins," Nature Methods, 2012, vol. 9(10), 26 pages.
Le Poul et al., "Adaption of Aequorin Functional Assay to High Throughput Screening," Journal of Biomolecular Screening, 2002, vol. 7(1), pp. 57-65.
Ledford "Bioengineers look beyond patents: Synthetic-biology company pushes open-source models," Nature, Jul. 2013, vol. 499, No. 7456, pp. 16-17.
Liu et al., "Biased signaling pathways in β2-adrenergic receptor characterized by 19F-NMR," Science, 2012, vol. 335(6072), 12 pages.
Massie et al., "Construction of a Helper-Free Recombinant Adenovirus That Expresses Polyomavirus Large T Antigen," Mol. Cell. Biol., 1986, vol. 6(8), pp. 2872-2883.
Nagai et al., "Circularly permuted green fluorescent proteins engineered to sense $Ca^{2}+$," Proceedings of the National Academy of Sciences, 2001, vol. 98(6), pp. 3197-3202.
Nakai et al., "A high signal-to-noise $Ca^{2}+$ probe composed of a single green fluorescent protein," Nature Biotechnology, 2001, vol. 19, pp. 137-141.
Nausch et al., "Differential patterning of cGMP in vascular smooth muscle cells revealed by single GFP-linked biosensors," Proceedings of the National Academy of Sciences, 2008, vol. 105(1), pp. 365-370.
Ni et al., "Signaling Diversity of PKA Achieved Via a Ca2+-cAMP-PKA Oscillatory Circuit," Nature Chemical Biology, 2011, vol. 7(1), 15 pages.
Oancea et al., "Green Fluorescent Protein (GFP)-tagged Cysteine-rich Domains from Protein Kinase C as Fluorescent Indicators for Diacylglycerol Signaling in Living Cells," The Journal of Cell Biology, 1998, vol. 140(3), pp. 485-498.
Okumoto et al., "Quantitative Imaging with Fluorescent Biosensors," Annu. Rev. Plant Biol., 2012, vo. 63, pp. 663-706.
Palmer et al., "Design and application of genetically encoded biosensors," Trends in Biotechnology, 2011, vol. 29(3), 18 pages.
Pletnev et al., "A Crystallographic Study of Bright Far-Red Fluorescent Protein mKate Reveals pH-induced cis-trans Isomerization of the Chromophore," The Journal of Biological Chemistry, 2008, vol. 283(43), pp. 28980-28987.
Ponsioen et al. "Detecting cAMP-induced Epac activation by fluorescence resonance energy transfer: Epac as a novel cAMP indicator," EMBO Reports, Dec. 2004, vol. 5, No. 12, pp. 1176-1180.
Prinz et al. "Novel, isotype-specific sensors for protein kinase a subunit interaction based on bioluminescence resonance energy transfer (BRET)." Cellular Signalling, Oct. 2006, vol. 18, No. 10, pp. 1616-1625 (Abstract Only).
Raehal et al., "Morphine Side Effects in β-Arrestin 2 Knockout Mice," The Journal of Pharmacology and Experimental Therapeutics, 2005, vol. 314(3), pp. 1195-1201.
Rajagopal et al., "Quantifying Ligand Bias at Seven-Transmembrane Receptors," Molecular Pharmacology, 2011, vol. 80(3), 28 pages.
Rajagopal et al., "Teaching old receptors new tricks: biasing seven-transmembrane receptors," Nature Reviews Drug Discovery, 2010, vol. 9(5), pp. 373-386.
Rehmann et al. "Structure of Epac2 in complex with a cyclic AMP analogue and RAP1B," Nature, Sep. 2008, vol. 455, No. 7209, pp. 124-127 (Abstract Only).
Rehmann et al. "Structure of the cyclic-AMP-responsive exchange factor Epac2 in its auto-inhibited state," Nature, Feb. 2006, vol. 439, No. 7076, pp. 625-628 (Abstract Only).

(56) References Cited

OTHER PUBLICATIONS

Salonikidis et al. "An Ion-insensitive cAMP Biosensor for Long Term Quantitative Ratiometric Fluorescence Resonance Energy Transfer (FRET) Measurements under Variable Physiological Conditions," Journal of Biological Chemistry, Jul. 2011, vol. 286, No. 26, pp. 23419-23431.
Schroeder et al., "FLIPR: A New Instrument for Accurate, High Throughput Optical Screening," Journal of Biomolecular Screening, 1996, vol. 1(2), pp. 75-80.
Shaner et al. "A guide to choosing fluorescent proteins," Nature Methods, Dec. 2005, vol. 2, No. 12, pp. 905-909.
Shaner et al. "Improving the photostability of bright monomeric orange and red fluorescent proteins," Nature Methods, Jun. 2008, vol. 5, No. 6, pp. 545-551 (Abstract Only).
Shaner et al. "A bright monomeric green fluorescent protein derived from Branchiostoma lanceolatum," Nature Methods, May 2013, vol. 10, No. 5, pp. 407-409 (Abstract Only).
Shaw et al., "Preferential transformation of human neuronal cells by human adenoviruses and the origin of HEK 293 cells," The FASEB Journal, 2002, vol. 16, pp. 869-871.
Shcherbo et al. "Practical and reliable FRET/FLIM pair of fluorescent proteins," BMC Biotechnology, Mar. 2009, vol. 9, 24, 6 pages.
Shui et al., "Circular Permutation of Red Fluorescent Proteins," PLoS ONE, 2011, vol. 6(5), e20505, 9 pages.
Subach et al. "Conversion of Red Fluorescent Protein into a Bright Blue Probe," Chemistry & Biology, Oct. 2008, vol. 15, No. 10, pp. 1116-1124.
Szymczak et al., "Correction of multi-gene deficiency in vivo using a single 'self-cleaving' 2A peptide-based retroviral vector," Nature Biotechnology, 2004, vol. 22(5), pp. 589-594.
Tewson et al., "Simultaneous Detection of $Ca^{2+}$ and Diacylglycerol Signaling in Living Cells," PLoS ONE, 2012, vol. 7(8), e42791, 6 pages.
Topell et al. "Circularly permuted variants of the green fluorescent protein," FEBS Letters, Aug. 1999, vol. 457, No. 2, pp. 283-289.
Tsutsui et al. "Improving membrane voltage measurements using FRET with new fluorescent proteins," Nature Methods, Aug. 2008, vol. 5, No. 8,683-685 (Abstract Only).
Van Der Wal et al., "Monitoring Agonist-induced Phospholipase C Activation in Live Cells by Fluorescence Resonance Energy Transfer," The Journal of Biological Chemistry, 2001, vol. 276(18), pp. 15337-15344.
White et al., "Characterization of a $Ca^{2+}$ Response to Both UTP and ATP at Human P2Y11 Receptors: Evidence for Agonist-Specific Signaling," Molecular Pharmacology, 2003, vol. 63(6), pp. 1356-1363.

Willoughby et al. "Live-cell imaging of cAMP dynamics," Nature Methods, Jan. 2008, vol. 5, No. 1, 29-36 (Abstract Only).
Woehler et al. "Signal/Noise Analysis of FRET-Based Sensors," Biophysical Journal, Oct. 2010, vol. 99, No. 7, pp. 2344-2354.
Xu et al. "A bioluminescence resonance energy transfer (BRET) system: application to interacting circadian clock proteins," Proc. Natl. Acad. Sci. U.S.A., Jan. 1999, vol. 96, No. 1, pp. 151-156.
Zaccolo et al. "A genetically encoded, fluorescent indicator for cyclic AMP in living cells," Nature Cell Biology, Jan. 2000, vol. 2, No. 1, pp. 25-29 (Abstract Only).
Zaccolo et al. "Discrete microdomains with high concentration of cAMP in stimulated rat neonatal cardiac myocytes," Science, Mar. 2002, vol. 295, No. 5560, pp. 1711-1715 (Abstract Only).
Zhang et al. "Generation and identification of recombinant adenovirus by liposome-mediated transfection and PCR analysis," Biotechniques, Nov. 1993, vol. 15, No. 5, pp. 868-872 (Abstract Only).
Zhang et al., "A Sample Statistical Parameter for Use in Evaluation and Validation of High Throughput Screening Assays," Journal of Biomolecular Screening, 1999, vol. 4(2), pp. 67-73.
Zhang et al. "Genetically encoded reporters of protein kinase A activity reveal impact of substrate tethering," Proceedings of the National Academy of Sciences, Dec. 2001, vol. 98, No. 26, pp. 14997-15002.
Zhao et al., "An Expanded Palette of Genetically Encoded $Ca^{2+}$ Indicators," Science, 2011, vol. 333(6051), pp. 1888-1891.
International Search Report and Written Opinion for International (PCT) Patent Application No. PCT/US2013/031889, dated Jul. 15, 2013, 13 pages.
International Preliminary Report on Patentability for International (PCT) Patent Application No. PCT/US2013/031889, dated Sep. 25, 2014, 9 pages.
Extended European Search Report for European Patent Application No. 13761664.5, dated Jul. 22, 2015, 7 pages.
Official Action for U.S. Appl. No. 14/384,464, dated Feb. 5, 2016 6 pages Restriction Requirement.
Official Action for U.S. Appl. No. 14/384,464, dated May 2, 2016 8 pages.
Notice of Allowance for U.S. Appl. No. 14/384,464, dated Sep. 7, 2016 8 pages.
Burns et al., "Protein Kinase C Contains Two Phorbol Ester Binding Domains," J. Biol. Chem., 1991, vol. 266(27), pp. 18330-8337.
Dries et al., "A Single Residue in the C1 Domain Sensitizes Novel Protein Kinase C Isoforms to Cellular Diacylglycerol Production," J. Biol. Chem., 2007, vol. 282(2), pp. 826-830.
Hurley et al., "Taxonomy and function of C1 protein kinase C homology domains," Protein Sci., 1997, vol. 6, pp. 477-480.
Nikolaev et al. "Novel Single Chain cAMP Sensors for Receptor-induced Signal Propagation," The Journal of Biological Chemistry, Sep. 2004, vol. 279, No. 36, pp. 37215-37218.

DAG – sensor | 2A | R-GECO

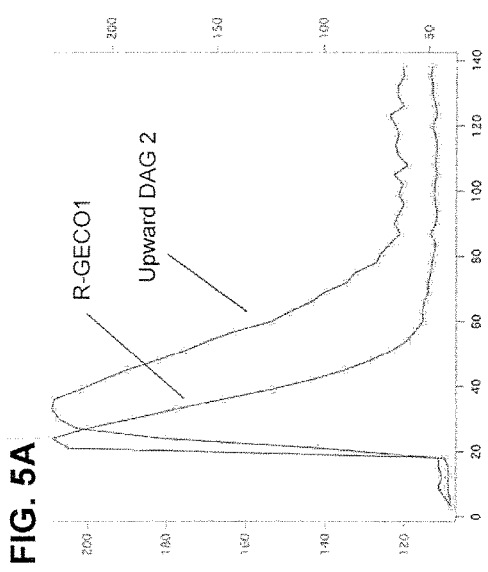
FIG. 5A
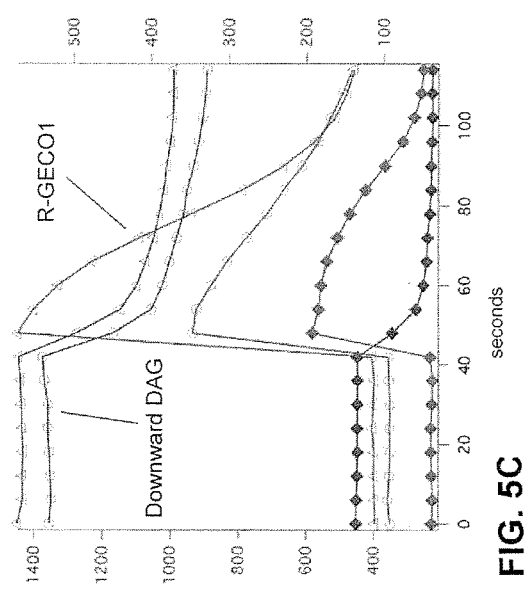
FIG. 5C
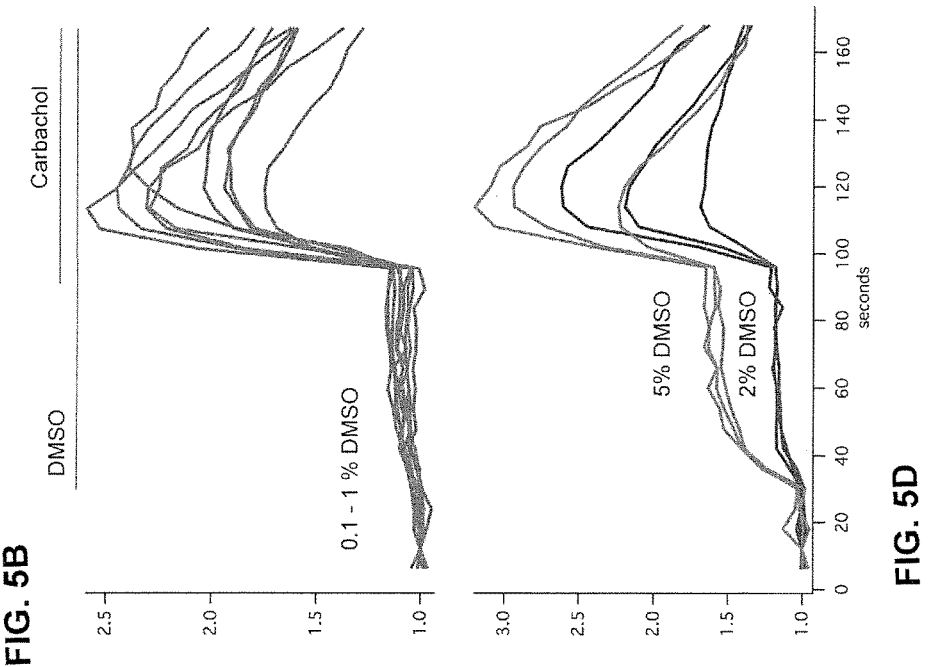
FIG. 5B
FIG. 5D

GENETICALLY ENCODED FLUORESCENT SENSORS FOR DETECTING INTRACELLULAR SIGNALLING THROUGH DIACYLGLYCEROL PATHWAYS

CROSS-REFERENCE TO RELATED APPLICATIONS

This application claims the benefit of priority under 35 U.S.C. § 119(e) from U.S. Provisional Application Ser. No. 61/611,406, filed Mar. 15, 2012, the contents of which are incorporated herein in their entirety by this reference.

GOVERNMENT SUPPORT

This invention was made with government support under NIH grant 1R43MH096670-01A1 awarded by the National Institute of Mental Health. The government has certain rights in this invention.

REFERENCE TO SEQUENCE LISTING

This application contains a Sequence Listing submitted electronically as a text file by EFS-Web. The text file, named "6666-2-PCT_Sequence Listing_ST25", has a size in bytes of 354 KB, and was recorded on Mar. 15, 2013. The information contained in the text file is incorporated herein by reference in its entirety pursuant to 37 CFR § 1.52(e)(5).

FIELD OF THE INVENTION

The field of the present invention is design and construction of fluorescent biological sensors for detection and measurement of intracellular analytes.

BACKGROUND OF THE INVENTION

Cell signaling involves the concerted activity of multiple second messenger pathways. It is the balance of these different signaling components, coordinated in both space and time, that ultimately dictate the response of the cell. While this is well understood in theory, the practice of measuring signaling is often reduced to two time points—before and after drug—and to a single second messenger. When kinetic measurements of signaling are possible, a new level of precision and insight guide new experiments and optimized assays. In the cases that it has been possible to image multiple components of a signaling pathway in the same cells (1-5), the interplay between the different components has provided new insights into the biological system and the downstream consequences of a drug's actions.

Multiplex sensors capable of simultaneously detecting different signaling components serve an important role in understanding complex biological pathways and assessing the biological relevance of a particular drug (8). For example, many drugs act at G-protein coupled receptors on the cell surface. Some of these receptors couple to the heterotrimeric protein, Gq, which activates phospholipase C (PLC). PLC in turn cleave PIP2 to produce two second messengers: diacylglycerol (DAG), which remains in the plasma membrane, and inositol triphosphate (IP3), which diffuses through the cytosol to release stores of intracellular calcium ions (Ca2+). This coordinated increase, in both DAG and cytosolic Ca2+, triggers the activation of conventional isoforms of protein kinase C (cPKC) which then phosphorylate many different targets. To unambiguously resolve PLC pathway activation, and to better understand the kinetics of these coordinated, parallel signaling processes and their significance in health and disease, multiplex sensor systems are needed that can simultaneously measure multiple molecules such as DAG, PIP2 and Ca2+.

Optimal multiplex sensors must satisfy a number of criteria. First, they must be capable of working in living cells and provide kinetic data for each signaling pathway. This means they need to work in living cells and provide strong signals that can be sampled at 10 Hz. Additionally, each sensor needs to consume as little of the visible spectrum as possible so that there is minimal crosstalk with other sensors. Furthermore, each sensor has to specifically detect the analyte at physiologically relevant concentrations.

Fluorescent protein-based sensors meet many of the design criteria: they work in living cells, they produce strong signals that can be sampled repeatedly and quickly, and the protein domains they carry have evolved to specifically detect a particular second messenger (1). However, early sensors based upon Forster Resonance Energy Transfer (FRET) between two different fluorescent proteins, rarely produce the sort of robust signals necessary for automated detection. Furthermore, the broad absorption bands of the donor and acceptor fluorophores consume most of the visible spectrum (12, 13).

More recently, a new generation of fluorescent protein sensors has been developed that only uses one fluorescent protein, produces large changes in fluorescence, and has the potential for multiplexing. Many of these new sensors carry a single, circularly permuted fluorescent protein that converts analyte binding into changes in fluorescence intensity. The green fluorescent GCaMP Ca2+ sensors (14-16), the red R-GECO1 $Ca^{2+}$ sensor (17), the green ElectricPk voltage sensor (18), and the green cGMP sensor (19) use this approach. However, there continues to be a need in the art for additional novel fluorescent sensors that are robust, sensitive, can detect specific analytes and can be used in multiplex systems in real time and in relevant tissues and cell types. The invention of the present application addresses such need.

SUMMARY OF THE INVENTION

The present invention includes a diacylglycerol (DAG) sensor fusion protein comprising a PKC protein comprising a DAG binding domain and a fusion region, and a circularly permuted fluorescent protein, wherein the fusion region is located upstream from the DAG binding domain or within the DAG binding domain; wherein the fluorescent protein is fused with the PKC protein at a fusion site present within the fusion region; and wherein the fluorescence of the DAG sensor fusion protein changes upon binding to DAG.

In some embodiments, the PKC protein may be PKC-δ (delta), PKC-ε (epsilon), PKC-θ (theta), PKC-η (eta), PKC-α (alpha), PKC-β1 (beta 1), PKC-β11 (beta 11), PKC-γ (gamma), or PKC-ξ (zeta). In some embodiments, the PKC protein may be PKC-δ (delta), PKC-ε (epsilon), PKC-θ (theta) or PKC-η (eta). In some embodiments, the PKC protein may be PKC-δ delta.

In some embodiments, the DAG binding domain may comprise a C1 domain. In some embodiments, the fusion region may be located upstream of the C1, or within the C1domain. In some embodiments, the fusion region may comprise additions or deletions of amino acids. In some embodiments, the fusion region may comprise linker sequences.

In some embodiments, the circularly permuted fluorescent protein may comprise a circular permutation in a beta sheet near the chromophore of the fluorescent protein. In some embodiments, the fluorescence of the fusion protein may increase upon binding to DAG. In some embodiments, the fluorescence of the fusion protein may decrease upon binding to DAG.

In some embodiments, the DAG sensor fusion protein may comprise an amino acid sequence that is at least 90% identical to an amino acid sequence selected from SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36. In some embodiments, the DAG sensor fusion protein may comprise an amino acid sequence that is at least 90% identical to an amino acid sequence selected from the group SEQ ID NO:4, SEQ ID NO:5, SEQ ID NO:12, SEQ ID NO:15, SEQ ID NO:16, SEQ ID NO:17, SEQ ID NO:20, SEQ ID NO:21, SEQ ID NO: 22, SEQ ID NO:24, SEQ ID NO:30.

In some embodiments, the present invention includes a multiplex system for detecting one or more analytes comprising the DAG sensor fusion protein, and one or more additional fluorescent sensors, wherein the additional sensor specifically detects an analyte other than DAG. The additional fluorescent sensor may comprise a fluorescent sensor fusion protein comprising a fluorescent protein, or a fluorescent dye. In some embodiments, the DAG sensor fusion protein may comprise a fluorescent protein that is fluorescent in one region of the spectrum and the additional fluorescent sensor is fluorescent in another region of the spectrum. In some embodiments, the additional fluorescent sensor may be a PiP2 sensor, wherein the fluorescence of the PIP2 sensor changes upon binding to PIP2, or a Calcium sensor, wherein the fluorescence of the Calcium sensor changes upon binding to Calcium, or both.

In some embodiments, the PIP2 sensor may comprise a PLC protein portion that binds to PIP2 and a fluorescent protein.

In some embodiments, the present invention includes a nucleic acid sequence encoding the DAG sensor fusion protein. In some embodiments, it includes a nucleic acid molecule comprising such nucleic acid sequence. In some embodiments, the present invention includes a cell comprising such nucleic acid molecule. In some embodiments, the nucleic acid sequence encoding the DAG sensor fusion protein may be located in the genome of the cell. In some embodiments, the cell may further comprise one or more additional nucleic acid molecules that encode one or more additional fluorescent sensor proteins that specifically detect an analyte other than DAG. In some embodiments, the cell may be a CHO cell, a human Hela cell or a human embryonic kidney (HEK) cell.

In some embodiments, the present invention includes a PIP2 sensor comprising a PLC protein portion that binds to PIP2 and a fluorescent protein, wherein the fluorescence of the PIP2 sensor fusion protein changes upon binding to PIP2. In some embodiments, the fluorescent protein may be a dimerization-dependent fluorescent protein.

In some embodiments, the present invention includes a polypeptide comprising a DAG sensor fusion protein, wherein the DAG sensor fusion protein comprises an amino acid sequence that is at least 90% identical to an amino acid sequence selected from SEQ ID NO:4, SEQ ID NO:5, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36. In some embodiments, the present invention includes a nucleic acid sequence encoding such polypeptide.

In some embodiments, the present invention includes a polypeptide comprising an amino acid sequence that is at least 90% identical to an amino acid sequence selected from SEQ ID NO:70 and SEQ ID NO:71. In some embodiments, the present invention includes a nucleic acid sequence encoding such polypeptide.

BRIEF DESCRIPTION OF THE DRAWINGS

FIG. 4 shows that the response of the Upward DAG-Green sensor to M1 muscarinic acetylcholine receptor (GPCR) activation in living HEK 293 cells occurs in physiologic ranges. The EC50 values for carbachol stimulation are approximately 3 μM.

FIGS. 5A through 5D show that the Green fluorescent sensors Upward DAG2 (A and B) and Downward DAG (C and D) can be co-expressed with the red fluorescent R-GECO1 to simultaneously measure Ca2+ and DAG signaling in living cells. The responses (mean pixel intensity) of individual cells are plotted in A and C. The left axis is green fluorescence (arbitrary units) and the right axis represents red fluorescence. The effect of DMSO on the DAG sensors is negligible at final concentrations of 0.1 to 1%, but detectable at 2% or greater (B and D).

DETAILED DESCRIPTION OF THE INVENTION

The present invention is directed at the design and production of novel fluorescent sensors that can be used in multiplex detection systems and assays. Described herein is the design and construction of a novel Diacyl Glycerol (DAG) sensor that specifically detects intracellular DAG. Further described is a PIP2 sensor that specifically detects intracellular PIP2. Both sensors provide strong fluorescence signals in live cells and can be used in live cell assays in real time, on standard fluorescent plate readers or live cell imaging systems. Additionally, they can be combined with one another, and/or with other sensors, such as a $Ca^{2+}$ sensor, to provide simultaneous detection and measurement of multiple molecules or analytes in multiplex detection systems.

In one aspect, the present invention includes a DAG sensor that can be used to detect changes in DAG concentration in living cells. The DAG sensor of the present invention is based on a design that converts the DAG activation-dependent conformational changes of the PKC protein into a change in fluorescence. Because DAG is involved in many intracellular signaling pathways, including a wide variety of G-Protein Coupled Receptors (GPCRs), the DAG sensor of the present invention is useful in drug discovery, basic research focused on cell signal transduction, and research into the mechanism of diseases associated with DAG dependent signal transduction, such as type II diabetes.

In one embodiment, the DAG sensor comprises a fusion protein comprising a PKC protein containing a DAG binding domain and a fusion region, and a fluorescent protein wherein the fluorescent protein is fused with the PKC protein at a fusion site present within the fusion region and wherein the fluorescence of the DAG sensor fusion protein changes upon binding to DAG.

Figure 1:
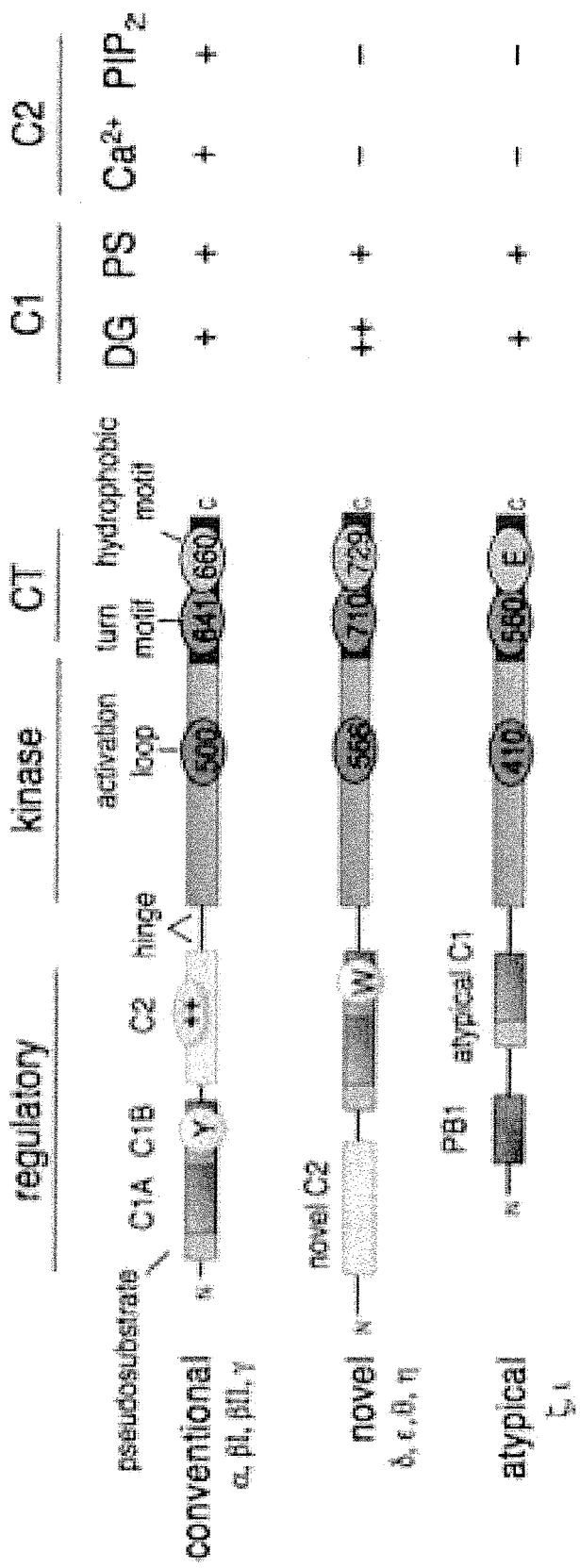
FIG. 1 is a schematic drawing depicting the domain structure of various isoforms of Protein Kinase C.

The term PKC protein refers to the protein Kinase C. A number of isoforms of PKC are known in the art and are encompassed by the present invention. These include, without limitation, conventional PKC isoforms such as a (alpha), β1 (beta 1), βII (beta 11) and γ (gamma); novel isoforms such as δ (delta), ε (epsilon), θ (theta) and η (eta); as well as atypical isoforms such as the ξ (zeta) isoform. The PKC isoforms have been isolated from a large number of species, including without limitation, *drosophila, xenopus,* cow, mouse, rat, rabbit, human, etc. The amino acid sequences of these isoforms, as well as the nucleotide sequences of nucleic acid molecules encoding them, are available through public databases such as Genbank and are expressly incorporated herein. FIG. 1 contains a schematic representation depicting a comparison of the domain structures of various PKC isoforms. As shown in FIG. 1, all PKC isoforms contain a regulatory region comprising a pseudosubstrate domain, a DAG binding C1 domain which comprises the subdomains C1a and C1b, and a calcium binding C2 domain; a kinase region comprising an activation loop, and a C terminal (CT) region; and a hinge region that connects the regulatory region and the kinase region. The pseudosubstrate domain lies upstream of the C1 domain. The conventional PKC isoforms, such as α, β1, βII and γ respond to both DAG and calcium through the binding domains C1 and C2 respectively. The PKC isoforms delta, epsilon, theta and eta contain a novel C2 domain that does not respond to calcium levels, and a C1 domain that has a very high affinity for DAG. The atypical PKC isoform lacks the C2 domain. For example, in the PKC delta isoform represented by SEQ ID NO:1 the pseudosubstrate domain extends from approximately amino acid 140 to amino acid 152. The C1 domain extends from approximately amino acid 158 to 280. The C1 domain comprises the C1a and C1b domains; C1a domain extends from approximately amino acid 158 to 208, while the C1b domain extends from approximately amino acid 230 to 280.

The presence of the novel non-functional C2 and a high affinity C1 domain makes the novel PKC isoforms particularly desirable in the construction of DAG sensors. However, the conventional isoforms can also be used in the construction of DAG sensors by removal or mutation of the C2 domain such that it does not respond to calcium, and the C1 domain can be converted to have a high affinity to DAG with a single mutation (22). Even the low affinity C1 domains of the conventional PKCs can be used to produce a sensor capable of indicating changes in DAG as GFP fused to the C1 domain of the conventional PKC gamma has been shown to translocate in response to DAG signaling (41).

Reference to a protein (or polypeptide) herein includes full-length proteins, fusion proteins, or any fragment, domain, conformational epitope, or homolog of such proteins. As used herein, the term "homolog" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation. A homolog can have either enhanced, decreased, or substantially similar properties as compared to the naturally occurring protein or peptide. Homologs can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis. A homolog of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homolog comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

Accordingly, the term PKC protein includes a full length PKC isoform, or truncated or mutated versions of it that contain, at a minimum, a DAG binding domain and a fusion region. The term DAG binding domain refers to a portion or region of the PKC protein that is capable of binding to DAG. In some embodiments, the term DAG binding domain refers to the full C1 domain of the PKC. In some embodiments, the DAG binding domain refers to a truncated or mutated version of the C1 domain or a fragment of the C1 domain, such as C1a or C1b or fragments thereof, that maintains the ability to bind to DAG.

The term fusion region refers to a region of the PKC protein which contains the fusion sites at which the fluorescent protein is inserted. Without wishing to be bound by theory it is believed that the binding of the C1 domain to DAG leads to large conformational changes in the fusion region of the PKC protein, which in turn alters the chromophore environment of the fluorescent protein, thereby producing a change in the fluorescence.

In some embodiments the fusion region lies upstream of the DAG binding domain. In some embodiments it is located in the region between the pseudosubstrate domain and the C1 domain. In some embodiments it is located within the DAG binding domain. In some embodiments it is located within the C1 domain. In some embodiments it is located within the C1 domain, upstream of the C1b domain. In some embodiments it is located in the C1a domain or the region between C1a and C1b domains. In some embodiments, it is located downstream of the DAG binding domain. In some embodiments it is located in the hinge region that lies between the C1 domain and the kinase domain.

In some embodiments the fusion region comprises the native amino acid sequence of the PKC protein, and the fluorescent protein is inserted at fusion sites within the native PKC protein sequence. In some embodiments the fusion region may comprise additions or deletions of amino acids that make the sequence deviate from the native sequence. For example, in various embodiments, the fusion region may comprise addition of at least 1, 2, 3, 4, 5, 6, 7, 8, 9, 10, 11, 12, 13, 14, 15, 16, 17, 18, 19, or 20 amino acids to the native sequence. In various embodiments, the fusion region may comprise deletions of at least 1, 2, 3, 4, 5, 6, 7, 8 9, 10, 11, 12, 13, 14, 15, 16, 17, 18, 19, 20, 21, or 22 amino acids from the native sequence. In some embodiments the fusion region may comprise conservative substitutions of the amino acids of the native sequence. For example, as shown in Table 2 in some embodiments the fusion region comprises the region between amino acid position about 150 to amino acid position about 173, and may further comprise additions or deletions of amino acids to this region.

In some embodiments the fusion region further comprises linker sequences that may be present at the N terminal and/or C terminal ends of the circularly permuted fluorescence protein and that link the circularly permuted protein to the PKC protein. Linkers containing amino acids with side chains that give the linker ridged structure are particularly important to converting the conformational changes of the PKC to changes in the structure of the fluorescent protein barrel. Similarly, linkers with bulky amino acids that can form a surface/structure capable of occluding the hole in the side of the barrel produced by circular permutation are best capable of producing large changes in fluorescence by protecting the chromophore environment in one configuration and in another configuration producing a large hole in the side of the protein barrel that renders the chromophore less fluorescent. The linker sequences may be at least 1, 2, 3, 4, 5, 6, 7, 8, 9, or 10 amino acids long. Examples of such linkers include, without limitation, LE, AI, PV, SH, TR, FN, or ENNHLS. In some embodiments the linker sequence may comprise the sequence LE or TR. It is well known that minor adjustments in the linkers interconnecting the circularly permuted fluorescent protein and the analyte-sensing domains can have a large impact on the amplitude of the fluorescence change (14, 15).

Example 1 describes in detail the design and construction of DAG sensors using PKC delta [SEQ ID NO:1]. Briefly, a series of genetically encoded, fluorescent DAG sensors were constructed. Sixty four candidates were produced that fused a circularly permuted green fluorescent protein [SEQ ID NO:2] to full length or truncated PKCδ. See Table 1. Two robust prototype sensors called Upward DAG (G17.2B, SEQ ID NO:4) (in which fluorescence increases upon binding to DAG) and Downward DAG (G23, SEQ ID NO:17) (in which fluorescence decreases upon binding to DAG) were recovered from this initial effort (20). In these two sensors, the circularly permuted green fluorescent protein and the linker were positioned either between the pseudosubstrate and the C1 domain of PKCδ or after the first amino acid of the C1 domain. An additional 156 variants of the original Upward and Downward DAG sensors were created and a total of thirty sensors were recovered. See Table 2.

The complete amino acid sequences of these sensors are represented by SEQ ID NO:4 (G17.2B, also referred to as Upward DAG), SEQ ID NO:5 (G17-18, also referred to as Upward DAG2), SEQ ID NO:6 (G17-19), SEQ ID NO:7 (G18-20), SEQ ID NO:8 (G19-17), SEQ ID NO:9 (G19-18), SEQ ID NO:10 (G19-20), SEQ ID NO:11 (G20-17), SEQ ID NO:12 (G20-28, also referred to as Downward DAG2), SEQ ID NO:13 (G21-17), SEQ ID NO:14 (G21-19), SEQ ID NO:15 (G21-20), SEQ ID NO:16 (G21-23), SEQ ID NO:17 (G23, also referred to as Downward DAG), SEQ ID NO:18 (G23-18), SEQ ID NO:19 (G23-19), SEQ ID NO:20 (G27-19), SEQ ID NO:21 (G27-22), SEQ ID NO:22 (G28-18), SEQ ID NO:23 (G28-27), SEQ ID NO:24 (G29-18), SEQ ID NO:25 (G29-23), SEQ ID NO:26 (G29-24), SEQ ID NO:27 (G30-21), SEQ ID NO:28 (G19-30), SEQ ID NO:29 (G21-30), SEQ ID NO:30 (G23-30), SEQ ID NO:31 (G24-30), SEQ ID NO:32 (G28-30), SEQ ID NO:33 (G29-30).

The nucleotide sequences encoding these sensors are provided in SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, respectively.

The details of the fusion region and the specific fusion sites are presented in Tables 1 and 2. The amino acid positions detailed in Example 1 and Tables 1 and 2, are in reference to SEQ ID NO:1.

Example 1 further describes the construction of three additional DAG sensors in which a circularly permuted red fluorescent protein (cpMapple) [SEQ ID NO:3] was fused to a truncated PKCδ. The complete amino acid sequences of these sensors are represented by SEQ ID NO:34 (R17-2b), SEQ ID NO:35 (R19), and SEQ ID NO:36 (R20). The nucleotide sequences encoding these sensors are provided in SEQ ID NO:67, SEQ ID NO:68, SEQ ID NO:69, respectively.

Thus, described herein are novel DAG sensor proteins comprising an amino acid sequence represented by SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36.

In some embodiments, the amino acid sequences consist or consist essentially of any of the aforementioned SEQ ID NOs. In some embodiments, the amino acid sequences comprise any of the aforementioned SEQ ID NOs., optionally with one or more conservative amino acid substitutions (e.g., with 1, 2, 3, 4, 5, 6, 7, 8, 9, 10, 11, 12, 13, 14, 15, 16, 17, 18, 19, 20 or a range between any two of the aforementioned numbers, or more than twenty conservative amino acid substitutions, so long as the desired function of the sensor is maintained (i.e. substantially maintained). Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. 157:105 (1982)), or on the basis of the ability to assume similar polypeptide secondary structure (Chou and Fasman, Adv. Enzymol. 47: 45 (1978)), or tertiary or quaternary structures. In some embodiments, the number of amino acid substitutions in the sequences may be expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present can be substituted with a conservative amino acid(s), so long as the desired function of the sensor is substantially maintained. Also included are amino acid sequences that possess at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent or more identity to any of the aforementioned SEQ ID NOs., so long as the desired function of the sensor is substantially maintained.

Further described herein are nucleic acid sequences that encode the aforementioned DAG sensor proteins. In some embodiments these are represented by SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, and SEQ ID NO:69.

In some embodiments, the nucleic acid sequence can consist or consist essentially of any of the aforementioned SEQ ID NOs. Also provided are nucleic acid sequences that possess at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent or more identity to any of the aforementioned SEQ ID NOs. Further included are nucleic acid molecules that hybridize to, or are the complements of the aforementioned molecules. Nucleic acids that encode the sensors having stated amino acid sequences, as well as variants, and fragments thereof are also included. These sequences include all degenerate sequences related to a specific amino acid sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular amino acid and nucleic acid sequence may not be written out herein, it is understood that each and every sequence is in fact disclosed and described herein through the disclosed polypeptide sequences.

It is noted that while the present invention is exemplified with the protein PKC-delta, the disclosure is applicable to other PKC isoforms and based on the disclosure of this application, one skilled in the art will be readily able to construct and use DAG sensors using other isoforms. For example, the novel PKC isoforms ε (epsilon), θ (theta) and η (eta) have similar structure, sequence, and binding properties as the delta isoform, and may be substituted for the delta isoform. The conventional PKC isoforms, such as α, β1, β11 and γ which respond to both DAG and calcium through binding domains C1 and C2 respectively, may be used in the construction of a DAG sensor by removal or mutation of the C2 domain such that it does not respond to calcium; additionally, their C1 domain can be converted to have a high affinity to DAG.

The DAG sensor further comprises a circularly permuted fluorescent protein. In a circularly permuted fluorescent protein the N and the C termini of the protein are placed adjacent to the chromophore. A number of fluorescent proteins are known in the art and may be circularly permuted to be used in the construction of the sensor of the present invention. The examples of these include without limitation, green fluorescent protein (GFP), and its variants such as red fluorescent protein, yellow fluorescent protein, enhanced green fluorescent protein (EGFP), enhanced yellow fluorescent protein (EYFP), Emerald, mApple, mPlum, mCherry, tdTomato, mStrawberry, J-Red, DsRed-monomer, mOrange, MKO, mCitrine, Venus, YPet, CyPet, mCFPm, Cerluean and T-Sapphire. Such fluorescent proteins are discussed in Shaner et al., A guide to choosing fluorescent proteins, Nature methods, 2:12, 905-909 (2005), and are expressly incorporated herein. Additional examples of fluorescent proteins include, mKOK, mUKG (44), Clover, Ruby (45), epFP650, epFP670 (46), mKate (47), tagRFP (48), mRag-GFP, mTAgBFP and EBFP2 (49). A number of circularly permuted fluorescent proteins are described in the art and may be used in the present invention. (Baird et al., Nagai et al, Nakai et al, Shui et al).

Fluorescent proteins typically exhibit a beta barrel structure containing the chromophore. For example, green fluorescent protein consists of eleven β-sheets that form a barrel shaped structure with six alpha helices containing the covalently bonded chromophore 4-(p-hydroxybenzylidene)imidazolidin-5-one (HBI) running through the center. This barrel of eleven β-sheets protects the cell from the chromophore, isolates the chromophore from the environment around the protein, and most importantly stabilizes the chromophore in a relatively ridged conformation that makes the chromophore fluorescent. When analyte sensing domains are fused to the original N- and C-termini of the fluorescent protein, their movements do not produce changes in fluorescence. However, when the original N- and C-termini are fused with a short linker, and new N- and C-termini are introduced in the middle of one of the beta sheets of the barrel, a circularly permuted fluorescent protein is produced with new properties. Analyte sensing domains fused to these new termini can produce very large changes in fluorescence. Without wishing to be bound by theory, it is believed that circular permutation in a beta sheet of the barrel near the chromophore allows a sensor to create a difference in the chromophore environment, thereby producing a change in fluorescence. Thus, for instance in the Calcium sensor GCaMP3 (described in United States Patent Application 20120034691), the calcium binding domains are placed adjacent to the chromophore of the circularly permuted green fluorescent protein. In one conformation there is an opening in the side of the beta barrel of the fluorescent protein and the chromophore is solvent accessible. When the binding domains move in response to activation by calcium, the hole is closed, and the new environment of the chromophore causes it to become fluorescent.

As exemplified herein, in some embodiments, the sensor comprises a circularly permuted green fluorescent protein described in Zhao 2011 (17). This version comprises EGFP circularly permuted around amino acids 149-144 [SEQ ID NO:2]. In another embodiment, the sensor comprises a circularly permuted red fluorescent protein (Mapple) [SEQ ID NO:3]. The circularly permuted red fluorescent protein is not analogous to the circularly permuted green fluorescent protein, indicating that different fluorescent proteins can be circularly permuted in different places and used effectively in the sensors of the present invention.

The fluorescence of the DAG sensor may increase upon binding of the DAG to the sensor, as in the Upward DAG and Upward DAG2 sensors, or decrease upon binding of the DAG to the sensor, as in the Downward DAG and Downward DAG2 sensors. Such properties of the sensors are indicated in Table 2.

Further described herein is a novel sensor that detects Phosphatidylinositol 4,5-bisphosphate or $PIP_2$. Phospholipase C hydrolyses PIP2 to produce DAG and IP3. The PIP2 sensor was created by fusing the pleckstrin homology (PH) domain of PLCδ to two different components of the recently described dimerization-dependent red fluorescent proteins (26). The Pleckstrin homology domain, roughly 100 amino acids in size, is a feature found in many proteins (42). In the case of the phospholipse C delta, the PH domain of the protein specifically binds to PIP2 (43). Previous work has shown that the translocation of the PLCδ PH domain can be used to measure PIP2 turnover (27), and if the PH domains carry FRET pairs of fluorescent proteins a small change in FRET occurs when PLC is activated (28). To create a more robust sensor that does not involve FRET, and which produces a larger signal with a single fluorescent protein, we fused the PH domain to each member of the ddRFP pair. The design and construction of the PIP2 sensor is described in Example 4.

One advantage of sensors constructed with single fluorescent proteins is that they use less of the visible spectrum than FRET-based systems. This means that different sensors of different colors can be combined to monitor multiple signaling pathways simultaneously. The sensors described in the present application produce large changes in fluorescence that can be readily detected even on simple fluorescent plate readers. Because the sensors are based upon single fluorescent proteins, they can be readily multiplexed with other fluorescent protein based sensors, including without limitation, the calcium sensor R-GECO1 described previously in Zhao et al. 2011 (17), the R-CAMP sensor who structure has been described and deposited with the Protein Data Bank DOI:10.2210/pdb3u0k/pdb or the PIP2 sensor described herein. They can also be used with fluorescent dyes. A number of such dyes are known and available commercially. These include without limitation, voltage sensitive membrane dyes such as Di-4-ANEPPS, and Di-8ANEPPS. They could also be used with $Ca^{2+}$ indicator dyes such as Fluo-3, Fluo-4, Rhod-2, Oregon Green, Calcium Green, Calcium Orange, Calcium Crimson, Fura Red or Calcein. They could also be used with bioluminescent reporters, such as cAMP-Glo (commercially available from Promega). In multiplex assays the different sensor proteins may be encoded by different expression vectors and coexpressed, or may be coupled to produce stoichiometrically balanced quantities of each sensor. Examples 2-7 contain examples of various multiplex assays.

Such multiplexing improves the quality of the information produced in a screen in several ways. First, the simultaneous detection of multiple components of a signaling pathway provides an unambiguous read-out for a particular pathway. Second, detection of two different signals can be used to improve assay performance/reliability. Finally, the use of multiplex sensors such as these have the potential to provide new views of agonist-biased signaling by providing relative ratios of the activity of different signaling components (8). The multiplex sensors described here offer new opportunities for live cell assays by producing large, reproducible changes in fluorescence that can be detected on standard fluorescence plate readers used in laboratory automation. These live cell assays require no additional reagents, cell lysis, or complex liquid handling steps. The sensors are ready for routine use on standard equipment, and even better signals can be obtained with plate readers that can measure the response of the sensors in every well over time. The advent of multiplex sensors for both Ca2+ and cAMP for example (2, 4), shows that cells can produce anti-phase, cyclic patterns of signaling that can only be detected by collecting the responses of the two sensors over time. Similarly, the Ca2+ and DAG/PIP2 responses shown herein in examples 2-7 are quite different, with different rates of onset and return to baseline. As further demonstrated in Example 8, these interesting and biologically relevant patterns of signaling can be captured in microplate format, by measuring multiple signals over several time points at 0.1 to 5 Hz, with the Molecular Devices Fluorescent Imaging Plate Reader (FLIPR) and Hamamatsu FDSS (31, 32).

Also provided herein are vectors comprising the sensor-encoding nucleic acid sequences. Examples of suitable vectors include, but are not limited to, plasmids, artificial chromosomes, such as BACs, YACs, or PACs, and viral vectors. As used herein, vectors are agents that transport the disclosed nucleic acids into a cell without degradation and, optionally, include a promoter yielding expression of the nucleic acid molecule in the cells into which it is delivered.

Viral vectors are, for example, Adenovirus, Adeno-associated virus, herpes virus, Vaccinia virus, Polio virus, Sindbis, and other RNA viruses, including these viruses with the HIV backbone. Any viral families which share the properties of these viruses which make them suitable for use as vectors are suitable. Retroviral vectors, in general are described by Coffin et al., Retorviruses, Cold Spring Harbor Laboratory Press (1997), which is incorporated by reference herein for the vectors and methods of making them. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

Non-viral based vectors, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. .beta.-actin promoter or EF1.alpha. promoter, or from hybrid or chimeric promoters (e.g., CMV promoter fused to the .beta.-actin promoter). Promoters from the host cell or related species are also useful herein. Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the .beta.-actin promoter, the EFLalpha. promoter, and the retroviral long terminal repeat (LTR).

Cells comprising the sensors of the present invention, the sensor-encoding nucleic acid sequences or vectors comprising the sensor-encoding nucleic acid sequence are provided. The cell can be, for example, a eukaryotic or prokaryotic cell. Suitable cells include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), insect cells (for example, Sf9), human cells and plant cells. Suitable human cells include, for example, HeLa cells or human embryonic kidney (HEK) cells. Cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Optionally, the sensor-encoding nucleic acid sequence may be located in the genome of the cell.

Methods of making the provided cells are known and the method of transformation and choice of expression vector will depend on the host system selected. Transformation and transfection methods are described, e.g., in F. Ausubel et al., Current Protocols in Molecular Biology, John Wiley & Sons, New York, N.Y., (1998), and, as described above, expression vectors may be chosen from examples known in the art. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide or, for example, complexing a protein or peptide with another compound or tethering the protein, such as by a glycerophosphatidyl inositol (GPI) anchor. Such modifications can be considered to be mutations, for example, if the modification is different than the post-translational modification that occurs in the natural, wild-type protein or peptide.

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast *Saccharomyces*: Cell Cycle and Cell Biology, Pringle et al., eds., Cold Spring Harbor Laboratory Press (1997); The Yeast *Saccharomyces*: Gene Expression, Jones et al., eds., Cold Spring Harbor Laboratory Press (1993); The Yeast *Saccharomyces*: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, N.Y. (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

EXAMPLES

Example 1 Illustrates the Design and Construction of the DAG Biosensors

Sixty four different prototypes of a DAG sensor were created by fusing a circularly permuted enhanced green fluorescent protein from the calcium sensor G-GECO (cpEGFP) previously described in Zhao et al. 2011 to 30 different positions within the PKC-delta isoform. The sequence of the cpGFP is represented by SEQ ID NO:2 and the full length sequence of the PKC-delta isoform is represented by SEQ ID NO:1. As detailed in table 1, cpEGFP was inserted at various fusion sites in the full length PKC-delta, or fragments of PKC delta comprising N terminal truncation. Additionally, some of the constructs contained a deletion in the region immediately adjacent to the cpGFP insertion site. The length of the deletions ranged from 1 amino acid to 68 amino acids.

PCR amplification was used to generate fragments of PKC-delta and cpEGFP of G-GECO. Different combinations of PKC fragments were then paired with the cpEGFP amplicon and cloned into a modified version of the mammalian expression vector pcDNA3.1 using the In-Fusion Cloning system (Clonetech Laboratories Inc, Mountain View, Calif.). The pcDNA3.1 vector was obtained from Life Technologies (Grand Island, N.Y.). As detailed in table 1, thirty two of the prototypes involved inserting the cpEGFP into the full length PKC delta, and an additional 32 constructs were created in which the N-terminal region of PKC delta containing the C2 domain was deleted.

To test the functionality of the 64 fusion proteins, each construct was coexpressed with the M1 acetylcholine receptor, which couples to the Gq signaling pathway, in HEK 293 cells, and the fluorescence measured as described below.

HEK 293 cells (21) were cultured in EMEM supplemented with 10% fetal bovine serum and Penicillin-Streptomycin at 37° C. in 5% CO2. The cells and Eagle's Minimum Essential Medium (EMEM) were purchased from ATCC (Manassas, Va.). Prior to cell seeding, 96-well glass-bottom plates were coated with Poly-D-Lysine. Cells were seeded on the plates, transfected using Lipofectamine 2000 Transfection Reagent according to the manufacturer's protocol, and incubated for 24-48 hours at 37° C. in 5% $CO_2$. 60 ng of sensor DNA was co-transfected with 40 ng of human M1 muscarinic acetylcholine receptor per well. Pen-Strep liquid and Lipofectamine 2000 were obtained from Life Technologies (Grand Island, N.Y.). Poly-D-Lysine was purchased from Fisher Scientific (Pittsburgh, Pa.).

EMEM culture medium was replaced with 1×DPBS prior to screening transfected cells for fluorescence. A Zeiss Axiovert S 100TV inverted microscope equipped with computer controlled excitation/emission filter wheels, shutters, and a Qimaging Retiga Exi CCD camera (Surrey, BC Canada) was used to image cells at 25° C. using the 10× objective lens. 480±20 nm excitation and 535±25 nm emission filters were used resolve the green fluorescence from the DAG sensors, and 572±20 nm and 630±30 nm filters were used to collect the R-GECO signal. Cells were analyzed for increases or decreases in fluorescence intensity upon addition of Carbachol, PdBU, DMSO or Ionomycin. To analyze the image stacks, background fluorescence was defined as a region of the image that contained no cells. The average value of this region was subtracted frame by frame from the measurements of the mean pixel values of the fluorescent cells. Fluorescence intensity data was plotted and analyzed with IGOR (Wavemetrics, Oswego Ore.).

For transient expression and screening in an automated fluorescence plate reader, HEK 293T cells were cultured in Corning Co-Star Polystyrene 96 well plates coated with Poly-D-Lysine. HEK293T cells were plated at 35,0000 cells/well in 100 µl growth medium per well without antibiotics so that the cells would be 90-95% confluent at the time of transfection (approximately 24 hours later). For each transfection (i.e. one well in a 96-well plate), 160 ng of plasmid DNA (120 ng sensor+40 ng receptor) was diluted in 25 µl of Opti-MEM, 0.48 ul of lipofectamine 2000 was diluted in 25 µl of Opti-MEM, and these were then mixed and added to the cells. Cells were incubated in this mixture for 4 to 6 hours, and then the mixture was replaced with fresh medium. Prior to scanning a plate on the Biotek Synergy Mx, EMEM culture medium was replaced with 250 µl of 1×DPBS per well. Plates were read at 25° C., using monochromators set to 488/20 nm excitation and 530/20 nm emission to resolve the green fluorescence from the DAG sensor.

Figure 3A:
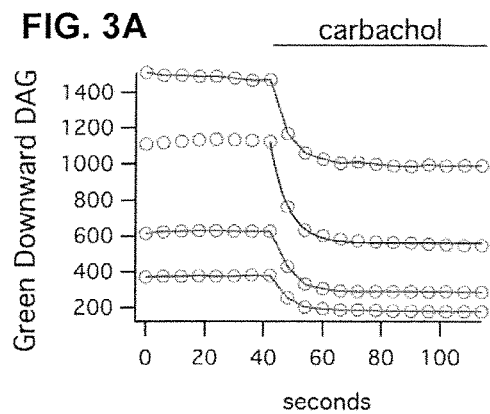
FIGS. 3A through 3E show the responses of Green Downward DAG and Upward DAG sensors. (A) Carbachol stimulation of the M1 receptor on cells expressing the Downward DAG sensor produces a 40% loss in fluorescence that occurs over 15 seconds (mean fluorescence over time of 4 cells). (B) The Upward DAG sensor shows a fluorescence increase of 45% over a similar time scale. (C) The signals generated by either sensor return to baseline quite slowly. (D) The apparent EC50 for carbacol-stimulated Upward DAG response is 3.5 uM. (E) The carbachol stimulation does not appear to activate all of the sensor pool in the cell since direct activation of the sensors with a subsequent application of PDBu produces an additional increase in fluorescence.
Figure 3B:
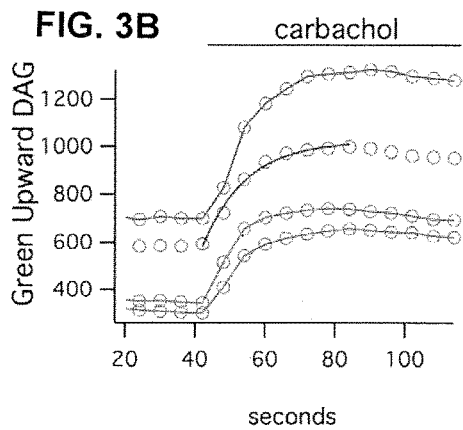
Figure 3C:
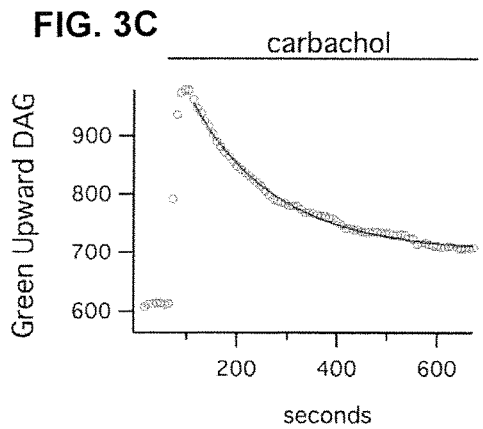

Two robust prototype sensors, Upward DAG and Downward DAG were recovered from this initial effort (20). Application of carbachol, an agonist of the M1 acetylcholine receptor, produced a remarkable a 45% increase in fluorescence in the Green Upward DAG sensor (FIG. 3B) and 40% decrease in fluorescence in the Green Downward DAG sensor (FIG. 3A). These changes were easily detected in time-lapse imaging and occurred in all transfected cells with remarkably little cell to cell variability. The increase or decrease of the signal produced by the Upward or Downward DAG, respectively, was reasonably fit by a single exponential function with a time constant of 6 to 11 seconds. The signals then returned to baseline quite slowly (t–170 seconds, FIG. 3C).

Figure 3D:
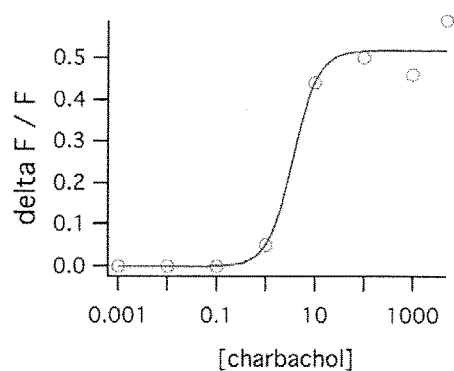
Figure 3E:
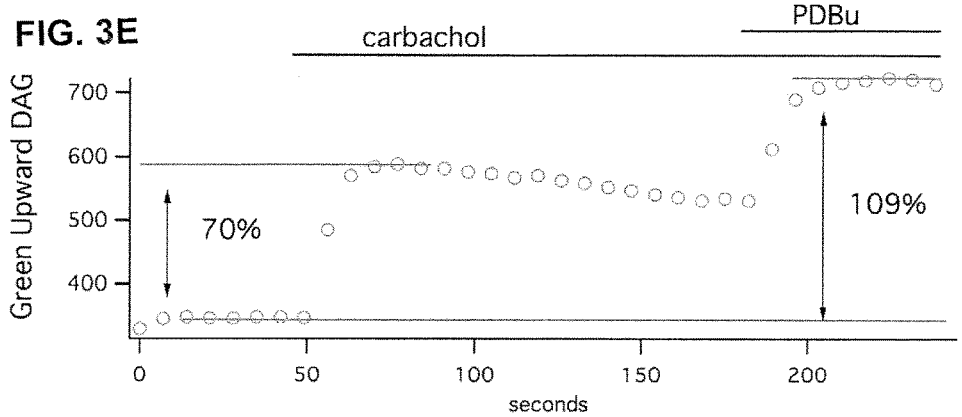

Both the Upward and Downward DAG sensors showed robust changes in fluorescence that are an order of magnitude larger than the previously reported, FRET-based DAG sensors. In transient expression it is possible to produce high concentrations of the protein-based sensor than the analyte itself [Falkenburger et al]. To test whether our measurements of the maximal sensor responses might be an underestimate, cells were first stimulated with carbachol and then the phorbol ester PDBu was added to directly activate any remaining sensors within the cell (FIG. 3D). This produced an additional doubling of the change in intensity, indicating that not all of the sensors in a given cell were activated by the carbachol, and that larger changes in fluorescence might be seen at lower intracellular concentrations of sensor, such as in the context of stable cell lines or transgenic animals.

Surprisingly, one sensor increases fluorescence as a result of activation (Upward DAG), while an insertion only 6 amino acids away produced a sensor that decreases fluorescence as a result of activation (Downward DAG). To our knowledge, this is the first example of small change in the position of the fluorescent protein producing an inversion of the signal produced by the sensor.

To optimize these prototype sensors, we created an additional 156 variants of the original Upward DAG and Downward DAG sensors, which helped identify additional 28 DAG sensors which produce large responses. The design of all thirty sensors is summarized in Table 2. As detailed in table 2, all sensors contain an N-terminal truncation of PKC delta that eliminates the C2 domain. The truncation was at L122. Thus, all sensors contain E123-Q150, with the table 2 beginning at Q150. Left side of the table lists the PKC delta protein sequence upstream of the inserted cpEGFP (see central green column)—In a given row, the final amino acid before the green column indicates the amino acid of PKC delta after which the cpEGFP is inserted. In all but one of these sensors, the cpEGFP and the linker were either positioned between the pseudosubstrate domain and the C1 domain of PKCδ, or in the C1a domain of PKCδ. Note that the PcpG30-21 sensor does not follow the general organization of the table. In this sensor, the insertion site of cpEGFP was well upstream of the insertion sites in the rest of the sensors. The amino acid after which cpEGFP was inserted was E134. Thus, this sensor is missing D135-H154 of the wild type PKC.

Similarly DAG sensors comprising a red fluorescent protein were constructed in which the circularly permuted Mapple protein [SEQ ID NO:3] was fused to a truncated PKCδ and in which the red fluorescence of the sensor increased upon binding to DAG. The complete amino acid sequence of the sensors are provided as SEQ ID NO:34, SEQ ID NO:35 and SEQ ID NO:36.

Figures 2A, 2B:
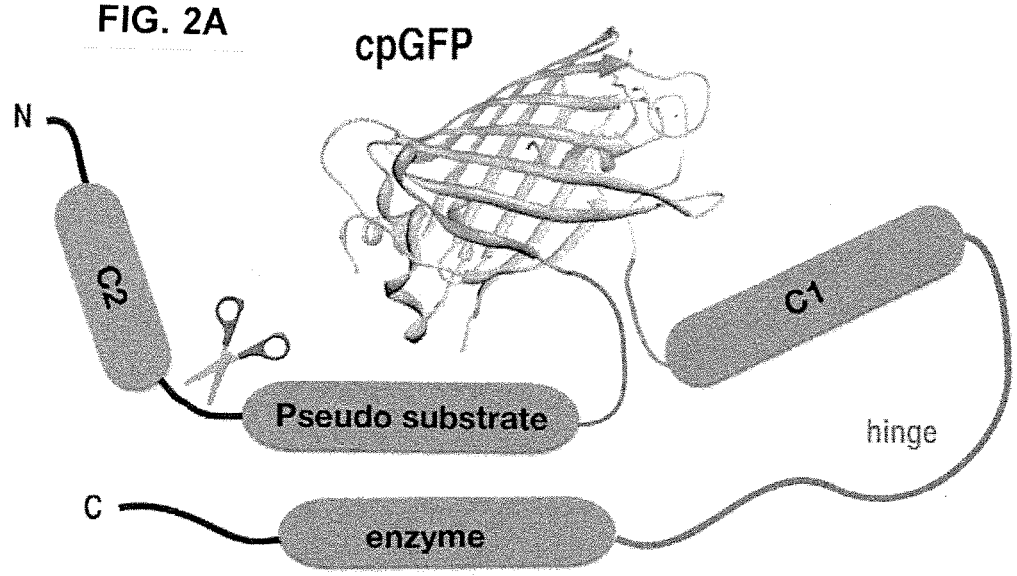
FIGS. 2A and 2B. (A) is a schematic diagram, illustrating the design of a prototype of DAG sensor. (B) shows the design of a construct in which a DAG sensor is coupled to a calcium sensor to produce stoichiometrically balanced quantities of each sensor.
Figure 4A:
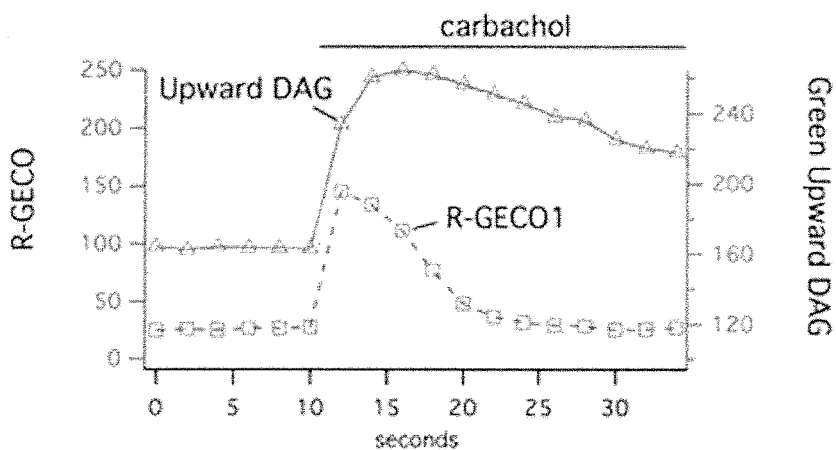
FIGS. 4A through 4C show that pairing the Green Upward and Downward DAG sensors with R-GECO makes it possible to simultaneously measure DAG and Ca2+ signaling in single cells. (A) The Green Upward DAG sensor response is considerably slower than the red Ca2+ response in response to carbachol stimulation of the M1 receptor. (B) Similar kinetics occur with the Downward DAG sensor. (C) The two sensors can be activated independently: ionomycin, which should raise intracellular Ca2+ without affecting DAG levels produces a change in R-GECO but not Downward DAG, while the subsequent addition of PDBu activates Downward DAG (arrows indicate stimulus artifact).
Figure 4B:
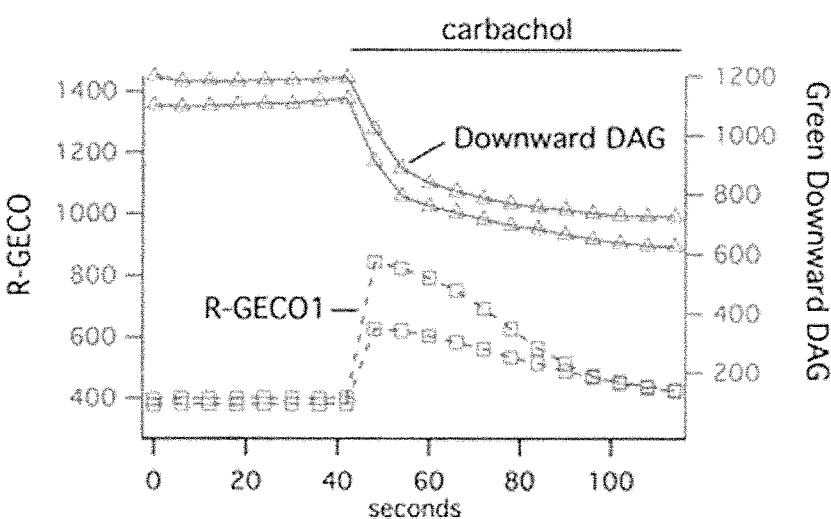

Example 2 Illustrates that a DAG Sensor can be Coupled with a Calcium Sensor in a Fusion Protein to Simultaneously Measure DAG and Calcium Signaling in Single Cells To multiplex the expression of the DAG sensor with a $Ca^{2+}$ sensor, we fused the coding regions of Green Upward DAG or Green Downward DAG to a cotranslational self-cleaving 2A [Szymczak et al.] peptide followed by R-GECO1 (FIG. 2B) to produce stoichiometrically balanced proportions of the two sensors. R-GECO1 is a red fluorescent $Ca^{2+}$ sensor described in Zhao et al [17] based on a circularly permuted red fluorescent protein mApple [Shaner et al] with excitation and emission properties that are easily distinguished from the green fluorescent DAG sensors. In cells transiently expressing this dual sensor system, stimulation of the M1 receptor produced a fast rise in intracellular Ca2+, as detected by changes in the red fluorescence channel, and a much slower rise in DAG, as detected in the green fluorescence channel (FIG. 4). The Ca2+ returns to baseline in ~20 seconds, while the DAG levels remain high for 200-300 seconds. This occurs for either the Downward or Upward DAG sensors paired with R-GECO1.

Figure 4C:
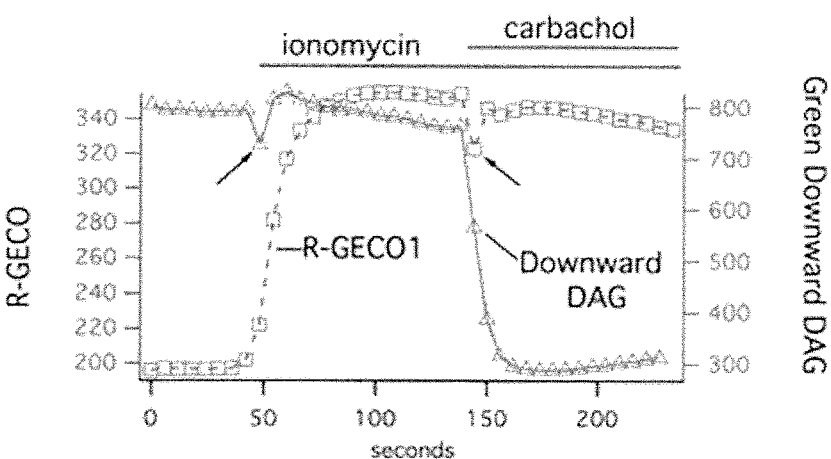

To test for the independence of the signals being detected by these sensors, we increased intracellular Ca2+ by applying ionomycin. This triggered a robust R-GECO1 response and no detectable change in the DAG sensor, which was subsequently activated by the addition of PDBu (FIG. 4C).

Example 3 Illustrates that DAG Sensors can be Co-Expressed with a Calcium Sensor to Simultaneously Measure DAG and Calcium Signaling in Single Cells The Green Upward DAG2 and Downward DAG were co-expressed with the red fluorescent R-GECO1 to simultaneously measure Ca2+ and DAG signaling in living cells. The responses (mean pixel intensity) of individual cells upon stimulation of the M1 receptor by carbachol are plotted in FIG. 5A, the left axis is green fluorescence (arbitrary units) and the right axis represents red fluorescence. Both the onset of the Ca2+ response and the return to baseline was considerably quicker than the DAG response, which is consistent with previous measurements (24, 25).

Many compound libraries are carried by DMSO, a vehicle that can cause artifacts in live cell assays. To test the effects of DMSO on the DAG assay, DMSO of different concentrations was added to the culture, followed later by carbachol to evoke the maximal sensor response (FIG. 5B). At moderate final concentrations of 0.1 to 1%, the DMSO produced no effect, while at higher concentrations artifactual, DMSO triggered changes in fluorescence did occur. The effect of DMSO on the DAG sensors was negligible at final concentrations of 0.1 to 1%, but detectable at 2% or greater.

Example 4 Illustrates the Design and Construction of a PIP2 Sensor

Figure 6A:
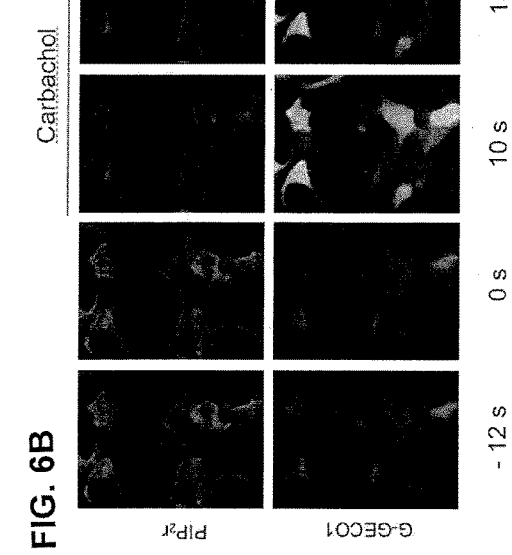
FIGS. 6A through 6D show multiplexing by DAG, PIP2, and Ca2+ sensors. The red PIP2 sensor was coexpressed with the G-GECO1 Ca2 sensor and the M1 receptor. Carbachol addition triggered a simultaneous increase in green fluorescence and decrease in red fluorescence (A & B). To test for interactions between the Ca2+ increase and DAG (C) or PIP2r (D) sensors, ionomycin was added to the culture, followed later by carbachol or PdBU.
Figure 6B:
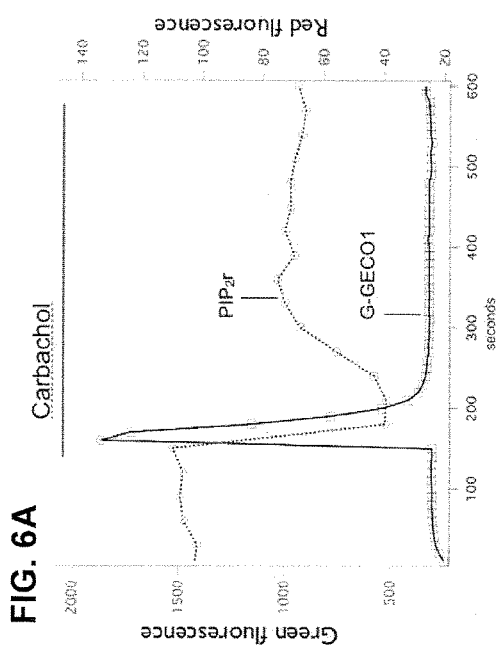

Phospholipase C hydrolyses PIP2 to produce both DAG and IP3. To independently check the fidelity and kinetics of the DAG sensors, we created a red fluorescent PIP2 sensor by fusing the pleckstrin homology (PH) domain of PLCδ to two different components of the recently described dimerization-dependent red fluorescent proteins (26). Previous work has shown that the translocation of the PLCδ PH domain can be used to measure PIP2 turnover (27), and if the PH domains carry FRET pairs of fluorescent proteins a small change in FRET occurs when PLC is activated (28). To create a more robust sensor that does not involve FRET, and uses less of the visible spectrum, we fused the PH domain of PLCδ to each member of the ddRFP pair (26). One pair of constructs produced a particularly strong red fluorescent signal at the membrane that rapidly disappeared with M1 receptor activation (FIGS. 6A and B). Because this sensor relies on the fluorescence of one protein, rather than a FRET pair, it could be multiplexed with the green fluorescent DAG sensors for simultaneous measurement of both PIP2 and DAG in living cells. The amino acid sequences of this pair of constructs forming a novel PIP2 sensor are shown as SEQ ID NO:70 and SEQ ID NO:71, and the nucleotide sequences encoding them are shown as SEQ ID NO:72 and SEQ ID NO:73.

Example 5 Illustrates Multiplexing with DAG, PIP2, and Ca2+ Sensors

Figure 6C:
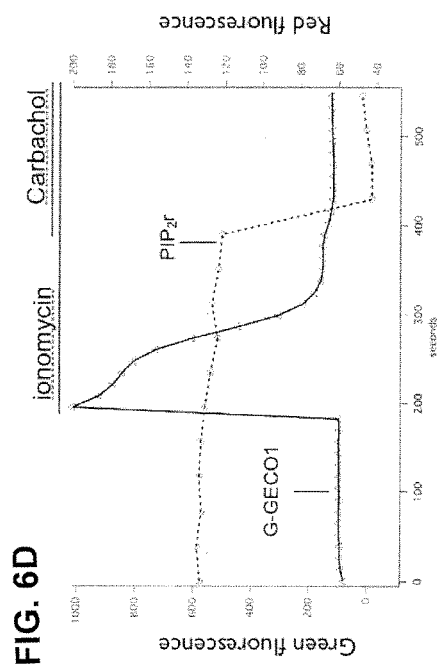
Figure 6D:
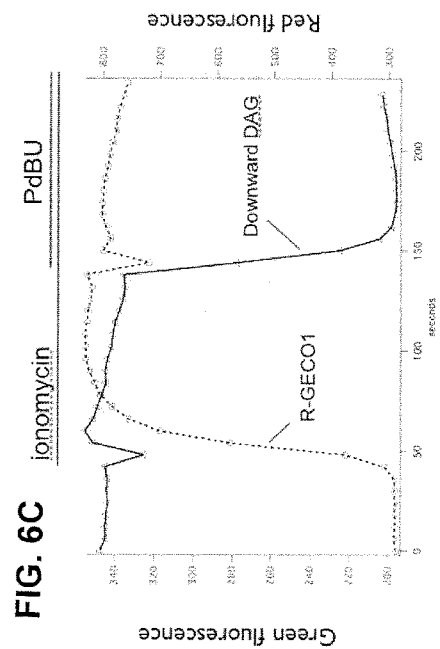

The red PIP2 sensor was coexpressed with the G-GECO1 $Ca^{2+}$ sensor (17) and the M1 receptor. Stimulation of the M1 receptor by carbachol addition produced a rapid, simultaneous rise in Ca2+ and fall in PIP2 levels. (FIGS. 6A and B). Changes in Ca2+ can have profound effects on many cellular processes. To explore the relationship between intracellular Ca2+ levels and the signals produced by our DAG and PIP2 sensors, we first raised Ca2+ levels by adding the ionophore ionomycin, and then activated the DAG sensors with PdBU and the PIP2r sensors with M1 receptor activation. Raising intracellular Ca2+ had no apparent effect on the DAG and PIP2 levels (FIGS. 6C and D).

Figure 7B:
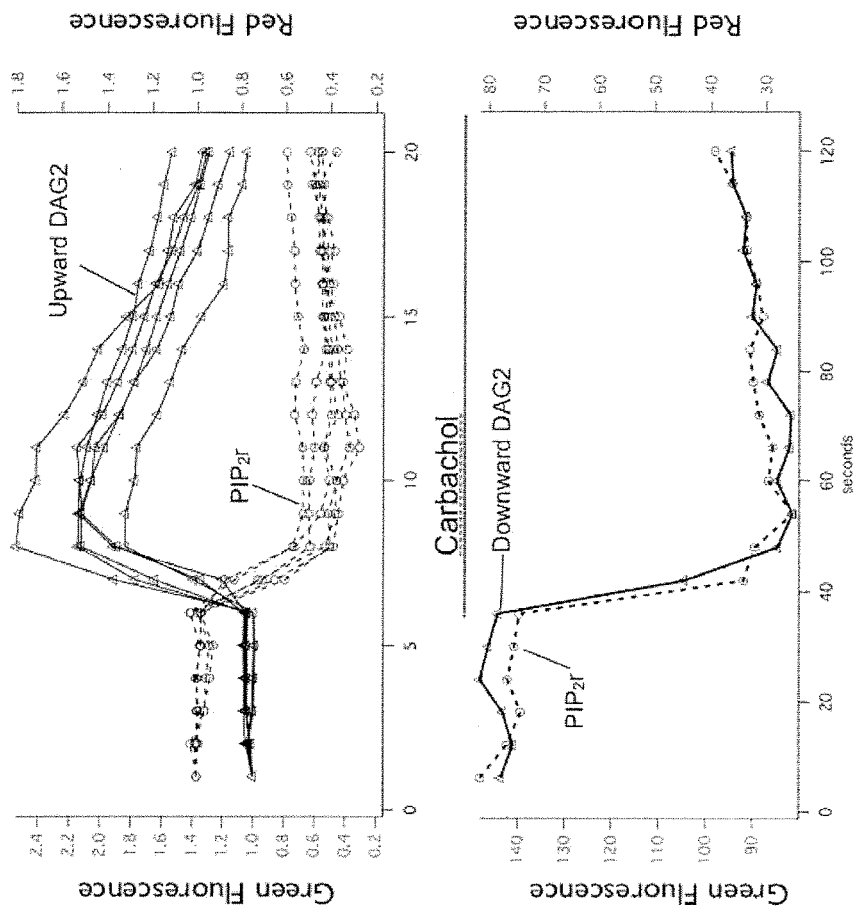
FIGS. 7A and 7B show that the PIP2r and DAG sensors can be co-expressed and measured simultaneously. Stimulation of phospholipase C cleaves PIP2 and produces DAG, which is clearly seen in living cells as the red fluorescence of the PIP2r vanishes and the Upward DAG2 sensor increases in fluorescence (A). This is reproducible from cell to cell (B, upper panel). The apparent return to baseline for the Upward DAG2 sensor is considerably faster than the Downward DAG2 or PIP2r sensors, which may be caused by photobleaching during the experiment.
Figure 7A:
Figure 8A:
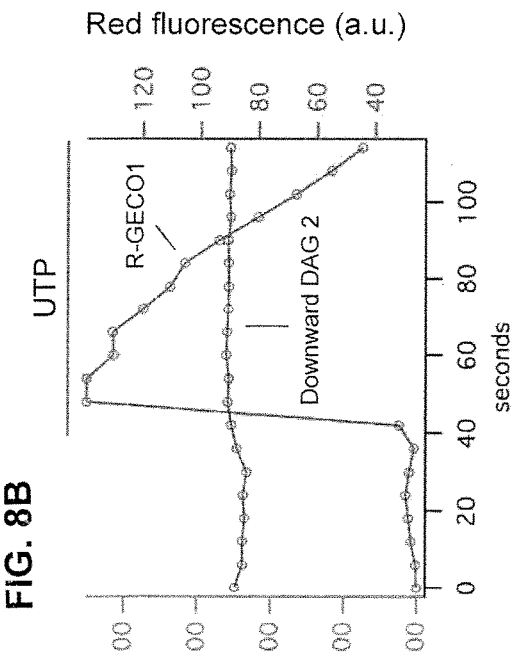
FIGS. 8A through 8D show the effect of ATP on activation of the PLC pathway. In HEK cells expressing the human P2Y11 receptor, the addition of ATP (A and C) or UTP (B and D) produces a transient increase in Ca2+ that is consistent with receptor activation. However the simultaneous recording of the Upward (C and D) or Downward (A and B) DAG2 sensors reveals that the ATP is activating the PLC pathway, while UTP is producing a Ca2+ transient through a different pathway.
Figure 8B:
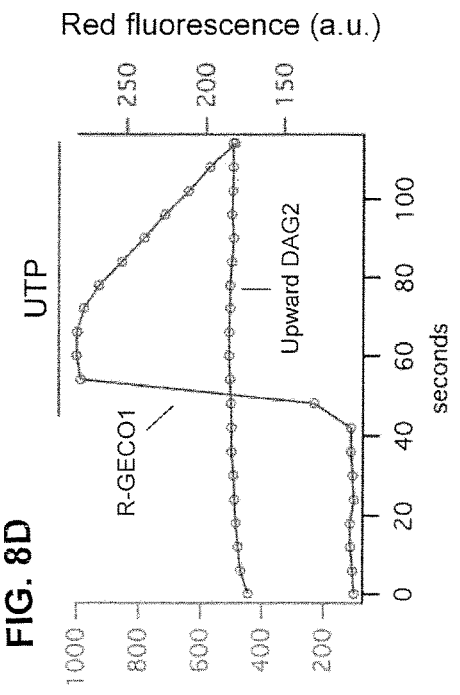
Figure 8C:
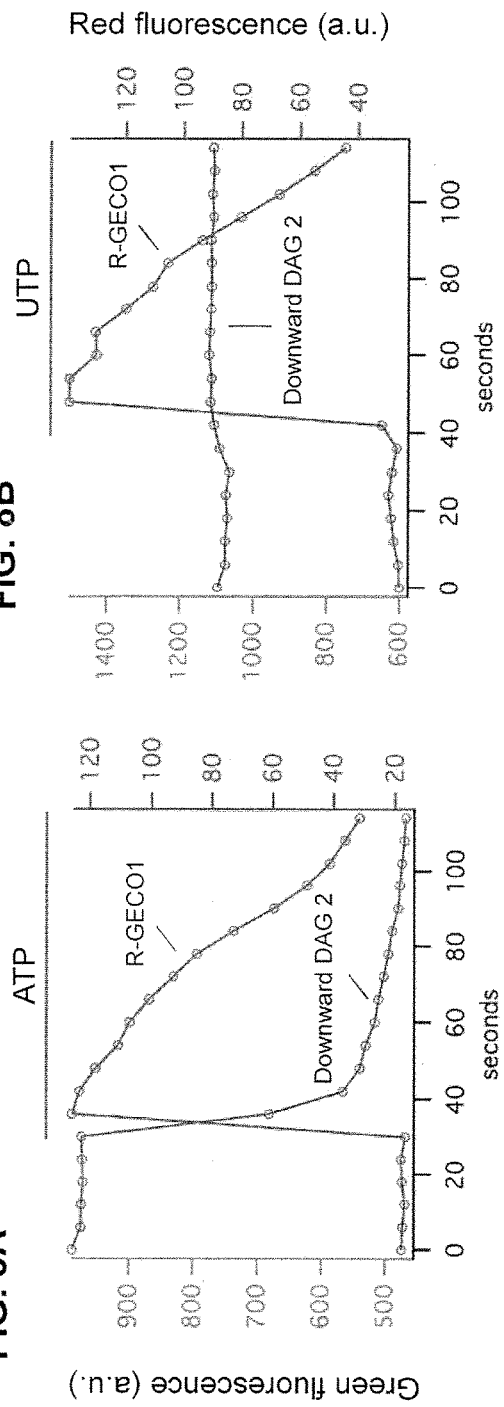
Figure 8D:
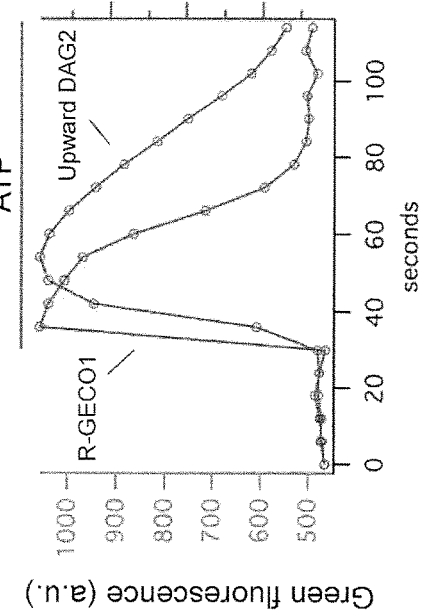

Example 6 Illustrates the Use of Multiplex PIP2 and DAG Sensors in Detection of PLC Activation Stimulation of phospholipase C cleaves PIP2 and produces DAG. Co-expression of the Upward DAG2 or Downward DAG2 sensor with the PIP2r sensor provides a new view of both the substrate and product of phospholipase C (FIG. 7). To our knowledge, this is the first time that genetically encoded biosensors have been used to simultaneously measure substrate and product. M1 receptor activation produced a remarkable change in the intensity and distribution of both sensors. As expected, the PIP2r sensor rapidly leaves the membrane and the red fluorescence decreases while the Upward DAG sensor translocates to the membrane and the green fluorescence increases (FIG. 7A). The onset of the response of the Upward and Downward DAG2 sensors, as well as PIP2r, is kinetically quite similar. However the return to baseline is considerably slower for the Downward DAG2 and PIP2r sensors (FIG. 7B). Because this return to baseline varies depending upon our sampling rate, our interpretation is that the apparent return to baseline for Upward DAG2 is artificially accelerated by photobleaching, and similarly prolonged in the cases of Downward DAG2 and PIP2r.

Example 7 Illustrates the Use of Multiplex DAG and Calcium Sensors

It has been reported that ATP acting at the P2Y11 receptor produces inositol phosphate turnover and transient Ca2+ signaling consistent with Gq signaling, while UTP acting at the same receptor only triggers a Ca2+ response (29). To explore whether multiplex sensors could be used to detect this distinct signaling pattern, we expressed the human P2Y11 receptor with combinations of the Downward DAG2, or Upward DAG2, and R-GECO1 sensors. In HEK 293 cells, both ATP and UTP triggered a Ca2+ response that was identical in terms of kinetics and is consistent with receptor activation. (FIG. 8). The Upward and Downward DAG2 sensors, however, revealed that the ATP triggers signaling via the phospholipase C pathway, while the UTP is causing a Ca2+ transient in a very different way. This UTP effect could be seen in cells that expressed only the sensor, without the P2Y11 receptor, so these results are likely to be due to the action of UTP on a receptor intrinsic to this cell line, unlike what White and colleagues saw with a different cell line (29).

Figure 9C:
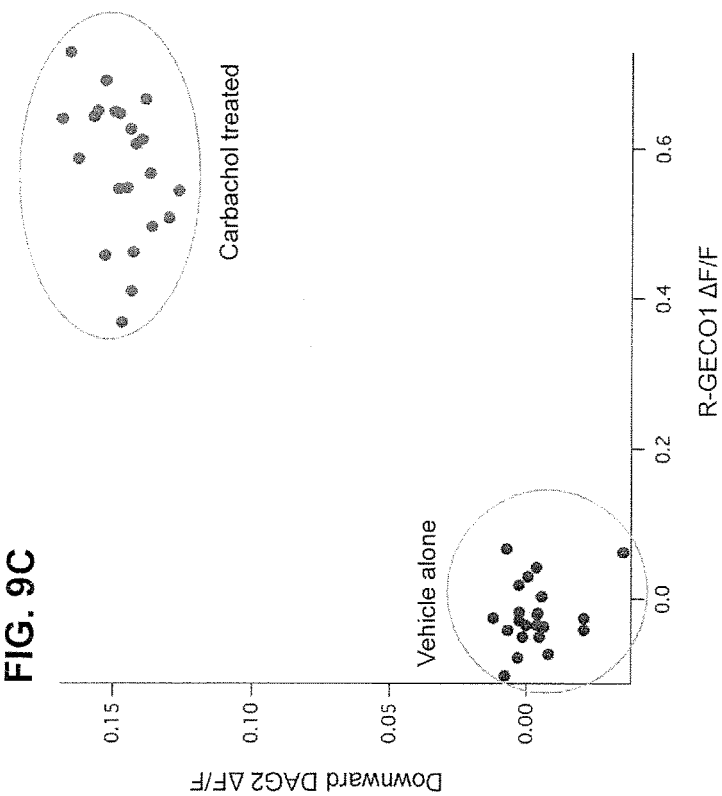
FIGS. 9A through 9C show that the DAG sensors described here are compatible with automated drug discovery. The Downward DAG2 sensor co-expressed with the M1 (A) or P2Y11 (B) receptor produces a consistent, reproducible signal (Z'>0.6) on a standard fluorescence plate reader. (C) Multiplexing the DAG sensors with R-GECO produces a two dimensional surface on which the negative control wells and positive carbachol responses are unambiguously separated.
Figure 9A:
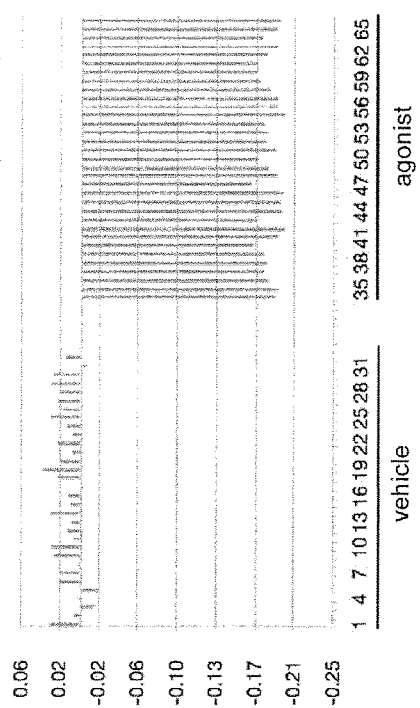

Example 8 Illustrates that the DAG Sensors Described Here are Compatible with Automated Drug Discovery Protein-based, fluorescent biosensors have often worked at the microscope, under exacting experimental control, and failed to make an impact on the field of laboratory automation and screening. To test whether the fluorescent DAG sensors described here would be suitable for routine applications and automated screening, we co-expressed the M1 or P2Y11 receptors with the Downward DAG2 sensor in HEK293T cells plated on a 96 well, Corning Co-Star polystyrene plate. Media was replaced with PBS, and the fluorescence of each well before and after the addition of drug was measured using a standard plate reader. The change in fluorescence was measured for addition of vehicle alone as well as vehicle carrying carbachol or ATP. Using only the signal provided by Downward DAG2, we were able to observe a consistent, reproducible signal (Z' values of 0.6 or greater) ((30) FIG. 9A).

Figure 9B:
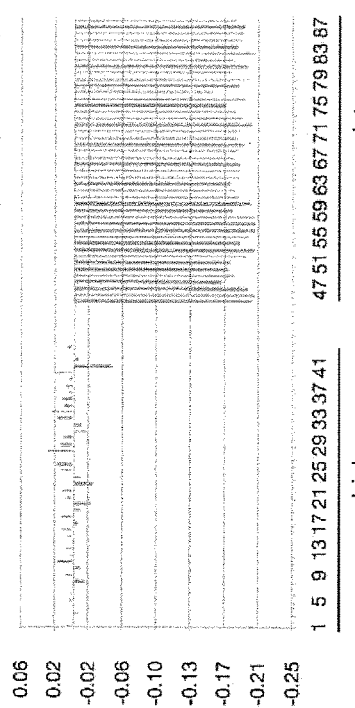

Multiplex sensors offer the opportunity to improve an assay by making multiple, simultaneous, independent measurements. When both the green and red fluorescence measurements were captured from wells of cells expressing both the R-GECO1 Ca2+ sensor and the Downward DAG2 sensor, it was possible to plot the response to M1 receptor activation in terms of both sensors. Multiplexing the DAG sensors with R-GECO produces a two dimensional surface on which the negative control wells and positive carbachol responses are unambiguously separated (FIG. 9B). This reveals that there is a strong correlation between the amplitude of the two signals, and even more importantly, that the two independent signals can be used to increase the stringency of the assay, and separation between stimulated and unstimulated cells (FIG. 9B).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims. The examples are provided for the purpose of illustration and are not intended to limit the scope of the present invention. Each publication, sequence or other reference disclosed below and elsewhere herein is incorporated herein by reference in its entirety, to the extent that there is no inconsistency with the present disclosure.

REFERENCES (1) Depry, C.; Mehta, S.; Zhang, J. Multiplexed visualization of dynamic signaling networks using genetically encoded fluorescent protein-based biosensors. Pflugers Arch—Eur J Physiol 2012, 1-9.

(2) Aye-Han, N.-N.; Allen, M. D.; Ni, Q.; Zhang, J. Parallel tracking of cAMP and PKA signaling dynamics in living cells with FRET-based fluorescent biosensors. Mol Biosyst 2012, 8, 1435-1440.

(3) Zaccolo, M. cAMP and Ca2+ interplay: a matter of oscillation patterns. Trends in neurosciences 2003.

(4) Borodinsky, L. N. Second Messenger Pas de Deux: The Coordinated Dance Between Calcium and cAMP. Science's STKE 2006, 2006, pe22-pe22.

(5) Ni, Q.; Ganesan, A.; Aye-Han, N.-N.; Gao, X.; Allen, M. D.; Levchenko, A.; Zhang, J. Signaling diversity of PKA achieved via a Ca2+-cAMP-PKA oscillatory circuit. Nat. Chem. Biol. 2011, 7, 34-40.

(6) Violin, J. D.; Lefkowitz, R. J. Beta-arrestin-biased ligands at seven-transmembrane receptors. Trends Pharmacol. Sci. 2007, 28, 416-422.

(7) Rajagopal, S.; Ahn, S.; Rominger, D. H.; Gowen-MacDonald, W.; Lam, C. M.; DeWire, S. M.; Violin, J. D.; Lefkowitz, R. J. Quantifying Ligand Bias at Seven-Transmembrane Receptors. Molecular Pharmacology 2011, 80, 367-377.

(8) Rajagopal, S.; Rajagopal, K.; Lefkowitz, R. J. Teaching old receptors new tricks: biasing seven-transmembrane receptors. Nat Rev Drug Discov 2010, 9, 373-386.

(9) Liu, J. J.; Horst, R.; Katritch, V.; Stevens, R. C.; Wuthrich, K. Biased Signaling Pathways in 2-Adrenergic Receptor Characterized by 19F-NMR. Science 2012, 335, 1106-1110.

(10) Sauliere, A.; Bellot, M.; Paris, H.; Denis, C.; Finana, F.; Hansen, J. T.; Altie, M.-F.; Seguelas, M.-H.; Pathak, A.; Hansen, J. L.; Senard, J.-M.; Gales, C. Deciphering biased-agonism complexity reveals a new active AT1 receptor entity. Nat. Chem. Biol. 2012, 8, 622-630.

(11) Raehal, K. M.; Walker, J. K. L.; Bohn, L. M. Morphine side effects in beta-arrestin 2 knockout mice. J. Pharmacol. Exp. Ther. 2005, 314, 1195-1201.

(12) Palmer, A. E.; Qin, Y.; Park, J. G.; McCombs, J. E. Design and application of genetically encoded biosensors. Trends Biotechnol. 2011, 29, 144-152.

(13) Ibraheem, A.; Campbell, R. E. Designs and applications of fluorescent protein based biosensors. Current Opinion in Chemical Biology 2010, 14, 30-36.

(14) Akerboom, J.; Rivera, J. D. V.; Guilbe, M. M. R.; Malave, E. C. A.; Hernandez, H. H.; Tian, L.; Hires, S. A.; Marvin, J. S.; looger, L. L.; Schreiter, E. R. Crystal Structures of the GCaMP Calcium Sensor Reveal the Mechanism of Fluorescence Signal Change and Aid Rational Design. Journal of Biological Chemistry 2008, 284, 6455-6464.

(15) Akerboom, J.; Chen, T.-W.; Wardill, T. J.; Tian, L.; Marvin, J. S.; Mutlu, S.; Calderon, N. C.; Esposti, F.; Borghuis, B. G.; Sun, X. R.; Gordus, A.; Orger, M. B.; Portugues, R.; Engert, F.; Macklin, J. J.; Filosa, A.; Aggarwal, A.; Kerr, R. A.; Takagi, R.; Kracun, S.; Shigetomi, E.; Khakh, B. S.; Baier, H.; Lagnado, L.; Wang, S. S.-H.; Bargmann, C. I.; Kimmel, B. E.; Jayaraman, V.; Svoboda, K.; Kim, D. S.; Schreiter, E. R.; Looger, L. L. Optimization of a GCaMP Calcium Indicator for Neural Activity Imaging. J. Neurosci. 2012, 32, 13819-13840.

(16) Nakai, J.; Ohkura, M.; Imoto, K. A high signal-to-noise Ca(2+) probe composed of a single green fluorescent protein. Nature Biotechnology 2001, 19, 137-141.

(17) Zhao, Y.; Araki, S.; Wu, J.; Teramoto, T.; Chang, Y. F.; Nakano, M.; Abdelfattah, A. S.; Fujiwara, M.; Ishihara, T.; Nagai, T.; Campbell, R. E. An Expanded Palette of Genetically Encoded Ca2+ Indicators. Science 2011.

(18) Barnett, L.; Platisa, J.; Popovic, M.; Pieribone, V. A.; Hughes, T. A fluorescent, genetically-encoded voltage probe capable of resolving action potentials. PLoS ONE 2012, 7, e43454.

(19) Nausch, L. W. M.; Ledoux, J.; Bonev, A. D.; Nelson, M. T.; Dostmann, W. R. Differential patterning of cGMP in vascular smooth muscle cells revealed by single GFP-linked biosensors. Proceedings of the National Academy of Sciences 2007, 105, 365.

(20) Tewson, P.; Westenberg, M.; Zhao, Y.; Campbell, R. E.; Quinn, A. M.; Hughes, T. E. Simultaneous Detection of Ca2+ and Diacylglycerol Signaling in Living Cells. PLoS ONE 2012, 7, e42791.

(21) Shaw, G.; Morse, S.; Ararat, M.; Graham, F. L. Preferential transformation of human neuronal cells by human adenoviruses and the origin of HEK 293 cells. The FASEB Journal 2002, 16, 869-871.

(22) Dries, D. R.; Gallegos, L. L.; Newton, A. C. A single residue in the C1 domain sensitizes novel protein kinase C isoforms to cellular diacylglycerol production. J. Biol. Chem. 2007, 282, 826-830.

(23) Giorgione, J. R.; Lin, J.-H.; McCammon, J. A.; Newton, A. C. Increased membrane affinity of the C1 domain of protein kinase Cdelta compensates for the lack of involvement of its C2 domain in membrane recruitment. J. Biol. Chem. 2006, 281, 1660-1669.

(24) Jensen, J. B.; Lyssand, J. S.; Hague, C.; Hille, B. Fluorescence changes reveal kinetic steps of muscarinic receptor-mediated modulation of phosphoinositides and Kv7.2/7.3 K+ channels. J. Gen. Physiol. 2009, 133, 347-359.

(25) Falkenburger, B. H.; Jensen, J. B.; Hille, B. Kinetics of M1 muscarinic receptor and G protein signaling to phospholipase C in living cells. J. Gen. Physiol. 2010, 135, 81-97.

(26) Alford, S. C.; Abdelfattah, A. S.; Ding, Y.; Campbell, R. E. A Fluorogenic Red Fluorescent Protein Heterodimer. Chem. Biol. 2012, 19, 353-360.
(27) Kavran, J. M.; Klein, D. E.; Lee, A.; Falasca, M.; Isakoff, S. J.; Skolnik, E. Y.; Lemmon, M. A. Specificity and promiscuity in phosphoinositide binding by pleckstrin homology domains. J. Biol. Chem. 1998, 273, 30497-30508.
(28) van der Wal, J. Monitoring Agonist-induced Phospholipase C Activation in Live Cells by Fluorescence Resonance Energy Transfer. Journal of Biological Chemistry 2001, 276, 15337-15344.
(29) White, P. J.; Webb, T. E.; Boarder, M. R. Characterization of a Ca2+ response to both UTP and ATP at human P2Y11 receptors: evidence for agonist-specific signaling. Molecular Pharmacology 2003, 63, 1356-1363.
(30) Zhang, J.; Chung, T.; Oldenburg, K. A Simple Statistical Parameter for Use in Evaluation and Validation of High Throughput Screening Assays. Journal of Biomolecular Screening 1999, 4, 67-73.
(31) Schroeder, K. S. FLIPR: A New Instrument for Accurate, High Throughput Optical Screening. Journal of Biomolecular Screening 1996, 1, 75-80.
(32) Poul, E. L.; Hisada, S.; Mizuguchi, Y.; Dupriez, V. J.; Burgeon, E.; Detheux, M. Adaptation of Aequorin Functional Assay to High Throughput Screening. Journal of Biomolecular Screening 2002, 7, 57-65.
(33) Shaner et al., A guide to choosing fluorescent proteins, Nature methods 2005, 2:12, 905-909.
(34) United States Patent Application 20120034691
(35) Carlson, H. J., Cotton, D. W., and Campbell, R. E. (2010). Circularly permuted monomeric red fluorescent proteins with new termini in the β-sheet. Protein Science 19, 1490-1499.
(36) Baird et al. G S, Zacharias D A, Tsien R Y (1999) Circular permutation and receptor insertion within green fluorescent proteins. Proc Natl Acad Sci USA 96: 11241-11246
(37) Nagai T, Sawano A, Park E S, Miyawaki A (2001) Circularly permuted green fluorescent proteins engineered to sense Ca2+. Proc Natl Acad Sci USA 98: 3197-3202.
(38) Nakai J, Ohkura M, Imoto K (2001) A high signal-to-noise Ca(2+) probe composed of a single green fluorescent protein. Nat Biotechnol 19: 137-141.
(39) Shui B, Wang Q, Lee F, Byrnes U, Chudakov D M, et al. (2011) Circular Permutation of Red Fluorescent Proteins. PLoS ONE 6(5): e20505. doi:10.1371/journal.pone.0020505
(40) Szymczak A L, Workman C J, Wang Y, Vignali K M, Dilioglou S, et al. (2004) Correction of multi-gene deficiency in vivo using a single "self-cleaving" 2A peptide-based retroviral vector. Nature Biotechnology 22: 589-594. doi:10.1038/nbt957.
(41) Oancea, E., Teruel, M. N., Quest, A. F. G., and Meyer, T. (1998). Green fluorescent protein (GFP)-tagged cysteine-rich domains from protein kinase C as fluorescent indicators for diacylglycerol signaling in living cells. J. Cell Biol. 140, 485-498.
(42) Shaw, G. (1996). The pleckstrin homology domain: An intriguing multifunctional protein module. Bioessays 18, 35-46.
(43) Cifuentes, M. E., Honkanen, L., and Rebecchi, M. J. (1993). Proteolytic fragments of phosphoinositide-specific phospholipase C-delta 1. Catalytic and membrane binding properties.
(44) Tsutsui, H., Karasawa, S., Okamura, Y., and Miyawaki, A. (2008). Improving membrane voltage measurements using FRET with new fluorescent proteins. Nature Methods 5, 683-685.
(45) Lam, A. J., St-Pierre, F., Gong, Y., Marshall, J. D., Cranfill, P. J., Baird, M. A., McKeown, M. R., Wiedenmann, J., Davidson, M. W., Schnitzer, M. J., et al. (2012). Improving FRET dynamic range with bright green and red fluorescent proteins. Nature Methods 9, 1005-1012.
(46) Shcherbo, D., Shemiakina, Ryabova, A. V., Luker, K. E., Schmidt, B. T., Souslova, E. A., Gorodnicheva, T. V., Strukova, L., Shidlovskiy, K. M., Britanova, O. V., et al. (2010). Near-infrared fluorescent proteins. Nature Methods 7, 827-829.
(47) Pletnev, S., Shcherbo, D., Chudakov, D. M., Pletneva, N., Merzlyak, E. M., Wlodawer, A., Dauter, Z., and Pletnev, V. (2008). A crystallographic study of bright far-red fluorescent protein mKate reveals pH-induced cis-trans isomerization of the chromophore. J. Biol. Chem. 283, 28980-28987.
(48) Merzlyak, E. M., Goedhart, J., Shcherbo, D., Bulina, M. E., Shcheglov, A. S., Fradkov, A. F., Gaintzeva, A., Lukyanov, K. A., Lukyanov, S., and Gadella, T. W. (2007). Bright monomeric red fluorescent protein with an extended fluorescence lifetime. Nature Methods 4, 555-557.
(49) Subach, O. M., Gundorov, I. S., Yoshimura, M., Subach, F. V., Zhang, J., Grüenwald, D., Souslova, E. A., Chudakov, D. M., and Verkhusha, V. V. (2008). Conversion of Red Fluorescent Protein into a Bright Blue Probe. Chem. Biol. 15, 1116-1124.

TABLE 1

Candidate sensor structural information, including cpEGFP positions, truncation sites, and amino acid deletions in PKC delta.

| Sensor | cpEGFP position | Truncation site | Deletion |
| --- | --- | --- | --- |
| PcpG1 | C280 | | |
| PcpG2 | I282 | | |
| PcpG3 | L286 | | |
| PcpG4 | A290 | | |
| PcpG5 | Q296 | | |
| PcpG6 | S302 | | |
| PcpG7 | E308 | | |
| PcpG8 | Y313 | | |
| PcpG9 | T320 | | |
| PcpG10 | E325 | | |
| PcpG11 | G332 | | |
| PcpG12 | I337 | | |
| PcpG13 | K343 | | |
| PcpG14 | N348 | | |
| PcpG15 | Y448 | | |
| PcpG16 | D217 | | |
| PcpG17 | N158 | | |
| PcpG1 2B | C280 | L122 | |
| PcpG2 2B | I282 | L122 | |
| PcpG3 2B | L286 | L122 | |
| PcpG4 2B | A290 | L122 | |
| PcpG5 2B | Q296 | L122 | |
| PcpG6 2B | S302 | L122 | |
| PcpG7 2B | E308 | L122 | |
| PcpG8 2B | Y313 | L122 | |
| PcpG9 2B | T320 | L122 | |
| PcpG10 2B | E325 | L122 | |
| PcpG11 2B | G332 | L122 | |
| PcpG12 2B | I337 | L122 | |
| PcpG13 2B | K343 | L122 | |
| PcpG14 2B | N348 | L122 | |
| PcpG15 2B | Y448 | L122 | |
| PcpG16 2B | D217 | L122 | |
| PcpG17 2A | N158 | L91 | |

TABLE 1-continued

Candidate sensor structural information, including cpEGFP positions, truncation sites, and amino acid deletions in PKC delta.

| Sensor | cpEGFP position | Truncation site | Deletion |
|---|---|---|---|
| PcpG17 2B | N158 | L122 | |
| PcpG17 2C | N158 | L106 | |
| PcpG17 2D | N158 | Q129 | |
| PcpG17 2A | N158 | K138 | |
| PcpG18 2B | K157 | L122 | |
| PcpG19 2B | I156 | L122 | |
| PcpG20 2B | Y155 | L122 | |
| PcpG21 2B | H154 | L122 | |
| PcpG22 2B | I153 | L122 | |
| PcpG23 2B | K152 | L122 | |
| Downward DAG | | | |
| PcpG24 2B | H159 | L122 | |
| PcpG25 2B | E160 | L122 | |
| PcpG26 2B | F161 | L122 | |
| PcpG27 2B | I162 | L122 | |
| PcpG28 2B | A163 | L122 | |
| PcpG29 2B | T164 | L122 | |
| PcpG30 2B | E134 | L122 | |
| PcpG1-2 | C280 | | G281-I282 |
| PcpG1-3 | C280 | | G281-L286 |
| PcpG1-4 | C280 | | G281-A290 |
| PcpG1-5 | C280 | | G281-Q296 |
| PcpG1-6 | C280 | | G281-S302 |
| PcpG1-7 | C280 | | G281-E308 |
| PcpG1-8 | C280 | | G281-Y313 |
| PcpG1-9 | C280 | | G281-T320 |
| PcpG1-10 | C280 | | G281-E325 |
| PcpG1-11 | C280 | | G281-G332 |
| PcpG1-12 | C280 | | G281-I337 |
| PcpG1-13 | C280 | | G281-K343 |
| PcpG1-14 | C280 | | G281-N348 |

TABLE 2

| PKC Delta | % Change | Sensor Domain<br>Q A K I H Y I K N H E F I A T<br>150 | Linker<br>F F | cpEGFP<br>G | Linker<br>Q P T F C S | Sensor Domain<br>173 |
|---|---|---|---|---|---|---|
| wildtype | | Q A K I H Y I K N H E F I A T | L E | | T R | H E F I A T F F G Q |
| Upward DAG | | | | | | |
| G17.2B | 50 | Q A K I H Y I K N | L E | | T R | N H E F I A T F F G |
| G17-18 | 105 | Q A K I H Y I K N | L E | | T R | *N* H E F I A T F F |
| Upward DAG2 | | | | | | |
| G17-19 | 12 | Q A K I H Y I K | L E | | T R | *K N* H E F I A T F F |
| G18-20 | -31 | Q A K I H Y I K | L E | | T R | *I K N* H E F I A T F |
| G19-17 | 34 | Q A K I H Y I | L E | | T R | - - H E F I A T F F G |
| G19-18 | 32 | Q A K I H Y I | L E | | T R | - *N* H E F I A T F F |
| G19-20 | -23 | Q A K I H Y I | L E | | T R | *I K N* H E F I A T F F |
| G20-17 | -42 | Q A K I H Y | L E | | T R | - - H E F I A T F G Q |
| G20-28 | -49 | Q A K I H Y | L E | | T R | - - T F G Q P T |
| DownwardDAG2 | | | | | | |
| G21-17 | 38 | Q A K I H | L E | | T R | - - - - H E F I A T F F G |
| G21-19 | 38 | Q A K I H | L E | | T R | - - *K N* H E F I A T F F G |
| G21-20 | 46 | Q A K I H | L E | | T R | - *I K N* H E F I A T F F G |
| G21-23 | -48 | Q A K I H | L E | | T R | - - - - N H E F I A T F F G Q P T F C S |
| G23 | -46 | Q A K | L E | | T R | - - - - - - H E F I A T F G |
| Downward DAG | | | | | | |
| G23-18 | 35 | Q A K | L E | | T R | - - - - *K N* H E F I A T F G |
| G23-19 | 36 | Q A K | L E | | T R | - - - *I K N* H E F I A T F F G |
| G27-19 | -46 | Q A K I H Y I K N H E F I | L E | | T R | *K N* H E F I A T F F G Q P T F C S |
| G27-22 | -45 | Q A K I H Y I K N H E F I | L E | | T R | *N* H E F I A T F F G Q P T F C S |
| G28-18 | 111 | Q A K I H Y I K N H E F I A | L E | | T R | *A* T F F G Q P T F C S |
| G28-27 | -10 | Q A K I H Y I K N H E F I A | L E | | T R | *N H E F I A T F F* G Q P T F C S |
| G29-18 | 56 | Q A K I H Y I K N H E F I A T | L E | | T R | *I H Y I K N H E F I A T F F* G Q P T F C S |
| G29-23 | -18 | Q A K I H Y I K N H E F I A T | L E | | T R | *E F I A T F F* G Q P T F C S |
| G29-24 | 16 | Q A K I H Y I K N H E F I A T | L E | | T R | - - - - - - - - - - - - - - - - - - |
| G30-21* | -23 | E D V D C K Q S M R S E | L E | | T R | - - - - - - - - - Y I K N H E F |

TABLE 2-continued

| | | DAG Sensing Domain | | |
|---|---|---|---|---|
| G19-30 | 13 | Q A K I H Y I | L E | T R D E A K F P T M N R R G A I K Q A K I H Y I K N H E F I A T F F |
| G21-30 | 44 | Q A K I H | L E | T R D E A K F P T M N R R G A I K Q A K I H Y I K N H E F I A T F F G Q |
| G23-30 | 96 | Q A K | L E | T R D E A K F P T M N R R G A I K Q A K I H Y I K N H E F I A T F F G Q |
| G24-30 | 34 | Q A K I H Y I K N H | L E | T R D E A K F P T M N R R G A I K Q A K I H Y I K N H E F I A T F F G Q |
| G28-30 | -10 | Q A K I H Y I K N H E F I A | L E | T R D E A K F P T M N R R G A I K Q A K I H Y I K N H E F I A T F F G Q |
| G29-30 | -29 | Q A K I H Y I K N H E F I A T | L E | T R D E A K F P T M N R R G A I K Q A K I H Y I K N H E F I A T F F G Q |
| R17.2B | | Q A K I H Y I K N | P V V | cpMapple T R H E F I A T F F G Q P T F C |
| R19 | | Q A K I H Y I | P V V | cpMapple T R K N H E F I A T F F G Q P T F C |
| R20 | | Q A K I H Y | P V V | cpMapple T R I K N H E F I A T F F G Q P T F C |

Left side lists DAG sensor sequence upstream of the inserted FP (central column) Amino acid position within PKC delta where FP is inserted is indicated relative to the wild type PKC Delta.

Right side lists DAG sensor sequence downstream of the inserted FP (central column). In some cases, there are amino acid insertions or deletions from wild type PKC delta.

All sensors contain an N-terminal trucation of PKC delta that eliminates the C2 domain. Truncation at L122. All sensors contain E123-Q150 with one exception noted, *PcpG30-21 sensor does not follow the general organization of the table. In this sensor, the insertion site of eGFP was upstream of the insertion sites in the rest of the sensors after position E134. Amino acids D135-H154 are deleted in this sensor.

deletion of PKC delta sensor domain residues indicated by -
insertions indicated in bold italics

What is claimed is:

1. A nucleic acid molecule comprising an expression control sequence operably linked to a nucleotide sequence encoding a protein comprising
   a. a protein kinase C (PKC) protein comprising a DAG binding domain and a fusion region; and,
   b. a circularly permuted fluorescent protein,
   wherein the fusion region is located between the pseudo substrate domain and the DAG binding domain, or within the DAG binding domain;
   wherein the fluorescent protein is fused with the PKC protein at a fusion site present within the fusion region; and,
   wherein the fluorescence of the DAG sensor fusion protein changes upon binding to DAG.

2. The nucleic acid molecule of claim 1, wherein the expression control sequence comprises one or more components selected from the group consisting of a promoter sequence, an enhancer sequence, a response element, a protein recognition site, a protein binding site, and a transcription start site.

3. The nucleic acid molecule of claim 2, wherein the promoter is an inducible promoter, a constitutive promoter, or a cell-specific promoter.

4. The nucleic acid molecule of claim 2, wherein the promoter is selected from the group consisting of a mammalian promoter, a polyoma virus promoter, a Simian Virus 40 (SV4) promoter, an adenovirus promoter, a retroviral promoter, a hepatitis B virus promoter, a Herpes virus promoter, and a cytomegalovirus (CMV) promoter.

5. The nucleic acid molecule of claim 2, wherein the promoter is a beta-actin promoter, a EF1-alpha promoter, hybrids thereof, or combinations thereof.

6. The nucleic acid molecule of claim 1, wherein the PKC protein is selected from the group consisting of PKC-δ (delta), PKC-ε (epsilon), PKC-θ (theta), PKC-η (eta), PKC-α (alpha), PKC-β1 (beta 1), PKC-β11 (beta 11), PKC-γ (gamma), and PKC-ξ (zeta).

7. The nucleic acid molecule of claim 1, wherein the fusion region comprises an addition or deletion up to 10 amino acids.

8. The nucleic acid molecule of claim 1, wherein the fusion region further comprises linker sequences.

9. The nucleic acid molecule of claim 1, wherein the encoded protein comprises an amino acid sequence at least 90% identical to an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36.

10. The nucleic acid molecule of claim 1, comprising a nucleotide sequence selected from the group consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, and SEQ ID NO:66.

11. A kit comprising the nucleic acid molecule of claim 1.

12. A viral vector comprising the nucleic acid molecule of claim 1.

13. A cell comprising the nucleic acid molecule of claim 1.

14. The cell of claim 13, further comprising one or more additional nucleic acid molecules that encode one or more additional fluorescent sensor proteins that specifically detect an analyte other than DAG.

15. A method of detecting diacylglycerol in a cell, comprising:
   a. exposing a cell comprising the nucleic acid molecule of claim 1 to light that excites the circularly permuted fluorescent protein; and,
   b. measuring the amount of fluorescent light produced by the cell at a wavelength corresponding to the emission wavelength of the fluorescent protein, thereby detecting diacylglycerol in the cell.

16. A method of detecting activation of the phospholipase C (PLC) pathway in a cell, comprising:
   a. exposing a cell comprising the nucleic acid molecule of claim 1 to light that excites the circularly permuted fluorescent protein; and,
   b. determining the level of diacylglycerol in the cell by measuring the amount of fluorescent light produced by the cell at a wavelength corresponding to the emission wavelength of the fluorescent protein;
   wherein a level of diacylglycerol greater than a basal level indicates activation of the phospholipase C pathway.

17. A method of identifying a compound that modulates the level of diacylglycerol in a cell, comprising:
   contacting a test compound with a cell comprising the nucleic acid molecule of claim 1;
   exposing the cell to light that excites the circularly permuted fluorescent protein; and,
   measuring the amount of fluorescent light produced by the cell at a wavelength corresponding to the emission wavelength of the fluorescent protein;
   wherein a change in the amount of fluorescent light produced by the cell indicates the test compound modulates the level of diacylglycerol in the cell.

18. A method of identifying a compound capable of modulating the activity of the phospholipase C (PLC) pathway in a cell, comprising:
   a. contacting a test compound with a cell comprising the nucleic acid molecule of claim 1;
   b. exposing the cell to light that excites the circularly permuted fluorescent protein; and,
   c. measuring the amount of fluorescent light produced by the cell at a wavelength corresponding to the emission wavelength of the fluorescent protein;
   wherein a change in the amount of fluorescent light produced by the cell indicates the compound modulates the PLC pathway.

* * * * *

SEQUENCE LISTING

<160> NUMBER OF SEQ ID NOS: 73

<210> SEQ ID NO 1
<211> LENGTH: 676
<212> TYPE: PRT
<213> ORGANISM: Homo sapiens

<400> SEQUENCE: 1

Met Ala Pro Phe Leu Arg Ile Ala Phe Asn Ser Tyr Glu Leu Gly Ser
1               5                   10                  15

Leu Gln Ala Glu Asp Glu Ala Asn Gln Pro Phe Cys Ala Val Lys Met
            20                  25                  30

Lys Glu Ala Leu Ser Thr Glu Arg Gly Lys Thr Leu Val Gln Lys Lys
        35                  40                  45

Pro Thr Met Tyr Pro Glu Trp Lys Ser Thr Phe Asp Ala His Ile Tyr
    50                  55                  60

Glu Gly Arg Val Ile Gln Ile Val Leu Met Arg Ala Ala Glu Glu Pro
65                  70                  75                  80

Val Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
            100                 105                 110

Lys Val Leu Met Ser Val Gln Tyr Phe Leu Glu Asp Val Asp Cys Lys
        115                 120                 125

Gln Ser Met Arg Ser Glu Asp Glu Ala Lys Phe Pro Thr Met Asn Arg
    130                 135                 140

Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
            180                 185                 190

Asn Ala Ala Ile His Lys Lys Cys Ile Asp Lys Ile Ile Gly Arg Cys
        195                 200                 205

Thr Gly Thr Ala Ala Asn Ser Arg Asp Thr Ile Phe Gln Lys Glu Arg
    210                 215                 220

Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
                245                 250                 255

Gln Gly Leu Lys Cys Glu Asp Cys Gly Met Asn Val His His Lys Cys
            260                 265                 270

Arg Glu Lys Val Ala Asn Leu Cys Gly Ile Asn Gln Lys Leu Leu Ala
        275                 280                 285

Glu Ala Leu Asn Gln Val Thr Gln Arg Ala Ser Arg Arg Ser Asp Ser
    290                 295                 300

Ala Ser Ser Glu Pro Val Gly Ile Tyr Gln Gly Phe Glu Lys Lys Thr
305                 310                 315                 320

Gly Val Ala Gly Glu Asp Met Gln Asp Asn Ser Gly Thr Tyr Gly Lys
                325                 330                 335

Ile Trp Glu Gly Ser Ser Lys Cys Asn Ile Asn Asn Phe Ile Phe His
            340                 345                 350

Lys Val Leu Gly Lys Gly Ser Phe Gly Lys Val Leu Leu Gly Glu Leu
        355                 360                 365

```
Lys Gly Arg Gly Glu Tyr Phe Ala Ile Lys Ala Leu Lys Lys Asp Val
    370                 375                 380
Val Leu Ile Asp Asp Val Glu Cys Thr Met Val Glu Lys Arg Val
385                 390                 395                 400
Leu Thr Leu Ala Ala Glu Asn Pro Phe Leu Thr His Leu Ile Cys Thr
                405                 410                 415
Phe Gln Thr Lys Asp His Leu Phe Phe Val Met Glu Phe Leu Asn Gly
            420                 425                 430
Gly Asp Leu Met Tyr His Ile Gln Asp Lys Gly Arg Phe Glu Leu Tyr
        435                 440                 445
Arg Ala Thr Phe Tyr Ala Ala Glu Ile Met Cys Gly Leu Gln Phe Leu
    450                 455                 460
His Ser Lys Gly Ile Ile Tyr Arg Asp Leu Lys Leu Asp Asn Val Leu
465                 470                 475                 480
Leu Asp Arg Asp Gly His Ile Lys Ile Ala Asp Phe Gly Met Cys Lys
                485                 490                 495
Glu Asn Ile Phe Gly Glu Ser Arg Ala Ser Thr Phe Cys Gly Thr Pro
            500                 505                 510
Asp Tyr Ile Ala Pro Glu Ile Leu Gln Gly Leu Lys Tyr Thr Phe Ser
        515                 520                 525
Val Asp Trp Trp Ser Phe Gly Val Leu Leu Tyr Glu Met Leu Ile Gly
    530                 535                 540
Gln Ser Pro Phe His Gly Asp Asp Glu Asp Glu Leu Phe Glu Ser Ile
545                 550                 555                 560
Arg Val Asp Thr Pro His Tyr Pro Arg Trp Ile Thr Lys Glu Ser Lys
                565                 570                 575
Asp Ile Leu Glu Lys Leu Phe Glu Arg Glu Pro Thr Lys Arg Leu Gly
            580                 585                 590
Val Thr Gly Asn Ile Lys Ile His Pro Phe Phe Lys Thr Ile Asn Trp
        595                 600                 605
Thr Leu Leu Glu Lys Arg Arg Leu Glu Pro Pro Phe Arg Pro Lys Val
    610                 615                 620
Lys Ser Pro Arg Asp Tyr Ser Asn Phe Asp Gln Glu Phe Leu Asn Glu
625                 630                 635                 640
Lys Ala Arg Leu Ser Tyr Ser Asp Lys Asn Leu Ile Asp Ser Met Asp
                645                 650                 655
Gln Ser Ala Phe Ala Gly Phe Ser Phe Val Asn Pro Lys Phe Glu His
            660                 665                 670
Leu Leu Glu Asp
            675

<210> SEQ ID NO 2
<211> LENGTH: 204
<212> TYPE: PRT
<213> ORGANISM: Artificial Sequence
<220> FEATURE:
<223> OTHER INFORMATION: Synthetic sequence, cpEGFP

<400> SEQUENCE: 2

Asn Val Tyr Ile Lys Ala Asp Lys Gln Lys Asn Gly Ile Lys Ala Asn
1               5                   10                  15
Phe Lys Ile Arg His Asn Ile Glu Asp Gly Gly Val Gln Leu Ala Tyr
            20                  25                  30
His Tyr Gln Gln Asn Thr Pro Ile Gly Asp Gly Pro Val Leu Leu Pro
        35                  40                  45
```

```
Asp Asn His Tyr Leu Ser Val Gln Ser Ile Leu Ser Lys Asp Pro Asn
    50                  55                  60

Glu Lys Arg Asp His Met Val Leu Leu Glu Phe Val Thr Ala Ala Gly
 65              70                  75                  80

Ile Thr Leu Gly Met Asp Glu Leu Tyr Lys Gly Gly Thr Gly Gly Ser
                 85                  90                  95

Met Val Ser Lys Gly Glu Glu Leu Phe Thr Gly Val Val Pro Ile Gln
                100                 105                 110

Val Glu Leu Asp Gly Asp Val Asn Gly His Lys Phe Ser Val Ser Gly
            115                 120                 125

Glu Gly Glu Gly Asp Ala Thr Tyr Gly Lys Leu Thr Leu Lys Phe Ile
130                 135                 140

Cys Thr Thr Gly Lys Leu Pro Val Pro Trp Pro Thr Leu Val Thr Thr
145                 150                 155                 160

Leu Thr Tyr Gly Val Gln Cys Phe Ser Arg Tyr Pro Asp His Met Lys
                165                 170                 175

Gln His Asp Phe Phe Lys Ser Ala Met Pro Glu Gly Tyr Ile Gln Glu
            180                 185                 190

Arg Thr Ile Phe Phe Lys Asp Asp Gly Asn Tyr Lys
        195                 200

<210> SEQ ID NO 3
<211> LENGTH: 241
<212> TYPE: PRT
<213> ORGANISM: Artificial Sequence
<220> FEATURE:
<223> OTHER INFORMATION: Synthetic sequence, cpApple

<400> SEQUENCE: 3

Ser Glu Arg Met Tyr Pro Glu Asp Gly Ala Leu Lys Ser Glu Ile Lys
  1               5                  10                  15

Lys Gly Leu Arg Leu Lys Asp Gly Gly His Tyr Ala Ala Glu Val Lys
                 20                  25                  30

Thr Thr Tyr Lys Ala Lys Lys Pro Val Gln Leu Pro Gly Ala Tyr Ile
             35                  40                  45

Val Asp Ile Lys Leu Asp Ile Val Ser His Asn Glu Asp Tyr Thr Ile
 50                  55                  60

Val Glu Gln Cys Glu Arg Ala Glu Gly Arg His Ser Thr Gly Gly Met
 65                  70                  75                  80

Asp Glu Leu Tyr Lys Gly Gly Thr Gly Gly Ser Leu Val Ser Lys Gly
                 85                  90                  95

Glu Glu Asp Asn Met Ala Ile Ile Lys Glu Phe Met Arg Phe Lys Val
                100                 105                 110

His Met Glu Gly Ser Val Asn Gly His Glu Phe Glu Ile Glu Gly Glu
            115                 120                 125

Gly Glu Gly Arg Pro Tyr Glu Ala Phe Gln Thr Ala Lys Leu Lys Val
130                 135                 140

Thr Lys Gly Gly Pro Leu Pro Phe Ala Trp Asp Ile Leu Ser Pro Gln
145                 150                 155                 160

Phe Met Tyr Gly Ser Lys Ala Tyr Ile Lys His Pro Ala Asp Ile Pro
                165                 170                 175

Asp Tyr Phe Lys Leu Ser Phe Pro Glu Gly Phe Arg Trp Glu Arg Val
            180                 185                 190

Met Asn Phe Glu Asp Gly Gly Ile Ile His Val Asn Gln Asp Ser Ser
        195                 200                 205
```

-continued

```
Leu Gln Asp Gly Val Phe Ile Tyr Lys Val Lys Leu Arg Gly Thr Asn
210                 215                 220

Phe Pro Pro Asp Gly Pro Val Met Gln Lys Lys Thr Met Gly Trp Glu
225                 230                 235                 240

Ala

<210> SEQ ID NO 4
<211> LENGTH: 800
<212> TYPE: PRT
<213> ORGANISM: Artificial Sequence
<220> FEATURE:
<223> OTHER INFORMATION: Synthetic sequence, a.a. sequence of sensor 1
      [G17.2B]

<400> SEQUENCE: 4

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
                20                  25                  30

His Tyr Ile Lys Asn Leu Glu Asn Val Tyr Ile Lys Ala Asp Lys Gln
            35                  40                  45

Lys Asn Gly Ile Lys Ala Asn Phe Lys Ile Arg His Asn Ile Glu Asp
50                  55                  60

Gly Gly Val Gln Leu Ala Tyr His Tyr Gln Gln Asn Thr Pro Ile Gly
65                  70                  75                  80

Asp Gly Pro Val Leu Leu Pro Asp Asn His Tyr Leu Ser Val Gln Ser
                85                  90                  95

Ile Leu Ser Lys Asp Pro Asn Glu Lys Arg Asp His Met Val Leu Leu
            100                 105                 110

Glu Phe Val Thr Ala Ala Gly Ile Thr Leu Gly Met Asp Glu Leu Tyr
        115                 120                 125

Lys Gly Gly Thr Gly Gly Ser Met Val Ser Lys Gly Glu Glu Leu Phe
    130                 135                 140

Thr Gly Val Val Pro Ile Gln Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Ile Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Thr Arg His Glu Phe Ile Ala Thr
        275                 280                 285

Phe Phe Gly Gln Pro Thr Phe Cys Ser Val Cys Lys Asp Phe Val Trp
    290                 295                 300

Gly Leu Asn Lys Gln Gly Tyr Lys Cys Arg Gln Cys Asn Ala Ala Ile
305                 310                 315                 320
```

-continued

His Lys Lys Cys Ile Asp Lys Ile Ile Gly Arg Cys Thr Gly Thr Ala
              325                 330                 335

Ala Asn Ser Arg Asp Thr Ile Phe Gln Lys Glu Arg Phe Asn Ile Asp
              340                 345                 350

Met Pro His Arg Phe Lys Val His Asn Tyr Met Ser Pro Thr Phe Cys
              355                 360                 365

Asp His Cys Gly Ser Leu Leu Trp Gly Leu Val Lys Gln Gly Leu Lys
              370                 375             380

Cys Glu Asp Cys Gly Met Asn Val His His Lys Cys Arg Glu Lys Val
385                 390                 395                 400

Ala Asn Leu Cys Gly Ile Asn Gln Lys Leu Leu Ala Glu Ala Leu Asn
                  405                 410                 415

Gln Val Thr Gln Arg Ala Ser Arg Ser Asp Ser Ala Ser Ser Glu
              420                 425                 430

Pro Val Gly Ile Tyr Gln Gly Phe Glu Lys Lys Thr Gly Val Ala Gly
              435                 440                 445

Glu Asp Met Gln Asp Asn Ser Gly Thr Tyr Gly Lys Ile Trp Glu Gly
              450                 455                 460

Ser Ser Lys Cys Asn Ile Asn Asn Phe Ile Phe His Lys Val Leu Gly
465                 470                 475                 480

Lys Gly Ser Phe Gly Lys Val Leu Leu Gly Glu Leu Lys Gly Arg Gly
                  485                 490                 495

Glu Tyr Phe Ala Ile Lys Ala Leu Lys Lys Asp Val Val Leu Ile Asp
                  500                 505                 510

Asp Asp Val Glu Cys Thr Met Val Glu Lys Arg Val Leu Thr Leu Ala
              515                 520                 525

Ala Glu Asn Pro Phe Leu Thr His Leu Ile Cys Thr Phe Gln Thr Lys
530                 535                 540

Asp His Leu Phe Phe Val Met Glu Phe Leu Asn Gly Gly Asp Leu Met
545                 550                 555                 560

Tyr His Ile Gln Asp Lys Gly Arg Phe Glu Leu Tyr Arg Ala Thr Phe
              565                 570                 575

Tyr Ala Ala Glu Ile Met Cys Gly Leu Gln Phe Leu His Ser Lys Gly
              580                 585                 590

Ile Ile Tyr Arg Asp Leu Lys Leu Asp Asn Val Leu Leu Asp Arg Asp
              595                 600                 605

Gly His Ile Lys Ile Ala Asp Phe Gly Met Cys Lys Glu Asn Ile Phe
              610                 615                 620

Gly Glu Ser Arg Ala Ser Thr Phe Cys Gly Thr Pro Asp Tyr Ile Ala
625                 630                 635                 640

Pro Glu Ile Leu Gln Gly Leu Lys Tyr Thr Phe Ser Val Asp Trp Trp
                  645                 650                 655

Ser Phe Gly Val Leu Leu Tyr Glu Met Leu Ile Gly Gln Ser Pro Phe
                  660                 665                 670

His Gly Asp Asp Glu Asp Glu Leu Phe Glu Ser Ile Arg Val Asp Thr
              675                 680                 685

Pro His Tyr Pro Arg Trp Ile Thr Lys Glu Ser Lys Asp Ile Leu Glu
              690                 695                 700

Lys Leu Phe Glu Arg Glu Pro Thr Lys Arg Leu Gly Val Thr Gly Asn
705                 710                 715                 720

Ile Lys Ile His Pro Phe Phe Lys Thr Ile Asn Trp Thr Leu Leu Glu
                  725                 730                 735

Lys Arg Arg Leu Glu Pro Pro Phe Arg Pro Lys Val Lys Ser Pro Arg

```
                740                 745                 750
Asp Tyr Ser Asn Phe Asp Gln Glu Phe Leu Asn Glu Lys Ala Arg Leu
        755                 760                 765

Ser Tyr Ser Asp Lys Asn Leu Ile Asp Ser Met Asp Gln Ser Ala Phe
        770                 775                 780

Ala Gly Phe Ser Phe Val Asn Pro Lys Phe Glu His Leu Leu Glu Asp
785                 790                 795                 800

<210> SEQ ID NO 5
<211> LENGTH: 801
<212> TYPE: PRT
<213> ORGANISM: Artificial Sequence
<220> FEATURE:
<223> OTHER INFORMATION: Synthetic sequence, a.a. sequence of sensor 2
      [G17-18]

<400> SEQUENCE: 5

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
                20                  25                  30

His Tyr Ile Lys Asn Leu Glu Asn Val Tyr Ile Lys Ala Asp Lys Gln
            35                  40                  45

Lys Asn Gly Ile Lys Ala Asn Phe Lys Ile Arg His Asn Ile Glu Asp
50                  55                  60

Gly Gly Val Gln Leu Ala Tyr His Tyr Gln Gln Asn Thr Pro Ile Gly
65                  70                  75                  80

Asp Gly Pro Val Leu Leu Pro Asp Asn His Tyr Leu Ser Val Gln Ser
                85                  90                  95

Ile Leu Ser Lys Asp Pro Asn Glu Lys Arg Asp His Met Val Leu Leu
            100                 105                 110

Glu Phe Val Thr Ala Ala Gly Ile Thr Leu Gly Met Asp Glu Leu Tyr
        115                 120                 125

Lys Gly Gly Thr Gly Gly Ser Met Val Ser Lys Gly Glu Glu Leu Phe
130                 135                 140

Thr Gly Val Val Pro Ile Gln Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
210                 215                 220

Pro Glu Gly Tyr Ile Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Thr Arg Asn His Glu Phe Ile Ala
        275                 280                 285

Thr Phe Phe Gly Gln Pro Thr Phe Cys Ser Val Cys Lys Asp Phe Val
290                 295                 300
```

-continued

```
Trp Gly Leu Asn Lys Gln Gly Tyr Lys Cys Arg Gln Cys Asn Ala Ala
305                 310                 315                 320

Ile His Lys Lys Cys Ile Asp Lys Ile Ile Gly Arg Cys Thr Gly Thr
                325                 330                 335

Ala Ala Asn Ser Arg Asp Thr Ile Phe Gln Lys Glu Arg Phe Asn Ile
            340                 345                 350

Asp Met Pro His Arg Phe Lys Val His Asn Tyr Met Ser Pro Thr Phe
        355                 360                 365

Cys Asp His Cys Gly Ser Leu Leu Trp Gly Leu Val Lys Gln Gly Leu
    370                 375                 380

Lys Cys Glu Asp Cys Gly Met Asn Val His His Lys Cys Arg Glu Lys
385                 390                 395                 400

Val Ala Asn Leu Cys Gly Ile Asn Gln Lys Leu Leu Ala Glu Ala Leu
                405                 410                 415

Asn Gln Val Thr Gln Arg Ala Ser Arg Arg Ser Asp Ser Ala Ser Ser
            420                 425                 430

Glu Pro Val Gly Ile Tyr Gln Gly Phe Glu Lys Lys Thr Gly Val Ala
        435                 440                 445

Gly Glu Asp Met Gln Asp Asn Ser Gly Thr Tyr Gly Lys Ile Trp Glu
    450                 455                 460

Gly Ser Ser Lys Cys Asn Ile Asn Asn Phe Ile Phe His Lys Val Leu
465                 470                 475                 480

Gly Lys Gly Ser Phe Gly Lys Val Leu Leu Gly Glu Leu Lys Gly Arg
                485                 490                 495

Gly Glu Tyr Phe Ala Ile Lys Ala Leu Lys Lys Asp Val Val Leu Ile
            500                 505                 510

Asp Asp Asp Val Glu Cys Thr Met Val Glu Lys Arg Val Leu Thr Leu
        515                 520                 525

Ala Ala Glu Asn Pro Phe Leu Thr His Leu Ile Cys Thr Phe Gln Thr
    530                 535                 540

Lys Asp His Leu Phe Phe Val Met Glu Phe Leu Asn Gly Gly Asp Leu
545                 550                 555                 560

Met Tyr His Ile Gln Asp Lys Gly Arg Phe Glu Leu Tyr Arg Ala Thr
                565                 570                 575

Phe Tyr Ala Ala Glu Ile Met Cys Gly Leu Gln Phe Leu His Ser Lys
            580                 585                 590

Gly Ile Ile Tyr Arg Asp Leu Lys Leu Asp Asn Val Leu Leu Asp Arg
        595                 600                 605

Asp Gly His Ile Lys Ile Ala Asp Phe Gly Met Cys Lys Glu Asn Ile
    610                 615                 620

Phe Gly Glu Ser Arg Ala Ser Thr Phe Cys Gly Thr Pro Asp Tyr Ile
625                 630                 635                 640

Ala Pro Glu Ile Leu Gln Gly Leu Lys Tyr Thr Phe Ser Val Asp Trp
                645                 650                 655

Trp Ser Phe Gly Val Leu Leu Tyr Glu Met Leu Ile Gly Gln Ser Pro
            660                 665                 670

Phe His Gly Asp Asp Glu Asp Glu Leu Phe Glu Ser Ile Arg Val Asp
        675                 680                 685

Thr Pro His Tyr Pro Arg Trp Ile Thr Lys Glu Ser Lys Asp Ile Leu
    690                 695                 700

Glu Lys Leu Phe Glu Arg Glu Pro Thr Lys Arg Leu Gly Val Thr Gly
705                 710                 715                 720

Asn Ile Lys Ile His Pro Phe Phe Lys Thr Ile Asn Trp Thr Leu Leu
```

```
                    725                 730                 735
Glu Lys Arg Arg Leu Glu Pro Pro Phe Arg Pro Lys Val Lys Ser Pro
                740                 745                 750

Arg Asp Tyr Ser Asn Phe Asp Gln Glu Phe Leu Asn Glu Lys Ala Arg
                755                 760                 765

Leu Ser Tyr Ser Asp Lys Asn Leu Ile Asp Ser Met Asp Gln Ser Ala
            770                 775                 780

Phe Ala Gly Phe Ser Phe Val Asn Pro Lys Phe Glu His Leu Leu Glu
785                 790                 795                 800

Asp

<210> SEQ ID NO 6
<211> LENGTH: 802
<212> TYPE: PRT
<213> ORGANISM: Artificial Sequence
<220> FEATURE:
<223> OTHER INFORMATION: Synthetic sequence, a.a. sequence of sensor 3
      [G17-19]

<400> SEQUENCE: 6

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
                20                  25                  30

His Tyr Ile Lys Asn Leu Glu Asn Val Tyr Ile Lys Ala Asp Lys Gln
            35                  40                  45

Lys Asn Gly Ile Lys Ala Asn Phe Lys Ile Arg His Asn Ile Glu Asp
50                  55                  60

Gly Gly Val Gln Leu Ala Tyr His Tyr Gln Gln Asn Thr Pro Ile Gly
65                  70                  75                  80

Asp Gly Pro Val Leu Leu Pro Asp Asn His Tyr Leu Ser Val Gln Ser
                85                  90                  95

Ile Leu Ser Lys Asp Pro Asn Glu Lys Arg Asp His Met Val Leu Leu
            100                 105                 110

Glu Phe Val Thr Ala Ala Gly Ile Thr Leu Gly Met Asp Glu Leu Tyr
        115                 120                 125

Lys Gly Gly Thr Gly Gly Ser Met Val Ser Lys Gly Glu Glu Leu Phe
    130                 135                 140

Thr Gly Val Val Pro Ile Gln Val Glu Leu Asp Gly Asp Val Asn Gly
145                 150                 155                 160

His Lys Phe Ser Val Ser Gly Glu Gly Glu Gly Asp Ala Thr Tyr Gly
                165                 170                 175

Lys Leu Thr Leu Lys Phe Ile Cys Thr Thr Gly Lys Leu Pro Val Pro
            180                 185                 190

Trp Pro Thr Leu Val Thr Thr Leu Thr Tyr Gly Val Gln Cys Phe Ser
        195                 200                 205

Arg Tyr Pro Asp His Met Lys Gln His Asp Phe Phe Lys Ser Ala Met
    210                 215                 220

Pro Glu Gly Tyr Ile Gln Glu Arg Thr Ile Phe Phe Lys Asp Asp Gly
225                 230                 235                 240

Asn Tyr Lys Thr Arg Ala Glu Val Lys Phe Glu Gly Asp Thr Leu Val
                245                 250                 255

Asn Arg Ile Glu Leu Lys Gly Ile Asp Phe Lys Glu Asp Gly Asn Ile
            260                 265                 270

Leu Gly His Lys Leu Glu Tyr Asn Thr Arg Lys Asn His Glu Phe Ile
```

-continued

```
                275                 280                 285
Ala Thr Phe Phe Gly Gln Pro Thr Phe Cys Ser Val Cys Lys Asp Phe
290                 295                 300

Val Trp Gly Leu Asn Lys Gln Gly Tyr Lys Cys Arg Gln Cys Asn Ala
305                 310                 315                 320

Ala Ile His Lys Lys Cys Ile Asp Lys Ile Gly Arg Cys Thr Gly
                325                 330                 335

Thr Ala Ala Asn Ser Arg Asp Thr Ile Phe Gln Lys Glu Arg Phe Asn
                340                 345                 350

Ile Asp Met Pro His Arg Phe Lys Val His Asn Tyr Met Ser Pro Thr
                355                 360                 365

Phe Cys Asp His Cys Gly Ser Leu Leu Trp Gly Leu Val Lys Gln Gly
370                 375                 380

Leu Lys Cys Glu Asp Cys Gly Met Asn Val His His Lys Cys Arg Glu
385                 390                 395                 400

Lys Val Ala Asn Leu Cys Gly Ile Asn Gln Lys Leu Leu Ala Glu Ala
                405                 410                 415

Leu Asn Gln Val Thr Gln Arg Ala Ser Arg Ser Asp Ser Ala Ser
                420                 425                 430

Ser Glu Pro Val Gly Ile Tyr Gln Gly Phe Glu Lys Lys Thr Gly Val
                435                 440                 445

Ala Gly Glu Asp Met Gln Asp Asn Ser Gly Thr Tyr Gly Lys Ile Trp
450                 455                 460

Glu Gly Ser Ser Lys Cys Asn Ile Asn Asn Phe Ile Phe His Lys Val
465                 470                 475                 480

Leu Gly Lys Gly Ser Phe Gly Lys Val Leu Leu Gly Glu Leu Lys Gly
                485                 490                 495

Arg Gly Glu Tyr Phe Ala Ile Lys Ala Leu Lys Lys Asp Val Val Leu
                500                 505                 510

Ile Asp Asp Asp Val Glu Cys Thr Met Val Glu Lys Arg Val Leu Thr
                515                 520                 525

Leu Ala Ala Glu Asn Pro Phe Leu Thr His Leu Ile Cys Thr Phe Gln
530                 535                 540

Thr Lys Asp His Leu Phe Phe Val Met Glu Phe Leu Asn Gly Gly Asp
545                 550                 555                 560

Leu Met Tyr His Ile Gln Asp Lys Gly Arg Phe Glu Leu Tyr Arg Ala
                565                 570                 575

Thr Phe Tyr Ala Ala Glu Ile Met Cys Gly Leu Gln Phe Leu His Ser
                580                 585                 590

Lys Gly Ile Ile Tyr Arg Asp Leu Lys Leu Asp Asn Val Leu Leu Asp
                595                 600                 605

Arg Asp Gly His Ile Lys Ile Ala Asp Phe Gly Met Cys Lys Glu Asn
                610                 615                 620

Ile Phe Gly Glu Ser Arg Ala Ser Thr Phe Cys Gly Thr Pro Asp Tyr
625                 630                 635                 640

Ile Ala Pro Glu Ile Leu Gln Gly Leu Lys Tyr Thr Phe Ser Val Asp
                645                 650                 655

Trp Trp Ser Phe Gly Val Leu Leu Tyr Glu Met Leu Ile Gly Gln Ser
                660                 665                 670

Pro Phe His Gly Asp Asp Glu Asp Glu Leu Phe Glu Ser Ile Arg Val
                675                 680                 685

Asp Thr Pro His Tyr Pro Arg Trp Ile Thr Lys Glu Ser Lys Asp Ile
                690                 695                 700
```

-continued

```
Leu Glu Lys Leu Phe Glu Arg Glu Pro Thr Lys Arg Leu Gly Val Thr
705                 710                 715                 720

Gly Asn Ile Lys Ile His Pro Phe Phe Lys Thr Ile Asn Trp Thr Leu
            725                 730                 735

Leu Glu Lys Arg Arg Leu Glu Pro Pro Phe Arg Pro Lys Val Lys Ser
        740                 745                 750

Pro Arg Asp Tyr Ser Asn Phe Asp Gln Glu Phe Leu Asn Glu Lys Ala
    755                 760                 765

Arg Leu Ser Tyr Ser Asp Lys Asn Leu Ile Asp Ser Met Asp Gln Ser
770                 775                 780

Ala Phe Ala Gly Phe Ser Phe Val Asn Pro Lys Phe Glu His Leu Leu
785                 790                 795                 800

Glu Asp

<210> SEQ ID NO 7
<211> LENGTH: 802
<212> TYPE: PRT
<213> ORGANISM: Artificial Sequence
<220> FEATURE:
<223> OTHER INFORMATION: Synthetic sequence, a.a. sequence of sensor 4
      [G18-20]

<400> SEQUENCE: 7

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Leu Glu Asn Val Tyr Ile Lys Ala Asp Lys Gln Lys
        35                  40                  45

Asn Gly Ile Lys Ala Asn Phe Lys Ile Arg His Asn Ile Glu Asp Gly
    50                  55                  60

Gly Val Gln Leu Ala Tyr His Tyr Gln Gln Asn Thr Pro Ile Gly Asp
65                  70                  75                  80

Gly Pro Val Leu Leu Pro Asp Asn His Tyr Leu Ser Val Gln Ser Ile
                85                  90                  95

Leu Ser Lys Asp Pro Asn Glu Lys Arg Asp His Met Val Leu Leu Glu
            100                 105                 110

Phe Val Thr Ala Ala Gly Ile Thr Leu Gly Met Asp Glu Leu Tyr Lys
        115                 120                 125

Gly Gly Thr Gly Gly Ser Met Val Ser Lys Gly Glu Glu Leu Phe Thr
    130                 135                 140

Gly Val Val Pro Ile Gln Val Glu Leu Asp Gly Asp Val Asn Gly His
145                 150                 155                 160

Lys Phe Ser Val Ser Gly Glu Gly Glu Gly Asp Ala Thr Tyr Gly Lys
                165                 170                 175

Leu Thr Leu Lys Phe Ile Cys Thr Thr Gly Lys Leu Pro Val Pro Trp
            180                 185                 190

Pro Thr Leu Val Thr Thr Leu Thr Tyr Gly Val Gln Cys Phe Ser Arg
        195                 200                 205

Tyr Pro Asp His Met Lys Gln His Asp Phe Phe Lys Ser Ala Met Pro
    210                 215                 220

Glu Gly Tyr Ile Gln Glu Arg Thr Ile Phe Phe Lys Asp Asp Gly Asn
225                 230                 235                 240

Tyr Lys Thr Arg Ala Glu Val Lys Phe Glu Gly Asp Thr Leu Val Asn
                245                 250                 255
```

-continued

```
Arg Ile Glu Leu Lys Gly Ile Asp Phe Lys Glu Asp Gly Asn Ile Leu
                260                 265                 270

Gly His Lys Leu Glu Tyr Asn Thr Arg Ile Lys Asn His Glu Phe Ile
            275                 280                 285

Ala Thr Phe Phe Gly Gln Pro Thr Phe Cys Ser Val Cys Lys Asp Phe
290                 295                 300

Val Trp Gly Leu Asn Lys Gln Gly Tyr Lys Cys Arg Gln Cys Asn Ala
305                 310                 315                 320

Ala Ile His Lys Lys Cys Ile Asp Lys Ile Ile Gly Arg Cys Thr Gly
                325                 330                 335

Thr Ala Ala Asn Ser Arg Asp Thr Ile Phe Gln Lys Glu Arg Phe Asn
                340                 345                 350

Ile Asp Met Pro His Arg Phe Lys Val His Asn Tyr Met Ser Pro Thr
                355                 360                 365

Phe Cys Asp His Cys Gly Ser Leu Leu Trp Gly Leu Val Lys Gln Gly
            370                 375                 380

Leu Lys Cys Glu Asp Cys Gly Met Asn Val His His Lys Cys Arg Glu
385                 390                 395                 400

Lys Val Ala Asn Leu Cys Gly Ile Asn Gln Lys Leu Leu Ala Glu Ala
                405                 410                 415

Leu Asn Gln Val Thr Gln Arg Ala Ser Arg Ser Asp Ser Ala Ser
                420                 425                 430

Ser Glu Pro Val Gly Ile Tyr Gln Gly Phe Glu Lys Lys Thr Gly Val
            435                 440                 445

Ala Gly Glu Asp Met Gln Asp Asn Ser Gly Thr Tyr Gly Lys Ile Trp
            450                 455                 460

Glu Gly Ser Ser Lys Cys Asn Ile Asn Asn Phe Ile Phe His Lys Val
465                 470                 475                 480

Leu Gly Lys Gly Ser Phe Gly Lys Val Leu Leu Gly Glu Leu Lys Gly
                485                 490                 495

Arg Gly Glu Tyr Phe Ala Ile Lys Ala Leu Lys Lys Asp Val Val Leu
            500                 505                 510

Ile Asp Asp Asp Val Glu Cys Thr Met Val Glu Lys Arg Val Leu Thr
            515                 520                 525

Leu Ala Ala Glu Asn Pro Phe Leu Thr His Leu Ile Cys Thr Phe Gln
530                 535                 540

Thr Lys Asp His Leu Phe Phe Val Met Glu Phe Leu Asn Gly Gly Asp
545                 550                 555                 560

Leu Met Tyr His Ile Gln Asp Lys Gly Arg Phe Glu Leu Tyr Arg Ala
                565                 570                 575

Thr Phe Tyr Ala Ala Glu Ile Met Cys Gly Leu Gln Phe Leu His Ser
            580                 585                 590

Lys Gly Ile Ile Tyr Arg Asp Leu Lys Leu Asp Asn Val Leu Leu Asp
                595                 600                 605

Arg Asp Gly His Ile Lys Ile Ala Asp Phe Gly Met Cys Lys Glu Asn
            610                 615                 620

Ile Phe Gly Glu Ser Arg Ala Ser Thr Phe Cys Gly Thr Pro Asp Tyr
625                 630                 635                 640

Ile Ala Pro Glu Ile Leu Gln Gly Leu Lys Tyr Thr Phe Ser Val Asp
                645                 650                 655

Trp Trp Ser Phe Gly Val Leu Leu Tyr Glu Met Leu Ile Gly Gln Ser
            660                 665                 670
```

```
Pro Phe His Gly Asp Asp Glu Asp Glu Leu Phe Glu Ser Ile Arg Val
            675                 680                 685

Asp Thr Pro His Tyr Pro Arg Trp Ile Thr Lys Glu Ser Lys Asp Ile
690                 695                 700

Leu Glu Lys Leu Phe Glu Arg Glu Pro Thr Lys Arg Leu Gly Val Thr
705                 710                 715                 720

Gly Asn Ile Lys Ile His Pro Phe Phe Lys Thr Ile Asn Trp Thr Leu
                725                 730                 735

Leu Glu Lys Arg Arg Leu Glu Pro Pro Phe Arg Pro Lys Val Lys Ser
                740                 745                 750

Pro Arg Asp Tyr Ser Asn Phe Asp Gln Glu Phe Leu Asn Glu Lys Ala
            755                 760                 765

Arg Leu Ser Tyr Ser Asp Lys Asn Leu Ile Asp Ser Met Asp Gln Ser
770                 775                 780

Ala Phe Ala Gly Phe Ser Val Asn Pro Lys Phe Glu His Leu Leu
785                 790                 795                 800

Glu Asp

<210> SEQ ID NO 8
<211> LENGTH: 798
<212> TYPE: PRT
<213> ORGANISM: Artificial Sequence
<220> FEATURE:
<223> OTHER INFORMATION: Synthetic sequence, a.a. sequence of sensor 5
      [G19-17]

<400> SEQUENCE: 8

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
                20                  25                  30

His Tyr Ile Leu Glu Asn Val Tyr Ile Lys Ala Asp Lys Gln Lys Asn
            35                  40                  45

Gly Ile Lys Ala Asn Phe Lys Ile Arg His Asn Ile Glu Asp Gly Gly
        50                  55                  60

Val Gln Leu Ala Tyr His Tyr Gln Gln Asn Thr Pro Ile Gly Asp Gly
65                  70                  75                  80

Pro Val Leu Leu Pro Asp Asn His Tyr Leu Ser Val Gln Ser Ile Leu
                85                  90                  95

Ser Lys Asp Pro Asn Glu Lys Arg Asp His Met Val Leu Leu Glu Phe
                100                 105                 110

Val Thr Ala Ala Gly Ile Thr Leu Gly Met Asp Glu Leu Tyr Lys Gly
            115                 120                 125

Gly Thr Gly Gly Ser Met Val Ser Lys Gly Glu Glu Leu Phe Thr Gly
        130                 135                 140

Val Val Pro Ile Gln Val Glu Leu Asp Gly Asp Val Asn Gly His Lys
145                 150                 155                 160

Phe Ser Val Ser Gly Glu Gly Glu Gly Asp Ala Thr Tyr Gly Lys Leu
                165                 170                 175

Thr Leu Lys Phe Ile Cys Thr Thr Gly Lys Leu Pro Val Pro Trp Pro
                180                 185                 190

Thr Leu Val Thr Thr Leu Thr Tyr Gly Val Gln Cys Phe Ser Arg Tyr
            195                 200                 205

Pro Asp His Met Lys Gln His Asp Phe Phe Lys Ser Ala Met Pro Glu
        210                 215                 220
```

```
Gly Tyr Ile Gln Glu Arg Thr Ile Phe Phe Lys Asp Asp Gly Asn Tyr
225                 230                 235                 240

Lys Thr Arg Ala Glu Val Lys Phe Glu Gly Asp Thr Leu Val Asn Arg
            245                 250                 255

Ile Glu Leu Lys Gly Ile Asp Phe Lys Glu Asp Gly Asn Ile Leu Gly
        260                 265                 270

His Lys Leu Glu Tyr Asn Thr Arg His Glu Phe Ile Ala Thr Phe Phe
    275                 280                 285

Gly Gln Pro Thr Phe Cys Ser Val Cys Lys Asp Phe Val Trp Gly Leu
290                 295                 300

Asn Lys Gln Gly Tyr Lys Cys Arg Gln Cys Asn Ala Ala Ile His Lys
305                 310                 315                 320

Lys Cys Ile Asp Lys Ile Ile Gly Arg Cys Thr Gly Thr Ala Ala Asn
            325                 330                 335

Ser Arg Asp Thr Ile Phe Gln Lys Glu Arg Phe Asn Ile Asp Met Pro
        340                 345                 350

His Arg Phe Lys Val His Asn Tyr Met Ser Pro Thr Phe Cys Asp His
    355                 360                 365

Cys Gly Ser Leu Leu Trp Gly Leu Val Lys Gln Gly Leu Lys Cys Glu
370                 375                 380

Asp Cys Gly Met Asn Val His His Lys Cys Arg Glu Lys Val Ala Asn
385                 390                 395                 400

Leu Cys Gly Ile Asn Gln Lys Leu Leu Ala Glu Ala Leu Asn Gln Val
            405                 410                 415

Thr Gln Arg Ala Ser Arg Arg Ser Asp Ser Ala Ser Ser Glu Pro Val
        420                 425                 430

Gly Ile Tyr Gln Gly Phe Glu Lys Lys Thr Gly Val Ala Gly Glu Asp
    435                 440                 445

Met Gln Asp Asn Ser Gly Thr Tyr Gly Lys Ile Trp Glu Gly Ser Ser
450                 455                 460

Lys Cys Asn Ile Asn Asn Phe Ile Phe His Lys Val Leu Gly Lys Gly
465                 470                 475                 480

Ser Phe Gly Lys Val Leu Leu Gly Glu Leu Lys Gly Arg Gly Glu Tyr
            485                 490                 495

Phe Ala Ile Lys Ala Leu Lys Lys Asp Val Val Leu Ile Asp Asp Asp
        500                 505                 510

Val Glu Cys Thr Met Val Glu Lys Arg Val Leu Thr Leu Ala Ala Glu
    515                 520                 525

Asn Pro Phe Leu Thr His Leu Ile Cys Thr Phe Gln Thr Lys Asp His
530                 535                 540

Leu Phe Phe Val Met Glu Phe Leu Asn Gly Gly Asp Leu Met Tyr His
545                 550                 555                 560

Ile Gln Asp Lys Gly Arg Phe Glu Leu Tyr Arg Ala Thr Phe Tyr Ala
            565                 570                 575

Ala Glu Ile Met Cys Gly Leu Gln Phe Leu His Ser Lys Gly Ile Ile
        580                 585                 590

Tyr Arg Asp Leu Lys Leu Asp Asn Val Leu Leu Asp Arg Asp Gly His
    595                 600                 605

Ile Lys Ile Ala Asp Phe Gly Met Cys Lys Glu Asn Ile Phe Gly Glu
610                 615                 620

Ser Arg Ala Ser Thr Phe Cys Gly Thr Pro Asp Tyr Ile Ala Pro Glu
625                 630                 635                 640

Ile Leu Gln Gly Leu Lys Tyr Thr Phe Ser Val Asp Trp Trp Ser Phe
```

```
            645                 650                 655
Gly Val Leu Leu Tyr Glu Met Leu Ile Gly Gln Ser Pro Phe His Gly
            660                 665                 670

Asp Asp Glu Asp Glu Leu Phe Glu Ser Ile Arg Val Asp Thr Pro His
            675                 680                 685

Tyr Pro Arg Trp Ile Thr Lys Glu Ser Lys Asp Ile Leu Glu Lys Leu
            690                 695                 700

Phe Glu Arg Glu Pro Thr Lys Arg Leu Gly Val Thr Gly Asn Ile Lys
705                 710                 715                 720

Ile His Pro Phe Phe Lys Thr Ile Asn Trp Thr Leu Leu Glu Lys Arg
                725                 730                 735

Arg Leu Glu Pro Pro Phe Arg Pro Lys Val Lys Ser Pro Arg Asp Tyr
            740                 745                 750

Ser Asn Phe Asp Gln Glu Phe Leu Asn Glu Lys Ala Arg Leu Ser Tyr
            755                 760                 765

Ser Asp Lys Asn Leu Ile Asp Ser Met Asp Gln Ser Ala Phe Ala Gly
            770                 775                 780

Phe Ser Phe Val Asn Pro Lys Phe Glu His Leu Leu Glu Asp
785                 790                 795
```

<210> SEQ ID NO 9
<211> LENGTH: 799
<212> TYPE: PRT
<213> ORGANISM: Artificial Sequence
<220> FEATURE:
<223> OTHER INFORMATION: Synthetic sequence, a.a. sequence of sensor 6 [G19-18]

<400> SEQUENCE: 9

```
Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Leu Glu Asn Val Tyr Ile Lys Ala Asp Lys Gln Lys Asn
            35                  40                  45

Gly Ile Lys Ala Asn Phe Lys Ile Arg His Asn Ile Glu Asp Gly Gly
        50                  55                  60

Val Gln Leu Ala Tyr His Tyr Gln Gln Asn Thr Pro Ile Gly Asp Gly
65              70                  75                  80

Pro Val Leu Leu Pro Asp Asn His Tyr Leu Ser Val Gln Ser Ile Leu
                85                  90                  95

Ser Lys Asp Pro Asn Glu Lys Arg Asp His Met Val Leu Leu Glu Phe
            100                 105                 110

Val Thr Ala Ala Gly Ile Thr Leu Gly Met Asp Glu Leu Tyr Lys Gly
            115                 120                 125

Gly Thr Gly Gly Ser Met Val Ser Lys Gly Glu Glu Leu Phe Thr Gly
        130                 135                 140

Val Val Pro Ile Gln Val Glu Leu Asp Gly Asp Val Asn Gly His Lys
145                 150                 155                 160

Phe Ser Val Ser Gly Glu Gly Glu Gly Asp Ala Thr Tyr Gly Lys Leu
                165                 170                 175

Thr Leu Lys Phe Ile Cys Thr Thr Gly Lys Leu Pro Val Pro Trp Pro
            180                 185                 190

Thr Leu Val Thr Thr Leu Thr Tyr Gly Val Gln Cys Phe Ser Arg Tyr
            195                 200                 205
```

```
Pro Asp His Met Lys Gln His Asp Phe Phe Lys Ser Ala Met Pro Glu
    210                 215                 220

Gly Tyr Ile Gln Glu Arg Thr Ile Phe Phe Lys Asp Asp Gly Asn Tyr
225                 230                 235                 240

Lys Thr Arg Ala Glu Val Lys Phe Glu Gly Asp Thr Leu Val Asn Arg
                245                 250                 255

Ile Glu Leu Lys Gly Ile Asp Phe Lys Glu Asp Gly Asn Ile Leu Gly
                260                 265                 270

His Lys Leu Glu Tyr Asn Thr Arg Asn His Glu Phe Ile Ala Thr Phe
    275                 280                 285

Phe Gly Gln Pro Thr Phe Cys Ser Val Cys Lys Asp Phe Val Trp Gly
290                 295                 300

Leu Asn Lys Gln Gly Tyr Lys Cys Arg Gln Cys Asn Ala Ala Ile His
305                 310                 315                 320

Lys Lys Cys Ile Asp Lys Ile Ile Gly Arg Cys Thr Gly Thr Ala Ala
                325                 330                 335

Asn Ser Arg Asp Thr Ile Phe Gln Lys Glu Arg Phe Asn Ile Asp Met
                340                 345                 350

Pro His Arg Phe Lys Val His Asn Tyr Met Ser Pro Thr Phe Cys Asp
            355                 360                 365

His Cys Gly Ser Leu Leu Trp Gly Leu Val Lys Gln Gly Leu Lys Cys
370                 375                 380

Glu Asp Cys Gly Met Asn Val His His Lys Cys Arg Glu Lys Val Ala
385                 390                 395                 400

Asn Leu Cys Gly Ile Asn Gln Lys Leu Leu Ala Glu Ala Leu Asn Gln
                405                 410                 415

Val Thr Gln Arg Ala Ser Arg Arg Ser Asp Ser Ala Ser Ser Glu Pro
            420                 425                 430

Val Gly Ile Tyr Gln Gly Phe Glu Lys Lys Thr Gly Val Ala Gly Glu
            435                 440                 445

Asp Met Gln Asp Asn Ser Gly Thr Tyr Gly Lys Ile Trp Glu Gly Ser
    450                 455                 460

Ser Lys Cys Asn Ile Asn Asn Phe Ile Phe His Lys Val Leu Gly Lys
465                 470                 475                 480

Gly Ser Phe Gly Lys Val Leu Leu Gly Glu Leu Lys Gly Arg Gly Glu
                485                 490                 495

Tyr Phe Ala Ile Lys Ala Leu Lys Lys Asp Val Val Leu Ile Asp Asp
                500                 505                 510

Asp Val Glu Cys Thr Met Val Glu Lys Arg Val Leu Thr Leu Ala Ala
    515                 520                 525

Glu Asn Pro Phe Leu Thr His Leu Ile Cys Thr Phe Gln Thr Lys Asp
    530                 535                 540

His Leu Phe Phe Val Met Glu Phe Leu Asn Gly Gly Asp Leu Met Tyr
545                 550                 555                 560

His Ile Gln Asp Lys Gly Arg Phe Glu Leu Tyr Arg Ala Thr Phe Tyr
                565                 570                 575

Ala Ala Glu Ile Met Cys Gly Leu Gln Phe Leu His Ser Lys Gly Ile
            580                 585                 590

Ile Tyr Arg Asp Leu Lys Leu Asp Asn Val Leu Leu Asp Arg Asp Gly
            595                 600                 605

His Ile Lys Ile Ala Asp Phe Gly Met Cys Lys Glu Asn Ile Phe Gly
    610                 615                 620

Glu Ser Arg Ala Ser Thr Phe Cys Gly Thr Pro Asp Tyr Ile Ala Pro
```

```
                625                 630                 635                 640
Glu Ile Leu Gln Gly Leu Lys Tyr Thr Phe Ser Val Asp Trp Trp Ser
                        645                 650                 655
Phe Gly Val Leu Leu Tyr Glu Met Leu Ile Gly Gln Ser Pro Phe His
                660                 665                 670
Gly Asp Glu Asp Glu Leu Phe Glu Ser Ile Arg Val Asp Thr Pro
                675                 680                 685
His Tyr Pro Arg Trp Ile Thr Lys Glu Ser Lys Asp Ile Leu Glu Lys
                690                 695                 700
Leu Phe Glu Arg Glu Pro Thr Lys Arg Leu Gly Val Thr Gly Asn Ile
705                 710                 715                 720
Lys Ile His Pro Phe Phe Lys Thr Ile Asn Trp Thr Leu Leu Glu Lys
                        725                 730                 735
Arg Arg Leu Glu Pro Pro Phe Arg Pro Lys Val Lys Ser Pro Arg Asp
                740                 745                 750
Tyr Ser Asn Phe Asp Gln Glu Phe Leu Asn Glu Lys Ala Arg Leu Ser
                755                 760                 765
Tyr Ser Asp Lys Asn Leu Ile Asp Ser Met Asp Gln Ser Ala Phe Ala
                770                 775                 780
Gly Phe Ser Phe Val Asn Pro Lys Phe Glu His Leu Leu Glu Asp
785                 790                 795
```

<210> SEQ ID NO 10
<211> LENGTH: 801
<212> TYPE: PRT
<213> ORGANISM: Artificial Sequence
<220> FEATURE:
<223> OTHER INFORMATION: Synthetic sequence, a.a. sequence of sensor 7
    [G19-20]

<400> SEQUENCE: 10

```
Met Glu Asp Val Asp Cys Lys Gln Ser Met Arg Ser Glu Asp Glu Ala
1               5                   10                  15
Lys Phe Pro Thr Met Asn Arg Arg Gly Ala Ile Lys Gln Ala Lys Ile
                20                  25                  30
His Tyr Ile Leu Glu Asn Val Tyr Ile Lys Ala Asp Lys Gln Lys Asn
                35                  40                  45
Gly Ile Lys Ala Asn Phe Lys Ile Arg His Asn Ile Glu Asp Gly Gly
            50                  55                  60
Val Gln Leu Ala Tyr His Tyr Gln Gln Asn Thr Pro Ile Gly Asp Gly
65              70                  75                  80
Pro Val Leu Leu Pro Asp Asn His Tyr Leu Ser Val Gln Ser Ile Leu
                85                  90                  95
Ser Lys Asp Pro Asn Glu Lys Arg Asp His Met Val Leu Leu Glu Phe
                100                 105                 110
Val Thr Ala Ala Gly Ile Thr Leu Gly Met Asp Glu Leu Tyr Lys Gly
                115                 120                 125
Gly Thr Gly Gly Ser Met Val Ser Lys Gly Glu Glu Leu Phe Thr Gly
            130                 135                 140
Val Val Pro Ile Gln Val Glu Leu Asp Gly Asp Val Asn Gly His Lys
145                 150                 155                 160
Phe Ser Val Ser Gly Glu Gly Glu Gly Asp Ala Thr Tyr Gly Lys Leu
                165                 170                 175
Thr Leu Lys Phe Ile Cys Thr Thr Gly Lys Leu Pro Val Pro Trp Pro
                180                 185                 190
```

```
Thr Leu Val Thr Thr Leu Thr Tyr Gly Val Gln Cys Phe Ser Arg Tyr
            195                 200                 205

Pro Asp His Met Lys Gln His Asp Phe Phe Lys Ser Ala Met Pro Glu
210                 215                 220

Gly Tyr Ile Gln Glu Arg Thr Ile Phe Phe Lys Asp Asp Gly Asn Tyr
225                 230                 235                 240

Lys Thr Arg Ala Glu Val Lys Phe Glu Gly Asp Thr Leu Val Asn Arg
                245                 250                 255

Ile Glu Leu Lys Gly Ile Asp Phe Lys Glu Asp Gly Asn Ile Leu Gly
            260                 265                 270

His Lys Leu Glu Tyr Asn Thr Arg Ile Lys Asn His Glu Phe Ile Ala
        275                 280                 285

Thr Phe Phe Gly Gln Pro Thr Phe Cys Ser Val Cys Lys Asp Phe Val
    290                 295                 300

Trp Gly Leu Asn Lys Gln Gly Tyr Lys Cys Arg Gln Cys Asn Ala Ala
305                 310                 315                 320

Ile His Lys Lys Cys Ile Asp Lys Ile Ile Gly Arg Cys Thr Gly Thr
                325                 330                 335

Ala Ala Asn Ser Arg Asp Thr Ile Phe Gln Lys Glu Arg Phe Asn Ile
            340                 345                 350

Asp Met Pro His Arg Phe Lys Val His Asn Tyr Met Ser Pro Thr Phe
        355                 360                 365

Cys Asp His Cys Gly Ser Leu Leu Trp Gly Leu Val Lys Gln Gly Leu
    370                 375                 380

Lys Cys Glu Asp Cys Gly Met Asn Val His His Lys Cys Arg Glu Lys
385                 390                 395                 400

Val Ala Asn Leu Cys Gly Ile Asn Gln Lys Leu Leu Ala Glu Ala Leu
                405                 410                 415

Asn Gln Val Thr Gln Arg Ala Ser Arg Arg Ser Asp Ser Ala Ser Ser
            420                 425                 430

Glu Pro Val Gly Ile Tyr Gln Gly Phe Glu Lys Lys Thr Gly Val Ala
        435                 440                 445

Gly Glu Asp Met Gln Asp Asn Ser Gly Thr Tyr Gly Lys Ile Trp Glu
    450                 455                 460

Gly Ser Ser Lys Cys Asn Ile Asn Asn Phe Ile Phe His Lys Val Leu
465                 470                 475                 480

Gly Lys Gly Ser Phe Gly Lys Val Leu Leu Gly Glu Leu Lys Gly Arg
                485                 490                 495

Gly Glu Tyr Phe Ala Ile Lys Ala Leu Lys Lys Asp Val Val Leu Ile
            500                 505                 510

Asp Asp Asp Val Glu Cys Thr Met Val Glu Lys Arg Val Leu Thr Leu
        515                 520                 525

Ala Ala Glu Asn Pro Phe Leu Thr His Leu Ile Cys Thr Phe Gln Thr
    530                 535                 540

Lys Asp His Leu Phe Phe Val Met Glu Phe Leu Asn Gly Gly Asp Leu
545                 550                 555                 560

Met Tyr His Ile Gln Asp Lys Gly Arg Phe Glu Leu Tyr Arg Ala Thr
                565                 570                 575

Phe Tyr Ala Ala Glu Ile Met Cys Gly Leu Gln Phe Leu His Ser Lys
            580                 585                 590

Gly Ile Ile Tyr Arg Asp Leu Lys Leu Asp Asn Val Leu Leu Asp Arg
        595                 600                 605

Asp Gly His Ile Lys Ile Ala Asp Phe Gly Met Cys Lys Glu Asn Ile
```

```
                610                 615                 620
Phe Gly Glu Ser Arg Ala Ser Thr Phe Cys Gly Thr Pro Asp Tyr Ile
625                 630                 635                 640

Ala Pro Glu Ile Leu Gln Gly Leu Lys Tyr Thr Phe Ser Val Asp Trp
                645                 650                 655

Trp Ser Phe Gly Val Leu Leu Tyr Glu Met Leu Ile Gly Gln Ser Pro
                660                 665                 670

Phe His Gly Asp Asp Glu Asp Glu Leu Phe Glu Ser Ile Arg Val Asp
                675                 680                 685

Thr Pro His Tyr Pro Arg Trp Ile Thr Lys Glu Ser Lys Asp Ile Leu
                690                 695                 700

Glu Lys Leu Phe Glu Arg Glu Pro Thr Lys Arg Leu Gly Val Thr Gly
705                 710                 715                 720

Asn Ile Lys Ile His Pro Phe Phe Lys Thr Ile Asn Trp Thr Leu Leu
                725                 730                 735

Glu Lys Arg Arg Leu Glu Pro Pro Phe Arg Pro Lys Val Lys Ser Pro
                740                 745                 750

Arg Asp Tyr Ser Asn Phe Asp Gln Glu Phe Leu Asn Glu Lys Ala Arg
                755                 760                 765

Leu Ser Tyr Ser Asp Lys Asn Leu Ile Asp Ser Met Asp Gln Ser Ala
                770                 775                 780

Phe Ala Gly Phe Ser Phe Val Asn Pro Lys Phe Glu His Leu Leu Glu
785                 790                 795                 800

Asp

<210> SEQ ID NO 11
<211> LENGTH: 797
<212> TYPE: PRT
<213> ORGANISM: Artificial Sequence
<220> FEATURE:
<223> OTHER INFORMATION: Synthetic sequence, a.a. sequence of sensor 8
      [G20-17]

<400> SEQUENCE: 11

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
                20                  25                  30

His Tyr Leu Glu Asn Val Tyr Ile Lys Ala Asp Lys Gln Lys Asn Gly
                35                  40                  45

Ile Lys Ala Asn Phe Lys Ile Arg His Asn Ile Glu Asp Gly Gly Val
50                  55                  60

Gln Leu Ala Tyr His Tyr Gln Gln Asn Thr Pro Ile Gly Asp Gly Pro
65                  70                  75                  80

Val Leu Leu Pro Asp Asn His Tyr Leu Ser Val Gln Ser Ile Leu Ser
                85                  90                  95

Lys Asp Pro Asn Glu Lys Arg Asp His Met Val Leu Leu Glu Phe Val
                100                 105                 110

Thr Ala Ala Gly Ile Thr Leu Gly Met Asp Glu Leu Tyr Lys Gly Gly
                115                 120                 125

Thr Gly Gly Ser Met Val Ser Lys Gly Glu Glu Leu Phe Thr Gly Val
                130                 135                 140

Val Pro Ile Gln Val Glu Leu Asp Gly Asp Val Asn Gly His Lys Phe
145                 150                 155                 160

Ser Val Ser Gly Glu Gly Glu Gly Asp Ala Thr Tyr Gly Lys Leu Thr
```

```
                165                 170                 175
Leu Lys Phe Ile Cys Thr Thr Gly Lys Leu Pro Val Pro Trp Pro Thr
                180                 185                 190
Leu Val Thr Thr Leu Thr Tyr Gly Val Gln Cys Phe Ser Arg Tyr Pro
                195                 200                 205
Asp His Met Lys Gln His Asp Phe Phe Lys Ser Ala Met Pro Glu Gly
                210                 215                 220
Tyr Ile Gln Glu Arg Thr Ile Phe Phe Lys Asp Asp Gly Asn Tyr Lys
225                 230                 235                 240
Thr Arg Ala Glu Val Lys Phe Glu Gly Asp Thr Leu Val Asn Arg Ile
                245                 250                 255
Glu Leu Lys Gly Ile Asp Phe Lys Glu Asp Gly Asn Ile Leu Gly His
                260                 265                 270
Lys Leu Glu Tyr Asn Thr Arg His Glu Phe Ile Ala Thr Phe Phe Gly
                275                 280                 285
Gln Pro Thr Phe Cys Ser Val Cys Lys Asp Phe Val Trp Gly Leu Asn
                290                 295                 300
Lys Gln Gly Tyr Lys Cys Arg Gln Cys Asn Ala Ala Ile His Lys Lys
305                 310                 315                 320
Cys Ile Asp Lys Ile Ile Gly Arg Cys Thr Gly Ala Ala Asn Ser
                325                 330                 335
Arg Asp Thr Ile Phe Gln Lys Glu Arg Phe Asn Ile Asp Met Pro His
                340                 345                 350
Arg Phe Lys Val His Asn Tyr Met Ser Pro Thr Phe Cys Asp His Cys
                355                 360                 365
Gly Ser Leu Leu Trp Gly Leu Val Lys Gln Gly Leu Lys Cys Glu Asp
                370                 375                 380
Cys Gly Met Asn Val His His Lys Cys Arg Glu Lys Val Ala Asn Leu
385                 390                 395                 400
Cys Gly Ile Asn Gln Lys Leu Leu Ala Glu Ala Leu Asn Gln Val Thr
                405                 410                 415
Gln Arg Ala Ser Arg Arg Ser Asp Ser Ala Ser Ser Glu Pro Val Gly
                420                 425                 430
Ile Tyr Gln Gly Phe Glu Lys Lys Thr Gly Val Ala Gly Glu Asp Met
                435                 440                 445
Gln Asp Asn Ser Gly Thr Tyr Gly Lys Ile Trp Glu Gly Ser Ser Lys
                450                 455                 460
Cys Asn Ile Asn Asn Phe Ile Phe His Lys Val Leu Gly Lys Gly Ser
465                 470                 475                 480
Phe Gly Lys Val Leu Leu Gly Glu Leu Lys Gly Arg Gly Glu Tyr Phe
                485                 490                 495
Ala Ile Lys Ala Leu Lys Lys Asp Val Val Leu Ile Asp Asp Asp Val
                500                 505                 510
Glu Cys Thr Met Val Glu Lys Arg Val Leu Thr Leu Ala Ala Glu Asn
                515                 520                 525
Pro Phe Leu Thr His Leu Ile Cys Thr Phe Gln Thr Lys Asp His Leu
                530                 535                 540
Phe Phe Val Met Glu Phe Leu Asn Gly Gly Asp Leu Met Tyr His Ile
545                 550                 555                 560
Gln Asp Lys Gly Arg Phe Glu Leu Tyr Arg Ala Thr Phe Tyr Ala Ala
                565                 570                 575
Glu Ile Met Cys Gly Leu Gln Phe Leu His Ser Lys Gly Ile Ile Tyr
                580                 585                 590
```

```
Arg Asp Leu Lys Leu Asp Asn Val Leu Leu Asp Arg Asp Gly His Ile
        595                 600                 605

Lys Ile Ala Asp Phe Gly Met Cys Lys Glu Asn Ile Phe Gly Glu Ser
        610                 615                 620

Arg Ala Ser Thr Phe Cys Gly Thr Pro Asp Tyr Ile Ala Pro Glu Ile
625                 630                 635                 640

Leu Gln Gly Leu Lys Tyr Thr Phe Ser Val Asp Trp Trp Ser Phe Gly
                645                 650                 655

Val Leu Leu Tyr Glu Met Leu Ile Gly Gln Ser Pro Phe His Gly Asp
                660                 665                 670

Asp Glu Asp Glu Leu Phe Glu Ser Ile Arg Val Asp Thr Pro His Tyr
            675                 680                 685

Pro Arg Trp Ile Thr Lys Glu Ser Lys Asp Ile Leu Glu Lys Leu Phe
        690                 695                 700

Glu Arg Glu Pro Thr Lys Arg Leu Gly Val Thr Gly Asn Ile Lys Ile
705                 710                 715                 720

His Pro Phe Phe Lys Thr Ile Asn Trp Thr Leu Leu Glu Lys Arg Arg
                725                 730                 735

Leu Glu Pro Pro Phe Arg Pro Lys Val Lys Ser Pro Arg Asp Tyr Ser
                740                 745                 750

Asn Phe Asp Gln Glu Phe Leu Asn Glu Lys Ala Arg Leu Ser Tyr Ser
            755                 760                 765

Asp Lys Asn Leu Ile Asp Ser Met Asp Gln Ser Ala Phe Ala Gly Phe
        770                 775                 780

Ser Phe Val Asn Pro Lys Phe Glu His Leu Leu Glu Asp
785                 790                 795

<210> SEQ ID NO 12
<211> LENGTH: 792
<212> TYPE: PRT
<213> ORGANISM: Artificial Sequence
<220> FEATURE:
<223> OTHER INFORMATION: Synthetic sequence, a.a. sequence of sensor 9
      [G20-28]

<400> SEQUENCE: 12

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Leu Glu Asn Val Tyr Ile Lys Ala Asp Lys Gln Lys Asn Gly
        35                  40                  45

Ile Lys Ala Asn Phe Lys Ile Arg His Asn Ile Glu Asp Gly Gly Val
    50                  55                  60

Gln Leu Ala Tyr His Tyr Gln Gln Asn Thr Pro Ile Gly Asp Gly Pro
65                  70                  75                  80

Val Leu Leu Pro Asp Asn His Tyr Leu Ser Val Gln Ser Ile Leu Ser
                85                  90                  95

Lys Asp Pro Asn Glu Lys Arg Asp His Met Val Leu Leu Glu Phe Val
            100                 105                 110

Thr Ala Ala Gly Ile Thr Leu Gly Met Asp Glu Leu Tyr Lys Gly Gly
        115                 120                 125

Thr Gly Gly Ser Met Val Ser Lys Gly Glu Glu Leu Phe Thr Gly Val
    130                 135                 140

Val Pro Ile Gln Val Glu Leu Asp Gly Asp Val Asn Gly His Lys Phe
```

-continued

```
            145                 150                 155                 160
Ser Val Ser Gly Glu Gly Glu Gly Asp Ala Thr Tyr Gly Lys Leu Thr
                    165                 170                 175
Leu Lys Phe Ile Cys Thr Thr Gly Lys Leu Pro Val Pro Trp Pro Thr
                    180                 185                 190
Leu Val Thr Thr Leu Thr Tyr Gly Val Gln Cys Phe Ser Arg Tyr Pro
                    195                 200                 205
Asp His Met Lys Gln His Asp Phe Phe Lys Ser Ala Met Pro Glu Gly
                    210                 215                 220
Tyr Ile Gln Glu Arg Thr Ile Phe Phe Lys Asp Asp Gly Asn Tyr Lys
225                 230                 235                 240
Thr Arg Ala Glu Val Lys Phe Glu Gly Asp Thr Leu Val Asn Arg Ile
                    245                 250                 255
Glu Leu Lys Gly Ile Asp Phe Lys Glu Asp Gly Asn Ile Leu Gly His
                    260                 265                 270
Lys Leu Glu Tyr Asn Thr Arg Thr Phe Phe Gly Gln Pro Thr Phe Cys
                    275                 280                 285
Ser Val Cys Lys Asp Phe Val Trp Gly Leu Asn Lys Gln Gly Tyr Lys
                    290                 295                 300
Cys Arg Gln Cys Asn Ala Ala Ile His Lys Lys Cys Ile Asp Lys Ile
305                 310                 315                 320
Ile Gly Arg Cys Thr Gly Thr Ala Ala Asn Ser Arg Asp Thr Ile Phe
                    325                 330                 335
Gln Lys Glu Arg Phe Asn Ile Asp Met Pro His Arg Phe Lys Val His
                    340                 345                 350
Asn Tyr Met Ser Pro Thr Phe Cys Asp His Cys Gly Ser Leu Leu Trp
                    355                 360                 365
Gly Leu Val Lys Gln Gly Leu Lys Cys Glu Asp Cys Gly Met Asn Val
                    370                 375                 380
His His Lys Cys Arg Glu Lys Val Ala Asn Leu Cys Gly Ile Asn Gln
385                 390                 395                 400
Lys Leu Leu Ala Glu Ala Leu Asn Gln Val Thr Gln Arg Ala Ser Arg
                    405                 410                 415
Arg Ser Asp Ser Ala Ser Ser Glu Pro Val Gly Ile Tyr Gln Gly Phe
                    420                 425                 430
Glu Lys Lys Thr Gly Val Ala Gly Glu Asp Met Gln Asp Asn Ser Gly
                    435                 440                 445
Thr Tyr Gly Lys Ile Trp Glu Gly Ser Ser Lys Cys Asn Ile Asn Asn
                    450                 455                 460
Phe Ile Phe His Lys Val Leu Gly Lys Gly Ser Phe Gly Lys Val Leu
465                 470                 475                 480
Leu Gly Glu Leu Lys Gly Arg Gly Glu Tyr Phe Ala Ile Lys Ala Leu
                    485                 490                 495
Lys Lys Asp Val Val Leu Ile Asp Asp Val Glu Cys Thr Met Val
                    500                 505                 510
Glu Lys Arg Val Leu Thr Leu Ala Ala Glu Asn Pro Phe Leu Thr His
                    515                 520                 525
Leu Ile Cys Thr Phe Gln Thr Lys Asp His Leu Phe Phe Val Met Glu
                    530                 535                 540
Phe Leu Asn Gly Gly Asp Leu Met Tyr His Ile Gln Asp Lys Gly Arg
545                 550                 555                 560
Phe Glu Leu Tyr Arg Ala Thr Phe Tyr Ala Ala Glu Ile Met Cys Gly
                    565                 570                 575
```

```
Leu Gln Phe Leu His Ser Lys Gly Ile Ile Tyr Arg Asp Leu Lys Leu
            580                 585                 590

Asp Asn Val Leu Leu Asp Arg Asp Gly His Ile Lys Ile Ala Asp Phe
            595                 600                 605

Gly Met Cys Lys Glu Asn Ile Phe Gly Glu Ser Arg Ala Ser Thr Phe
            610                 615                 620

Cys Gly Thr Pro Asp Tyr Ile Ala Pro Glu Ile Leu Gln Gly Leu Lys
625                 630                 635                 640

Tyr Thr Phe Ser Val Asp Trp Trp Ser Phe Gly Val Leu Leu Tyr Glu
            645                 650                 655

Met Leu Ile Gly Gln Ser Pro Phe His Gly Asp Glu Asp Glu Leu
            660                 665                 670

Phe Glu Ser Ile Arg Val Asp Thr Pro His Tyr Pro Arg Trp Ile Thr
            675                 680                 685

Lys Glu Ser Lys Asp Ile Leu Glu Lys Leu Phe Glu Arg Glu Pro Thr
            690                 695                 700

Lys Arg Leu Gly Val Thr Gly Asn Ile Lys Ile His Pro Phe Phe Lys
705                 710                 715                 720

Thr Ile Asn Trp Thr Leu Leu Glu Lys Arg Arg Leu Glu Pro Pro Phe
            725                 730                 735

Arg Pro Lys Val Lys Ser Pro Arg Asp Tyr Ser Asn Phe Asp Gln Glu
            740                 745                 750

Phe Leu Asn Glu Lys Ala Arg Leu Ser Tyr Ser Asp Lys Asn Leu Ile
            755                 760                 765

Asp Ser Met Asp Gln Ser Ala Phe Ala Gly Phe Ser Phe Val Asn Pro
            770                 775                 780

Lys Phe Glu His Leu Leu Glu Asp
785                 790

<210> SEQ ID NO 13
<211> LENGTH: 796
<212> TYPE: PRT
<213> ORGANISM: Artificial Sequence
<220> FEATURE:
<223> OTHER INFORMATION: Synthetic sequence, a.a. sequence of sensor 10
      [G21-17]

<400> SEQUENCE: 13

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Leu Glu Asn Val Tyr Ile Lys Ala Asp Lys Gln Lys Asn Gly Ile
            35                  40                  45

Lys Ala Asn Phe Lys Ile Arg His Asn Ile Glu Asp Gly Gly Val Gln
        50                  55                  60

Leu Ala Tyr His Tyr Gln Gln Asn Thr Pro Ile Gly Asp Gly Pro Val
65                  70                  75                  80

Leu Leu Pro Asp Asn His Tyr Leu Ser Val Gln Ser Ile Leu Ser Lys
            85                  90                  95

Asp Pro Asn Glu Lys Arg Asp His Met Val Leu Leu Glu Phe Val Thr
            100                 105                 110

Ala Ala Gly Ile Thr Leu Gly Met Asp Glu Leu Tyr Lys Gly Gly Thr
            115                 120                 125

Gly Gly Ser Met Val Ser Lys Gly Glu Glu Leu Phe Thr Gly Val Val
```

```
                130             135             140
Pro Ile Gln Val Glu Leu Asp Gly Asp Val Asn Gly His Lys Phe Ser
145                 150                 155                 160

Val Ser Gly Glu Gly Glu Gly Asp Ala Thr Tyr Gly Lys Leu Thr Leu
                165                 170                 175

Lys Phe Ile Cys Thr Thr Gly Lys Leu Pro Val Pro Trp Pro Thr Leu
                180                 185                 190

Val Thr Thr Leu Thr Tyr Gly Val Gln Cys Phe Ser Arg Tyr Pro Asp
                195                 200                 205

His Met Lys Gln His Asp Phe Phe Lys Ser Ala Met Pro Glu Gly Tyr
            210                 215                 220

Ile Gln Glu Arg Thr Ile Phe Phe Lys Asp Asp Gly Asn Tyr Lys Thr
225                 230                 235                 240

Arg Ala Glu Val Lys Phe Glu Gly Asp Thr Leu Val Asn Arg Ile Glu
                245                 250                 255

Leu Lys Gly Ile Asp Phe Lys Glu Asp Gly Asn Ile Leu Gly His Lys
                260                 265                 270

Leu Glu Tyr Asn Thr Arg His Glu Phe Ile Ala Thr Phe Phe Gly Gln
            275                 280                 285

Pro Thr Phe Cys Ser Val Cys Lys Asp Phe Val Trp Gly Leu Asn Lys
            290                 295                 300

Gln Gly Tyr Lys Cys Arg Gln Cys Asn Ala Ala Ile His Lys Lys Cys
305                 310                 315                 320

Ile Asp Lys Ile Ile Gly Arg Cys Thr Gly Thr Ala Ala Asn Ser Arg
                325                 330                 335

Asp Thr Ile Phe Gln Lys Glu Arg Phe Asn Ile Asp Met Pro His Arg
                340                 345                 350

Phe Lys Val His Asn Tyr Met Ser Pro Thr Phe Cys Asp His Cys Gly
            355                 360                 365

Ser Leu Leu Trp Gly Leu Val Lys Gln Gly Leu Lys Cys Glu Asp Cys
370                 375                 380

Gly Met Asn Val His His Lys Cys Arg Glu Lys Val Ala Asn Leu Cys
385                 390                 395                 400

Gly Ile Asn Gln Lys Leu Leu Ala Glu Ala Leu Asn Gln Val Thr Gln
                405                 410                 415

Arg Ala Ser Arg Arg Ser Asp Ser Ala Ser Ser Glu Pro Val Gly Ile
                420                 425                 430

Tyr Gln Gly Phe Glu Lys Lys Thr Gly Val Ala Gly Glu Asp Met Gln
            435                 440                 445

Asp Asn Ser Gly Thr Tyr Gly Lys Ile Trp Glu Gly Ser Ser Lys Cys
            450                 455                 460

Asn Ile Asn Asn Phe Ile Phe His Lys Val Leu Gly Lys Gly Ser Phe
465                 470                 475                 480

Gly Lys Val Leu Leu Gly Glu Leu Lys Gly Arg Gly Glu Tyr Phe Ala
                485                 490                 495

Ile Lys Ala Leu Lys Lys Asp Val Val Leu Ile Asp Asp Asp Val Glu
                500                 505                 510

Cys Thr Met Val Glu Lys Arg Val Leu Thr Leu Ala Ala Glu Asn Pro
            515                 520                 525

Phe Leu Thr His Leu Ile Cys Thr Phe Gln Thr Lys Asp His Leu Phe
            530                 535                 540

Phe Val Met Glu Phe Leu Asn Gly Gly Asp Leu Met Tyr His Ile Gln
545                 550                 555                 560
```

Asp Lys Gly Arg Phe Glu Leu Tyr Arg Ala Thr Phe Tyr Ala Ala Glu
            565                 570                 575

Ile Met Cys Gly Leu Gln Phe Leu His Ser Lys Gly Ile Ile Tyr Arg
            580                 585                 590

Asp Leu Lys Leu Asp Asn Val Leu Leu Asp Arg Asp Gly His Ile Lys
            595                 600                 605

Ile Ala Asp Phe Gly Met Cys Lys Glu Asn Ile Phe Gly Glu Ser Arg
            610                 615                 620

Ala Ser Thr Phe Cys Gly Thr Pro Asp Tyr Ile Ala Pro Glu Ile Leu
625                 630                 635                 640

Gln Gly Leu Lys Tyr Thr Phe Ser Val Asp Trp Trp Ser Phe Gly Val
            645                 650                 655

Leu Leu Tyr Glu Met Leu Ile Gly Gln Ser Pro Phe His Gly Asp Asp
            660                 665                 670

Glu Asp Glu Leu Phe Glu Ser Ile Arg Val Asp Thr Pro His Tyr Pro
            675                 680                 685

Arg Trp Ile Thr Lys Glu Ser Lys Asp Ile Leu Glu Lys Leu Phe Glu
            690                 695                 700

Arg Glu Pro Thr Lys Arg Leu Gly Val Thr Gly Asn Ile Lys Ile His
705                 710                 715                 720

Pro Phe Phe Lys Thr Ile Asn Trp Thr Leu Leu Glu Lys Arg Arg Leu
            725                 730                 735

Glu Pro Pro Phe Arg Pro Lys Val Lys Ser Pro Arg Asp Tyr Ser Asn
            740                 745                 750

Phe Asp Gln Glu Phe Leu Asn Glu Lys Ala Arg Leu Ser Tyr Ser Asp
            755                 760                 765

Lys Asn Leu Ile Asp Ser Met Asp Gln Ser Ala Phe Ala Gly Phe Ser
            770                 775                 780

Phe Val Asn Pro Lys Phe Glu His Leu Leu Glu Asp
785                 790                 795

<210> SEQ ID NO 14
<211> LENGTH: 798
<212> TYPE: PRT
<213> ORGANISM: Artificial Sequence
<220> FEATURE:
<223> OTHER INFORMATION: Synthetic sequence, a.a. sequence of sensor 11
      [G21-19]

<400> SEQUENCE: 14

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Leu Glu Asn Val Tyr Ile Lys Ala Asp Lys Gln Lys Asn Gly Ile
            35                  40                  45

Lys Ala Asn Phe Lys Ile Arg His Asn Ile Glu Asp Gly Gly Val Gln
            50                  55                  60

Leu Ala Tyr His Tyr Gln Gln Asn Thr Pro Ile Gly Asp Gly Pro Val
65                  70                  75                  80

Leu Leu Pro Asp Asn His Tyr Leu Ser Val Gln Ser Ile Leu Ser Lys
            85                  90                  95

Asp Pro Asn Glu Lys Arg Asp His Met Val Leu Leu Glu Phe Val Thr
            100                 105                 110

Ala Ala Gly Ile Thr Leu Gly Met Asp Glu Leu Tyr Lys Gly Gly Thr

```
            115                 120                 125
Gly Gly Ser Met Val Ser Lys Gly Glu Glu Leu Phe Thr Gly Val Val
            130                 135                 140
Pro Ile Gln Val Glu Leu Asp Gly Asp Val Asn Gly His Lys Phe Ser
145                 150                 155                 160
Val Ser Gly Glu Gly Glu Gly Asp Ala Thr Tyr Gly Lys Leu Thr Leu
                165                 170                 175
Lys Phe Ile Cys Thr Thr Gly Lys Leu Pro Val Pro Trp Pro Thr Leu
                180                 185                 190
Val Thr Thr Leu Thr Tyr Gly Val Gln Cys Phe Ser Arg Tyr Pro Asp
            195                 200                 205
His Met Lys Gln His Asp Phe Phe Lys Ser Ala Met Pro Glu Gly Tyr
            210                 215                 220
Ile Gln Glu Arg Thr Ile Phe Phe Lys Asp Asp Gly Asn Tyr Lys Thr
225                 230                 235                 240
Arg Ala Glu Val Lys Phe Glu Gly Asp Thr Leu Val Asn Arg Ile Glu
                245                 250                 255
Leu Lys Gly Ile Asp Phe Lys Glu Asp Gly Asn Ile Leu Gly His Lys
                260                 265                 270
Leu Glu Tyr Asn Thr Arg Lys Asn His Glu Phe Ile Ala Thr Phe Phe
            275                 280                 285
Gly Gln Pro Thr Phe Cys Ser Val Cys Lys Asp Phe Val Trp Gly Leu
            290                 295                 300
Asn Lys Gln Gly Tyr Lys Cys Arg Gln Cys Asn Ala Ala Ile His Lys
305                 310                 315                 320
Lys Cys Ile Asp Lys Ile Ile Gly Arg Cys Thr Gly Thr Ala Ala Asn
                325                 330                 335
Ser Arg Asp Thr Ile Phe Gln Lys Glu Arg Phe Asn Ile Asp Met Pro
            340                 345                 350
His Arg Phe Lys Val His Asn Tyr Met Ser Pro Thr Phe Cys Asp His
            355                 360                 365
Cys Gly Ser Leu Leu Trp Gly Leu Val Lys Gln Gly Leu Lys Cys Glu
            370                 375                 380
Asp Cys Gly Met Asn Val His His Lys Cys Arg Glu Lys Val Ala Asn
385                 390                 395                 400
Leu Cys Gly Ile Asn Gln Lys Leu Leu Ala Glu Ala Leu Asn Gln Val
                405                 410                 415
Thr Gln Arg Ala Ser Arg Arg Ser Asp Ser Ala Ser Ser Glu Pro Val
            420                 425                 430
Gly Ile Tyr Gln Gly Phe Glu Lys Lys Thr Gly Val Ala Gly Glu Asp
            435                 440                 445
Met Gln Asp Asn Ser Gly Thr Tyr Gly Lys Ile Trp Glu Gly Ser Ser
            450                 455                 460
Lys Cys Asn Ile Asn Asn Phe Ile Phe His Lys Val Leu Gly Lys Gly
465                 470                 475                 480
Ser Phe Gly Lys Val Leu Leu Gly Glu Leu Lys Gly Arg Gly Glu Tyr
                485                 490                 495
Phe Ala Ile Lys Ala Leu Lys Lys Asp Val Val Leu Ile Asp Asp Asp
                500                 505                 510
Val Glu Cys Thr Met Val Glu Lys Arg Val Leu Thr Leu Ala Ala Glu
            515                 520                 525
Asn Pro Phe Leu Thr His Leu Ile Cys Thr Phe Gln Thr Lys Asp His
            530                 535                 540
```

Leu Phe Phe Val Met Glu Phe Leu Asn Gly Gly Asp Leu Met Tyr His
545                 550                 555                 560

Ile Gln Asp Lys Gly Arg Phe Glu Leu Tyr Arg Ala Thr Phe Tyr Ala
            565                 570                 575

Ala Glu Ile Met Cys Gly Leu Gln Phe Leu His Ser Lys Gly Ile Ile
        580                 585                 590

Tyr Arg Asp Leu Lys Leu Asp Asn Val Leu Leu Asp Arg Asp Gly His
    595                 600                 605

Ile Lys Ile Ala Asp Phe Gly Met Cys Lys Glu Asn Ile Phe Gly Glu
610                 615                 620

Ser Arg Ala Ser Thr Phe Cys Gly Thr Pro Asp Tyr Ile Ala Pro Glu
625                 630                 635                 640

Ile Leu Gln Gly Leu Lys Tyr Thr Phe Ser Val Asp Trp Trp Ser Phe
                645                 650                 655

Gly Val Leu Leu Tyr Glu Met Leu Ile Gly Gln Ser Pro Phe His Gly
            660                 665                 670

Asp Asp Glu Asp Glu Leu Phe Glu Ser Ile Arg Val Asp Thr Pro His
        675                 680                 685

Tyr Pro Arg Trp Ile Thr Lys Glu Ser Lys Asp Ile Leu Glu Lys Leu
    690                 695                 700

Phe Glu Arg Glu Pro Thr Lys Arg Leu Gly Val Thr Gly Asn Ile Lys
705                 710                 715                 720

Ile His Pro Phe Phe Lys Thr Ile Asn Trp Thr Leu Leu Glu Lys Arg
                725                 730                 735

Arg Leu Glu Pro Pro Phe Arg Pro Lys Val Lys Ser Pro Arg Asp Tyr
            740                 745                 750

Ser Asn Phe Asp Gln Glu Phe Leu Asn Glu Lys Ala Arg Leu Ser Tyr
        755                 760                 765

Ser Asp Lys Asn Leu Ile Asp Ser Met Asp Gln Ser Ala Phe Ala Gly
    770                 775                 780

Phe Ser Phe Val Asn Pro Lys Phe Glu His Leu Leu Glu Asp
785                 790                 795

<210> SEQ ID NO 15
<211> LENGTH: 799
<212> TYPE: PRT
<213> ORGANISM: Artificial Sequence
<220> FEATURE:
<223> OTHER INFORMATION: Synthetic sequence, a.a. sequence of sensor 12
      [G21-20]

<400> SEQUENCE: 15

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Leu Glu Asn Val Tyr Ile Lys Ala Asp Lys Gln Lys Asn Gly Ile
        35                  40                  45

Lys Ala Asn Phe Lys Ile Arg His Asn Ile Glu Asp Gly Gly Val Gln
    50                  55                  60

Leu Ala Tyr His Tyr Gln Gln Asn Thr Pro Ile Gly Asp Gly Pro Val
65                  70                  75                  80

Leu Leu Pro Asp Asn His Tyr Leu Ser Val Gln Ser Ile Leu Ser Lys
                85                  90                  95

Asp Pro Asn Glu Lys Arg Asp His Met Val Leu Leu Glu Phe Val Thr

-continued

```
                100                 105                 110
Ala Ala Gly Ile Thr Leu Gly Met Asp Glu Leu Tyr Lys Gly Gly Thr
            115                 120                 125
Gly Gly Ser Met Val Ser Lys Gly Glu Leu Phe Thr Gly Val Val
            130                 135             140
Pro Ile Gln Val Glu Leu Asp Gly Asp Val Asn Gly His Lys Phe Ser
145                 150                 155                 160
Val Ser Gly Glu Gly Glu Gly Asp Ala Thr Tyr Gly Lys Leu Thr Leu
                165                 170                 175
Lys Phe Ile Cys Thr Thr Gly Lys Leu Pro Val Pro Trp Pro Thr Leu
            180                 185                 190
Val Thr Thr Leu Thr Tyr Gly Val Gln Cys Phe Ser Arg Tyr Pro Asp
            195                 200                 205
His Met Lys Gln His Asp Phe Phe Lys Ser Ala Met Pro Glu Gly Tyr
            210                 215                 220
Ile Gln Glu Arg Thr Ile Phe Phe Lys Asp Asp Gly Asn Tyr Lys Thr
225                 230                 235                 240
Arg Ala Glu Val Lys Phe Glu Gly Asp Thr Leu Val Asn Arg Ile Glu
                245                 250                 255
Leu Lys Gly Ile Asp Phe Lys Glu Asp Gly Asn Ile Leu Gly His Lys
                260                 265                 270
Leu Glu Tyr Asn Thr Arg Ile Lys Asn His Glu Phe Ile Ala Thr Phe
            275                 280                 285
Phe Gly Gln Pro Thr Phe Cys Ser Val Cys Lys Asp Phe Val Trp Gly
            290                 295                 300
Leu Asn Lys Gln Gly Tyr Lys Cys Arg Gln Cys Asn Ala Ala Ile His
305                 310                 315                 320
Lys Lys Cys Ile Asp Lys Ile Ile Gly Arg Cys Thr Gly Thr Ala Ala
                325                 330                 335
Asn Ser Arg Asp Thr Ile Phe Gln Lys Glu Arg Phe Asn Ile Asp Met
            340                 345                 350
Pro His Arg Phe Lys Val His Asn Tyr Met Ser Pro Thr Phe Cys Asp
            355                 360                 365
His Cys Gly Ser Leu Leu Trp Gly Leu Val Lys Gln Gly Leu Lys Cys
            370                 375             380
Glu Asp Cys Gly Met Asn Val His His Lys Cys Arg Glu Lys Val Ala
385                 390                 395                 400
Asn Leu Cys Gly Ile Asn Gln Lys Leu Leu Ala Glu Ala Leu Asn Gln
                405                 410                 415
Val Thr Gln Arg Ala Ser Arg Arg Ser Asp Ser Ala Ser Ser Glu Pro
                420                 425                 430
Val Gly Ile Tyr Gln Gly Phe Glu Lys Lys Thr Gly Val Ala Gly Glu
            435                 440                 445
Asp Met Gln Asp Asn Ser Gly Thr Tyr Gly Lys Ile Trp Glu Gly Ser
            450                 455             460
Ser Lys Cys Asn Ile Asn Asn Phe Ile Phe His Lys Val Leu Gly Lys
465                 470                 475                 480
Gly Ser Phe Gly Lys Val Leu Leu Gly Glu Leu Lys Gly Arg Gly Glu
                485                 490                 495
Tyr Phe Ala Ile Lys Ala Leu Lys Lys Asp Val Val Leu Ile Asp Asp
                500                 505                 510
Asp Val Glu Cys Thr Met Val Glu Lys Arg Val Leu Thr Leu Ala Ala
            515                 520                 525
```

```
Glu Asn Pro Phe Leu Thr His Leu Ile Cys Thr Phe Gln Thr Lys Asp
            530                 535                 540

His Leu Phe Phe Val Met Glu Phe Leu Asn Gly Gly Asp Leu Met Tyr
545                 550                 555                 560

His Ile Gln Asp Lys Gly Arg Phe Glu Leu Tyr Arg Ala Thr Phe Tyr
            565                 570                 575

Ala Ala Glu Ile Met Cys Gly Leu Gln Phe Leu His Ser Lys Gly Ile
            580                 585                 590

Ile Tyr Arg Asp Leu Lys Leu Asp Asn Val Leu Leu Asp Arg Asp Gly
            595                 600                 605

His Ile Lys Ile Ala Asp Phe Gly Met Cys Lys Glu Asn Ile Phe Gly
            610                 615                 620

Glu Ser Arg Ala Ser Thr Phe Cys Gly Thr Pro Asp Tyr Ile Ala Pro
625                 630                 635                 640

Glu Ile Leu Gln Gly Leu Lys Tyr Thr Phe Ser Val Asp Trp Trp Ser
            645                 650                 655

Phe Gly Val Leu Leu Tyr Glu Met Leu Ile Gly Gln Ser Pro Phe His
            660                 665                 670

Gly Asp Asp Glu Asp Glu Leu Phe Glu Ser Ile Arg Val Asp Thr Pro
            675                 680                 685

His Tyr Pro Arg Trp Ile Thr Lys Glu Ser Lys Asp Ile Leu Glu Lys
            690                 695                 700

Leu Phe Glu Arg Glu Pro Thr Lys Arg Leu Gly Val Thr Gly Asn Ile
705                 710                 715                 720

Lys Ile His Pro Phe Phe Lys Thr Ile Asn Trp Thr Leu Leu Glu Lys
            725                 730                 735

Arg Arg Leu Glu Pro Pro Phe Arg Pro Lys Val Lys Ser Pro Arg Asp
            740                 745                 750

Tyr Ser Asn Phe Asp Gln Glu Phe Leu Asn Glu Lys Ala Arg Leu Ser
            755                 760                 765

Tyr Ser Asp Lys Asn Leu Ile Asp Ser Met Asp Gln Ser Ala Phe Ala
            770                 775                 780

Gly Phe Ser Phe Val Asn Pro Lys Phe Glu His Leu Leu Glu Asp
785                 790                 795

<210> SEQ ID NO 16
<211> LENGTH: 802
<212> TYPE: PRT
<213> ORGANISM: Artificial Sequence
<220> FEATURE:
<223> OTHER INFORMATION: Synthetic sequence, a.a. sequence of sensor 13
      [G21-23]

<400> SEQUENCE: 16

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Leu Glu Asn Val Tyr Ile Lys Ala Asp Lys Gln Lys Asn Gly Ile
            35                  40                  45

Lys Ala Asn Phe Lys Ile Arg His Asn Ile Glu Asp Gly Gly Val Gln
            50                  55                  60

Leu Ala Tyr His Tyr Gln Gln Asn Thr Pro Ile Gly Asp Gly Pro Val
65                  70                  75                  80

Leu Leu Pro Asp Asn His Tyr Leu Ser Val Gln Ser Ile Leu Ser Lys
```

-continued

```
                    85                  90                  95
Asp Pro Asn Glu Lys Arg Asp His Met Val Leu Leu Glu Phe Val Thr
                100                 105                 110
Ala Ala Gly Ile Thr Leu Gly Met Asp Glu Leu Tyr Lys Gly Gly Thr
                115                 120                 125
Gly Gly Ser Met Val Ser Lys Gly Glu Glu Leu Phe Thr Gly Val Val
            130                 135                 140
Pro Ile Gln Val Glu Leu Asp Gly Asp Val Asn Gly His Lys Phe Ser
145                 150                 155                 160
Val Ser Gly Glu Gly Glu Gly Asp Ala Thr Tyr Gly Lys Leu Thr Leu
                165                 170                 175
Lys Phe Ile Cys Thr Thr Gly Lys Leu Pro Val Pro Trp Pro Thr Leu
                180                 185                 190
Val Thr Thr Leu Thr Tyr Gly Val Gln Cys Phe Ser Arg Tyr Pro Asp
                195                 200                 205
His Met Lys Gln His Asp Phe Phe Lys Ser Ala Met Pro Glu Gly Tyr
            210                 215                 220
Ile Gln Glu Arg Thr Ile Phe Phe Lys Asp Asp Gly Asn Tyr Lys Thr
225                 230                 235                 240
Arg Ala Glu Val Lys Phe Glu Gly Asp Thr Leu Val Asn Arg Ile Glu
                245                 250                 255
Leu Lys Gly Ile Asp Phe Lys Glu Asp Gly Asn Ile Leu Gly His Lys
                260                 265                 270
Leu Glu Tyr Asn Thr Arg Ile His Tyr Ile Lys Asn His Glu Phe Ile
                275                 280                 285
Ala Thr Phe Phe Gly Gln Pro Thr Phe Cys Ser Val Cys Lys Asp Phe
            290                 295                 300
Val Trp Gly Leu Asn Lys Gln Gly Tyr Lys Cys Arg Gln Cys Asn Ala
305                 310                 315                 320
Ala Ile His Lys Lys Cys Ile Asp Lys Ile Ile Gly Arg Cys Thr Gly
                325                 330                 335
Thr Ala Ala Asn Ser Arg Asp Thr Ile Phe Gln Lys Glu Arg Phe Asn
                340                 345                 350
Ile Asp Met Pro His Arg Phe Lys Val His Asn Tyr Met Ser Pro Thr
                355                 360                 365
Phe Cys Asp His Cys Gly Ser Leu Leu Trp Gly Leu Val Lys Gln Gly
            370                 375                 380
Leu Lys Cys Glu Asp Cys Gly Met Asn Val His His Lys Cys Arg Glu
385                 390                 395                 400
Lys Val Ala Asn Leu Cys Gly Ile Asn Gln Lys Leu Leu Ala Glu Ala
                405                 410                 415
Leu Asn Gln Val Thr Gln Arg Ala Ser Arg Ser Asp Ser Ala Ser
                420                 425                 430
Ser Glu Pro Val Gly Ile Tyr Gln Gly Phe Glu Lys Lys Thr Gly Val
            435                 440                 445
Ala Gly Glu Asp Met Gln Asp Asn Ser Gly Thr Tyr Gly Lys Ile Trp
            450                 455                 460
Glu Gly Ser Ser Lys Cys Asn Ile Asn Asn Phe Ile Phe His Lys Val
465                 470                 475                 480
Leu Gly Lys Gly Ser Phe Gly Lys Val Leu Leu Gly Glu Leu Lys Gly
                485                 490                 495
Arg Gly Glu Tyr Phe Ala Ile Lys Ala Leu Lys Lys Asp Val Val Leu
            500                 505                 510
```

```
Ile Asp Asp Asp Val Glu Cys Thr Met Val Glu Lys Arg Val Leu Thr
            515                 520                 525

Leu Ala Ala Glu Asn Pro Phe Leu Thr His Leu Ile Cys Thr Phe Gln
530                 535                 540

Thr Lys Asp His Leu Phe Phe Val Met Glu Phe Leu Asn Gly Gly Asp
545                 550                 555                 560

Leu Met Tyr His Ile Gln Asp Lys Gly Arg Phe Glu Leu Tyr Arg Ala
            565                 570                 575

Thr Phe Tyr Ala Ala Glu Ile Met Cys Gly Leu Gln Phe Leu His Ser
            580                 585                 590

Lys Gly Ile Ile Tyr Arg Asp Leu Lys Leu Asp Asn Val Leu Leu Asp
            595                 600                 605

Arg Asp Gly His Ile Lys Ile Ala Asp Phe Gly Met Cys Lys Glu Asn
            610                 615                 620

Ile Phe Gly Glu Ser Arg Ala Ser Thr Phe Cys Gly Thr Pro Asp Tyr
625                 630                 635                 640

Ile Ala Pro Glu Ile Leu Gln Gly Leu Lys Tyr Thr Phe Ser Val Asp
            645                 650                 655

Trp Trp Ser Phe Gly Val Leu Leu Tyr Glu Met Leu Ile Gly Gln Ser
            660                 665                 670

Pro Phe His Gly Asp Asp Glu Asp Glu Leu Phe Glu Ser Ile Arg Val
            675                 680                 685

Asp Thr Pro His Tyr Pro Arg Trp Ile Thr Lys Glu Ser Lys Asp Ile
            690                 695                 700

Leu Glu Lys Leu Phe Glu Arg Glu Pro Thr Lys Arg Leu Gly Val Thr
705                 710                 715                 720

Gly Asn Ile Lys Ile His Pro Phe Phe Lys Thr Ile Asn Trp Thr Leu
            725                 730                 735

Leu Glu Lys Arg Arg Leu Glu Pro Pro Phe Arg Pro Lys Val Lys Ser
            740                 745                 750

Pro Arg Asp Tyr Ser Asn Phe Asp Gln Glu Phe Leu Asn Glu Lys Ala
            755                 760                 765

Arg Leu Ser Tyr Ser Asp Lys Asn Leu Ile Asp Ser Met Asp Gln Ser
            770                 775                 780

Ala Phe Ala Gly Phe Ser Phe Val Asn Pro Lys Phe Glu His Leu Leu
785                 790                 795                 800

Glu Asp

<210> SEQ ID NO 17
<211> LENGTH: 800
<212> TYPE: PRT
<213> ORGANISM: Artificial Sequence
<220> FEATURE:
<223> OTHER INFORMATION: Synthetic sequence, a.a. sequence of sensor 14
      [G23]

<400> SEQUENCE: 17

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Leu
            20                  25                  30

Glu Asn Val Tyr Ile Lys Ala Asp Lys Gln Lys Asn Gly Ile Lys Ala
            35                  40                  45

Asn Phe Lys Ile Arg His Asn Ile Glu Asp Gly Gly Val Gln Leu Ala
        50                  55                  60
```

```
Tyr His Tyr Gln Gln Asn Thr Pro Ile Gly Asp Gly Pro Val Leu Leu
 65                  70                  75                  80

Pro Asp Asn His Tyr Leu Ser Val Gln Ser Ile Leu Ser Lys Asp Pro
                 85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Gly Thr Gly Gly
        115                 120                 125

Ser Met Val Ser Lys Gly Glu Glu Leu Phe Thr Gly Val Val Pro Ile
130                 135                 140

Gln Val Glu Leu Asp Gly Asp Val Asn Gly His Lys Phe Ser Val Ser
145                 150                 155                 160

Gly Glu Gly Glu Gly Asp Ala Thr Tyr Gly Lys Leu Thr Leu Lys Phe
                165                 170                 175

Ile Cys Thr Thr Gly Lys Leu Pro Val Pro Trp Pro Thr Leu Val Thr
            180                 185                 190

Thr Leu Thr Tyr Gly Val Gln Cys Phe Ser Arg Tyr Pro Asp His Met
        195                 200                 205

Lys Gln His Asp Phe Phe Lys Ser Ala Met Pro Glu Gly Tyr Ile Gln
210                 215                 220

Glu Arg Thr Ile Phe Phe Lys Asp Asp Gly Asn Tyr Lys Thr Arg Ala
225                 230                 235                 240

Glu Val Lys Phe Glu Gly Asp Thr Leu Val Asn Arg Ile Glu Leu Lys
                245                 250                 255

Gly Ile Asp Phe Lys Glu Asp Gly Asn Ile Leu Gly His Lys Leu Glu
            260                 265                 270

Tyr Asn Thr Arg Ile His Tyr Ile Lys Asn His Glu Phe Ile Ala Thr
        275                 280                 285

Phe Phe Gly Gln Pro Thr Phe Cys Ser Val Cys Lys Asp Phe Val Trp
290                 295                 300

Gly Leu Asn Lys Gln Gly Tyr Lys Cys Arg Gln Cys Asn Ala Ala Ile
305                 310                 315                 320

His Lys Lys Cys Ile Asp Lys Ile Ile Gly Arg Cys Thr Gly Thr Ala
                325                 330                 335

Ala Asn Ser Arg Asp Thr Ile Phe Gln Lys Glu Arg Phe Asn Ile Asp
            340                 345                 350

Met Pro His Arg Phe Lys Val His Asn Tyr Met Ser Pro Thr Phe Cys
        355                 360                 365

Asp His Cys Gly Ser Leu Leu Trp Gly Leu Val Lys Gln Gly Leu Lys
                375                 380
        370

Cys Glu Asp Cys Gly Met Asn Val His His Lys Cys Arg Glu Lys Val
385                 390                 395                 400

Ala Asn Leu Cys Gly Ile Asn Gln Lys Leu Leu Ala Glu Ala Leu Asn
                405                 410                 415

Gln Val Thr Gln Arg Ala Ser Arg Arg Ser Asp Ser Ala Ser Ser Glu
            420                 425                 430

Pro Val Gly Ile Tyr Gln Gly Phe Glu Lys Lys Thr Gly Val Ala Gly
        435                 440                 445

Glu Asp Met Gln Asp Asn Ser Gly Thr Tyr Gly Lys Ile Trp Glu Gly
    450                 455                 460

Ser Ser Lys Cys Asn Ile Asn Asn Phe Ile Phe His Lys Val Leu Gly
465                 470                 475                 480
```

```
Lys Gly Ser Phe Gly Lys Val Leu Leu Gly Glu Leu Lys Gly Arg Gly
                485                 490                 495
Glu Tyr Phe Ala Ile Lys Ala Leu Lys Lys Asp Val Val Leu Ile Asp
            500                 505                 510
Asp Asp Val Glu Cys Thr Met Val Glu Lys Arg Val Leu Thr Leu Ala
        515                 520                 525
Ala Glu Asn Pro Phe Leu Thr His Leu Ile Cys Thr Phe Gln Thr Lys
    530                 535                 540
Asp His Leu Phe Phe Val Met Glu Phe Leu Asn Gly Gly Asp Leu Met
545                 550                 555                 560
Tyr His Ile Gln Asp Lys Gly Arg Phe Glu Leu Tyr Arg Ala Thr Phe
                565                 570                 575
Tyr Ala Ala Glu Ile Met Cys Gly Leu Gln Phe Leu His Ser Lys Gly
            580                 585                 590
Ile Ile Tyr Arg Asp Leu Lys Leu Asp Asn Val Leu Leu Asp Arg Asp
        595                 600                 605
Gly His Ile Lys Ile Ala Asp Phe Gly Met Cys Lys Glu Asn Ile Phe
    610                 615                 620
Gly Glu Ser Arg Ala Ser Thr Phe Cys Gly Thr Pro Asp Tyr Ile Ala
625                 630                 635                 640
Pro Glu Ile Leu Gln Gly Leu Lys Tyr Thr Phe Ser Val Asp Trp Trp
                645                 650                 655
Ser Phe Gly Val Leu Leu Tyr Glu Met Leu Ile Gly Gln Ser Pro Phe
            660                 665                 670
His Gly Asp Asp Glu Asp Glu Leu Phe Glu Ser Ile Arg Val Asp Thr
        675                 680                 685
Pro His Tyr Pro Arg Trp Ile Thr Lys Glu Ser Lys Asp Ile Leu Glu
    690                 695                 700
Lys Leu Phe Glu Arg Glu Pro Thr Lys Arg Leu Gly Val Thr Gly Asn
705                 710                 715                 720
Ile Lys Ile His Pro Phe Phe Lys Thr Ile Asn Trp Thr Leu Leu Glu
                725                 730                 735
Lys Arg Arg Leu Glu Pro Pro Phe Arg Pro Lys Val Lys Ser Pro Arg
            740                 745                 750
Asp Tyr Ser Asn Phe Asp Gln Glu Phe Leu Asn Glu Lys Ala Arg Leu
        755                 760                 765
Ser Tyr Ser Asp Lys Asn Leu Ile Asp Ser Met Asp Gln Ser Ala Phe
    770                 775                 780
Ala Gly Phe Ser Phe Val Asn Pro Lys Phe Glu His Leu Leu Glu Asp
785                 790                 795                 800
```

<210> SEQ ID NO 18
<211> LENGTH: 795
<212> TYPE: PRT
<213> ORGANISM: Artificial Sequence
<220> FEATURE:
<223> OTHER INFORMATION: Synthetic sequence, a.a. sequence of sensor 15
      [G23-18]

<400> SEQUENCE: 18

```
Met Glu Asp Val Asp Cys Lys Gln Ser Met Arg Ser Glu Asp Glu Ala
1               5                   10                  15
Lys Phe Pro Thr Met Asn Arg Arg Gly Ala Ile Lys Gln Ala Lys Leu
            20                  25                  30
Glu Asn Val Tyr Ile Lys Ala Asp Lys Gln Lys Asn Gly Ile Lys Ala
        35                  40                  45
```

```
Asn Phe Lys Ile Arg His Asn Ile Glu Asp Gly Gly Val Gln Leu Ala
     50                  55                  60

Tyr His Tyr Gln Gln Asn Thr Pro Ile Gly Asp Gly Pro Val Leu Leu
 65                  70                  75                  80

Pro Asp Asn His Tyr Leu Ser Val Gln Ser Ile Leu Ser Lys Asp Pro
                 85                  90                  95

Asn Glu Lys Arg Asp His Met Val Leu Leu Glu Phe Val Thr Ala Ala
                100                 105                 110

Gly Ile Thr Leu Gly Met Asp Glu Leu Tyr Lys Gly Gly Thr Gly Gly
                115                 120                 125

Ser Met Val Ser Lys Gly Glu Glu Leu Phe Thr Gly Val Val Pro Ile
        130                 135                 140

Gln Val Glu Leu Asp Gly Asp Val Asn Gly His Lys Phe Ser Val Ser
145                 150                 155                 160

Gly Glu Gly Glu Gly Asp Ala Thr Tyr Gly Lys Leu Thr Leu Lys Phe
                    165                 170                 175

Ile Cys Thr Thr Gly Lys Leu Pro Val Pro Trp Pro Thr Leu Val Thr
                180                 185                 190

Thr Leu Thr Tyr Gly Val Gln Cys Phe Ser Arg Tyr Pro Asp His Met
        195                 200                 205

Lys Gln His Asp Phe Phe Lys Ser Ala Met Pro Glu Gly Tyr Ile Gln
    210                 215                 220

Glu Arg Thr Ile Phe Phe Lys Asp Asp Gly Asn Tyr Lys Thr Arg Ala
225                 230                 235                 240

Glu Val Lys Phe Glu Gly Asp Thr Leu Val Asn Arg Ile Glu Leu Lys
                245                 250                 255

Gly Ile Asp Phe Lys Glu Asp Gly Asn Ile Leu Gly His Lys Leu Glu
                260                 265                 270

Tyr Asn Thr Arg Asn His Glu Phe Ile Ala Thr Phe Phe Gly Gln Pro
        275                 280                 285

Thr Phe Cys Ser Val Cys Lys Asp Phe Val Trp Gly Leu Asn Lys Gln
    290                 295                 300

Gly Tyr Lys Cys Arg Gln Cys Asn Ala Ala Ile His Lys Lys Cys Ile
305                 310                 315                 320

Asp Lys Ile Ile Gly Arg Cys Thr Gly Thr Ala Ala Asn Ser Arg Asp
                325                 330                 335

Thr Ile Phe Gln Lys Glu Arg Phe Asn Ile Asp Met Pro His Arg Phe
                340                 345                 350

Lys Val His Asn Tyr Met Ser Pro Thr Phe Cys Asp His Cys Gly Ser
        355                 360                 365

Leu Leu Trp Gly Leu Val Lys Gln Gly Leu Lys Cys Glu Asp Cys Gly
    370                 375                 380

Met Asn Val His His Lys Cys Arg Glu Lys Val Ala Asn Leu Cys Gly
385                 390                 395                 400

Ile Asn Gln Lys Leu Leu Ala Glu Ala Leu Asn Gln Val Thr Gln Arg
                405                 410                 415

Ala Ser Arg Arg Ser Asp Ser Ala Ser Ser Glu Pro Val Gly Ile Tyr
                420                 425                 430

Gln Gly Phe Glu Lys Lys Thr Gly Val Ala Gly Glu Asp Met Gln Asp
        435                 440                 445

Asn Ser Gly Thr Tyr Gly Lys Ile Trp Glu Gly Ser Ser Lys Cys Asn
    450                 455                 460
```

```
Ile Asn Asn Phe Ile Phe His Lys Val Leu Gly Lys Gly Ser Phe Gly
465                 470                 475                 480

Lys Val Leu Leu Gly Glu Leu Lys Gly Arg Gly Glu Tyr Phe Ala Ile
                485                 490                 495

Lys Ala Leu Lys Lys Asp Val Val Leu Ile Asp Asp Asp Val Glu Cys
            500                 505                 510

Thr Met Val Glu Lys Arg Val Leu Thr Leu Ala Ala Glu Asn Pro Phe
        515                 520                 525

Leu Thr His Leu Ile Cys Thr Phe Gln Thr Lys Asp His Leu Phe Phe
    530                 535                 540

Val Met Glu Phe Leu Asn Gly Gly Asp Leu Met Tyr His Ile Gln Asp
545                 550                 555                 560

Lys Gly Arg Phe Glu Leu Tyr Arg Ala Thr Phe Tyr Ala Ala Glu Ile
                565                 570                 575

Met Cys Gly Leu Gln Phe Leu His Ser Lys Gly Ile Ile Tyr Arg Asp
            580                 585                 590

Leu Lys Leu Asp Asn Val Leu Leu Asp Arg Asp Gly His Ile Lys Ile
        595                 600                 605

Ala Asp Phe Gly Met Cys Lys Glu Asn Ile Phe Gly Glu Ser Arg Ala
610                 615                 620

Ser Thr Phe Cys Gly Thr Pro Asp Tyr Ile Ala Pro Glu Ile Leu Gln
625                 630                 635                 640

Gly Leu Lys Tyr Thr Phe Ser Val Asp Trp Trp Ser Phe Gly Val Leu
                645                 650                 655

Leu Tyr Glu Met Leu Ile Gly Gln Ser Pro Phe His Gly Asp Asp Glu
            660                 665                 670

Asp Glu Leu Phe Glu Ser Ile Arg Val Asp Thr Pro His Tyr Pro Arg
        675                 680                 685

Trp Ile Thr Lys Glu Ser Lys Asp Ile Leu Glu Lys Leu Phe Glu Arg
690                 695                 700

Glu Pro Thr Lys Arg Leu Gly Val Thr Gly Asn Ile Lys Ile His Pro
705                 710                 715                 720

Phe Phe Lys Thr Ile Asn Trp Thr Leu Leu Glu Lys Arg Arg Leu Glu
                725                 730                 735

Pro Pro Phe Arg Pro Lys Val Lys Ser Pro Arg Asp Tyr Ser Asn Phe
            740                 745                 750

Asp Gln Glu Phe Leu Asn Glu Lys Ala Arg Leu Ser Tyr Ser Asp Lys
        755                 760                 765

Asn Leu Ile Asp Ser Met Asp Gln Ser Ala Phe Ala Gly Phe Ser Phe
    770                 775                 780

Val Asn Pro Lys Phe Glu His Leu Leu Glu Asp
785                 790                 795

<210> SEQ ID NO 19
<211> LENGTH: 796
<212> TYPE: PRT
<213> ORGANISM: Artificial Sequence
<220> FEATURE:
<223> OTHER INFORMATION: Synthetic sequence, a.a. sequence of sensor 16
      [G23-19]

<400> SEQUENCE: 19

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Leu
            20                  25                  30
```

-continued

```
Glu Asn Val Tyr Ile Lys Ala Asp Lys Gln Lys Asn Gly Ile Lys Ala
             35                  40                  45

Asn Phe Lys Ile Arg His Asn Ile Glu Asp Gly Gly Val Gln Leu Ala
     50                  55                  60

Tyr His Tyr Gln Gln Asn Thr Pro Ile Gly Asp Gly Pro Val Leu Leu
 65                  70                  75                  80

Pro Asp Asn His Tyr Leu Ser Val Gln Ser Ile Leu Ser Lys Asp Pro
                 85                  90                  95

Asn Glu Lys Arg Asp His Met Val Leu Leu Glu Phe Val Thr Ala Ala
                100                 105                 110

Gly Ile Thr Leu Gly Met Asp Glu Leu Tyr Lys Gly Thr Gly Gly
                115                 120                 125

Ser Met Val Ser Lys Gly Glu Glu Leu Phe Thr Gly Val Val Pro Ile
    130                 135                 140

Gln Val Glu Leu Asp Gly Asp Val Asn Gly His Lys Phe Ser Val Ser
145                 150                 155                 160

Gly Glu Gly Glu Gly Asp Ala Thr Tyr Gly Lys Leu Thr Leu Lys Phe
                165                 170                 175

Ile Cys Thr Thr Gly Lys Leu Pro Val Pro Trp Pro Thr Leu Val Thr
                180                 185                 190

Thr Leu Thr Tyr Gly Val Gln Cys Phe Ser Arg Tyr Pro Asp His Met
            195                 200                 205

Lys Gln His Asp Phe Phe Lys Ser Ala Met Pro Glu Gly Tyr Ile Gln
    210                 215                 220

Glu Arg Thr Ile Phe Phe Lys Asp Asp Gly Asn Tyr Lys Thr Arg Ala
225                 230                 235                 240

Glu Val Lys Phe Glu Gly Asp Thr Leu Val Asn Arg Ile Glu Leu Lys
                245                 250                 255

Gly Ile Asp Phe Lys Glu Asp Gly Asn Ile Leu Gly His Lys Leu Glu
                260                 265                 270

Tyr Asn Thr Arg Lys Asn His Glu Phe Ile Ala Thr Phe Phe Gly Gln
            275                 280                 285

Pro Thr Phe Cys Ser Val Cys Lys Asp Phe Val Trp Gly Leu Asn Lys
    290                 295                 300

Gln Gly Tyr Lys Cys Arg Gln Cys Asn Ala Ala Ile His Lys Lys Cys
305                 310                 315                 320

Ile Asp Lys Ile Ile Gly Arg Cys Thr Gly Thr Ala Ala Asn Ser Arg
                325                 330                 335

Asp Thr Ile Phe Gln Lys Glu Arg Phe Asn Ile Asp Met Pro His Arg
            340                 345                 350

Phe Lys Val His Asn Tyr Met Ser Pro Thr Phe Cys Asp His Cys Gly
    355                 360                 365

Ser Leu Leu Trp Gly Leu Val Lys Gln Gly Leu Lys Cys Glu Asp Cys
370                 375                 380

Gly Met Asn Val His His Lys Cys Arg Glu Lys Val Ala Asn Leu Cys
385                 390                 395                 400

Gly Ile Asn Gln Lys Leu Leu Ala Glu Ala Leu Asn Gln Val Thr Gln
                405                 410                 415

Arg Ala Ser Arg Arg Ser Asp Ser Ala Ser Ser Glu Pro Val Gly Ile
            420                 425                 430

Tyr Gln Gly Phe Glu Lys Lys Thr Gly Val Ala Gly Glu Asp Met Gln
    435                 440                 445
```

```
Asp Asn Ser Gly Thr Tyr Gly Lys Ile Trp Glu Gly Ser Ser Lys Cys
    450                 455                 460

Asn Ile Asn Asn Phe Ile Phe His Lys Val Leu Gly Lys Gly Ser Phe
465                 470                 475                 480

Gly Lys Val Leu Leu Gly Glu Leu Lys Gly Arg Gly Glu Tyr Phe Ala
                485                 490                 495

Ile Lys Ala Leu Lys Lys Asp Val Val Leu Ile Asp Asp Val Glu
            500                 505                 510

Cys Thr Met Val Glu Lys Arg Val Leu Thr Leu Ala Ala Glu Asn Pro
        515                 520                 525

Phe Leu Thr His Leu Ile Cys Thr Phe Gln Thr Lys Asp His Leu Phe
    530                 535                 540

Phe Val Met Glu Phe Leu Asn Gly Gly Asp Leu Met Tyr His Ile Gln
545                 550                 555                 560

Asp Lys Gly Arg Phe Glu Leu Tyr Arg Ala Thr Phe Tyr Ala Ala Glu
                565                 570                 575

Ile Met Cys Gly Leu Gln Phe Leu His Ser Lys Gly Ile Ile Tyr Arg
            580                 585                 590

Asp Leu Lys Leu Asp Asn Val Leu Leu Asp Arg Asp Gly His Ile Lys
        595                 600                 605

Ile Ala Asp Phe Gly Met Cys Lys Glu Asn Ile Phe Gly Glu Ser Arg
    610                 615                 620

Ala Ser Thr Phe Cys Gly Thr Pro Asp Tyr Ile Ala Pro Glu Ile Leu
625                 630                 635                 640

Gln Gly Leu Lys Tyr Thr Phe Ser Val Asp Trp Trp Ser Phe Gly Val
                645                 650                 655

Leu Leu Tyr Glu Met Leu Ile Gly Gln Ser Pro Phe His Gly Asp Asp
            660                 665                 670

Glu Asp Glu Leu Phe Glu Ser Ile Arg Val Asp Thr Pro His Tyr Pro
        675                 680                 685

Arg Trp Ile Thr Lys Glu Ser Lys Asp Ile Leu Glu Lys Leu Phe Glu
    690                 695                 700

Arg Glu Pro Thr Lys Arg Leu Gly Val Thr Gly Asn Ile Lys Ile His
705                 710                 715                 720

Pro Phe Phe Lys Thr Ile Asn Trp Thr Leu Leu Glu Lys Arg Arg Leu
                725                 730                 735

Glu Pro Pro Phe Arg Pro Lys Val Lys Ser Pro Arg Asp Tyr Ser Asn
            740                 745                 750

Phe Asp Gln Glu Phe Leu Asn Glu Lys Ala Arg Leu Ser Tyr Ser Asp
        755                 760                 765

Lys Asn Leu Ile Asp Ser Met Asp Gln Ser Ala Phe Ala Gly Phe Ser
    770                 775                 780

Phe Val Asn Pro Lys Phe Glu His Leu Leu Glu Asp
785                 790                 795

<210> SEQ ID NO 20
<211> LENGTH: 806
<212> TYPE: PRT
<213> ORGANISM: Artificial Sequence
<220> FEATURE:
<223> OTHER INFORMATION: Synthetic sequence, a.a. sequence of sensor 17
      [G27-19]

<400> SEQUENCE: 20

Met Glu Asp Val Asp Cys Lys Gln Ser Met Arg Ser Glu Asp Glu Ala
1               5                   10                  15
```

-continued

```
Lys Phe Pro Thr Met Asn Arg Arg Gly Ala Ile Lys Gln Ala Lys Ile
             20                  25                  30
His Tyr Ile Lys Asn His Glu Phe Ile Leu Glu Asn Val Tyr Ile Lys
         35                  40                  45
Ala Asp Lys Gln Lys Asn Gly Ile Lys Ala Asn Phe Lys Ile Arg His
 50                  55                  60
Asn Ile Glu Asp Gly Gly Val Gln Leu Ala Tyr His Tyr Gln Gln Asn
 65                  70                  75                  80
Thr Pro Ile Gly Asp Gly Pro Val Leu Leu Pro Asp Asn His Tyr Leu
                 85                  90                  95
Ser Val Gln Ser Ile Leu Ser Lys Asp Pro Asn Glu Lys Arg Asp His
             100                 105                 110
Met Val Leu Leu Glu Phe Val Thr Ala Ala Gly Ile Thr Leu Gly Met
         115                 120                 125
Asp Glu Leu Tyr Lys Gly Gly Thr Gly Gly Ser Met Val Ser Lys Gly
130                 135                 140
Glu Glu Leu Phe Thr Gly Val Val Pro Ile Gln Val Glu Leu Asp Gly
145                 150                 155                 160
Asp Val Asn Gly His Lys Phe Ser Val Ser Gly Glu Gly Glu Gly Asp
                 165                 170                 175
Ala Thr Tyr Gly Lys Leu Thr Leu Lys Phe Ile Cys Thr Thr Gly Lys
             180                 185                 190
Leu Pro Val Pro Trp Pro Thr Leu Val Thr Thr Leu Thr Tyr Gly Val
         195                 200                 205
Gln Cys Phe Ser Arg Tyr Pro Asp His Met Lys Gln His Asp Phe Phe
     210                 215                 220
Lys Ser Ala Met Pro Glu Gly Tyr Ile Gln Glu Arg Thr Ile Phe Phe
225                 230                 235                 240
Lys Asp Asp Gly Asn Tyr Lys Thr Arg Ala Glu Val Lys Phe Glu Gly
                 245                 250                 255
Asp Thr Leu Val Asn Arg Ile Glu Leu Lys Gly Ile Asp Phe Lys Glu
             260                 265                 270
Asp Gly Asn Ile Leu Gly His Lys Leu Glu Tyr Asn Thr Arg Lys Asn
         275                 280                 285
His Glu Phe Ile Ala Thr Phe Phe Gly Gln Pro Thr Phe Cys Ser Val
     290                 295                 300
Cys Lys Asp Phe Val Trp Gly Leu Asn Lys Gln Gly Tyr Lys Cys Arg
305                 310                 315                 320
Gln Cys Asn Ala Ala Ile His Lys Lys Cys Ile Asp Lys Ile Ile Gly
                 325                 330                 335
Arg Cys Thr Gly Thr Ala Ala Asn Ser Arg Asp Thr Ile Phe Gln Lys
             340                 345                 350
Glu Arg Phe Asn Ile Asp Met Pro His Arg Phe Lys Val His Asn Tyr
         355                 360                 365
Met Ser Pro Thr Phe Cys Asp His Cys Gly Ser Leu Leu Trp Gly Leu
     370                 375                 380
Val Lys Gln Gly Leu Lys Cys Glu Asp Cys Gly Met Asn Val His His
385                 390                 395                 400
Lys Cys Arg Glu Lys Val Ala Asn Leu Cys Gly Ile Asn Gln Lys Leu
                 405                 410                 415
Leu Ala Glu Ala Leu Asn Gln Val Thr Gln Arg Ala Ser Arg Arg Ser
             420                 425                 430
```

```
Asp Ser Ala Ser Ser Glu Pro Val Gly Ile Tyr Gln Gly Phe Glu Lys
            435                 440                 445

Lys Thr Gly Val Ala Gly Glu Asp Met Gln Asp Asn Ser Gly Thr Tyr
450                 455                 460

Gly Lys Ile Trp Glu Gly Ser Ser Lys Cys Asn Ile Asn Asn Phe Ile
465                 470                 475                 480

Phe His Lys Val Leu Gly Lys Gly Ser Phe Gly Lys Val Leu Leu Gly
                485                 490                 495

Glu Leu Lys Gly Arg Gly Glu Tyr Phe Ala Ile Lys Ala Leu Lys Lys
            500                 505                 510

Asp Val Val Leu Ile Asp Asp Val Glu Cys Thr Met Val Glu Lys
            515                 520                 525

Arg Val Leu Thr Leu Ala Ala Glu Asn Pro Phe Leu Thr His Leu Ile
            530                 535                 540

Cys Thr Phe Gln Thr Lys Asp His Leu Phe Phe Val Met Glu Phe Leu
545                 550                 555                 560

Asn Gly Gly Asp Leu Met Tyr His Ile Gln Asp Lys Gly Arg Phe Glu
                565                 570                 575

Leu Tyr Arg Ala Thr Phe Tyr Ala Ala Glu Ile Met Cys Gly Leu Gln
            580                 585                 590

Phe Leu His Ser Lys Gly Ile Ile Tyr Arg Asp Leu Lys Leu Asp Asn
            595                 600                 605

Val Leu Leu Asp Arg Asp Gly His Ile Lys Ile Ala Asp Phe Gly Met
            610                 615                 620

Cys Lys Glu Asn Ile Phe Gly Glu Ser Arg Ala Ser Thr Phe Cys Gly
625                 630                 635                 640

Thr Pro Asp Tyr Ile Ala Pro Glu Ile Leu Gln Gly Leu Lys Tyr Thr
                645                 650                 655

Phe Ser Val Asp Trp Trp Ser Phe Gly Val Leu Leu Tyr Glu Met Leu
            660                 665                 670

Ile Gly Gln Ser Pro Phe His Gly Asp Asp Glu Asp Glu Leu Phe Glu
            675                 680                 685

Ser Ile Arg Val Asp Thr Pro His Tyr Pro Arg Trp Ile Thr Lys Glu
690                 695                 700

Ser Lys Asp Ile Leu Glu Lys Leu Phe Glu Arg Glu Pro Thr Lys Arg
705                 710                 715                 720

Leu Gly Val Thr Gly Asn Ile Lys Ile His Pro Phe Phe Lys Thr Ile
                725                 730                 735

Asn Trp Thr Leu Leu Glu Lys Arg Arg Leu Glu Pro Pro Phe Arg Pro
            740                 745                 750

Lys Val Lys Ser Pro Arg Asp Tyr Ser Asn Phe Asp Gln Glu Phe Leu
            755                 760                 765

Asn Glu Lys Ala Arg Leu Ser Tyr Ser Asp Lys Asn Leu Ile Asp Ser
            770                 775                 780

Met Asp Gln Ser Ala Phe Ala Gly Phe Ser Phe Val Asn Pro Lys Phe
785                 790                 795                 800

Glu His Leu Leu Glu Asp
                805

<210> SEQ ID NO 21
<211> LENGTH: 809
<212> TYPE: PRT
<213> ORGANISM: Artificial Sequence
<220> FEATURE:
<223> OTHER INFORMATION: Synthetic sequence, a.a. sequence of sensor 18
```

[G27-22]

<400> SEQUENCE: 21

```
Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Leu Glu Asn Val Tyr Ile Lys
        35                  40                  45

Ala Asp Lys Gln Lys Asn Gly Ile Lys Ala Asn Phe Lys Ile Arg His
    50                  55                  60

Asn Ile Glu Asp Gly Gly Val Gln Leu Ala Tyr His Tyr Gln Gln Asn
65                  70                  75                  80

Thr Pro Ile Gly Asp Gly Pro Val Leu Leu Pro Asp Asn His Tyr Leu
                85                  90                  95

Ser Val Gln Ser Ile Leu Ser Lys Asp Pro Asn Glu Lys Arg Asp His
            100                 105                 110

Met Val Leu Leu Glu Phe Val Thr Ala Ala Gly Ile Thr Leu Gly Met
        115                 120                 125

Asp Glu Leu Tyr Lys Gly Gly Thr Gly Gly Ser Met Val Ser Lys Gly
    130                 135                 140

Glu Glu Leu Phe Thr Gly Val Val Pro Ile Gln Val Glu Leu Asp Gly
145                 150                 155                 160

Asp Val Asn Gly His Lys Phe Ser Val Ser Gly Glu Gly Glu Gly Asp
                165                 170                 175

Ala Thr Tyr Gly Lys Leu Thr Leu Lys Phe Ile Cys Thr Thr Gly Lys
            180                 185                 190

Leu Pro Val Pro Trp Pro Thr Leu Val Thr Thr Leu Thr Tyr Gly Val
        195                 200                 205

Gln Cys Phe Ser Arg Tyr Pro Asp His Met Lys Gln His Asp Phe Phe
    210                 215                 220

Lys Ser Ala Met Pro Glu Gly Tyr Ile Gln Glu Arg Thr Ile Phe Phe
225                 230                 235                 240

Lys Asp Asp Gly Asn Tyr Lys Thr Arg Ala Glu Val Lys Phe Glu Gly
                245                 250                 255

Asp Thr Leu Val Asn Arg Ile Glu Leu Lys Gly Ile Asp Phe Lys Glu
            260                 265                 270

Asp Gly Asn Ile Leu Gly His Lys Leu Glu Tyr Asn Thr Arg His Tyr
        275                 280                 285

Ile Lys Asn His Glu Phe Ile Ala Thr Phe Phe Gly Gln Pro Thr Phe
    290                 295                 300

Cys Ser Val Cys Lys Asp Phe Val Trp Gly Leu Asn Lys Gln Gly Tyr
305                 310                 315                 320

Lys Cys Arg Gln Cys Asn Ala Ala Ile His Lys Lys Cys Ile Asp Lys
                325                 330                 335

Ile Ile Gly Arg Cys Thr Gly Thr Ala Ala Asn Ser Arg Asp Thr Ile
            340                 345                 350

Phe Gln Lys Glu Arg Phe Asn Ile Asp Met Pro His Arg Phe Lys Val
        355                 360                 365

His Asn Tyr Met Ser Pro Thr Phe Cys Asp His Cys Gly Ser Leu Leu
    370                 375                 380

Trp Gly Leu Val Lys Gln Gly Leu Lys Cys Glu Asp Cys Gly Met Asn
385                 390                 395                 400
```

-continued

```
Val His His Lys Cys Arg Glu Lys Val Ala Asn Leu Cys Gly Ile Asn
                405                 410                 415
Gln Lys Leu Leu Ala Glu Ala Leu Asn Gln Val Thr Gln Arg Ala Ser
            420                 425                 430
Arg Arg Ser Asp Ser Ala Ser Ser Glu Pro Val Gly Ile Tyr Gln Gly
        435                 440                 445
Phe Glu Lys Lys Thr Gly Val Ala Gly Glu Asp Met Gln Asp Asn Ser
    450                 455                 460
Gly Thr Tyr Gly Lys Ile Trp Glu Gly Ser Ser Lys Cys Asn Ile Asn
465                 470                 475                 480
Asn Phe Ile Phe His Lys Val Leu Gly Lys Gly Ser Phe Gly Lys Val
                485                 490                 495
Leu Leu Gly Glu Leu Lys Gly Arg Gly Glu Tyr Phe Ala Ile Lys Ala
            500                 505                 510
Leu Lys Lys Asp Val Val Leu Ile Asp Asp Asp Val Glu Cys Thr Met
        515                 520                 525
Val Glu Lys Arg Val Leu Thr Leu Ala Ala Glu Asn Pro Phe Leu Thr
    530                 535                 540
His Leu Ile Cys Thr Phe Gln Thr Lys Asp His Leu Phe Phe Val Met
545                 550                 555                 560
Glu Phe Leu Asn Gly Gly Asp Leu Met Tyr His Ile Gln Asp Lys Gly
                565                 570                 575
Arg Phe Glu Leu Tyr Arg Ala Thr Phe Tyr Ala Ala Glu Ile Met Cys
            580                 585                 590
Gly Leu Gln Phe Leu His Ser Lys Gly Ile Ile Tyr Arg Asp Leu Lys
        595                 600                 605
Leu Asp Asn Val Leu Leu Asp Arg Asp Gly His Ile Lys Ile Ala Asp
    610                 615                 620
Phe Gly Met Cys Lys Glu Asn Ile Phe Gly Glu Ser Arg Ala Ser Thr
625                 630                 635                 640
Phe Cys Gly Thr Pro Asp Tyr Ile Ala Pro Glu Ile Leu Gln Gly Leu
                645                 650                 655
Lys Tyr Thr Phe Ser Val Asp Trp Trp Ser Phe Gly Val Leu Leu Tyr
            660                 665                 670
Glu Met Leu Ile Gly Gln Ser Pro Phe His Gly Asp Asp Glu Asp Glu
        675                 680                 685
Leu Phe Glu Ser Ile Arg Val Asp Thr Pro His Tyr Pro Arg Trp Ile
    690                 695                 700
Thr Lys Glu Ser Lys Asp Ile Leu Glu Lys Leu Phe Glu Arg Glu Pro
705                 710                 715                 720
Thr Lys Arg Leu Gly Val Thr Gly Asn Ile Lys Ile His Pro Phe Phe
                725                 730                 735
Lys Thr Ile Asn Trp Thr Leu Leu Glu Lys Arg Arg Leu Glu Pro Pro
            740                 745                 750
Phe Arg Pro Lys Val Lys Ser Pro Arg Asp Tyr Ser Asn Phe Asp Gln
        755                 760                 765
Glu Phe Leu Asn Glu Lys Ala Arg Leu Ser Tyr Ser Asp Lys Asn Leu
    770                 775                 780
Ile Asp Ser Met Asp Gln Ser Ala Phe Ala Gly Phe Ser Phe Val Asn
785                 790                 795                 800
Pro Lys Phe Glu His Leu Leu Glu Asp
                805
```

```
<210> SEQ ID NO 22
<211> LENGTH: 806
<212> TYPE: PRT
<213> ORGANISM: Artificial Sequence
<220> FEATURE:
<223> OTHER INFORMATION: Synthetic sequence, a.a. sequence of sensor 19
      [G28-18]

<400> SEQUENCE: 22
```

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Ala Leu Glu Asn Val Tyr Ile
        35                  40                  45

Lys Ala Asp Lys Gln Lys Asn Gly Ile Lys Ala Asn Phe Lys Ile Arg
    50                  55                  60

His Asn Ile Glu Asp Gly Gly Val Gln Leu Ala Tyr His Tyr Gln Gln
65                  70                  75                  80

Asn Thr Pro Ile Gly Asp Gly Pro Val Leu Leu Pro Asp Asn His Tyr
                85                  90                  95

Leu Ser Val Gln Ser Ile Leu Ser Lys Asp Pro Asn Glu Lys Arg Asp
            100                 105                 110

His Met Val Leu Leu Glu Phe Val Thr Ala Ala Gly Ile Thr Leu Gly
        115                 120                 125

Met Asp Glu Leu Tyr Lys Gly Gly Thr Gly Gly Ser Met Val Ser Lys
    130                 135                 140

Gly Glu Glu Leu Phe Thr Gly Val Val Pro Ile Gln Val Glu Leu Asp
145                 150                 155                 160

Gly Asp Val Asn Gly His Lys Phe Ser Val Ser Gly Glu Gly Glu Gly
                165                 170                 175

Asp Ala Thr Tyr Gly Lys Leu Thr Leu Lys Phe Ile Cys Thr Thr Gly
            180                 185                 190

Lys Leu Pro Val Pro Trp Pro Thr Leu Val Thr Thr Leu Thr Tyr Gly
        195                 200                 205

Val Gln Cys Phe Ser Arg Tyr Pro Asp His Met Lys Gln His Asp Phe
    210                 215                 220

Phe Lys Ser Ala Met Pro Glu Gly Tyr Ile Gln Glu Arg Thr Ile Phe
225                 230                 235                 240

Phe Lys Asp Asp Gly Asn Tyr Lys Thr Arg Ala Glu Val Lys Phe Glu
                245                 250                 255

Gly Asp Thr Leu Val Asn Arg Ile Glu Leu Lys Gly Ile Asp Phe Lys
            260                 265                 270

Glu Asp Gly Asn Ile Leu Gly His Lys Leu Glu Tyr Asn Thr Arg Asn
        275                 280                 285

His Glu Phe Ile Ala Thr Phe Phe Gly Gln Pro Thr Phe Cys Ser Val
    290                 295                 300

Cys Lys Asp Phe Val Trp Gly Leu Asn Lys Gln Gly Tyr Lys Cys Arg
305                 310                 315                 320

Gln Cys Asn Ala Ala Ile His Lys Lys Cys Ile Asp Lys Ile Ile Gly
                325                 330                 335

Arg Cys Thr Gly Thr Ala Ala Asn Ser Arg Asp Thr Ile Phe Gln Lys
            340                 345                 350

Glu Arg Phe Asn Ile Asp Met Pro His Arg Phe Lys Val His Asn Tyr
        355                 360                 365

-continued

```
Met Ser Pro Thr Phe Cys Asp His Cys Gly Ser Leu Leu Trp Gly Leu
    370             375             380
Val Lys Gln Gly Leu Lys Cys Glu Asp Cys Gly Met Asn Val His His
385             390             395             400
Lys Cys Arg Glu Lys Val Ala Asn Leu Cys Gly Ile Asn Gln Lys Leu
            405             410             415
Leu Ala Glu Ala Leu Asn Gln Val Thr Gln Arg Ala Ser Arg Arg Ser
        420             425             430
Asp Ser Ala Ser Ser Glu Pro Val Gly Ile Tyr Gln Gly Phe Glu Lys
        435             440             445
Lys Thr Gly Val Ala Gly Glu Asp Met Gln Asp Asn Ser Gly Thr Tyr
    450             455             460
Gly Lys Ile Trp Glu Gly Ser Ser Lys Cys Asn Ile Asn Asn Phe Ile
465             470             475             480
Phe His Lys Val Leu Gly Lys Gly Ser Phe Gly Lys Val Leu Leu Gly
            485             490             495
Glu Leu Lys Gly Arg Gly Glu Tyr Phe Ala Ile Lys Ala Leu Lys Lys
        500             505             510
Asp Val Val Leu Ile Asp Asp Val Glu Cys Thr Met Val Glu Lys
        515             520             525
Arg Val Leu Thr Leu Ala Ala Glu Asn Pro Phe Leu Thr His Leu Ile
    530             535             540
Cys Thr Phe Gln Thr Lys Asp His Leu Phe Phe Val Met Glu Phe Leu
545             550             555             560
Asn Gly Gly Asp Leu Met Tyr His Ile Gln Asp Lys Gly Arg Phe Glu
            565             570             575
Leu Tyr Arg Ala Thr Phe Tyr Ala Ala Glu Ile Met Cys Gly Leu Gln
        580             585             590
Phe Leu His Ser Lys Gly Ile Ile Tyr Arg Asp Leu Lys Leu Asp Asn
        595             600             605
Val Leu Leu Asp Arg Asp Gly His Ile Lys Ile Ala Asp Phe Gly Met
    610             615             620
Cys Lys Glu Asn Ile Phe Gly Glu Ser Arg Ala Ser Thr Phe Cys Gly
625             630             635             640
Thr Pro Asp Tyr Ile Ala Pro Glu Ile Leu Gln Gly Leu Lys Tyr Thr
            645             650             655
Phe Ser Val Asp Trp Trp Ser Phe Gly Val Leu Leu Tyr Glu Met Leu
        660             665             670
Ile Gly Gln Ser Pro Phe His Gly Asp Asp Glu Asp Glu Leu Phe Glu
        675             680             685
Ser Ile Arg Val Asp Thr Pro His Tyr Pro Arg Trp Ile Thr Lys Glu
    690             695             700
Ser Lys Asp Ile Leu Glu Lys Leu Phe Glu Arg Glu Pro Thr Lys Arg
705             710             715             720
Leu Gly Val Thr Gly Asn Ile Lys Ile His Pro Phe Phe Lys Thr Ile
            725             730             735
Asn Trp Thr Leu Leu Glu Lys Arg Arg Leu Glu Pro Pro Phe Arg Pro
        740             745             750
Lys Val Lys Ser Pro Arg Asp Tyr Ser Asn Phe Asp Gln Glu Phe Leu
        755             760             765
Asn Glu Lys Ala Arg Leu Ser Tyr Ser Asp Lys Asn Leu Ile Asp Ser
    770             775             780
Met Asp Gln Ser Ala Phe Ala Gly Phe Ser Phe Val Asn Pro Lys Phe
```

```
785                 790                 795                 800
Glu His Leu Leu Glu Asp
                805

<210> SEQ ID NO 23
<211> LENGTH: 801
<212> TYPE: PRT
<213> ORGANISM: Artificial Sequence
<220> FEATURE:
<223> OTHER INFORMATION: Synthetic sequence, a.a. sequence of sensor 20
      [G28-27]

<400> SEQUENCE: 23

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Ala Leu Glu Asn Val Tyr Ile
        35                  40                  45

Lys Ala Asp Lys Gln Lys Asn Gly Ile Lys Ala Asn Phe Lys Ile Arg
    50                  55                  60

His Asn Ile Glu Asp Gly Gly Val Gln Leu Ala Tyr His Tyr Gln Gln
65                  70                  75                  80

Asn Thr Pro Ile Gly Asp Gly Pro Val Leu Leu Pro Asp Asn His Tyr
                85                  90                  95

Leu Ser Val Gln Ser Ile Leu Ser Lys Asp Pro Asn Glu Lys Arg Asp
            100                 105                 110

His Met Val Leu Leu Glu Phe Val Thr Ala Ala Gly Ile Thr Leu Gly
        115                 120                 125

Met Asp Glu Leu Tyr Lys Gly Gly Thr Gly Gly Ser Met Val Ser Lys
    130                 135                 140

Gly Glu Glu Leu Phe Thr Gly Val Val Pro Ile Gln Val Glu Leu Asp
145                 150                 155                 160

Gly Asp Val Asn Gly His Lys Phe Ser Val Ser Gly Glu Gly Glu Gly
                165                 170                 175

Asp Ala Thr Tyr Gly Lys Leu Thr Leu Lys Phe Ile Cys Thr Thr Gly
            180                 185                 190

Lys Leu Pro Val Pro Trp Pro Thr Leu Val Thr Thr Leu Thr Tyr Gly
        195                 200                 205

Val Gln Cys Phe Ser Arg Tyr Pro Asp His Met Lys Gln His Asp Phe
    210                 215                 220

Phe Lys Ser Ala Met Pro Glu Gly Tyr Ile Gln Glu Arg Thr Ile Phe
225                 230                 235                 240

Phe Lys Asp Asp Gly Asn Tyr Lys Thr Arg Ala Glu Val Lys Phe Glu
                245                 250                 255

Gly Asp Thr Leu Val Asn Arg Ile Glu Leu Lys Gly Ile Asp Phe Lys
            260                 265                 270

Glu Asp Gly Asn Ile Leu Gly His Lys Leu Glu Tyr Asn Thr Arg Ala
        275                 280                 285

Thr Phe Phe Gly Gln Pro Thr Phe Cys Ser Val Cys Lys Asp Phe Val
    290                 295                 300

Trp Gly Leu Asn Lys Gln Gly Tyr Lys Cys Arg Gln Cys Asn Ala Ala
305                 310                 315                 320

Ile His Lys Lys Cys Ile Asp Lys Ile Ile Gly Arg Cys Thr Gly Thr
                325                 330                 335
```

```
Ala Ala Asn Ser Arg Asp Thr Ile Phe Gln Lys Glu Arg Phe Asn Ile
            340                 345                 350

Asp Met Pro His Arg Phe Lys Val His Asn Tyr Met Ser Pro Thr Phe
        355                 360                 365

Cys Asp His Cys Gly Ser Leu Leu Trp Gly Leu Val Lys Gln Gly Leu
    370                 375                 380

Lys Cys Glu Asp Cys Gly Met Asn Val His His Lys Cys Arg Glu Lys
385                 390                 395                 400

Val Ala Asn Leu Cys Gly Ile Asn Gln Lys Leu Leu Ala Glu Ala Leu
            405                 410                 415

Asn Gln Val Thr Gln Arg Ala Ser Arg Arg Ser Asp Ser Ala Ser Ser
        420                 425                 430

Glu Pro Val Gly Ile Tyr Gln Gly Phe Glu Lys Lys Thr Gly Val Ala
        435                 440                 445

Gly Glu Asp Met Gln Asp Asn Ser Gly Thr Tyr Gly Lys Ile Trp Glu
        450                 455                 460

Gly Ser Ser Lys Cys Asn Ile Asn Asn Phe Ile Phe His Lys Val Leu
465                 470                 475                 480

Gly Lys Gly Ser Phe Gly Lys Val Leu Leu Gly Glu Leu Lys Gly Arg
            485                 490                 495

Gly Glu Tyr Phe Ala Ile Lys Ala Leu Lys Lys Asp Val Val Leu Ile
        500                 505                 510

Asp Asp Asp Val Glu Cys Thr Met Val Glu Lys Arg Val Leu Thr Leu
        515                 520                 525

Ala Ala Glu Asn Pro Phe Leu Thr His Leu Ile Cys Thr Phe Gln Thr
    530                 535                 540

Lys Asp His Leu Phe Phe Val Met Glu Phe Leu Asn Gly Gly Asp Leu
545                 550                 555                 560

Met Tyr His Ile Gln Asp Lys Gly Arg Phe Glu Leu Tyr Arg Ala Thr
            565                 570                 575

Phe Tyr Ala Ala Glu Ile Met Cys Gly Leu Gln Phe Leu His Ser Lys
        580                 585                 590

Gly Ile Ile Tyr Arg Asp Leu Lys Leu Asp Asn Val Leu Leu Asp Arg
        595                 600                 605

Asp Gly His Ile Lys Ile Ala Asp Phe Gly Met Cys Lys Glu Asn Ile
    610                 615                 620

Phe Gly Glu Ser Arg Ala Ser Thr Phe Cys Gly Thr Pro Asp Tyr Ile
625                 630                 635                 640

Ala Pro Glu Ile Leu Gln Gly Leu Lys Tyr Thr Phe Ser Val Asp Trp
            645                 650                 655

Trp Ser Phe Gly Val Leu Leu Tyr Glu Met Leu Ile Gly Gln Ser Pro
        660                 665                 670

Phe His Gly Asp Asp Glu Asp Glu Leu Phe Glu Ser Ile Arg Val Asp
        675                 680                 685

Thr Pro His Tyr Pro Arg Trp Ile Thr Lys Glu Ser Lys Asp Ile Leu
    690                 695                 700

Glu Lys Leu Phe Glu Arg Glu Pro Thr Lys Arg Leu Gly Val Thr Gly
705                 710                 715                 720

Asn Ile Lys Ile His Pro Phe Phe Lys Thr Ile Asn Trp Thr Leu Leu
            725                 730                 735

Glu Lys Arg Arg Leu Glu Pro Pro Phe Arg Pro Lys Val Lys Ser Pro
        740                 745                 750

Arg Asp Tyr Ser Asn Phe Asp Gln Glu Phe Leu Asn Glu Lys Ala Arg
```

```
                    755                 760                 765
Leu Ser Tyr Ser Asp Lys Asn Leu Ile Asp Ser Met Asp Gln Ser Ala
            770                 775                 780

Phe Ala Gly Phe Ser Phe Val Asn Pro Lys Phe Glu His Leu Leu Glu
785                 790                 795                 800

Asp

<210> SEQ ID NO 24
<211> LENGTH: 807
<212> TYPE: PRT
<213> ORGANISM: Artificial Sequence
<220> FEATURE:
<223> OTHER INFORMATION: Synthetic sequence, a.a. sequence of sensor 21
      [G29-18]

<400> SEQUENCE: 24

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Ala Thr Leu Glu Asn Val Tyr
        35                  40                  45

Ile Lys Ala Asp Lys Gln Lys Asn Gly Ile Lys Ala Asn Phe Lys Ile
    50                  55                  60

Arg His Asn Ile Glu Asp Gly Gly Val Gln Leu Ala Tyr His Tyr Gln
65                  70                  75                  80

Gln Asn Thr Pro Ile Gly Asp Gly Pro Val Leu Leu Pro Asp Asn His
                85                  90                  95

Tyr Leu Ser Val Gln Ser Ile Leu Ser Lys Asp Pro Asn Glu Lys Arg
            100                 105                 110

Asp His Met Val Leu Leu Glu Phe Val Thr Ala Ala Gly Ile Thr Leu
        115                 120                 125

Gly Met Asp Glu Leu Tyr Lys Gly Gly Thr Gly Gly Ser Met Val Ser
    130                 135                 140

Lys Gly Glu Glu Leu Phe Thr Gly Val Val Pro Ile Gln Val Glu Leu
145                 150                 155                 160

Asp Gly Asp Val Asn Gly His Lys Phe Ser Val Ser Gly Glu Gly Glu
                165                 170                 175

Gly Asp Ala Thr Tyr Gly Lys Leu Thr Leu Lys Phe Ile Cys Thr Thr
            180                 185                 190

Gly Lys Leu Pro Val Pro Trp Pro Thr Leu Val Thr Thr Leu Thr Tyr
        195                 200                 205

Gly Val Gln Cys Phe Ser Arg Tyr Pro Asp His Met Lys Gln His Asp
    210                 215                 220

Phe Phe Lys Ser Ala Met Pro Glu Gly Tyr Ile Gln Glu Arg Thr Ile
225                 230                 235                 240

Phe Phe Lys Asp Asp Gly Asn Tyr Lys Thr Arg Ala Glu Val Lys Phe
                245                 250                 255

Glu Gly Asp Thr Leu Val Asn Arg Ile Glu Leu Lys Gly Ile Asp Phe
            260                 265                 270

Lys Glu Asp Gly Asn Ile Leu Gly His Lys Leu Glu Tyr Asn Thr Arg
        275                 280                 285

Asn His Glu Phe Ile Ala Thr Phe Gly Gln Pro Thr Phe Cys Ser
    290                 295                 300

Val Cys Lys Asp Phe Val Trp Gly Leu Asn Lys Gln Gly Tyr Lys Cys
```

-continued

```
            305                 310                 315                 320
Arg Gln Cys Asn Ala Ala Ile His Lys Lys Cys Ile Asp Lys Ile Ile
                    325                 330                 335
Gly Arg Cys Thr Gly Thr Ala Ala Asn Ser Arg Asp Thr Ile Phe Gln
                    340                 345                 350
Lys Glu Arg Phe Asn Ile Asp Met Pro His Arg Phe Lys Val His Asn
                    355                 360                 365
Tyr Met Ser Pro Thr Phe Cys Asp His Cys Gly Ser Leu Leu Trp Gly
                    370                 375                 380
Leu Val Lys Gln Gly Leu Lys Cys Glu Asp Cys Gly Met Asn Val His
385                 390                 395                 400
His Lys Cys Arg Glu Lys Val Ala Asn Leu Cys Gly Ile Asn Gln Lys
                    405                 410                 415
Leu Leu Ala Glu Ala Leu Asn Gln Val Thr Gln Arg Ala Ser Arg Arg
                    420                 425                 430
Ser Asp Ser Ala Ser Ser Glu Pro Val Gly Ile Tyr Gln Gly Phe Glu
                    435                 440                 445
Lys Lys Thr Gly Val Ala Gly Glu Asp Met Gln Asp Asn Ser Gly Thr
                    450                 455                 460
Tyr Gly Lys Ile Trp Glu Gly Ser Ser Lys Cys Asn Ile Asn Asn Phe
465                 470                 475                 480
Ile Phe His Lys Val Leu Gly Lys Gly Ser Phe Gly Lys Val Leu Leu
                    485                 490                 495
Gly Glu Leu Lys Gly Arg Gly Glu Tyr Phe Ala Ile Lys Ala Leu Lys
                    500                 505                 510
Lys Asp Val Val Leu Ile Asp Asp Asp Val Glu Cys Thr Met Val Glu
                    515                 520                 525
Lys Arg Val Leu Thr Leu Ala Ala Glu Asn Pro Phe Leu Thr His Leu
                    530                 535                 540
Ile Cys Thr Phe Gln Thr Lys Asp His Leu Phe Phe Val Met Glu Phe
545                 550                 555                 560
Leu Asn Gly Gly Asp Leu Met Tyr His Ile Gln Asp Lys Gly Arg Phe
                    565                 570                 575
Glu Leu Tyr Arg Ala Thr Phe Tyr Ala Ala Glu Ile Met Cys Gly Leu
                    580                 585                 590
Gln Phe Leu His Ser Lys Gly Ile Ile Tyr Arg Asp Leu Lys Leu Asp
                    595                 600                 605
Asn Val Leu Leu Asp Arg Asp Gly His Ile Lys Ile Ala Asp Phe Gly
                    610                 615                 620
Met Cys Lys Glu Asn Ile Phe Gly Glu Ser Arg Ala Ser Thr Phe Cys
625                 630                 635                 640
Gly Thr Pro Asp Tyr Ile Ala Pro Glu Ile Leu Gln Gly Leu Lys Tyr
                    645                 650                 655
Thr Phe Ser Val Asp Trp Trp Ser Phe Gly Val Leu Leu Tyr Glu Met
                    660                 665                 670
Leu Ile Gly Gln Ser Pro Phe His Gly Asp Asp Glu Asp Glu Leu Phe
                    675                 680                 685
Glu Ser Ile Arg Val Asp Thr Pro His Tyr Pro Arg Trp Ile Thr Lys
                    690                 695                 700
Glu Ser Lys Asp Ile Leu Glu Lys Leu Phe Glu Arg Glu Pro Thr Lys
705                 710                 715                 720
Arg Leu Gly Val Thr Gly Asn Ile Lys Ile His Pro Phe Phe Lys Thr
                    725                 730                 735
```

Ile Asn Trp Thr Leu Leu Glu Lys Arg Arg Leu Glu Pro Pro Phe Arg
            740                 745                 750

Pro Lys Val Lys Ser Pro Arg Asp Tyr Ser Asn Phe Asp Gln Glu Phe
            755                 760                 765

Leu Asn Glu Lys Ala Arg Leu Ser Tyr Ser Asp Lys Asn Leu Ile Asp
            770                 775                 780

Ser Met Asp Gln Ser Ala Phe Ala Gly Phe Ser Phe Val Asn Pro Lys
785                 790                 795                 800

Phe Glu His Leu Leu Glu Asp
            805

<210> SEQ ID NO 25
<211> LENGTH: 812
<212> TYPE: PRT
<213> ORGANISM: Artificial Sequence
<220> FEATURE:
<223> OTHER INFORMATION: Synthetic sequence, a.a. sequence of sensor 22
      [G29-23]

<400> SEQUENCE: 25

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Ala Thr Leu Glu Asn Val Tyr
            35                  40                  45

Ile Lys Ala Asp Lys Gln Lys Asn Gly Ile Lys Ala Asn Phe Lys Ile
        50                  55                  60

Arg His Asn Ile Glu Asp Gly Gly Val Gln Leu Ala Tyr His Tyr Gln
65                  70                  75                  80

Gln Asn Thr Pro Ile Gly Asp Gly Pro Val Leu Leu Pro Asp Asn His
            85                  90                  95

Tyr Leu Ser Val Gln Ser Ile Leu Ser Lys Asp Pro Asn Glu Lys Arg
            100                 105                 110

Asp His Met Val Leu Leu Glu Phe Val Thr Ala Ala Gly Ile Thr Leu
            115                 120                 125

Gly Met Asp Glu Leu Tyr Lys Gly Gly Thr Gly Gly Ser Met Val Ser
        130                 135                 140

Lys Gly Glu Glu Leu Phe Thr Gly Val Val Pro Ile Gln Val Glu Leu
145                 150                 155                 160

Asp Gly Asp Val Asn Gly His Lys Phe Ser Val Ser Gly Glu Gly Glu
            165                 170                 175

Gly Asp Ala Thr Tyr Gly Lys Leu Thr Leu Lys Phe Ile Cys Thr Thr
            180                 185                 190

Gly Lys Leu Pro Val Pro Trp Pro Thr Leu Val Thr Thr Leu Thr Tyr
            195                 200                 205

Gly Val Gln Cys Phe Ser Arg Tyr Pro Asp His Met Lys Gln His Asp
        210                 215                 220

Phe Phe Lys Ser Ala Met Pro Glu Gly Tyr Ile Gln Glu Arg Thr Ile
225                 230                 235                 240

Phe Phe Lys Asp Asp Gly Asn Tyr Lys Thr Arg Ala Glu Val Lys Phe
            245                 250                 255

Glu Gly Asp Thr Leu Val Asn Arg Ile Glu Leu Lys Gly Ile Asp Phe
            260                 265                 270

Lys Glu Asp Gly Asn Ile Leu Gly His Lys Leu Glu Tyr Asn Thr Arg

```
                275                 280                 285
Ile His Tyr Ile Lys Asn His Glu Phe Ile Ala Thr Phe Phe Gly Gln
            290                 295                 300
Pro Thr Phe Cys Ser Val Cys Lys Asp Phe Val Trp Gly Leu Asn Lys
305                 310                 315                 320
Gln Gly Tyr Lys Cys Arg Gln Cys Asn Ala Ile His Lys Lys Cys
            325                 330                 335
Ile Asp Lys Ile Ile Gly Arg Cys Thr Gly Thr Ala Ala Asn Ser Arg
            340                 345                 350
Asp Thr Ile Phe Gln Lys Glu Arg Phe Asn Ile Asp Met Pro His Arg
            355                 360                 365
Phe Lys Val His Asn Tyr Met Ser Pro Thr Phe Cys Asp His Cys Gly
            370                 375                 380
Ser Leu Leu Trp Gly Leu Val Lys Gln Gly Leu Lys Cys Glu Asp Cys
385                 390                 395                 400
Gly Met Asn Val His His Lys Cys Arg Glu Lys Val Ala Asn Leu Cys
            405                 410                 415
Gly Ile Asn Gln Lys Leu Leu Ala Glu Ala Leu Asn Gln Val Thr Gln
            420                 425                 430
Arg Ala Ser Arg Arg Ser Asp Ser Ala Ser Ser Glu Pro Val Gly Ile
            435                 440                 445
Tyr Gln Gly Phe Glu Lys Lys Thr Gly Val Ala Gly Glu Asp Met Gln
            450                 455                 460
Asp Asn Ser Gly Thr Tyr Gly Lys Ile Trp Glu Gly Ser Ser Lys Cys
465                 470                 475                 480
Asn Ile Asn Asn Phe Ile Phe His Lys Val Leu Gly Lys Gly Ser Phe
            485                 490                 495
Gly Lys Val Leu Leu Gly Glu Leu Lys Gly Arg Gly Glu Tyr Phe Ala
            500                 505                 510
Ile Lys Ala Leu Lys Lys Asp Val Val Leu Ile Asp Asp Asp Val Glu
            515                 520                 525
Cys Thr Met Val Glu Lys Arg Val Leu Thr Leu Ala Ala Glu Asn Pro
530                 535                 540
Phe Leu Thr His Leu Ile Cys Thr Phe Gln Thr Lys Asp His Leu Phe
545                 550                 555                 560
Phe Val Met Glu Phe Leu Asn Gly Gly Asp Leu Met Tyr His Ile Gln
            565                 570                 575
Asp Lys Gly Arg Phe Glu Leu Tyr Arg Ala Thr Phe Tyr Ala Ala Glu
            580                 585                 590
Ile Met Cys Gly Leu Gln Phe Leu His Ser Lys Gly Ile Ile Tyr Arg
            595                 600                 605
Asp Leu Lys Leu Asp Asn Val Leu Leu Asp Arg Asp Gly His Ile Lys
            610                 615                 620
Ile Ala Asp Phe Gly Met Cys Lys Glu Asn Ile Phe Gly Glu Ser Arg
625                 630                 635                 640
Ala Ser Thr Phe Cys Gly Thr Pro Asp Tyr Ile Ala Pro Glu Ile Leu
            645                 650                 655
Gln Gly Leu Lys Tyr Thr Phe Ser Val Asp Trp Trp Ser Phe Gly Val
            660                 665                 670
Leu Leu Tyr Glu Met Leu Ile Gly Gln Ser Pro Phe His Gly Asp Asp
            675                 680                 685
Glu Asp Glu Leu Phe Glu Ser Ile Arg Val Asp Thr Pro His Tyr Pro
            690                 695                 700
```

```
Arg Trp Ile Thr Lys Glu Ser Lys Asp Ile Leu Glu Lys Leu Phe Glu
705                 710                 715                 720

Arg Glu Pro Thr Lys Arg Leu Gly Val Thr Gly Asn Ile Lys Ile His
            725                 730                 735

Pro Phe Phe Lys Thr Ile Asn Trp Thr Leu Leu Glu Lys Arg Arg Leu
        740                 745                 750

Glu Pro Pro Phe Arg Pro Lys Val Lys Ser Pro Arg Asp Tyr Ser Asn
    755                 760                 765

Phe Asp Gln Glu Phe Leu Asn Glu Lys Ala Arg Leu Ser Tyr Ser Asp
770                 775                 780

Lys Asn Leu Ile Asp Ser Met Asp Gln Ser Ala Phe Ala Gly Phe Ser
785                 790                 795                 800

Phe Val Asn Pro Lys Phe Glu His Leu Leu Glu Asp
            805                 810
```

<210> SEQ ID NO 26
<211> LENGTH: 805
<212> TYPE: PRT
<213> ORGANISM: Artificial Sequence
<220> FEATURE:
<223> OTHER INFORMATION: Synthetic sequence, a.a. sequence of sensor 23
      [G29-24]

<400> SEQUENCE: 26

```
Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Ala Thr Leu Glu Asn Val Tyr
        35                  40                  45

Ile Lys Ala Asp Lys Gln Lys Asn Gly Ile Lys Ala Asn Phe Lys Ile
    50                  55                  60

Arg His Asn Ile Glu Asp Gly Gly Val Gln Leu Ala Tyr His Tyr Gln
65                  70                  75                  80

Gln Asn Thr Pro Ile Gly Asp Gly Pro Val Leu Leu Pro Asp Asn His
            85                  90                  95

Tyr Leu Ser Val Gln Ser Ile Leu Ser Lys Asp Pro Asn Glu Lys Arg
        100                 105                 110

Asp His Met Val Leu Leu Glu Phe Val Thr Ala Ala Gly Ile Thr Leu
    115                 120                 125

Gly Met Asp Glu Leu Tyr Lys Gly Gly Thr Gly Gly Ser Met Val Ser
130                 135                 140

Lys Gly Glu Glu Leu Phe Thr Gly Val Val Pro Ile Gln Val Glu Leu
145                 150                 155                 160

Asp Gly Asp Val Asn Gly His Lys Phe Ser Val Ser Gly Glu Gly Glu
            165                 170                 175

Gly Asp Ala Thr Tyr Gly Lys Leu Thr Leu Lys Phe Ile Cys Thr Thr
        180                 185                 190

Gly Lys Leu Pro Val Pro Trp Pro Thr Leu Val Thr Thr Leu Thr Tyr
    195                 200                 205

Gly Val Gln Cys Phe Ser Arg Tyr Pro Asp His Met Lys Gln His Asp
210                 215                 220

Phe Phe Lys Ser Ala Met Pro Glu Gly Tyr Ile Gln Glu Arg Thr Ile
225                 230                 235                 240

Phe Phe Lys Asp Asp Gly Asn Tyr Lys Thr Arg Ala Glu Val Lys Phe
```

-continued

```
                245                 250                 255
Glu Gly Asp Thr Leu Val Asn Arg Ile Glu Leu Lys Gly Ile Asp Phe
            260                 265                 270
Lys Glu Asp Gly Asn Ile Leu Gly His Lys Leu Glu Tyr Asn Thr Arg
        275                 280                 285
Glu Phe Ile Ala Thr Phe Phe Gly Gln Pro Thr Phe Cys Ser Val Cys
    290                 295                 300
Lys Asp Phe Val Trp Gly Leu Asn Lys Gln Gly Tyr Lys Cys Arg Gln
305                 310                 315                 320
Cys Asn Ala Ala Ile His Lys Lys Cys Ile Asp Lys Ile Ile Gly Arg
                325                 330                 335
Cys Thr Gly Thr Ala Ala Asn Ser Arg Asp Thr Ile Phe Gln Lys Glu
            340                 345                 350
Arg Phe Asn Ile Asp Met Pro His Arg Phe Lys Val His Asn Tyr Met
        355                 360                 365
Ser Pro Thr Phe Cys Asp His Cys Gly Ser Leu Leu Trp Gly Leu Val
    370                 375                 380
Lys Gln Gly Leu Lys Cys Glu Asp Cys Gly Met Asn Val His His Lys
385                 390                 395                 400
Cys Arg Glu Lys Val Ala Asn Leu Cys Gly Ile Asn Gln Lys Leu Leu
                405                 410                 415
Ala Glu Ala Leu Asn Gln Val Thr Gln Arg Ala Ser Arg Arg Ser Asp
            420                 425                 430
Ser Ala Ser Ser Glu Pro Val Gly Ile Tyr Gln Gly Phe Glu Lys Lys
        435                 440                 445
Thr Gly Val Ala Gly Glu Asp Met Gln Asp Asn Ser Gly Thr Tyr Gly
    450                 455                 460
Lys Ile Trp Glu Gly Ser Ser Lys Cys Asn Ile Asn Asn Phe Ile Phe
465                 470                 475                 480
His Lys Val Leu Gly Lys Gly Ser Phe Gly Lys Val Leu Leu Gly Glu
                485                 490                 495
Leu Lys Gly Arg Gly Glu Tyr Phe Ala Ile Lys Ala Leu Lys Lys Asp
            500                 505                 510
Val Val Leu Ile Asp Asp Asp Val Glu Cys Thr Met Val Glu Lys Arg
        515                 520                 525
Val Leu Thr Leu Ala Ala Glu Asn Pro Phe Leu Thr His Leu Ile Cys
    530                 535                 540
Thr Phe Gln Thr Lys Asp His Leu Phe Phe Val Met Glu Phe Leu Asn
545                 550                 555                 560
Gly Gly Asp Leu Met Tyr His Ile Gln Asp Lys Gly Arg Phe Glu Leu
                565                 570                 575
Tyr Arg Ala Thr Phe Tyr Ala Ala Glu Ile Met Cys Gly Leu Gln Phe
            580                 585                 590
Leu His Ser Lys Gly Ile Ile Tyr Arg Asp Leu Lys Leu Asp Asn Val
        595                 600                 605
Leu Leu Asp Arg Asp Gly His Ile Lys Ile Ala Asp Phe Gly Met Cys
    610                 615                 620
Lys Glu Asn Ile Phe Gly Glu Ser Arg Ala Ser Thr Phe Cys Gly Thr
625                 630                 635                 640
Pro Asp Tyr Ile Ala Pro Glu Ile Leu Gln Gly Leu Lys Tyr Thr Phe
                645                 650                 655
Ser Val Asp Trp Trp Ser Phe Gly Val Leu Leu Tyr Glu Met Leu Ile
            660                 665                 670
```

```
Gly Gln Ser Pro Phe His Gly Asp Asp Glu Asp Leu Phe Glu Ser
            675                 680                 685

Ile Arg Val Asp Thr Pro His Tyr Pro Arg Trp Ile Thr Lys Glu Ser
690                 695                 700

Lys Asp Ile Leu Glu Lys Leu Phe Glu Arg Glu Pro Thr Lys Arg Leu
705                 710                 715                 720

Gly Val Thr Gly Asn Ile Lys Ile His Pro Phe Phe Lys Thr Ile Asn
                725                 730                 735

Trp Thr Leu Leu Glu Lys Arg Arg Leu Glu Pro Pro Phe Arg Pro Lys
                740                 745                 750

Val Lys Ser Pro Arg Asp Tyr Ser Asn Phe Asp Gln Glu Phe Leu Asn
            755                 760                 765

Glu Lys Ala Arg Leu Ser Tyr Ser Asp Lys Asn Leu Ile Asp Ser Met
770                 775                 780

Asp Gln Ser Ala Phe Ala Gly Phe Ser Phe Val Asn Pro Lys Phe Glu
785                 790                 795                 800

His Leu Leu Glu Asp
                805

<210> SEQ ID NO 27
<211> LENGTH: 780
<212> TYPE: PRT
<213> ORGANISM: Artificial Sequence
<220> FEATURE:
<223> OTHER INFORMATION: Synthetic sequence, a.a. sequence of sensor 24
      [G30-21]

<400> SEQUENCE: 27

Met Glu Asp Val Asp Cys Lys Gln Ser Met Arg Ser Glu Leu Glu Asn
1               5                   10                  15

Val Tyr Ile Lys Ala Asp Lys Gln Lys Asn Gly Ile Lys Ala Asn Phe
            20                  25                  30

Lys Ile Arg His Asn Ile Glu Asp Gly Gly Val Gln Leu Ala Tyr His
        35                  40                  45

Tyr Gln Gln Asn Thr Pro Ile Gly Asp Gly Pro Val Leu Leu Pro Asp
    50                  55                  60

Asn His Tyr Leu Ser Val Gln Ser Ile Leu Ser Lys Asp Pro Asn Glu
65                  70                  75                  80

Lys Arg Asp His Met Val Leu Leu Glu Phe Val Thr Ala Ala Gly Ile
                85                  90                  95

Thr Leu Gly Met Asp Glu Leu Tyr Lys Gly Thr Gly Gly Ser Met
            100                 105                 110

Val Ser Lys Gly Glu Glu Leu Phe Thr Gly Val Val Pro Ile Gln Val
            115                 120                 125

Glu Leu Asp Gly Asp Val Asn Gly His Lys Phe Ser Val Ser Gly Glu
        130                 135                 140

Gly Glu Gly Asp Ala Thr Tyr Gly Lys Leu Thr Leu Lys Phe Ile Cys
145                 150                 155                 160

Thr Thr Gly Lys Leu Pro Val Pro Trp Pro Thr Leu Val Thr Thr Leu
                165                 170                 175

Thr Tyr Gly Val Gln Cys Phe Ser Arg Tyr Pro Asp His Met Lys Gln
            180                 185                 190

His Asp Phe Phe Lys Ser Ala Met Pro Glu Gly Tyr Ile Gln Glu Arg
        195                 200                 205

Thr Ile Phe Phe Lys Asp Asp Gly Asn Tyr Lys Thr Arg Ala Glu Val
```

```
              210                 215                 220
Lys Phe Glu Gly Asp Thr Leu Val Asn Arg Ile Glu Leu Lys Gly Ile
225                 230                 235                 240

Asp Phe Lys Glu Asp Gly Asn Ile Leu Gly His Lys Leu Glu Tyr Asn
                    245                 250                 255

Thr Arg Tyr Ile Lys Asn His Glu Phe Ile Ala Thr Phe Phe Gly Gln
                260                 265                 270

Pro Thr Phe Cys Ser Val Cys Lys Asp Phe Val Trp Gly Leu Asn Lys
                275                 280                 285

Gln Gly Tyr Lys Cys Arg Gln Cys Asn Ala Ala Ile His Lys Lys Cys
                290                 295                 300

Ile Asp Lys Ile Ile Gly Arg Cys Thr Gly Thr Ala Ala Asn Ser Arg
305                 310                 315                 320

Asp Thr Ile Phe Gln Lys Glu Arg Phe Asn Ile Asp Met Pro His Arg
                325                 330                 335

Phe Lys Val His Asn Tyr Met Ser Pro Thr Phe Cys Asp His Cys Gly
                340                 345                 350

Ser Leu Leu Trp Gly Leu Val Lys Gln Gly Leu Lys Cys Glu Asp Cys
                355                 360                 365

Gly Met Asn Val His His Lys Cys Arg Glu Lys Val Ala Asn Leu Cys
370                 375                 380

Gly Ile Asn Gln Lys Leu Leu Ala Glu Ala Leu Asn Gln Val Thr Gln
385                 390                 395                 400

Arg Ala Ser Arg Arg Ser Asp Ser Ala Ser Ser Glu Pro Val Gly Ile
                405                 410                 415

Tyr Gln Gly Phe Glu Lys Lys Thr Gly Val Ala Gly Glu Asp Met Gln
                420                 425                 430

Asp Asn Ser Gly Thr Tyr Gly Lys Ile Trp Glu Gly Ser Ser Lys Cys
                435                 440                 445

Asn Ile Asn Asn Phe Ile Phe His Lys Val Leu Gly Lys Gly Ser Phe
                450                 455                 460

Gly Lys Val Leu Leu Gly Glu Leu Lys Gly Arg Gly Glu Tyr Phe Ala
465                 470                 475                 480

Ile Lys Ala Leu Lys Lys Asp Val Val Leu Ile Asp Asp Asp Val Glu
                485                 490                 495

Cys Thr Met Val Glu Lys Arg Val Leu Thr Leu Ala Ala Glu Asn Pro
                500                 505                 510

Phe Leu Thr His Leu Ile Cys Thr Phe Gln Thr Lys Asp His Leu Phe
                515                 520                 525

Phe Val Met Glu Phe Leu Asn Gly Gly Asp Leu Met Tyr His Ile Gln
                530                 535                 540

Asp Lys Gly Arg Phe Glu Leu Tyr Arg Ala Thr Phe Tyr Ala Ala Glu
545                 550                 555                 560

Ile Met Cys Gly Leu Gln Phe Leu His Ser Lys Gly Ile Ile Tyr Arg
                565                 570                 575

Asp Leu Lys Leu Asp Asn Val Leu Leu Asp Arg Asp Gly His Ile Lys
                580                 585                 590

Ile Ala Asp Phe Gly Met Cys Lys Glu Asn Ile Phe Gly Glu Ser Arg
                595                 600                 605

Ala Ser Thr Phe Cys Gly Thr Pro Asp Tyr Ile Ala Pro Glu Ile Leu
                610                 615                 620

Gln Gly Leu Lys Tyr Thr Phe Ser Val Asp Trp Trp Ser Phe Gly Val
625                 630                 635                 640
```

```
Leu Leu Tyr Glu Met Leu Ile Gly Gln Ser Pro Phe His Gly Asp Asp
                645                 650                 655

Glu Asp Glu Leu Phe Glu Ser Ile Arg Val Asp Thr Pro His Tyr Pro
            660                 665                 670

Arg Trp Ile Thr Lys Glu Ser Lys Asp Ile Leu Glu Lys Leu Phe Glu
        675                 680                 685

Arg Glu Pro Thr Lys Arg Leu Gly Val Thr Gly Asn Ile Lys Ile His
    690                 695                 700

Pro Phe Phe Lys Thr Ile Asn Trp Thr Leu Leu Glu Lys Arg Arg Leu
705                 710                 715                 720

Glu Pro Pro Phe Arg Pro Lys Val Lys Ser Pro Arg Asp Tyr Ser Asn
                725                 730                 735

Phe Asp Gln Glu Phe Leu Asn Glu Lys Ala Arg Leu Ser Tyr Ser Asp
            740                 745                 750

Lys Asn Leu Ile Asp Ser Met Asp Gln Ser Ala Phe Ala Gly Phe Ser
        755                 760                 765

Phe Val Asn Pro Lys Phe Glu His Leu Leu Glu Asp
770                 775                 780

<210> SEQ ID NO 28
<211> LENGTH: 822
<212> TYPE: PRT
<213> ORGANISM: Artificial Sequence
<220> FEATURE:
<223> OTHER INFORMATION: Synthetic sequence, a.a. sequence of sensor 25
      [G19-30]

<400> SEQUENCE: 28

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Leu Glu Asn Val Tyr Ile Lys Ala Asp Lys Gln Lys Asn
        35                  40                  45

Gly Ile Lys Ala Asn Phe Lys Ile Arg His Asn Ile Glu Asp Gly Gly
    50                  55                  60

Val Gln Leu Ala Tyr His Tyr Gln Gln Asn Thr Pro Ile Gly Asp Gly
65                  70                  75                  80

Pro Val Leu Leu Pro Asp Asn His Tyr Leu Ser Val Gln Ser Ile Leu
                85                  90                  95

Ser Lys Asp Pro Asn Glu Lys Arg Asp His Met Val Leu Leu Glu Phe
            100                 105                 110

Val Thr Ala Ala Gly Ile Thr Leu Gly Met Asp Glu Leu Tyr Lys Gly
        115                 120                 125

Gly Thr Gly Gly Ser Met Val Ser Lys Gly Glu Glu Leu Phe Thr Gly
    130                 135                 140

Val Val Pro Ile Gln Val Glu Leu Asp Gly Asp Val Asn Gly His Lys
145                 150                 155                 160

Phe Ser Val Ser Gly Glu Gly Glu Gly Asp Ala Thr Tyr Gly Lys Leu
                165                 170                 175

Thr Leu Lys Phe Ile Cys Thr Thr Gly Lys Leu Pro Val Pro Trp Pro
            180                 185                 190

Thr Leu Val Thr Thr Leu Thr Tyr Gly Val Gln Cys Phe Ser Arg Tyr
        195                 200                 205

Pro Asp His Met Lys Gln His Asp Phe Phe Lys Ser Ala Met Pro Glu
```

```
              210                 215                 220
Gly Tyr Ile Gln Glu Arg Thr Ile Phe Phe Lys Asp Asp Gly Asn Tyr
225                 230                 235                 240

Lys Thr Arg Ala Glu Val Lys Phe Glu Gly Asp Thr Leu Val Asn Arg
                245                 250                 255

Ile Glu Leu Lys Gly Ile Asp Phe Lys Glu Asp Gly Asn Ile Leu Gly
                260                 265                 270

His Lys Leu Glu Tyr Asn Thr Arg Asp Glu Ala Lys Phe Pro Thr Met
                275                 280                 285

Asn Arg Arg Gly Ala Ile Lys Gln Ala Lys Ile His Tyr Ile Lys Asn
                290                 295                 300

His Glu Phe Ile Ala Thr Phe Phe Gly Gln Pro Thr Phe Cys Ser Val
305                 310                 315                 320

Cys Lys Asp Phe Val Trp Gly Leu Asn Lys Gln Gly Tyr Lys Cys Arg
                325                 330                 335

Gln Cys Asn Ala Ala Ile His Lys Lys Cys Ile Asp Lys Ile Ile Gly
                340                 345                 350

Arg Cys Thr Gly Thr Ala Ala Asn Ser Arg Asp Thr Ile Phe Gln Lys
                355                 360                 365

Glu Arg Phe Asn Ile Asp Met Pro His Arg Phe Lys Val His Asn Tyr
                370                 375                 380

Met Ser Pro Thr Phe Cys Asp His Cys Gly Ser Leu Leu Trp Gly Leu
385                 390                 395                 400

Val Lys Gln Gly Leu Lys Cys Glu Asp Cys Gly Met Asn Val His His
                405                 410                 415

Lys Cys Arg Glu Lys Val Ala Asn Leu Cys Gly Ile Asn Gln Lys Leu
                420                 425                 430

Leu Ala Glu Ala Leu Asn Gln Val Thr Gln Arg Ala Ser Arg Arg Ser
                435                 440                 445

Asp Ser Ala Ser Ser Glu Pro Val Gly Ile Tyr Gln Gly Phe Glu Lys
                450                 455                 460

Lys Thr Gly Val Ala Gly Glu Asp Met Gln Asp Asn Ser Gly Thr Tyr
465                 470                 475                 480

Gly Lys Ile Trp Glu Gly Ser Ser Lys Cys Asn Ile Asn Asn Phe Ile
                485                 490                 495

Phe His Lys Val Leu Gly Lys Gly Ser Phe Gly Lys Val Leu Leu Gly
                500                 505                 510

Glu Leu Lys Gly Arg Gly Glu Tyr Phe Ala Ile Lys Ala Leu Lys Lys
                515                 520                 525

Asp Val Val Leu Ile Asp Asp Val Glu Cys Thr Met Val Glu Lys
                530                 535                 540

Arg Val Leu Thr Leu Ala Ala Glu Asn Pro Phe Leu Thr His Leu Ile
545                 550                 555                 560

Cys Thr Phe Gln Thr Lys Asp His Leu Phe Phe Val Met Glu Phe Leu
                565                 570                 575

Asn Gly Gly Asp Leu Met Tyr His Ile Gln Asp Lys Gly Arg Phe Glu
                580                 585                 590

Leu Tyr Arg Ala Thr Phe Tyr Ala Ala Glu Ile Met Cys Gly Leu Gln
                595                 600                 605

Phe Leu His Ser Lys Gly Ile Ile Tyr Arg Asp Leu Lys Leu Asp Asn
                610                 615                 620

Val Leu Leu Asp Arg Asp Gly His Ile Lys Ile Ala Asp Phe Gly Met
625                 630                 635                 640
```

Cys Lys Glu Asn Ile Phe Gly Glu Ser Arg Ala Ser Thr Phe Cys Gly
                645                 650                 655

Thr Pro Asp Tyr Ile Ala Pro Glu Ile Leu Gln Gly Leu Lys Tyr Thr
            660                 665                 670

Phe Ser Val Asp Trp Trp Ser Phe Gly Val Leu Leu Tyr Glu Met Leu
        675                 680                 685

Ile Gly Gln Ser Pro Phe His Gly Asp Asp Glu Asp Glu Leu Phe Glu
    690                 695                 700

Ser Ile Arg Val Asp Thr Pro His Tyr Pro Arg Trp Ile Thr Lys Glu
705                 710                 715                 720

Ser Lys Asp Ile Leu Glu Lys Leu Phe Glu Arg Glu Pro Thr Lys Arg
                725                 730                 735

Leu Gly Val Thr Gly Asn Ile Lys Ile His Pro Phe Phe Lys Thr Ile
            740                 745                 750

Asn Trp Thr Leu Leu Glu Lys Arg Arg Leu Glu Pro Pro Phe Arg Pro
        755                 760                 765

Lys Val Lys Ser Pro Arg Asp Tyr Ser Asn Phe Asp Gln Glu Phe Leu
    770                 775                 780

Asn Glu Lys Ala Arg Leu Ser Tyr Ser Asp Lys Asn Leu Ile Asp Ser
785                 790                 795                 800

Met Asp Gln Ser Ala Phe Ala Gly Phe Ser Phe Val Asn Pro Lys Phe
                805                 810                 815

Glu His Leu Leu Glu Asp
                820

<210> SEQ ID NO 29
<211> LENGTH: 820
<212> TYPE: PRT
<213> ORGANISM: Artificial Sequence
<220> FEATURE:
<223> OTHER INFORMATION: Synthetic sequence, a.a. sequence of sensor 26
      [G21-30]

<400> SEQUENCE: 29

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Leu Glu Asn Val Tyr Ile Lys Ala Asp Lys Gln Lys Asn Gly Ile
        35                  40                  45

Lys Ala Asn Phe Lys Ile Arg His Asn Ile Glu Asp Gly Gly Val Gln
    50                  55                  60

Leu Ala Tyr His Tyr Gln Gln Asn Thr Pro Ile Gly Asp Gly Pro Val
65                  70                  75                  80

Leu Leu Pro Asp Asn His Tyr Leu Ser Val Gln Ser Ile Leu Ser Lys
                85                  90                  95

Asp Pro Asn Glu Lys Arg Asp His Met Val Leu Leu Glu Phe Val Thr
            100                 105                 110

Ala Ala Gly Ile Thr Leu Gly Met Asp Glu Leu Tyr Lys Gly Gly Thr
        115                 120                 125

Gly Gly Ser Met Val Ser Lys Gly Glu Glu Leu Phe Thr Gly Val Val
    130                 135                 140

Pro Ile Gln Val Glu Leu Asp Gly Asp Val Asn Gly His Lys Phe Ser
145                 150                 155                 160

Val Ser Gly Glu Gly Glu Gly Asp Ala Thr Tyr Gly Lys Leu Thr Leu

```
                165                 170                 175
Lys Phe Ile Cys Thr Thr Gly Lys Leu Pro Val Pro Trp Pro Thr Leu
            180                 185                 190

Val Thr Thr Leu Thr Tyr Gly Val Gln Cys Phe Ser Arg Tyr Pro Asp
            195                 200                 205

His Met Lys Gln His Asp Phe Phe Lys Ser Ala Met Pro Glu Gly Tyr
            210                 215                 220

Ile Gln Glu Arg Thr Ile Phe Phe Lys Asp Asp Gly Asn Tyr Lys Thr
225                 230                 235                 240

Arg Ala Glu Val Lys Phe Glu Gly Asp Thr Leu Val Asn Arg Ile Glu
                245                 250                 255

Leu Lys Gly Ile Asp Phe Lys Glu Asp Gly Asn Ile Leu Gly His Lys
                260                 265                 270

Leu Glu Tyr Asn Thr Arg Asp Glu Ala Lys Phe Pro Thr Met Asn Arg
                275                 280                 285

Arg Gly Ala Ile Lys Gln Ala Lys Ile His Tyr Ile Lys Asn His Glu
            290                 295                 300

Phe Ile Ala Thr Phe Phe Gly Gln Pro Thr Phe Cys Ser Val Cys Lys
305                 310                 315                 320

Asp Phe Val Trp Gly Leu Asn Lys Gln Gly Tyr Lys Cys Arg Gln Cys
                325                 330                 335

Asn Ala Ala Ile His Lys Lys Cys Ile Asp Lys Ile Ile Gly Arg Cys
                340                 345                 350

Thr Gly Thr Ala Ala Asn Ser Arg Asp Thr Ile Phe Gln Lys Glu Arg
            355                 360                 365

Phe Asn Ile Asp Met Pro His Arg Phe Lys Val His Asn Tyr Met Ser
370                 375                 380

Pro Thr Phe Cys Asp His Cys Gly Ser Leu Leu Trp Gly Leu Val Lys
385                 390                 395                 400

Gln Gly Leu Lys Cys Glu Asp Cys Gly Met Asn Val His His Lys Cys
                405                 410                 415

Arg Glu Lys Val Ala Asn Leu Cys Gly Ile Asn Gln Lys Leu Leu Ala
            420                 425                 430

Glu Ala Leu Asn Gln Val Thr Gln Arg Ala Ser Arg Arg Ser Asp Ser
            435                 440                 445

Ala Ser Ser Glu Pro Val Gly Ile Tyr Gln Gly Phe Glu Lys Lys Thr
            450                 455                 460

Gly Val Ala Gly Glu Asp Met Gln Asp Asn Ser Gly Thr Tyr Gly Lys
465                 470                 475                 480

Ile Trp Glu Gly Ser Ser Lys Cys Asn Ile Asn Asn Phe Ile Phe His
                485                 490                 495

Lys Val Leu Gly Lys Gly Ser Phe Gly Lys Val Leu Leu Gly Glu Leu
                500                 505                 510

Lys Gly Arg Gly Glu Tyr Phe Ala Ile Lys Ala Leu Lys Lys Asp Val
                515                 520                 525

Val Leu Ile Asp Asp Asp Val Glu Cys Thr Met Val Glu Lys Arg Val
            530                 535                 540

Leu Thr Leu Ala Ala Glu Asn Pro Phe Leu Thr His Leu Ile Cys Thr
545                 550                 555                 560

Phe Gln Thr Lys Asp His Leu Phe Phe Val Met Glu Phe Leu Asn Gly
                565                 570                 575

Gly Asp Leu Met Tyr His Ile Gln Asp Lys Gly Arg Phe Glu Leu Tyr
            580                 585                 590
```

-continued

```
Arg Ala Thr Phe Tyr Ala Ala Glu Ile Met Cys Gly Leu Gln Phe Leu
            595                 600                 605

His Ser Lys Gly Ile Ile Tyr Arg Asp Leu Lys Leu Asp Asn Val Leu
        610                 615                 620

Leu Asp Arg Asp Gly His Ile Lys Ile Ala Asp Phe Gly Met Cys Lys
625                 630                 635                 640

Glu Asn Ile Phe Gly Glu Ser Arg Ala Ser Thr Phe Cys Gly Thr Pro
                645                 650                 655

Asp Tyr Ile Ala Pro Glu Ile Leu Gln Gly Leu Lys Tyr Thr Phe Ser
            660                 665                 670

Val Asp Trp Trp Ser Phe Gly Val Leu Leu Tyr Glu Met Leu Ile Gly
        675                 680                 685

Gln Ser Pro Phe His Gly Asp Asp Glu Asp Glu Leu Phe Glu Ser Ile
    690                 695                 700

Arg Val Asp Thr Pro His Tyr Pro Arg Trp Ile Thr Lys Glu Ser Lys
705                 710                 715                 720

Asp Ile Leu Glu Lys Leu Phe Glu Arg Glu Pro Thr Lys Arg Leu Gly
                725                 730                 735

Val Thr Gly Asn Ile Lys Ile His Pro Phe Phe Lys Thr Ile Asn Trp
            740                 745                 750

Thr Leu Leu Glu Lys Arg Arg Leu Glu Pro Pro Phe Arg Pro Lys Val
        755                 760                 765

Lys Ser Pro Arg Asp Tyr Ser Asn Phe Asp Gln Glu Phe Leu Asn Glu
    770                 775                 780

Lys Ala Arg Leu Ser Tyr Ser Asp Lys Asn Leu Ile Asp Ser Met Asp
785                 790                 795                 800

Gln Ser Ala Phe Ala Gly Phe Ser Phe Val Asn Pro Lys Phe Glu His
                805                 810                 815

Leu Leu Glu Asp
            820
```

<210> SEQ ID NO 30
<211> LENGTH: 818
<212> TYPE: PRT
<213> ORGANISM: Artificial Sequence
<220> FEATURE:
<223> OTHER INFORMATION: Synthetic sequence, a.a. sequence of sensor 27
      [G23-30]

<400> SEQUENCE: 30

```
Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Leu
            20                  25                  30

Glu Asn Val Tyr Ile Lys Ala Asp Lys Gln Lys Asn Gly Ile Lys Ala
        35                  40                  45

Asn Phe Lys Ile Arg His Asn Ile Glu Asp Gly Gly Val Gln Leu Ala
    50                  55                  60

Tyr His Tyr Gln Gln Asn Thr Pro Ile Gly Asp Gly Pro Val Leu Leu
65                  70                  75                  80

Pro Asp Asn His Tyr Leu Ser Val Gln Ser Ile Leu Ser Lys Asp Pro
                85                  90                  95

Asn Glu Lys Arg Asp His Met Val Leu Leu Glu Phe Val Thr Ala Ala
            100                 105                 110

Gly Ile Thr Leu Gly Met Asp Glu Leu Tyr Lys Gly Gly Thr Gly Gly
```

-continued

```
                115                 120                 125
Ser Met Val Ser Lys Gly Glu Glu Leu Phe Thr Gly Val Pro Ile
130                 135                 140
Gln Val Glu Leu Asp Gly Asp Val Asn Gly His Lys Phe Ser Val Ser
145                 150                 155                 160
Gly Glu Gly Glu Gly Asp Ala Thr Tyr Gly Lys Leu Thr Leu Lys Phe
                165                 170                 175
Ile Cys Thr Thr Gly Lys Leu Pro Val Pro Trp Pro Thr Leu Val Thr
            180                 185                 190
Thr Leu Thr Tyr Gly Val Gln Cys Phe Ser Arg Tyr Pro Asp His Met
        195                 200                 205
Lys Gln His Asp Phe Phe Lys Ser Ala Met Pro Glu Gly Tyr Ile Gln
210                 215                 220
Glu Arg Thr Ile Phe Phe Lys Asp Asp Gly Asn Tyr Lys Thr Arg Ala
225                 230                 235                 240
Glu Val Lys Phe Glu Gly Asp Thr Leu Val Asn Arg Ile Glu Leu Lys
                245                 250                 255
Gly Ile Asp Phe Lys Glu Asp Gly Asn Ile Leu Gly His Lys Leu Glu
            260                 265                 270
Tyr Asn Thr Arg Asp Glu Ala Lys Phe Pro Thr Met Asn Arg Arg Gly
        275                 280                 285
Ala Ile Lys Gln Ala Lys Ile His Tyr Ile Lys Asn His Glu Phe Ile
290                 295                 300
Ala Thr Phe Phe Gly Gln Pro Thr Phe Cys Ser Val Cys Lys Asp Phe
305                 310                 315                 320
Val Trp Gly Leu Asn Lys Gln Gly Tyr Lys Cys Arg Gln Cys Asn Ala
                325                 330                 335
Ala Ile His Lys Lys Cys Ile Asp Lys Ile Ile Gly Arg Cys Thr Gly
            340                 345                 350
Thr Ala Ala Asn Ser Arg Asp Thr Ile Phe Gln Lys Glu Arg Phe Asn
        355                 360                 365
Ile Asp Met Pro His Arg Phe Lys Val His Asn Tyr Met Ser Pro Thr
370                 375                 380
Phe Cys Asp His Cys Gly Ser Leu Leu Trp Gly Leu Val Lys Gln Gly
385                 390                 395                 400
Leu Lys Cys Glu Asp Cys Gly Met Asn Val His His Lys Cys Arg Glu
                405                 410                 415
Lys Val Ala Asn Leu Cys Gly Ile Asn Gln Lys Leu Leu Ala Glu Ala
            420                 425                 430
Leu Asn Gln Val Thr Gln Arg Ala Ser Arg Arg Ser Asp Ser Ala Ser
        435                 440                 445
Ser Glu Pro Val Gly Ile Tyr Gln Gly Phe Glu Lys Lys Thr Gly Val
450                 455                 460
Ala Gly Glu Asp Met Gln Asp Asn Ser Gly Thr Tyr Gly Lys Ile Trp
465                 470                 475                 480
Glu Gly Ser Ser Lys Cys Asn Ile Asn Asn Phe Ile Phe His Lys Val
                485                 490                 495
Leu Gly Lys Gly Ser Phe Gly Lys Val Leu Leu Gly Glu Leu Lys Gly
            500                 505                 510
Arg Gly Glu Tyr Phe Ala Ile Lys Ala Leu Lys Lys Asp Val Val Leu
        515                 520                 525
Ile Asp Asp Asp Val Glu Cys Thr Met Val Glu Lys Arg Val Leu Thr
530                 535                 540
```

```
Leu Ala Ala Glu Asn Pro Phe Leu Thr His Leu Ile Cys Thr Phe Gln
545                 550                 555                 560

Thr Lys Asp His Leu Phe Phe Val Met Glu Phe Leu Asn Gly Gly Asp
                565                 570                 575

Leu Met Tyr His Ile Gln Asp Lys Gly Arg Phe Glu Leu Tyr Arg Ala
            580                 585                 590

Thr Phe Tyr Ala Ala Glu Ile Met Cys Gly Leu Gln Phe Leu His Ser
        595                 600                 605

Lys Gly Ile Ile Tyr Arg Asp Leu Lys Leu Asp Asn Val Leu Leu Asp
610                 615                 620

Arg Asp Gly His Ile Lys Ile Ala Asp Phe Gly Met Cys Lys Glu Asn
625                 630                 635                 640

Ile Phe Gly Glu Ser Arg Ala Ser Thr Phe Cys Gly Thr Pro Asp Tyr
                645                 650                 655

Ile Ala Pro Glu Ile Leu Gln Gly Leu Lys Tyr Thr Phe Ser Val Asp
            660                 665                 670

Trp Trp Ser Phe Gly Val Leu Leu Tyr Glu Met Leu Ile Gly Gln Ser
        675                 680                 685

Pro Phe His Gly Asp Asp Glu Asp Glu Leu Phe Glu Ser Ile Arg Val
    690                 695                 700

Asp Thr Pro His Tyr Pro Arg Trp Ile Thr Lys Glu Ser Lys Asp Ile
705                 710                 715                 720

Leu Glu Lys Leu Phe Glu Arg Glu Pro Thr Lys Arg Leu Gly Val Thr
                725                 730                 735

Gly Asn Ile Lys Ile His Pro Phe Phe Lys Thr Ile Asn Trp Thr Leu
            740                 745                 750

Leu Glu Lys Arg Arg Leu Glu Pro Pro Phe Arg Pro Lys Val Lys Ser
        755                 760                 765

Pro Arg Asp Tyr Ser Asn Phe Asp Gln Glu Phe Leu Asn Glu Lys Ala
    770                 775                 780

Arg Leu Ser Tyr Ser Asp Lys Asn Leu Ile Asp Ser Met Asp Gln Ser
785                 790                 795                 800

Ala Phe Ala Gly Phe Ser Phe Val Asn Pro Lys Phe Glu His Leu Leu
                805                 810                 815

Glu Asp

<210> SEQ ID NO 31
<211> LENGTH: 825
<212> TYPE: PRT
<213> ORGANISM: Artificial Sequence
<220> FEATURE:
<223> OTHER INFORMATION: Synthetic sequence, a.a. sequence of sensor 28
      [G24-30]

<400> SEQUENCE: 31

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Leu Glu Asn Val Tyr Ile Lys Ala Asp Lys
        35                  40                  45

Gln Lys Asn Gly Ile Lys Ala Asn Phe Lys Ile Arg His Asn Ile Glu
    50                  55                  60

Asp Gly Gly Val Gln Leu Ala Tyr His Tyr Gln Gln Asn Thr Pro Ile
65                  70                  75                  80
```

```
Gly Asp Gly Pro Val Leu Leu Pro Asp Asn His Tyr Leu Ser Val Gln
                 85                  90                  95

Ser Ile Leu Ser Lys Asp Pro Asn Glu Lys Arg Asp His Met Val Leu
            100                 105                 110

Leu Glu Phe Val Thr Ala Ala Gly Ile Thr Leu Gly Met Asp Glu Leu
        115                 120                 125

Tyr Lys Gly Gly Thr Gly Gly Ser Met Val Ser Lys Gly Glu Glu Leu
    130                 135                 140

Phe Thr Gly Val Val Pro Ile Gln Val Glu Leu Asp Gly Asp Val Asn
145                 150                 155                 160

Gly His Lys Phe Ser Val Ser Gly Glu Gly Glu Gly Asp Ala Thr Tyr
                165                 170                 175

Gly Lys Leu Thr Leu Lys Phe Ile Cys Thr Thr Gly Lys Leu Pro Val
            180                 185                 190

Pro Trp Pro Thr Leu Val Thr Thr Leu Thr Tyr Gly Val Gln Cys Phe
        195                 200                 205

Ser Arg Tyr Pro Asp His Met Lys Gln His Asp Phe Phe Lys Ser Ala
    210                 215                 220

Met Pro Glu Gly Tyr Ile Gln Glu Arg Thr Ile Phe Phe Lys Asp Asp
225                 230                 235                 240

Gly Asn Tyr Lys Thr Arg Ala Glu Val Lys Phe Glu Gly Asp Thr Leu
                245                 250                 255

Val Asn Arg Ile Glu Leu Lys Gly Ile Asp Phe Lys Glu Asp Gly Asn
            260                 265                 270

Ile Leu Gly His Lys Leu Glu Tyr Asn Thr Arg Asp Glu Ala Lys Phe
        275                 280                 285

Pro Thr Met Asn Arg Arg Gly Ala Ile Lys Gln Ala Lys Ile His Tyr
    290                 295                 300

Ile Lys Asn His Glu Phe Ile Ala Thr Phe Phe Gly Gln Pro Thr Phe
305                 310                 315                 320

Cys Ser Val Cys Lys Asp Phe Val Trp Gly Leu Asn Lys Gln Gly Tyr
                325                 330                 335

Lys Cys Arg Gln Cys Asn Ala Ala Ile His Lys Lys Cys Ile Asp Lys
            340                 345                 350

Ile Ile Gly Arg Cys Thr Gly Thr Ala Ala Asn Ser Arg Asp Thr Ile
        355                 360                 365

Phe Gln Lys Glu Arg Phe Asn Ile Asp Met Pro His Arg Phe Lys Val
    370                 375                 380

His Asn Tyr Met Ser Pro Thr Phe Cys Asp His Cys Gly Ser Leu Leu
385                 390                 395                 400

Trp Gly Leu Val Lys Gln Gly Leu Lys Cys Glu Asp Cys Gly Met Asn
                405                 410                 415

Val His His Lys Cys Arg Glu Lys Val Ala Asn Leu Cys Gly Ile Asn
            420                 425                 430

Gln Lys Leu Leu Ala Glu Ala Leu Asn Gln Val Thr Gln Arg Ala Ser
        435                 440                 445

Arg Arg Ser Asp Ser Ala Ser Ser Glu Pro Val Gly Ile Tyr Gln Gly
    450                 455                 460

Phe Glu Lys Lys Thr Gly Val Ala Gly Glu Asp Met Gln Asp Asn Ser
465                 470                 475                 480

Gly Thr Tyr Gly Lys Ile Trp Glu Gly Ser Ser Lys Cys Asn Ile Asn
                485                 490                 495
```

```
Asn Phe Ile Phe His Lys Val Leu Gly Lys Gly Ser Phe Gly Lys Val
                500                 505                 510

Leu Leu Gly Glu Leu Lys Gly Arg Gly Glu Tyr Phe Ala Ile Lys Ala
            515                 520                 525

Leu Lys Lys Asp Val Val Leu Ile Asp Asp Asp Val Glu Cys Thr Met
        530                 535                 540

Val Glu Lys Arg Val Leu Thr Leu Ala Ala Glu Asn Pro Phe Leu Thr
545                 550                 555                 560

His Leu Ile Cys Thr Phe Gln Thr Lys Asp His Leu Phe Phe Val Met
                565                 570                 575

Glu Phe Leu Asn Gly Gly Asp Leu Met Tyr His Ile Gln Asp Lys Gly
            580                 585                 590

Arg Phe Glu Leu Tyr Arg Ala Thr Phe Tyr Ala Ala Glu Ile Met Cys
        595                 600                 605

Gly Leu Gln Phe Leu His Ser Lys Gly Ile Ile Tyr Arg Asp Leu Lys
610                 615                 620

Leu Asp Asn Val Leu Leu Asp Arg Asp Gly His Ile Lys Ile Ala Asp
625                 630                 635                 640

Phe Gly Met Cys Lys Glu Asn Ile Phe Gly Glu Ser Arg Ala Ser Thr
                645                 650                 655

Phe Cys Gly Thr Pro Asp Tyr Ile Ala Pro Glu Ile Leu Gln Gly Leu
            660                 665                 670

Lys Tyr Thr Phe Ser Val Asp Trp Trp Ser Phe Gly Val Leu Leu Tyr
        675                 680                 685

Glu Met Leu Ile Gly Gln Ser Pro Phe His Gly Asp Asp Glu Asp Glu
            690                 695                 700

Leu Phe Glu Ser Ile Arg Val Asp Thr Pro His Tyr Pro Arg Trp Ile
705                 710                 715                 720

Thr Lys Glu Ser Lys Asp Ile Leu Glu Lys Leu Phe Glu Arg Glu Pro
                725                 730                 735

Thr Lys Arg Leu Gly Val Thr Gly Asn Ile Lys Ile His Pro Phe Phe
            740                 745                 750

Lys Thr Ile Asn Trp Thr Leu Leu Glu Lys Arg Arg Leu Glu Pro Pro
        755                 760                 765

Phe Arg Pro Lys Val Lys Ser Pro Arg Asp Tyr Ser Asn Phe Asp Gln
770                 775                 780

Glu Phe Leu Asn Glu Lys Ala Arg Leu Ser Tyr Ser Asp Lys Asn Leu
785                 790                 795                 800

Ile Asp Ser Met Asp Gln Ser Ala Phe Ala Gly Phe Ser Phe Val Asn
                805                 810                 815

Pro Lys Phe Glu His Leu Leu Glu Asp
            820                 825

<210> SEQ ID NO 32
<211> LENGTH: 829
<212> TYPE: PRT
<213> ORGANISM: Artificial Sequence
<220> FEATURE:
<223> OTHER INFORMATION: Synthetic sequence, a.a. sequence of sensor 29
      [G28-30]

<400> SEQUENCE: 32

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30
```

```
His Tyr Ile Lys Asn His Glu Phe Ile Ala Leu Glu Asn Val Tyr Ile
        35                  40                  45

Lys Ala Asp Lys Gln Lys Asn Gly Ile Lys Ala Asn Phe Lys Ile Arg
50                  55                  60

His Asn Ile Glu Asp Gly Gly Val Gln Leu Ala Tyr His Tyr Gln Gln
65                  70                  75                  80

Asn Thr Pro Ile Gly Asp Gly Pro Val Leu Leu Pro Asp Asn His Tyr
                85                  90                  95

Leu Ser Val Gln Ser Ile Leu Ser Lys Asp Pro Asn Glu Lys Arg Asp
                100                 105                 110

His Met Val Leu Leu Glu Phe Val Thr Ala Ala Gly Ile Thr Leu Gly
                115                 120                 125

Met Asp Glu Leu Tyr Lys Gly Gly Thr Gly Gly Ser Met Val Ser Lys
130                 135                 140

Gly Glu Glu Leu Phe Thr Gly Val Val Pro Ile Gln Val Glu Leu Asp
145                 150                 155                 160

Gly Asp Val Asn Gly His Lys Phe Ser Val Ser Gly Glu Gly Glu Gly
                165                 170                 175

Asp Ala Thr Tyr Gly Lys Leu Thr Leu Lys Phe Ile Cys Thr Thr Gly
                180                 185                 190

Lys Leu Pro Val Pro Trp Pro Thr Leu Val Thr Thr Leu Thr Tyr Gly
                195                 200                 205

Val Gln Cys Phe Ser Arg Tyr Pro Asp His Met Lys Gln His Asp Phe
                210                 215                 220

Phe Lys Ser Ala Met Pro Glu Gly Tyr Ile Gln Glu Arg Thr Ile Phe
225                 230                 235                 240

Phe Lys Asp Asp Gly Asn Tyr Lys Thr Arg Ala Glu Val Lys Phe Glu
                245                 250                 255

Gly Asp Thr Leu Val Asn Arg Ile Glu Leu Lys Gly Ile Asp Phe Lys
                260                 265                 270

Glu Asp Gly Asn Ile Leu Gly His Lys Leu Glu Tyr Asn Thr Arg Asp
                275                 280                 285

Glu Ala Lys Phe Pro Thr Met Asn Arg Arg Gly Ala Ile Lys Gln Ala
                290                 295                 300

Lys Ile His Tyr Ile Lys Asn His Glu Phe Ile Ala Thr Phe Phe Gly
305                 310                 315                 320

Gln Pro Thr Phe Cys Ser Val Cys Lys Asp Phe Val Trp Gly Leu Asn
                325                 330                 335

Lys Gln Gly Tyr Lys Cys Arg Gln Cys Asn Ala Ala Ile His Lys Lys
                340                 345                 350

Cys Ile Asp Lys Ile Ile Gly Arg Cys Thr Gly Thr Ala Ala Asn Ser
                355                 360                 365

Arg Asp Thr Ile Phe Gln Lys Glu Arg Phe Asn Ile Asp Met Pro His
370                 375                 380

Arg Phe Lys Val His Asn Tyr Met Ser Pro Thr Phe Cys Asp His Cys
385                 390                 395                 400

Gly Ser Leu Leu Trp Gly Leu Val Lys Gln Gly Leu Lys Cys Glu Asp
                405                 410                 415

Cys Gly Met Asn Val His His Lys Cys Arg Glu Lys Val Ala Asn Leu
                420                 425                 430

Cys Gly Ile Asn Gln Lys Leu Leu Ala Glu Ala Leu Asn Gln Val Thr
                435                 440                 445
```

```
Gln Arg Ala Ser Arg Arg Ser Asp Ser Ala Ser Ser Glu Pro Val Gly
    450                 455                 460

Ile Tyr Gln Gly Phe Glu Lys Lys Thr Gly Val Ala Gly Glu Asp Met
465                 470                 475                 480

Gln Asp Asn Ser Gly Thr Tyr Gly Lys Ile Trp Glu Gly Ser Ser Lys
            485                 490                 495

Cys Asn Ile Asn Asn Phe Ile Phe His Lys Val Leu Gly Lys Gly Ser
            500                 505                 510

Phe Gly Lys Val Leu Leu Gly Glu Leu Lys Gly Arg Gly Glu Tyr Phe
            515                 520                 525

Ala Ile Lys Ala Leu Lys Lys Asp Val Val Leu Ile Asp Asp Asp Val
530                 535                 540

Glu Cys Thr Met Val Glu Lys Arg Val Leu Thr Leu Ala Ala Glu Asn
545                 550                 555                 560

Pro Phe Leu Thr His Leu Ile Cys Thr Phe Gln Thr Lys Asp His Leu
                565                 570                 575

Phe Phe Val Met Glu Phe Leu Asn Gly Gly Asp Leu Met Tyr His Ile
            580                 585                 590

Gln Asp Lys Gly Arg Phe Glu Leu Tyr Arg Ala Thr Phe Tyr Ala Ala
            595                 600                 605

Glu Ile Met Cys Gly Leu Gln Phe Leu His Ser Lys Gly Ile Ile Tyr
610                 615                 620

Arg Asp Leu Lys Leu Asp Asn Val Leu Leu Asp Arg Asp Gly His Ile
625                 630                 635                 640

Lys Ile Ala Asp Phe Gly Met Cys Lys Glu Asn Ile Phe Gly Glu Ser
                645                 650                 655

Arg Ala Ser Thr Phe Cys Gly Thr Pro Asp Tyr Ile Ala Pro Glu Ile
            660                 665                 670

Leu Gln Gly Leu Lys Tyr Thr Phe Ser Val Asp Trp Ser Phe Gly
            675                 680                 685

Val Leu Leu Tyr Glu Met Leu Ile Gly Gln Ser Pro Phe His Gly Asp
690                 695                 700

Asp Glu Asp Glu Leu Phe Glu Ser Ile Arg Val Asp Thr Pro His Tyr
705                 710                 715                 720

Pro Arg Trp Ile Thr Lys Glu Ser Lys Asp Ile Leu Glu Lys Leu Phe
                725                 730                 735

Glu Arg Glu Pro Thr Lys Arg Leu Gly Val Thr Gly Asn Ile Lys Ile
            740                 745                 750

His Pro Phe Phe Lys Thr Ile Asn Trp Thr Leu Leu Glu Lys Arg Arg
            755                 760                 765

Leu Glu Pro Pro Phe Arg Pro Lys Val Lys Ser Pro Arg Asp Tyr Ser
770                 775                 780

Asn Phe Asp Gln Glu Phe Leu Asn Glu Lys Ala Arg Leu Ser Tyr Ser
785                 790                 795                 800

Asp Lys Asn Leu Ile Asp Ser Met Asp Gln Ser Ala Phe Ala Gly Phe
                805                 810                 815

Ser Phe Val Asn Pro Lys Phe Glu His Leu Leu Glu Asp
            820                 825
```

<210> SEQ ID NO 33
<211> LENGTH: 830
<212> TYPE: PRT
<213> ORGANISM: Artificial Sequence
<220> FEATURE:
<223> OTHER INFORMATION: Synthetic sequence, a.a. sequence of sensor 30

[G29-30]

<400> SEQUENCE: 33

```
Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn His Glu Phe Ile Ala Thr Leu Glu Asn Val Tyr
        35                  40                  45

Ile Lys Ala Asp Lys Gln Lys Asn Gly Ile Lys Ala Asn Phe Lys Ile
50                  55                  60

Arg His Asn Ile Glu Asp Gly Gly Val Gln Leu Ala Tyr His Tyr Gln
65                  70                  75                  80

Gln Asn Thr Pro Ile Gly Asp Gly Pro Val Leu Leu Pro Asp Asn His
                    85                  90                  95

Tyr Leu Ser Val Gln Ser Ile Leu Ser Lys Asp Pro Asn Glu Lys Arg
                100                 105                 110

Asp His Met Val Leu Leu Glu Phe Val Thr Ala Ala Gly Ile Thr Leu
            115                 120                 125

Gly Met Asp Glu Leu Tyr Lys Gly Gly Thr Gly Gly Ser Met Val Ser
130                 135                 140

Lys Gly Glu Glu Leu Phe Thr Gly Val Val Pro Ile Gln Val Glu Leu
145                 150                 155                 160

Asp Gly Asp Val Asn Gly His Lys Phe Ser Val Ser Gly Glu Gly Glu
                165                 170                 175

Gly Asp Ala Thr Tyr Gly Lys Leu Thr Leu Lys Phe Ile Cys Thr Thr
            180                 185                 190

Gly Lys Leu Pro Val Pro Trp Pro Thr Leu Val Thr Thr Leu Thr Tyr
        195                 200                 205

Gly Val Gln Cys Phe Ser Arg Tyr Pro Asp His Met Lys Gln His Asp
210                 215                 220

Phe Phe Lys Ser Ala Met Pro Glu Gly Tyr Ile Gln Glu Arg Thr Ile
225                 230                 235                 240

Phe Phe Lys Asp Asp Gly Asn Tyr Lys Thr Arg Ala Glu Val Lys Phe
                245                 250                 255

Glu Gly Asp Thr Leu Val Asn Arg Ile Glu Leu Lys Gly Ile Asp Phe
            260                 265                 270

Lys Glu Asp Gly Asn Ile Leu Gly His Lys Leu Glu Tyr Asn Thr Arg
        275                 280                 285

Asp Glu Ala Lys Phe Pro Thr Met Asn Arg Arg Gly Ala Ile Lys Gln
290                 295                 300

Ala Lys Ile His Tyr Ile Lys Asn His Glu Phe Ile Ala Thr Phe Phe
305                 310                 315                 320

Gly Gln Pro Thr Phe Cys Ser Val Cys Lys Asp Phe Val Trp Gly Leu
                325                 330                 335

Asn Lys Gln Gly Tyr Lys Cys Arg Gln Cys Asn Ala Ala Ile His Lys
            340                 345                 350

Lys Cys Ile Asp Lys Ile Ile Gly Arg Cys Thr Gly Thr Ala Ala Asn
        355                 360                 365

Ser Arg Asp Thr Ile Phe Gln Lys Glu Arg Phe Asn Ile Asp Met Pro
370                 375                 380

His Arg Phe Lys Val His Asn Tyr Met Ser Pro Thr Phe Cys Asp His
385                 390                 395                 400
```

```
Cys Gly Ser Leu Leu Trp Gly Leu Val Lys Gln Gly Leu Lys Cys Glu
                405                 410                 415

Asp Cys Gly Met Asn Val His His Lys Cys Arg Glu Lys Val Ala Asn
            420                 425                 430

Leu Cys Gly Ile Asn Gln Lys Leu Leu Ala Glu Ala Leu Asn Gln Val
            435                 440                 445

Thr Gln Arg Ala Ser Arg Arg Ser Asp Ser Ala Ser Ser Glu Pro Val
        450                 455                 460

Gly Ile Tyr Gln Gly Phe Glu Lys Lys Thr Gly Val Ala Gly Glu Asp
465                 470                 475                 480

Met Gln Asp Asn Ser Gly Thr Tyr Gly Lys Ile Trp Glu Gly Ser Ser
                485                 490                 495

Lys Cys Asn Ile Asn Asn Phe Ile Phe His Lys Val Leu Gly Lys Gly
            500                 505                 510

Ser Phe Gly Lys Val Leu Leu Gly Glu Leu Lys Gly Arg Gly Glu Tyr
        515                 520                 525

Phe Ala Ile Lys Ala Leu Lys Lys Asp Val Val Leu Ile Asp Asp Asp
530                 535                 540

Val Glu Cys Thr Met Val Glu Lys Arg Val Leu Thr Leu Ala Ala Glu
545                 550                 555                 560

Asn Pro Phe Leu Thr His Leu Ile Cys Thr Phe Gln Thr Lys Asp His
                565                 570                 575

Leu Phe Phe Val Met Glu Phe Leu Asn Gly Gly Asp Leu Met Tyr His
                580                 585                 590

Ile Gln Asp Lys Gly Arg Phe Glu Leu Tyr Arg Ala Thr Phe Tyr Ala
                595                 600                 605

Ala Glu Ile Met Cys Gly Leu Gln Phe Leu His Ser Lys Gly Ile Ile
        610                 615                 620

Tyr Arg Asp Leu Lys Leu Asp Asn Val Leu Leu Asp Arg Asp Gly His
625                 630                 635                 640

Ile Lys Ile Ala Asp Phe Gly Met Cys Lys Glu Asn Ile Phe Gly Glu
            645                 650                 655

Ser Arg Ala Ser Thr Phe Cys Gly Thr Pro Asp Tyr Ile Ala Pro Glu
            660                 665                 670

Ile Leu Gln Gly Leu Lys Tyr Thr Phe Ser Val Asp Trp Trp Ser Phe
        675                 680                 685

Gly Val Leu Leu Tyr Glu Met Leu Ile Gly Gln Ser Pro Phe His Gly
        690                 695                 700

Asp Asp Glu Asp Glu Leu Phe Glu Ser Ile Arg Val Asp Thr Pro His
705                 710                 715                 720

Tyr Pro Arg Trp Ile Thr Lys Glu Ser Lys Asp Ile Leu Glu Lys Leu
                725                 730                 735

Phe Glu Arg Glu Pro Thr Lys Arg Leu Gly Val Thr Gly Asn Ile Lys
            740                 745                 750

Ile His Pro Phe Phe Lys Thr Ile Asn Trp Thr Leu Leu Glu Lys Arg
        755                 760                 765

Arg Leu Glu Pro Pro Phe Arg Pro Lys Val Lys Ser Pro Arg Asp Tyr
770                 775                 780

Ser Asn Phe Asp Gln Glu Phe Leu Asn Glu Lys Ala Arg Leu Ser Tyr
785                 790                 795                 800

Ser Asp Lys Asn Leu Ile Asp Ser Met Asp Gln Ser Ala Phe Ala Gly
            805                 810                 815

Phe Ser Phe Val Asn Pro Lys Phe Glu His Leu Leu Glu Asp
```

<210> SEQ ID NO 34
<211> LENGTH: 801
<212> TYPE: PRT
<213> ORGANISM: Artificial Sequence
<220> FEATURE:
<223> OTHER INFORMATION: Synthetic sequence, a.a. sequence of sensor 31 [R17.2B]

<400> SEQUENCE: 34

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Ile Lys Asn Pro Val Val Ser Glu Arg Met Tyr Pro Glu Asp
        35                  40                  45

Gly Ala Leu Lys Ser Glu Ile Lys Lys Gly Leu Arg Leu Lys Asp Gly
    50                  55                  60

Gly His Tyr Ala Ala Glu Val Lys Thr Thr Tyr Lys Ala Lys Lys Pro
65                  70                  75                  80

Val Gln Leu Pro Gly Ala Tyr Ile Val Asp Ile Lys Leu Asp Ile Val
                85                  90                  95

Ser His Asn Glu Asp Tyr Thr Ile Val Glu Gln Cys Glu Arg Ala Glu
            100                 105                 110

Gly Arg His Ser Thr Gly Gly Met Asp Glu Leu Tyr Lys Gly Gly Thr
        115                 120                 125

Gly Gly Ser Leu Val Ser Lys Gly Glu Glu Asp Asn Met Ala Ile Ile
    130                 135                 140

Lys Glu Phe Met Arg Phe Lys Val His Met Glu Gly Ser Val Asn Gly
145                 150                 155                 160

His Glu Phe Glu Ile Glu Gly Glu Gly Glu Gly Arg Pro Tyr Glu Ala
                165                 170                 175

Phe Gln Thr Ala Lys Leu Lys Val Thr Lys Gly Gly Pro Leu Pro Phe
            180                 185                 190

Ala Trp Asp Ile Leu Ser Pro Gln Phe Met Tyr Gly Ser Lys Ala Tyr
        195                 200                 205

Ile Lys His Pro Ala Asp Ile Pro Asp Tyr Phe Lys Leu Ser Phe Pro
    210                 215                 220

Glu Gly Phe Arg Trp Glu Arg Val Met Asn Phe Glu Asp Gly Gly Ile
225                 230                 235                 240

Ile His Val Asn Gln Asp Ser Ser Leu Gln Asp Gly Val Phe Ile Tyr
                245                 250                 255

Lys Val Lys Leu Arg Gly Thr Asn Phe Pro Pro Asp Gly Pro Val Met
            260                 265                 270

Gln Lys Lys Thr Met Gly Trp Glu Ala Thr Arg His Glu Phe Ile Ala
        275                 280                 285

Thr Phe Phe Gly Gln Pro Thr Phe Cys Ser Val Cys Lys Asp Phe Val
    290                 295                 300

Trp Gly Leu Asn Lys Gln Gly Tyr Lys Cys Arg Gln Cys Asn Ala Ala
305                 310                 315                 320

Ile His Lys Lys Cys Ile Asp Lys Ile Ile Gly Arg Cys Thr Gly Thr
                325                 330                 335

Ala Ala Asn Ser Arg Asp Thr Ile Phe Gln Lys Glu Arg Phe Asn Ile
            340                 345                 350

```
Asp Met Pro His Arg Phe Lys Val His Asn Tyr Met Ser Pro Thr Phe
        355                 360                 365

Cys Asp His Cys Gly Ser Leu Leu Trp Gly Leu Val Lys Gln Gly Leu
    370                 375                 380

Lys Cys Glu Asp Cys Gly Met Asn Val His His Lys Cys Arg Glu Lys
385                 390                 395                 400

Val Ala Asn Leu Cys Gly Ile Asn Gln Lys Leu Leu Ala Glu Ala Leu
            405                 410                 415

Asn Gln Val Thr Gln Arg Ala Ser Arg Ser Asp Ser Ala Ser Ser
            420                 425                 430

Glu Pro Val Gly Ile Tyr Gln Gly Phe Glu Lys Lys Thr Gly Val Ala
            435                 440                 445

Gly Glu Asp Met Gln Asp Asn Ser Gly Thr Tyr Gly Lys Ile Trp Glu
450                 455                 460

Gly Ser Ser Lys Cys Asn Ile Asn Asn Phe Ile Phe His Lys Val Leu
465                 470                 475                 480

Gly Lys Gly Ser Phe Gly Lys Val Leu Leu Gly Glu Leu Lys Gly Arg
                485                 490                 495

Gly Glu Tyr Phe Ala Ile Lys Ala Leu Lys Lys Asp Val Val Leu Ile
                500                 505                 510

Asp Asp Asp Val Glu Cys Thr Met Val Glu Lys Arg Val Leu Thr Leu
        515                 520                 525

Ala Ala Glu Asn Pro Phe Leu Thr His Leu Ile Cys Thr Phe Gln Thr
        530                 535                 540

Lys Asp His Leu Phe Phe Val Met Glu Phe Leu Asn Gly Gly Asp Leu
545                 550                 555                 560

Met Tyr His Ile Gln Asp Lys Gly Arg Phe Glu Leu Tyr Arg Ala Thr
                565                 570                 575

Phe Tyr Ala Ala Glu Ile Met Cys Gly Leu Gln Phe Leu His Ser Lys
            580                 585                 590

Gly Ile Ile Tyr Arg Asp Leu Lys Leu Asp Asn Val Leu Leu Asp Arg
            595                 600                 605

Asp Gly His Ile Lys Ile Ala Asp Phe Gly Met Cys Lys Glu Asn Ile
610                 615                 620

Phe Gly Glu Ser Arg Ala Ser Thr Phe Cys Gly Thr Pro Asp Tyr Ile
625                 630                 635                 640

Ala Pro Glu Ile Leu Gln Gly Leu Lys Tyr Thr Phe Ser Val Asp Trp
                645                 650                 655

Trp Ser Phe Gly Val Leu Leu Tyr Glu Met Leu Ile Gly Gln Ser Pro
            660                 665                 670

Phe His Gly Asp Asp Glu Asp Glu Leu Phe Glu Ser Ile Arg Val Asp
            675                 680                 685

Thr Pro His Tyr Pro Arg Trp Ile Thr Lys Glu Ser Lys Asp Ile Leu
            690                 695                 700

Glu Lys Leu Phe Glu Arg Glu Pro Thr Lys Arg Leu Gly Val Thr Gly
705                 710                 715                 720

Asn Ile Lys Ile His Pro Phe Phe Lys Thr Ile Asn Trp Thr Leu Leu
                725                 730                 735

Glu Lys Arg Arg Leu Glu Pro Pro Phe Arg Pro Lys Val Lys Ser Pro
            740                 745                 750

Arg Asp Tyr Ser Asn Phe Asp Gln Glu Phe Leu Asn Glu Lys Ala Arg
            755                 760                 765

Leu Ser Tyr Ser Asp Lys Asn Leu Ile Asp Ser Met Asp Gln Ser Ala
```

-continued

```
                770                 775                 780
Phe Ala Gly Phe Ser Phe Val Asn Pro Lys Phe Glu His Leu Leu Glu
785                 790                 795                 800

Asp

<210> SEQ ID NO 35
<211> LENGTH: 801
<212> TYPE: PRT
<213> ORGANISM: Artificial Sequence
<220> FEATURE:
<223> OTHER INFORMATION: Synthetic sequence, a.a sequence of sensor 32
      [R19]

<400> SEQUENCE: 35

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
                20                  25                  30

His Tyr Ile Pro Val Val Ser Glu Arg Met Tyr Pro Glu Asp Gly Ala
            35                  40                  45

Leu Lys Ser Glu Ile Lys Lys Gly Leu Arg Leu Lys Asp Gly Gly His
50                  55                  60

Tyr Ala Ala Glu Val Lys Thr Thr Tyr Lys Ala Lys Lys Pro Val Gln
65                  70                  75                  80

Leu Pro Gly Ala Tyr Ile Val Asp Ile Lys Leu Asp Ile Val Ser His
                85                  90                  95

Asn Glu Asp Tyr Thr Ile Val Glu Gln Cys Glu Arg Ala Glu Gly Arg
            100                 105                 110

His Ser Thr Gly Gly Met Asp Glu Leu Tyr Lys Gly Gly Thr Gly Gly
            115                 120                 125

Ser Leu Val Ser Lys Gly Glu Glu Asp Asn Met Ala Ile Ile Lys Glu
130                 135                 140

Phe Met Arg Phe Lys Val His Met Glu Gly Ser Val Asn Gly His Glu
145                 150                 155                 160

Phe Glu Ile Glu Gly Glu Gly Glu Gly Arg Pro Tyr Glu Ala Phe Gln
                165                 170                 175

Thr Ala Lys Leu Lys Val Thr Lys Gly Gly Pro Leu Pro Phe Ala Trp
            180                 185                 190

Asp Ile Leu Ser Pro Gln Phe Met Tyr Gly Ser Lys Ala Tyr Ile Lys
            195                 200                 205

His Pro Ala Asp Ile Pro Asp Tyr Phe Lys Leu Ser Phe Pro Glu Gly
            210                 215                 220

Phe Arg Trp Glu Arg Val Met Asn Phe Glu Asp Gly Gly Ile Ile His
225                 230                 235                 240

Val Asn Gln Asp Ser Ser Leu Gln Asp Gly Val Phe Ile Tyr Lys Val
                245                 250                 255

Lys Leu Arg Gly Thr Asn Phe Pro Pro Asp Gly Pro Val Met Gln Lys
            260                 265                 270

Lys Thr Met Gly Trp Glu Ala Thr Arg Lys Asn His Glu Phe Ile Ala
            275                 280                 285

Thr Phe Phe Gly Gln Pro Thr Phe Cys Ser Val Cys Lys Asp Phe Val
            290                 295                 300

Trp Gly Leu Asn Lys Gln Gly Tyr Lys Cys Arg Gln Cys Asn Ala Ala
305                 310                 315                 320

Ile His Lys Lys Cys Ile Asp Lys Ile Ile Gly Arg Cys Thr Gly Thr
```

-continued

```
                325                 330                 335
Ala Ala Asn Ser Arg Asp Thr Ile Phe Gln Lys Glu Arg Phe Asn Ile
                340                 345                 350
Asp Met Pro His Arg Phe Lys Val His Asn Tyr Met Ser Pro Thr Phe
                355                 360                 365
Cys Asp His Cys Gly Ser Leu Leu Trp Gly Leu Val Lys Gln Gly Leu
                370                 375                 380
Lys Cys Glu Asp Cys Gly Met Asn Val His His Lys Cys Arg Glu Lys
385                 390                 395                 400
Val Ala Asn Leu Cys Gly Ile Asn Gln Lys Leu Leu Ala Glu Ala Leu
                405                 410                 415
Asn Gln Val Thr Gln Arg Ala Ser Arg Ser Asp Ser Ala Ser Ser
                420                 425                 430
Glu Pro Val Gly Ile Tyr Gln Gly Phe Glu Lys Lys Thr Gly Val Ala
                435                 440                 445
Gly Glu Asp Met Gln Asp Asn Ser Gly Thr Tyr Gly Lys Ile Trp Glu
                450                 455                 460
Gly Ser Ser Lys Cys Asn Ile Asn Asn Phe Ile Phe His Lys Val Leu
465                 470                 475                 480
Gly Lys Gly Ser Phe Gly Lys Val Leu Leu Gly Glu Leu Lys Gly Arg
                485                 490                 495
Gly Glu Tyr Phe Ala Ile Lys Ala Leu Lys Lys Asp Val Val Leu Ile
                500                 505                 510
Asp Asp Asp Val Glu Cys Thr Met Val Glu Lys Arg Val Leu Thr Leu
                515                 520                 525
Ala Ala Glu Asn Pro Phe Leu Thr His Leu Ile Cys Thr Phe Gln Thr
                530                 535                 540
Lys Asp His Leu Phe Phe Val Met Glu Phe Leu Asn Gly Gly Asp Leu
545                 550                 555                 560
Met Tyr His Ile Gln Asp Lys Gly Arg Phe Glu Leu Tyr Arg Ala Thr
                565                 570                 575
Phe Tyr Ala Ala Glu Ile Met Cys Gly Leu Gln Phe Leu His Ser Lys
                580                 585                 590
Gly Ile Ile Tyr Arg Asp Leu Lys Leu Asp Asn Val Leu Leu Asp Arg
                595                 600                 605
Asp Gly His Ile Lys Ile Ala Asp Phe Gly Met Cys Lys Glu Asn Ile
                610                 615                 620
Phe Gly Glu Ser Arg Ala Ser Thr Phe Cys Gly Thr Pro Asp Tyr Ile
625                 630                 635                 640
Ala Pro Glu Ile Leu Gln Gly Leu Lys Tyr Thr Phe Ser Val Asp Trp
                645                 650                 655
Trp Ser Phe Gly Val Leu Leu Tyr Glu Met Leu Ile Gly Gln Ser Pro
                660                 665                 670
Phe His Gly Asp Asp Glu Asp Glu Leu Phe Glu Ser Ile Arg Val Asp
                675                 680                 685
Thr Pro His Tyr Pro Arg Trp Ile Thr Lys Glu Ser Lys Asp Ile Leu
                690                 695                 700
Glu Lys Leu Phe Glu Arg Glu Pro Thr Lys Arg Leu Gly Val Thr Gly
705                 710                 715                 720
Asn Ile Lys Ile His Pro Phe Phe Lys Thr Ile Asn Trp Thr Leu Leu
                725                 730                 735
Glu Lys Arg Arg Leu Glu Pro Pro Phe Arg Pro Lys Val Lys Ser Pro
                740                 745                 750
```

```
Arg Asp Tyr Ser Asn Phe Asp Gln Glu Phe Leu Asn Glu Lys Ala Arg
        755                 760                 765

Leu Ser Tyr Ser Asp Lys Asn Leu Ile Asp Ser Met Asp Gln Ser Ala
770             775                 780

Phe Ala Gly Phe Ser Phe Val Asn Pro Lys Phe Glu His Leu Leu Glu
785             790                 795                 800

Asp

<210> SEQ ID NO 36
<211> LENGTH: 801
<212> TYPE: PRT
<213> ORGANISM: Artificial Sequence
<220> FEATURE:
<223> OTHER INFORMATION: Synthetic sequence, a.a. sequence of sensor 33
      [R20]

<400> SEQUENCE: 36

Met Glu Asp Val Asp Cys Lys Gln Ser Met Arg Ser Glu Asp Glu Ala
1               5                   10                  15

Lys Phe Pro Thr Met Asn Arg Arg Gly Ala Ile Lys Gln Ala Lys Ile
            20                  25                  30

His Tyr Pro Val Val Ser Glu Arg Met Tyr Pro Glu Asp Gly Ala Leu
        35                  40                  45

Lys Ser Glu Ile Lys Lys Gly Leu Arg Leu Lys Asp Gly Gly His Tyr
    50                  55                  60

Ala Ala Glu Val Lys Thr Thr Tyr Lys Ala Lys Lys Pro Val Gln Leu
65                  70                  75                  80

Pro Gly Ala Tyr Ile Val Asp Ile Lys Leu Asp Ile Val Ser His Asn
                85                  90                  95

Glu Asp Tyr Thr Ile Val Glu Gln Cys Glu Arg Ala Glu Gly Arg His
            100                 105                 110

Ser Thr Gly Gly Met Asp Glu Leu Tyr Lys Gly Gly Thr Gly Gly Ser
        115                 120                 125

Leu Val Ser Lys Gly Glu Glu Asp Asn Met Ala Ile Ile Lys Glu Phe
130                 135                 140

Met Arg Phe Lys Val His Met Glu Gly Ser Val Asn Gly His Glu Phe
145                 150                 155                 160

Glu Ile Glu Gly Glu Gly Glu Gly Arg Pro Tyr Glu Ala Phe Gln Thr
                165                 170                 175

Ala Lys Leu Lys Val Thr Lys Gly Gly Pro Leu Pro Phe Ala Trp Asp
            180                 185                 190

Ile Leu Ser Pro Gln Phe Met Tyr Gly Ser Lys Ala Tyr Ile Lys His
        195                 200                 205

Pro Ala Asp Ile Pro Asp Tyr Phe Lys Leu Ser Phe Pro Glu Gly Phe
    210                 215                 220

Arg Trp Glu Arg Val Met Asn Phe Glu Asp Gly Gly Ile Ile His Val
225                 230                 235                 240

Asn Gln Asp Ser Ser Leu Gln Asp Gly Val Phe Ile Tyr Lys Val Lys
                245                 250                 255

Leu Arg Gly Thr Asn Phe Pro Pro Asp Gly Pro Val Met Gln Lys Lys
            260                 265                 270

Thr Met Gly Trp Glu Ala Thr Arg Ile Lys Asn His Glu Phe Ile Ala
        275                 280                 285

Thr Phe Phe Gly Gln Pro Thr Phe Cys Ser Val Cys Lys Asp Phe Val
    290                 295                 300
```

-continued

```
Trp Gly Leu Asn Lys Gln Gly Tyr Lys Cys Arg Gln Cys Asn Ala Ala
305                 310                 315                 320

Ile His Lys Lys Cys Ile Asp Lys Ile Ile Gly Arg Cys Thr Gly Thr
                325                 330                 335

Ala Ala Asn Ser Arg Asp Thr Ile Phe Gln Lys Glu Arg Phe Asn Ile
                340                 345                 350

Asp Met Pro His Arg Phe Lys Val His Asn Tyr Met Ser Pro Thr Phe
                355                 360                 365

Cys Asp His Cys Gly Ser Leu Leu Trp Gly Leu Val Lys Gln Gly Leu
370                 375                 380

Lys Cys Glu Asp Cys Gly Met Asn Val His Lys Cys Arg Glu Lys
385                 390                 395                 400

Val Ala Asn Leu Cys Gly Ile Asn Gln Lys Leu Leu Ala Glu Ala Leu
                405                 410                 415

Asn Gln Val Thr Gln Arg Ala Ser Arg Arg Ser Asp Ser Ala Ser Ser
                420                 425                 430

Glu Pro Val Gly Ile Tyr Gln Gly Phe Glu Lys Lys Thr Gly Val Ala
                435                 440                 445

Gly Glu Asp Met Gln Asp Asn Ser Gly Thr Tyr Gly Lys Ile Trp Glu
450                 455                 460

Gly Ser Ser Lys Cys Asn Ile Asn Asn Phe Ile Phe His Lys Val Leu
465                 470                 475                 480

Gly Lys Gly Ser Phe Gly Lys Val Leu Leu Gly Glu Leu Lys Gly Arg
                485                 490                 495

Gly Glu Tyr Phe Ala Ile Lys Ala Leu Lys Lys Asp Val Val Leu Ile
                500                 505                 510

Asp Asp Asp Val Glu Cys Thr Met Val Glu Lys Arg Val Leu Thr Leu
                515                 520                 525

Ala Ala Glu Asn Pro Phe Leu Thr His Leu Ile Cys Thr Phe Gln Thr
530                 535                 540

Lys Asp His Leu Phe Phe Val Met Glu Phe Leu Asn Gly Gly Asp Leu
545                 550                 555                 560

Met Tyr His Ile Gln Asp Lys Gly Arg Phe Glu Leu Tyr Arg Ala Thr
                565                 570                 575

Phe Tyr Ala Ala Glu Ile Met Cys Gly Leu Gln Phe Leu His Ser Lys
                580                 585                 590

Gly Ile Ile Tyr Arg Asp Leu Lys Leu Asp Asn Val Leu Leu Asp Arg
                595                 600                 605

Asp Gly His Ile Lys Ile Ala Asp Phe Gly Met Cys Lys Glu Asn Ile
                610                 615                 620

Phe Gly Glu Ser Arg Ala Ser Thr Phe Cys Gly Thr Pro Asp Tyr Ile
625                 630                 635                 640

Ala Pro Glu Ile Leu Gln Gly Leu Lys Tyr Thr Phe Ser Val Asp Trp
                645                 650                 655

Trp Ser Phe Gly Val Leu Leu Tyr Glu Met Leu Ile Gly Gln Ser Pro
                660                 665                 670

Phe His Gly Asp Asp Glu Asp Glu Leu Phe Glu Ser Ile Arg Val Asp
                675                 680                 685

Thr Pro His Tyr Pro Arg Trp Ile Thr Lys Glu Ser Lys Asp Ile Leu
                690                 695                 700

Glu Lys Leu Phe Glu Arg Glu Pro Thr Lys Arg Leu Gly Val Thr Gly
705                 710                 715                 720
```

```
Asn Ile Lys Ile His Pro Phe Phe Lys Thr Ile Asn Trp Thr Leu Leu
                725                 730                 735

Glu Lys Arg Arg Leu Glu Pro Pro Phe Arg Pro Lys Val Lys Ser Pro
        740                 745                 750

Arg Asp Tyr Ser Asn Phe Asp Gln Glu Phe Leu Asn Glu Lys Ala Arg
            755                 760                 765

Leu Ser Tyr Ser Asp Lys Asn Leu Ile Asp Ser Met Asp Gln Ser Ala
        770                 775                 780

Phe Ala Gly Phe Ser Phe Val Asn Pro Lys Phe Glu His Leu Leu Glu
785                 790                 795                 800

Asp

<210> SEQ ID NO 37
<211> LENGTH: 2403
<212> TYPE: DNA
<213> ORGANISM: Artificial Sequence
<220> FEATURE:
<223> OTHER INFORMATION: Synthetic sequence, nt sequence of sensor 1
      [G17.2B]

<400> SEQUENCE: 37
atggaggacg tggattgcaa acagtctatg cgcagtgagg acgaggccaa gttcccaacg      60
atgaaccgcc gcggagccat caaacaggcc aaaatccact acatcaagaa cctcgagaac     120
gtctatatca aggccgacaa gcagaagaac ggcatcaagg cgaacttcaa gatccgccac     180
aacatcgagg acggcggcgt gcagctcgcc taccactacc agcagaacac ccccatcggc     240
gacggccccg tgctgctgcc cgacaaccac taccctgagc gtgcagtcca tactttcgaaa   300 gaccccaacg agaagcgcga tcacatggtc ctgctggagt tcgtgaccgc cgccgggatc     360
actctcggca tggacgagct gtacaagggc ggtaccggag ggagcatggt gagcaagggc     420
gaggagctgt tcaccggggt ggtgcccatc caggtcgagc tggacggcga cgtaaacggc     480
cacaagttca gcgtgtccgg cgagggtgag ggcgatgcca cctacggcaa gctgaccctg     540
aagttcatct gcaccaccgg caagctgccc gtgccctggc ccaccctcgt gaccaccctg     600
acctacggcg tgcagtgctt cagccgctac cccgaccaca tgaagcagca cgacttcttc     660
aagtccgcca tgcccgaagg ctacatccag gagcgcacca tcttcttcaa ggacgacggc     720
aactacaaga cccgcgccga ggtgaagttc gagggcgaca ccctggtgaa ccgcatcgag     780
ctgaagggca tcgacttcaa ggaggacggc aacatcctgg gcacaagct ggagtacaac     840 acgcgtcatg agtttatcgc cacctttctt gggcaaccca ccttctgttc tgtgtgcaaa     900
gactttgtct ggggcctcaa caagcaaggc tacaaatgca ggcaatgtaa cgctgccatc     960
cacaagaaat gcatcgacaa gatcatcggc agatgcactg gcaccgcggc aacagccgg    1020 gacactatat tccagaaaga acgcttcaac atcgacatgc cgcaccgctt caaggttcac    1080
aactacatga gccccacctt ctgtgaccac tgcggcagcc tgctctgggg actggtgaag    1140
cagggattaa agtgtgaaga ctgcggcatg aatgtgcacc ataaatgccg ggagaaggtg    1200
gccaacctct gcggcatcaa ccagaagctt ttggctgagg ccttgaacca agtcacccag    1260
agagcctccc ggagatcaga ctcagcctcc tcagagcctg ttgggatata tcagggtttc    1320
gagaagaaga ccggagttgc tggggaggac atgcaagaca cagtgggac ctacggcaag    1380 atctggagg gcagcagcaa gtgcaacatc aacaacttca tcttccacaa ggtcctgggc    1440
aaaggcagct cgggaaggt gctgcttgga gagctgaagg gcagaggaga gtactttgcc    1500
atcaaggccc tcaagaagga tgtggtcctg atcgacgacg acgtggagtg caccatggtt    1560
```

```
gagaagcggg tgctgacact tgccgcagag aatccctttc tcacccacct catctgcacc    1620
ttccagacca aggaccacct gttctttgtg atggagttcc tcaacggggg ggacctgatg    1680
taccacatcc aggacaaagg ccgctttgaa ctctaccgtg ccacgtttta tgccgctgag    1740
ataatgtgtg gactgcagtt tctacacagc aagggcatca tttacaggga cctcaaactg    1800
gacaatgtgc tgttggaccg ggatggccac atcaagattg ccgactttgg gatgtgcaaa    1860
gagaacatat tcggggagag ccgggccagc accttctgcg caccectga ctatatcgcc    1920 cctgagatcc tacagggcct gaagtacaca ttctctgtgg actggtggtc tttcggggtc    1980
cttctgtacg agatgctcat tggccagtcc cccttccatg tgatgatga ggatgaactc    2040 ttcgagtcca tccgtgtgga cacgccacat tatccccgct ggatcaccaa ggagtccaag    2100
gacatcctgg agaagctctt tgaaagggaa ccaaccaaga ggctgggagt gacgggaaac    2160
atcaaaatcc accccttctt caagaccata aactggactc tgctggaaaa gcggaggttg    2220
gagccaccct tcaggcccaa agtgaagtca cccagagact acagtaactt tgaccaggag    2280
ttcctgaacg agaaggcgcg cctctcctac agcgacaaga acctcatcga ctccatggac    2340
cagtctgcat tcgctggctt ctcctttgtg aaccccaaat tcgagcacct cctggaagat    2400
tag                                                                 2403
```

<210> SEQ ID NO 38
<211> LENGTH: 2406
<212> TYPE: DNA
<213> ORGANISM: Artificial Sequence
<220> FEATURE:
<223> OTHER INFORMATION: Synthetic sequence, nt sequence of sensor 2
      [G17-18]

<400> SEQUENCE: 38

```
atggaggacg tggattgcaa acagtctatg cgcagtgagg acgaggccaa gttcccaacg    60
atgaaccgcc gcggagccat caaacaggcc aaaatccact acatcaagaa cctcgagaac    120
gtctatatca aggccgacaa gcagaagaac ggcatcaagg cgaacttcaa gatccgccac    180
aacatcgagg acggcggcgt gcagctcgcc taccactacc agcagaacac ccccatcggc    240
gacggccccg tgctgctgcc cgacaaccac tacctgagcg tgcagtccat actttcgaaa    300
gaccccaacg agaagcgcga tcacatggtc ctgctggagt tcgtgaccgc cgccgggatc    360
actctcggca tggacgagct gtacaagggc ggtaccggag ggagcatggt gagcaagggc    420
gaggagctgt tcaccggggt ggtgcccatc caggtcgagc tggacggcga cgtaaacggc    480
cacaagttca gcgtgtccgg cgagggtgag ggcgatgcca cctacggcaa gctgaccctg    540
aagttcatct gcaccaccgg caagctgccc gtgccctggc ccaccctcgt gaccaccctg    600
acctacggcg tgcagtgctt cagccgctac cccgaccaca tgaagcagca cgacttcttc    660
aagtccgcca tgcccgaagg ctacatccag gagcgcacca tcttcttcaa ggacgacggc    720
aactacaaga cccgcgccga ggtgaagttc gagggcgaca ccctggtgaa ccgcatcgag    780
ctgaagggca tcgacttcaa ggaggacggc aacatcctgg ggcacaagct ggagtacaac    840
acgcgtaacc atgagtttat cgccaccttc tttgggcaac ccaccttctg ttctgtgtgc    900
aaagactttg tctgggcct caacaagcaa ggctacaaat gcaggcaatg taacgctgcc    960
atccacaaga aatgcatcga caagatcatc ggcagatgca ctggcaccgc ggccaacagc    1020
cgggacacta tattccagaa agaacgcttc aacatcgaca tgccgcaccg cttcaaggtt    1080
cacaactaca tgagccccac cttctgtgac cactgcggca gcctgctctg ggactggtg    1140
```

```
aagcagggat taaagtgtga agactgcggc atgaatgtgc accataaatg ccgggagaag    1200
gtggccaacc tctgcggcat caaccagaag cttttggctg aggccttgaa ccaagtcacc    1260
cagagagcct cccggagatc agactcagcc tcctcagagc ctgttgggat atatcagggt    1320
ttcgagaaga agaccggagt tgctggggag gacatgcaag acaacagtgg gacctacggc    1380
aagatctggg agggcagcag caagtgcaac atcaacaact tcatcttcca caaggtcctg    1440
ggcaaaggca gcttcgggaa ggtgctgctt ggagagctga agggcagagg agagtacttt    1500
gccatcaagg ccctcaagaa ggatgtggtc ctgatcgacg acgacgtgga gtgcaccatg    1560
gttgagaagc gggtgctgac acttgccgca gagaatccct ttctcaccca cctcatctgc    1620
accttccaga ccaaggacca cctgttcttt gtgatggagt tcctcaacgg ggggacctg    1680 atgtaccaca tccaggacaa aggccgcttt gaactctacc gtgccacgtt ttatgccgct    1740
gagataatgt gtggactgca gtttctacac agcaagggca tcatttacag ggacctcaaa    1800
ctggacaatg tgctgttgga ccgggatggc cacatcaaga ttgccgactt tgggatgtgc    1860
aaagagaaca tattcgggga gagccggccc agcaccttct gcggcacccc tgactatatc    1920
gcccctgaga tcctacaggg cctgaagtac acattctctg tggactggtg gtctttcggg    1980
gtccttctgt acgagatgct cattggccag tccccttcc atggtgatga tgaggatgaa    2040
ctcttcgagt ccatccgtgt ggacacgcca cattatcccc gctggatcac caaggagtcc    2100
aaggacatcc tggagaagct ctttgaaagg gaaccaacca agaggctggg agtgacggga    2160
aacatcaaaa tccaccccctt cttcaagacc ataaactgga ctctgctgga aaagcggagg    2220
ttggagccac ccttcaggcc caaagtgaag tcacccagag actacagtaa ctttgaccag    2280
gagttcctga cgagaaggc gcgcctctcc tacagcgaca agaacctcat cgactccatg    2340
gaccagtctg cattcgctgg cttctccttt gtgaacccca aattcgagca cctcctggaa    2400
gattag                                                              2406
```

<210> SEQ ID NO 39
<211> LENGTH: 2409
<212> TYPE: DNA
<213> ORGANISM: Artificial Sequence
<220> FEATURE:
<223> OTHER INFORMATION: Synthetic sequence, nt sequence of sensor 3
      [G17-19]

<400> SEQUENCE: 39

```
atggaggacg tggattgcaa acagtctatg cgcagtgagg acgaggccaa gttcccaacg     60
atgaaccgcc gcggagccat caaacaggcc aaaatccact acatcaagaa cctcgagaac    120
gtctatatca aggccgacaa gcagaagaac ggcatcaagg cgaacttcaa gatccgccac    180
aacatcgagg acggcggcgt gcagctcgcc taccactacc agcagaacac ccccatcggc    240
gacggccccg tgctgctgcc cgacaaccac tacctgagcg tgcagtccat actttcgaaa    300
gaccccaacg agaagcgcga tcacatggtc ctgctggagt tcgtgaccgc cgccgggatc    360
actctcggca tggacgagct gtacaagggc ggtaccggag ggagcatggt gagcaagggc    420
gaggagctgt tcaccggggt ggtgcccatc caggtcgagc tggacggcga cgtaaacggc    480
cacaagttca gcgtgtccgg cgagggtgag ggcgatgcca cctacggcaa gctgaccctg    540
aagttcatct gcaccaccgg caagctgccc gtgccctggc ccaccctcgt gaccaccctg    600
acctacggcg tgcagtgctt cagccgctac cccgaccaca tgaagcagca cgacttcttc    660
aagtccgcca tgcccgaagg ctacatccag gagcgcacca tcttcttcaa ggacgacggc    720
```

```
aactacaaga cccgcgccga ggtgaagttc gagggcgaca ccctggtgaa ccgcatcgag      780
ctgaagggca tcgacttcaa ggaggacggc aacatcctgg gcacaagct ggagtacaac       840 acgcgtaaga accatgagtt tatcgccacc ttctttgggc aacccacctt ctgttctgtg      900
tgcaaagact ttgtctgggg cctcaacaag caaggctaca aatgcaggca atgtaacgct      960
gccatccaca agaaatgcat cgacaagatc atcggcagat gcactggcac cgcggccaac     1020
agccgggaca ctatattcca gaaagaacgc ttcaacatcg acatgccgca ccgcttcaag     1080
gttcacaact acatgagccc caccttctgt gaccactgcg gcagcctgct ctggggactg     1140
gtgaagcagg gattaaagtg tgaagactgc ggcatgaatg tgcaccataa atgccgggag     1200
aaggtggcca acctctgcgg catcaaccag aagcttttgg ctgaggcctt gaaccaagtc     1260
acccagagag cctcccggag atcagactca gcctcctcag agcctgttgg gatatatcag     1320
ggtttcgaga agaagaccgg agttgctggg gaggacatgc aagacaacag tgggacctac     1380
ggcaagatct ggagggcag cagcaagtgc aacatcaaca acttcatctt ccacaaggtc      1440
ctgggcaaag gcagcttcgg gaaggtgctg cttggagagc tgaagggcag aggagagtac     1500
tttgccatca aggcccctcaa gaaggatgtg gtcctgatcg acgacgacgt ggagtgcacc    1560
atggttgaga gcgggtgct gacacttgcc gcagagaatc cctttctcac ccacctcatc      1620
tgcaccttcc agaccaagga ccacctgttc tttgtgatgg agttcctcaa cggggggggac    1680 ctgatgtacc acatccagga caaggccgc tttgaactct accgtgccac gttttatgcc      1740
gctgagataa tgtgtggact gcagtttcta cacagcaagg gcatcattta cagggacctc    1800
aaactggaca atgtgctgtt ggaccgggat ggccacatca agattgccga ctttgggatg     1860
tgcaaagaga acatattcgg ggagagccgg gccagcacct tctgcggcac ccctgactat     1920
atcgcccctg agatcctaca gggcctgaag tacacattct ctgtggactg gtggtctttc     1980 gggggtccttc tgtacgagat gctcattggc cagtccccct tccatggtga tgatgaggat    2040
gaactcttcg agtccatccg tgtggacacg ccacattatc cccgctggat caccaaggag     2100
tccaaggaca tcctggagaa gctcttttgaa agggaaccaa ccaagaggct gggagtgacg    2160
ggaaacatca aaatccaccc cttcttcaag accataaact ggactctgct ggaaaagcgg     2220
aggttggagc cacccttcag gcccaaagtg aagtcaccca gagactacag taactttgac     2280
caggagttcc tgaacgagaa ggcgcgcctc tcctacagcg acaagaacct catcgactcc     2340
atggaccagt ctgcattcgc tggcttctcc tttgtgaacc ccaaattcga gcacctcctg     2400
gaagattag                                                              2409
```

<210> SEQ ID NO 40
<211> LENGTH: 2409
<212> TYPE: DNA
<213> ORGANISM: Artificial Sequence
<220> FEATURE:
<223> OTHER INFORMATION: Synthetic sequence, nt sequence of sensor 4 [G18-20]

<400> SEQUENCE: 40

```
atggaggacg tggattgcaa acagtctatg cgcagtgagg acgaggccaa gttcccaacg       60
atgaaccgcc gcggagccat caaacaggcc aaaatccact acatcaagct cgagaacgtc      120
tatatcaagg ccgacaagca gaagaacggc atcaaggcga acttcaagat ccgccacaac      180
atcgaggacg cgggcgtgca gctcgcctac cactaccagc agaacacccc catcggcgac      240
ggccccgtgc tgctgcccga caaccactac ctgagcgtgc agtccatact ttcgaaagac      300
```

```
cccaacgaga agcgcgatca catggtcctg ctggagttcg tgaccgccgc cgggatcact    360
ctcggcatgg acgagctgta caagggcggt accggaggga gcatggtgag caagggcgag    420
gagctgttca ccggggtggt gcccatccag gtcgagctgg acggcgacgt aaacggccac    480
aagttcagcg tgtccggcga gggtgagggc gatgccacct acggcaagct gaccctgaag    540
ttcatctgca ccaccggcaa gctgcccgtg ccctggccca ccctcgtgac caccctgacc    600
tacggcgtgc agtgcttcag ccgctacccc gaccacatga gcagcacga cttcttcaag    660 tccgccatgc ccgaaggcta catccaggag cgcaccatct tcttcaagga cgacggcaac    720
tacaagaccc gcgccgaggt gaagttcgag ggcgacaccc tggtgaaccg catcgagctg    780
aagggcatcg acttcaagga ggacggcaac atcctggggc acaagctgga gtacaacacg    840
cgtatcaaga accatgagtt tatcgccacc ttctttgggc aacccacctt ctgttctgtg    900
tgcaaagact ttgtctgggg cctcaacaag caaggctaca atgcaggca atgtaacgct    960 gccatccaca gaaatgcat cgacaagatc atcggcagat gcactggcac cgcggccaac   1020
agccgggaca ctatattcca gaaagaacgc ttcaacatcg acatgccgca ccgcttcaag   1080
gttcacaact acatgagccc caccttctgt gaccactgcg gcagcctgct ctggggactg   1140
gtgaagcagg gattaaagtg tgaagactgc ggcatgaatg tgcaccataa atgccgggag   1200
aaggtggcca acctctgcgg catcaaccag aagcttttgg ctgaggcctt gaaccaagtc   1260
acccagagag cctcccggag atcagactca gcctcctcag agcctgttgg gatatatcag   1320
ggtttcgaga agaagaccgg agttgctggg gaggacatgc aagacaacag tgggacctac   1380
ggcaagatct gggagggcag cagcaagtgc aacatcaaca acttcatctt ccacaaggtc   1440
ctgggcaaag gcagcttcgg gaaggtgctg cttggagagc tgaagggcag aggagagtac   1500
tttgccatca aggccctcaa gaaggatgtg gtcctgatcg acgacgacgt ggagtgcacc   1560
atggttgaga gcgggtgct gacacttgcc gcagagaatc cctttctcac ccacctcatc   1620
tgcaccttcc agaccaagga ccacctgttc tttgtgatga gttcctcaa cggggggac   1680 ctgatgtacc acatccagga caaaggccgc tttgaactct accgtgccac gttttatgcc   1740
gctgagataa tgtgtggact gcagtttcta cacagcaagg gcatcattta cagggacctc   1800
aaactggaca atgtgctgtt ggaccgggat ggccacatca agattgccga ctttgggatg   1860
tgcaaagaga acatattcgg ggagagccgg gccagcacct tctgcggcac ccctgactat   1920
atcgcccctg agatcctaca gggcctgaag tacacattct ctgtggactg gtggtctttc   1980 gggtcttc tgtacgagat gctcattggc cagtccccct tccatggtga tgatgaggat   2040
gaactcttcg agtccatccg tgtggacacg ccacattatc ccgctggat caccaaggag   2100 tccaaggaca tcctggagaa gctctttgaa agggaaccaa ccaagaggct gggagtgacg   2160
ggaaacatca aaatccaccc cttcttcaag accataaact ggactctgct ggaaaagcgg   2220
aggttggagc cacccttcag gcccaaagtg aagtcaccca gagactacag taactttgac   2280
caggagttcc tgaacgagaa ggcgcgcctc tcctacagcg acaagaacct catcgactcc   2340
atggaccagt ctgcattcgc tggcttctcc tttgtgaacc caaaattcga gcacctcctg   2400
gaagattag                                                           2409
```

<210> SEQ ID NO 41
<211> LENGTH: 2397
<212> TYPE: DNA
<213> ORGANISM: Artificial Sequence
<220> FEATURE:

<223> OTHER INFORMATION: Synthetic sequence, nt sequence of sensor 5 [G19-17]

<400> SEQUENCE: 41

```
atggaggacg tggattgcaa acagtctatg cgcagtgagg acgaggccaa gttcccaacg      60
atgaaccgcc gcggagccat caaacaggcc aaaatccact catcctcga gaacgtctat     120
atcaaggccg acaagcagaa gaacggcatc aaggcgaact tcaagatccg ccacaacatc     180
gaggacggcg gcgtgcagct cgcctaccac taccagcaga acacccccat cggcgacggc     240
cccgtgctgc tgcccgacaa ccactacctg agcgtgcagt ccatactttc gaaagacccc     300
aacgagaagc gcgatcacat ggtcctgctg gagttcgtga ccgccgcgg gatcactctc      360
ggcatggacg agctgtacaa gggcggtacc ggagggagca tggtgagcaa gggcgaggag     420
ctgttcaccg gggtggtgcc catccaggtc gagctggacg gcgacgtaaa cggccacaag     480
ttcagcgtgt ccggcgaggg tgagggcgat gccacctacg gcaagctgac cctgaagttc     540
atctgcacca ccggcaagct gcccgtgccc tggcccaccc tcgtgaccac cctgacctac     600
ggcgtgcagt gcttcagccg ctaccccgac cacatgaagc agcacgactt cttcaagtcc     660
gccatgcccg aaggctacat ccaggagcgc accatcttct tcaaggacga cggcaactac     720
aagacccgcg ccgaggtgaa gttcgagggc gacaccctgg tgaaccgcat cgagctgaag     780
ggcatcgact tcaaggagga cggcaacatc ctggggcaca gctggagta caacacgcgt     840
catgagttta tcgccacctt ctttgggcaa cccacctt ctt gttctgtgtg caaagacttt      900
gtctggggcc tcaacaagca aggctacaaa tgcaggcaat gtaacgctgc catccacaag     960
aaatgcatcg acaagatcat cggcagatgc actggcaccg cggccaacag ccgggacact    1020
atattccaga aagaacgctt caacatcgac atgccgcacc gcttcaaggt tcacaactac    1080
atgagcccca ccttctgtga ccactgcggc agcctgctct ggggactggt gaagcaggga    1140
ttaaagtgtg aagactgcgg catgaatgtg caccataaat gccgggagaa ggtggccaac    1200
ctctgcggca tcaaccagaa gcttttggct gaggccttga accaagtcac ccagagagcc    1260
tcccggagat cagactcagc ctcctcagag cctgttggga tatatcaggg tttcgagaag    1320
aagaccggag ttgctgggga ggacatgcaa gacaacagtg ggacctacgg caagatctgg    1380
gagggcagca gcaagtgcaa catcaacaac ttcatcttcc acaaggtcct gggcaaaggc    1440
agcttcggga aggtgctgct ggagagctga agggcagag gagagtactt tgccatcaag    1500
gccctcaaga aggatgtggt cctgatcgac gacgacgtgg agtgcaccat ggttgagaag    1560
cgggtgctga cacttgccgc agagaatccc tttctcaccc acctcatctg caccttccag    1620
accaaggacc acctgttctt tgtgatggag ttcctcaacg ggggggacct gatgtaccac    1680
atccaggaca aaggccgctt tgaactctac cgtgccacgt tttatgccgc tgagataatg    1740
tgtggactgc agtttctaca cagcaagggc atcatttaca gggacctcaa actggacaat    1800
gtgctgttgg accgggatgg ccacatcaag attgccgact tgggatgtg caaagagaac    1860
atattcgggg agagccgggc cagcaccttc tgcggcaccc ctgactatat cgcccctgag    1920
atcctacagg gcctgaagta cacattctct gtggactggt ggtctttcgg ggtccttctg    1980
tacgagatgc tcattggcca gtcccccttc catggtgatg atgaggatga actcttcgag    2040
tccatccgtg tggacacgcc acattatccc cgctggatca ccaaggagtc caaggacatc    2100
ctggagaagc tctttgaaag ggaaccaacc aagaggctgg gagtgacggg aaacatcaaa    2160
atccaccccct tcttcaagac cataaactgg actctgctgg aaaagcggag gttggagcca    2220
```

```
cccttcaggc ccaaagtgaa gtcacccaga gactacagta actttgacca ggagttcctg    2280
aacgagaagg cgcgcctctc ctacagcgac aagaacctca tcgactccat ggaccagtct    2340
gcattcgctg gcttctcctt tgtgaacccc aaattcgagc acctcctgga agattag       2397

<210> SEQ ID NO 42
<211> LENGTH: 2400
<212> TYPE: DNA
<213> ORGANISM: Artificial Sequence
<220> FEATURE:
<223> OTHER INFORMATION: Synthetic sequence, nt sequence of sensor 6
      [G19-18]

<400> SEQUENCE: 42
atggaggacg tggattgcaa acagtctatg cgcagtgagg acgaggccaa gttcccaacg     60
atgaaccgcc gcggagccat caaacaggcc aaaatccact catcctcga gaacgtctat    120 atcaaggccg acaagcagaa aacggcatc aaggcgaact tcaagatccg ccacaacatc    180
gaggacggcg cgtgcagct cgcctaccac taccagcaga acaccccat cggcgacggc    240 cccgtgctgc tgcccgacaa ccactacctg agcgtgcagt ccatactttc gaaagacccc    300
aacgagaagc gcgatcacat ggtcctgctg gagttcgtga ccgccgcgg gatcactctc    360 ggcatggacg agctgtacaa gggcggtacc ggagggagca tggtgagcaa gggcgaggag    420
ctgttcaccg gggtggtgcc catccaggtc gagctggacg gcgacgtaaa cggccacaag    480
ttcagcgtgt ccggcgaggg tgagggcgat gccacctacg gcaagctgac cctgaagttc    540
atctgcacca ccggcaagct gcccgtgccc tggcccaccc tcgtgaccac cctgacctac    600
ggcgtgcagt gcttcagccg ctaccccgac cacatgaagc agcacgactt cttcaagtcc    660
gccatgcccg aaggctacat ccaggagcgc accatcttct tcaaggacga cggcaactac    720
aagacccgcg ccgaggtgaa gttcgagggc gacacctgg tgaaccgcat cgagctgaag    780
ggcatcgact tcaaggagga cggcaacatc ctggggcaca gctggagta caacacgcgt    840 aaccatgagt ttatcgccac cttctttggg caacccacct tctgttctgt gtgcaaagac    900
tttgtctggg gcctcaacaa gcaaggctac aaatgcaggc aatgtaacgc tgccatccac    960
aagaaatgca tcgacaagat catcggcaga tgcactggca ccgcgccaa cagccggac   1020 actatattcc agaaagaacg cttcaacatc gacatgccgc accgcttcaa ggttcacaac   1080
tacatgagcc caccttctg tgaccactgc ggcagcctgc tctggggact ggtgaagcag   1140
ggattaaagt gtgaagactg cggcatgaat gtgcaccata atgccggga aaggtggcc   1200 aacctctgcg gcatcaacca gaagcttttg gctgaggcct tgaaccaagt cacccagaga   1260
gcctcccgga gatcagactc agcctcctca gagcctgttg ggatatatca gggtttcgag   1320
aagaagaccg gagttgctgg ggaggacatg caagacaaca gtgggaccta cggcaagatc   1380
tgggagggca gcagcaagtg caacatcaac aacttcatct tccacaaggt cctgggcaaa   1440
ggcagcttcg ggaaggtgct gcttggagag ctgaagggca gggagagta ctttgccatc   1500 aaggccctca gaaggatgt ggtcctgatc gacgacgacg tggagtgcac catggttgag   1560
aagcgggtgc tgacacttgc cgcagagaat ccctttctca cccacctcat ctgcaccttc   1620
cagaccaagg accacctgtt ctttgtgatg gagttcctca cgggggggga cctgatgtac   1680
cacatccagg acaaaggccg ctttgaactc taccgtgcca cgttttatgc cgctgagata   1740
atgtgtggac tgcagtttct acacagcaag ggcatcattt acaggaccct caaactggac   1800
aatgtgctgt tggaccggga tggccacatc aagattgccg actttgggat gtgcaaagag   1860
```

| | |
|---|---|
| aacatattcg gggagagccg ggccagcacc ttctgcggca cccctgacta tatcgcccct | 1920 |
| gagatcctac agggcctgaa gtacacattc tctgtggact ggtggtcttt cggggtcctt | 1980 |
| ctgtacgaga tgctcattgg ccagtccccc ttccatggtg atgatgagga tgaactcttc | 2040 |
| gagtccatcc gtgtggacac gccacattat ccccgctgga tcaccaagga gtccaaggac | 2100 |
| atcctggaga agctctttga aagggaacca accaagaggc tgggagtgac gggaaacatc | 2160 |
| aaaatccacc ccttcttcaa gaccataaac tggactctgc tggaaaagcg gaggttggag | 2220 |
| ccacccttca ggcccaaagt gaagtcaccc agagactaca gtaactttga ccaggagttc | 2280 |
| ctgaacgaga aggcgcgcct ctcctacagc gacaagaacc tcatcgactc catggaccag | 2340 |
| tctgcattcg ctggcttctc ctttgtgaac cccaaattcg agcacctcct ggaagattag | 2400 |

<210> SEQ ID NO 43
<211> LENGTH: 2406
<212> TYPE: DNA
<213> ORGANISM: Artificial Sequence
<220> FEATURE:
<223> OTHER INFORMATION: Synthetic sequence, nt sequence of sensor 7
      [G19-20]

<400> SEQUENCE: 43

| | |
|---|---|
| atggaggacg tggattgcaa acagtctatg cgcagtgagg acgaggccaa gttcccaacg | 60 |
| atgaaccgcc gcggagccat caaacaggcc aaaatccact catcctcga gaacgtctat | 120 |
| atcaaggccg acaagcagaa gaacggcatc aaggcgaact tcaagatccg ccacaacatc | 180 |
| gaggacggcg gcgtgcagct cgcctaccac taccagcaga cacccccat cggcgacggc | 240 |
| cccgtgctgc tgcccgacaa ccactacctg agcgtgcagt ccatactttc gaaagacccc | 300 |
| aacgagaagc gcgatcacat ggtcctgctg gagttcgtga ccgccgcgg gatcactctc | 360 |
| ggcatggacg agctgtacaa gggcggtacc ggagggagca tggtgagcaa gggcgaggag | 420 |
| ctgttcaccg gggtggtgcc catccaggtc gagctggacg gcgacgtaaa cggccacaag | 480 |
| ttcagcgtgt ccggcgaggg tgagggcgat gccacctacg gcaagctgac cctgaagttc | 540 |
| atctgcacca ccggcaagct gcccgtgccc tggcccaccc tcgtgaccac cctgacctac | 600 |
| ggcgtgcagt gcttcagccg ctaccccgac cacatgaagc agcacgactt cttcaagtcc | 660 |
| gccatgcccg aaggctacat ccaggagcgc accatcttct tcaaggacga cggcaactac | 720 |
| aagacccgcg ccgaggtgaa gttcgagggc gacaccctgg tgaaccgcat cgagctgaag | 780 |
| ggcatcgact tcaaggagga cggcaacatc ctggggcaca gctggagta caacacgcgt | 840 |
| atcaagaacc atgagtttat cgccaccttc tttgggcaac ccaccttctg ttctgtgtgc | 900 |
| aaagactttg tctggggcct caacaagcaa ggctacaaat gcaggcaatg taacgctgcc | 960 |
| atccacaaga aatgcatcga caagatcatc ggcagatgac tggcaccgc ggccaacagc | 1020 |
| cgggacacta tattccagaa agaacgcttc aacatcgaca tgccgcaccg cttcaaggtt | 1080 |
| cacaactaca tgagccccac cttctgtgac cactgcggca gcctgctctg gggactggtg | 1140 |
| aagcagggat taaagtgtga agactgcggc atgaatgtgc accataaatg ccgggagaag | 1200 |
| gtggccaacc tctgcggcat caaccagaag ctttttggctg aggccttgaa ccaagtcacc | 1260 |
| cagagagcct cccggagatc agactcagcc tcctcagagc ctgttgggat atatcagggt | 1320 |
| ttcgagaaga gaccggagt tgctggggag gacatgcaag acaacagtgg gacctacggc | 1380 |
| aagatctggg agggcagcag caagtgcaac atcaacaact tcatcttcca caaggtcctg | 1440 |
| ggcaaaggca gcttcgggaa ggtgctgctt ggagagctga agggcagagg agagtacttt | 1500 |

| | |
|---|---|
| gccatcaagg ccctcaagaa ggatgtggtc ctgatcgacg acgacgtgga gtgcaccatg | 1560 |
| gttgagaagc gggtgctgac acttgccgca gagaatccct ttctcaccca cctcatctgc | 1620 |
| accttccaga ccaaggacca cctgttcttt gtgatggagt tcctcaacgg gggggacctg | 1680 |
| atgtaccaca tccaggacaa aggccgcttt gaactctacc gtgccacgtt ttatgccgct | 1740 |
| gagataatgt gtggactgca gtttctacac agcaagggca tcatttacag ggacctcaaa | 1800 |
| ctggacaatg tgctgttgga ccgggatggc acatcaaga ttgccgactt tgggatgtgc | 1860 |
| aaagagaaca tattcgggga gagccgggcc agcaccttct gcggcacccc tgactatatc | 1920 |
| gcccctgaga tcctacaggg cctgaagtac acattctctg tggactggtg gtctttcggg | 1980 |
| gtccttctgt acgagatgct cattggccag tcccccttcc atggtgatga tgaggatgaa | 2040 |
| ctcttcgagt ccatccgtgt ggacacgcca cattatcccc gctggatcac caaggagtcc | 2100 |
| aaggacatcc tggagaagct cttgaaagg gaaccaacca agaggctggg agtgacggga | 2160 |
| aacatcaaaa tccaccccct tcttcaagac cataaactgga ctctgctgga aaagcggagg | 2220 |
| ttggagccac ccttcaggcc caaagtgaag tcacccagag actacagtaa ctttgaccag | 2280 |
| gagttcctga cgagaaggc gcgcctctcc tacagcgaca agaacctcat cgactccatg | 2340 |
| gaccagtctg cattcgctgg cttctccttt gtgaaccca aattcgagca cctcctggaa | 2400 |
| gattag | 2406 |

<210> SEQ ID NO 44
<211> LENGTH: 2394
<212> TYPE: DNA
<213> ORGANISM: Artificial Sequence
<220> FEATURE:
<223> OTHER INFORMATION: Synthetic sequence, nt sequence of sensor 8
 [G20-17]

<400> SEQUENCE: 44

| | |
|---|---|
| atggaggacg tggattgcaa acagtctatg cgcagtgagg acgaggccaa gttcccaacg | 60 |
| atgaaccgcc gcggagccat caaacaggcc aaaatccact acctcgagaa cgtctatatc | 120 |
| aaggccgaca gcagaagaa cggcatcaag gcgaacttca agatccgcca caacatcgag | 180 |
| gacggcggcg tgcagctcgc ctaccactac agcagaaaca cccccatcgg cgacggcccc | 240 |
| gtgctgctgc ccgacaacca ctacctgagc gtgcagtcca actttcgaa agaccccaac | 300 |
| gagaagcgcg atcacatggt cctgctggag ttcgtgaccg ccgccgggat cactctcggc | 360 |
| atggacgagc tgtacaaggg cggtaccgga gggagcatgg tgagcaaggg cgaggagctg | 420 |
| ttcaccgggg tggtgcccat ccaggtcgag ctggacggcg acgtaaacgg ccacaagttc | 480 |
| agcgtgtccg gcgagggtga gggcgatgcc acctacggca agctgaccct gaagttcatc | 540 |
| tgcaccaccg gcaagctgcc cgtgccctgg cccaccctcg tgaccaccct gacctacggc | 600 |
| gtgcagtgct tcagccgcta ccccgaccac atgaagcagc acgacttctt caagtccgcc | 660 |
| atgcccgaag gctacatcca ggagcgcacc atcttcttca aggacgacgg caactacaag | 720 |
| acccgcgccg aggtgaagtt cgagggcgac accctggtga accgcatcga gctgaagggc | 780 |
| atcgacttca aggaggacgg caacatcctg gggcacaagc tggagtacaa cacgcgtcat | 840 |
| gagtttatcg ccaccttctt tgggcaaccc accttctgtt ctgtgtgcaa agactttgtc | 900 |
| tggggcctca caagcaagg ctacaaatgc aggcaatgta acgctgccat ccacaagaaa | 960 |
| tgcatcgaca agatcatcgg cagatgcact ggcaccgcgg ccaacagccg ggacactata | 1020 |
| ttccagaaag aacgcttcaa catcgacatg ccgcaccgct tcaaggttca caactacatg | 1080 |

-continued

| | |
|---|---|
| agccccacct tctgtgacca ctgcggcagc ctgctctggg gactggtgaa gcaggatta | 1140 |
| aagtgtgaag actgcggcat gaatgtgcac cataaatgcc gggagaaggt ggccaacctc | 1200 |
| tgcggcatca accagaagct tttggctgag gccttgaacc aagtcaccca gagagcctcc | 1260 |
| cggagatcag actcagcctc ctcagagcct gttgggatat atcagggttt cgagaagaag | 1320 |
| accggagttg ctggggagga catgcaagac aacagtggga cctacggcaa gatctgggag | 1380 |
| ggcagcagca agtgcaacat caacaacttc atcttccaca aggtcctggg caaaggcagc | 1440 |
| ttcgggaagg tgctgcttgg agagctgaag gcagaggag agtactttgc catcaaggcc | 1500 |
| ctcaagaagg atgtggtcct gatcgacgac gacgtggagt gcaccatggt tgagaagcgg | 1560 |
| gtgctgacac ttgccgcaga gaatcccttt ctcacccacc tcatctgcac cttccagacc | 1620 |
| aaggaccacc tgttctttgt gatggagttc ctcaacgggg gggacctgat gtaccacatc | 1680 |
| caggacaaag gccgctttga actctaccgt gccacgtttt atgccgctga gataatgtgt | 1740 |
| ggactgcagt ttctacacag caagggcatc atttacaggg acctcaaact ggacaatgtg | 1800 |
| ctgttggacc gggatggcca catcaagatt gccgactttg gatgtgcaa agagaacata | 1860 |
| ttcggggaga gccgggccag caccttctgc ggcacccctg actatatcgc ccctgagatc | 1920 |
| ctacagggcc tgaagtacac attctctgtg gactggtggt ctttcggggt ccttctgtac | 1980 |
| gagatgctca ttggccagtc ccccttccat ggtgatgatg aggatgaact cttcgagtcc | 2040 |
| atccgtgtgg acacgccaca ttatccccgc tggatcacca aggagtccaa ggacatcctg | 2100 |
| gagaagctct ttgaaaggga accaaccaag aggctgggag tgacgggaaa catcaaaatc | 2160 |
| caccccttct tcaagaccat aaactggact ctgctggaaa agcggaggtt ggagccaccc | 2220 |
| ttcaggccca aagtgaagtc acccagagac tacagtaact ttgaccagga gttcctgaac | 2280 |
| gagaaggcgc gcctctccta cagcgacaag aacctcatcg actccatgga ccagtctgca | 2340 |
| ttcgctggct tctcctttgt gaaccccaaa ttcgagcacc tcctggaaga ttag | 2394 |

<210> SEQ ID NO 45
<211> LENGTH: 2379
<212> TYPE: DNA
<213> ORGANISM: Artificial Sequence
<220> FEATURE:
<223> OTHER INFORMATION: Synthetic sequence, nt sequence of sensor 9
      [G20-28]

<400> SEQUENCE: 45

| | |
|---|---|
| atggaggacg tggattgcaa acagtctatg cgcagtgagg acgaggccaa gttcccaacg | 60 |
| atgaaccgcc gcggagccat caacaggcc aaaatccact acctcgagaa cgtctatatc | 120 |
| aaggccgaca gcagaagaa cggcatcaag gcgaacttca agatccgcca caacatcgag | 180 |
| gacggcggcg tgcagctcgc ctaccactac cagcagaaca ccccccatcgg cgacggcccc | 240 |
| gtgctgctgc ccgacaacca ctacctgagc gtgcagtcca ctttcgaa agaccccaac | 300 |
| gagaagcgcg atcacatggt cctgctggag ttcgtgaccg ccgcgggat cactctcggc | 360 |
| atggacgagc tgtacaaggg cggtaccgga gggagcatgg tgagcaaggg cgaggagctg | 420 |
| ttcaccgggg tggtgcccat ccaggtcgag ctggacggcg acgtaaacgg ccacaagttc | 480 |
| agcgtgtccg gcgagggtga gggcgatgcc acctacggca agctgaccct gaagttcatc | 540 |
| tgcaccaccg gcaagctgcc cgtgccctgg cccaccctcg tgaccaccct gacctacggc | 600 |
| gtgcagtgct tcagccgcta ccccgaccac atgaagcagc acgacttctt caagtccgcc | 660 |
| atgcccgaag gctacatcca ggagcgcacc atcttcttca aggacgacgg caactacaag | 720 |

```
acccgcgccg aggtgaagtt cgagggcgac accctggtga accgcatcga gctgaagggc    780
atcgacttca aggaggacgg caacatcctg gggcacaagc tggagtacaa cacgcgtacc    840
ttctttgggc aacccacctt ctgttctgtg tgcaaagact ttgtctgggg cctcaacaag    900
caaggctaca aatgcaggca atgtaacgct gccatccaca agaaatgcat cgacaagatc    960
atcggcagat gcactggcac cgcggccaac agccgggaca ctatattcca gaaagaacgc   1020
ttcaacatcg acatgccgca ccgcttcaag gttcacaact acatgagccc caccttctgt   1080
gaccactgcg gcagcctgct ctggggactg gtgaagcagg gattaaagtg tgaagactgc   1140
ggcatgaatg tgcaccataa atgccgggag aaggtggcca acctctgcgg catcaaccag   1200
aagcttttgg ctgaggcctt gaaccaagtc acccagagag cctcccggag atcagactca   1260
gcctcctcag agcctgttgg gatatatcag ggtttcgaga agaagaccgg agttgctggg   1320
gaggacatgc aagacaacag tgggacctac ggcaagatct ggagggcag cagcaagtgc   1380 aacatcaaca acttcatctt ccacaaggtc ctgggcaaag gcagcttcgg aaggtgctg   1440 cttggagagc tgaagggcag aggagagtac tttgccatca aggccctcaa gaaggatgtg   1500
gtcctgatcg acgacgacgt ggagtgcacc atggttgaga agcgggtgct gacacttgcc   1560
gcagagaatc cctttctcac ccacctcatc tgcaccttcc agaccaagga ccacctgttc   1620
tttgtgatgg agttcctcaa cggggggggac ctgatgtacc acatccagga caaggccgc   1680 tttgaactct accgtgccac gttttatgcc gctgagataa tgtgtggact gcagtttcta   1740
cacagcaagg gcatcattta cagggacctc aaactggaca atgtgctgtt ggaccgggat   1800
ggccacatca agattgccga ctttgggatg tgcaaagaga acatattcgg ggagagccgg   1860
gccagcacct tctgcggcac ccctgactat atcgcccctg agatcctaca gggcctgaag   1920
tacacattct ctgtggactg gtggtctttc ggggtccttc tgtacgagat gctcattggc   1980
cagtccccct tccatggtga tgatgaggat gaactcttcg agtccatccg tgtggacacg   2040
ccacattatc cccgctggat caccaaggag tccaaggaca tcctggagaa gctctttgaa   2100
agggaaccaa ccaagaggct gggagtgacg ggaaacatca aaatccaccc cttcttcaag   2160
accataaact ggactctgct ggaaaagcgg aggttggagc cacccttcag gcccaaagtg   2220
aagtcaccca gagactacag taactttgac caggagttcc tgaacgagaa ggcgcgcctc   2280
tcctacagcg acaagaacct catcgactcc atggaccagt ctgcattcgc tggcttctcc   2340
tttgtgaacc ccaaattcga gcacctcctg gaagattag                          2379
```

<210> SEQ ID NO 46
<211> LENGTH: 2391
<212> TYPE: DNA
<213> ORGANISM: Artificial Sequence
<220> FEATURE:
<223> OTHER INFORMATION: Synthetic sequence, nt sequence of sensor 10
      [G21-17]

<400> SEQUENCE: 46

```
atggaggacg tggattgcaa acagtctatg cgcagtgagg acgaggccaa gttcccaacg     60
atgaaccgcc gcggagccat caaacaggcc aaaatccacc tcgagaacgt ctatatcaag    120
gccgacaagc agaagaacgg catcaaggcg aacttcaaga tccgccacaa catcgaggac    180
ggcggcgtgc agctcgccta ccactaccag cagaacaccc ccatcggcga cggccccgtg    240
ctgctgcccg acaaccacta cctgagcgtg cagtccatac tttcgaaaga ccccaacgag    300
aagcgcgatc acatggtcct gctggagttc gtgaccgccg ccgggatcac tctcggcatg    360
```

```
gacgagctgt acaagggcgg taccggaggg agcatggtga gcaagggcga ggagctgttc      420
accggggtgg tgcccatcca ggtcgagctg gacggcgacg taaacggcca caagttcagc      480
gtgtccggcg agggtgaggg cgatgccacc tacggcaagc tgaccctgaa gttcatctgc      540
accaccggca agctgcccgt gccctggccc accctcgtga ccaccctgac ctacggcgtg      600
cagtgcttca gccgctaccc cgaccacatg aagcagcacg acttcttcaa gtccgccatg      660
cccgaaggct acatccagga gcgcaccatc ttcttcaagg acgacggcaa ctacaagacc      720
cgcgccgagg tgaagttcga gggcgacacc ctggtgaacc gcatcgagct gaagggcatc      780
gacttcaagg aggacggcaa catcctgggg cacaagctgg agtacaacac gcgtcatgag      840
tttatcgcca ccttctttgg caacccacc ttctgttctg tgtgcaaaga ctttgtctgg       900
ggcctcaaca gcaaggcta caatgcagg caatgtaacg ctgccatcca agaaaatgc         960
atcgacaaga tcatcggcag atgcactggc accgcggcca acagccggga cactatattc     1020
cagaaagaac gcttcaacat cgacatgccg caccgcttca aggttcacaa ctacatgagc     1080
cccaccttct gtgaccactg cggcagcctg ctctggggac tggtgaagca gggattaaag     1140
tgtgaagact gcggcatgaa tgtgcaccat aaatgccggg agaaggtggc caacctctgc     1200
ggcatcaacc agaagctttt ggctgaggcc ttgaaccaag tcacccagag agcctcccgg     1260
agatcagact cagcctcctc agagcctgtt gggatatatc agggtttcga gaagaagacc     1320
ggagttgctg gggaggacat gcaagacaac agtgggacct acggcaagat ctgggagggc     1380
agcagcaagt gcaacatcaa caacttcatc ttccacaagg tcctgggcaa aggcagcttc     1440
gggaaggtgc tgcttggaga gctgaagggc agaggagagt actttgccat caaggccctc     1500
aagaaggatg tggtcctgat cgacgacgac gtggagtgca ccatggttga agcgggtg       1560
ctgacacttg ccgcagagaa tccctttctc acccacctca tctgcacctt ccagaccaag     1620
gaccacctgt tctttgtgat ggagttcctc aacggggggg acctgatgta ccacatccag     1680
gacaaaggcc gctttgaact ctaccgtgcc acgttttatg ccgctgagat aatgtgtgga     1740
ctgcagtttc tacacagcaa gggcatcatt tacagggacc tcaaactgga caatgtgctg     1800
ttggaccggg atggccacat caagattgcc gactttggga tgtgcaaaga gaacatattc     1860
ggggagagcc gggccagcac cttctgcggc acccctgact atatcgcccc tgagatccta     1920
cagggcctga gtacacatt tctctgtggac tggtggtctt tcgggtcct tctgtacgag      1980
atgctcattg gccagtcccc cttccatggt gatgatgagg atgaactctt cgagtccatc     2040
cgtgtggaca cgccacatta tccccgctgg atcaccaagg agtccaagga catcctggag     2100
aagctctttg aaagggaacc aaccaagagg ctgggagtga cgggaaacat caaaatccac     2160
cccttcttca agaccataaa ctggactctg ctggaaaagc ggaggttgga gccacccttc     2220
aggcccaaag tgaagtcacc cagagactac agtaactttg accaggagtt cctgaacgag     2280
aaggcgcgcc tctcctacag cgacaagaac ctcatcgact ccatggacca gtctgcattc     2340
gctggcttct cctttgtgaa ccccaaattc gagcacctcc tggaagatta g              2391
```

<210> SEQ ID NO 47
<211> LENGTH: 2397
<212> TYPE: DNA
<213> ORGANISM: Artificial Sequence
<220> FEATURE:
<223> OTHER INFORMATION: Synthetic sequence, nt sequence of sensor 11
      [G21-19]

<400> SEQUENCE: 47

-continued

```
atggaggacg tggattgcaa acagtctatg cgcagtgagg acgaggccaa gttcccaacg      60
atgaaccgcc gcggagccat caaacaggcc aaaatccacc tcgagaacgt ctatatcaag     120
gccgacaagc agaagaacgg catcaaggcg aacttcaaga tccgccacaa catcgaggac     180
ggcggcgtgc agctcgccta ccactaccag cagaacaccc ccatcggcga cggcccgtg      240
ctgctgcccg acaaccacta cctgagcgtg cagtccatac tttcgaaaga ccccaacgag     300
aagcgcgatc acatggtcct gctggagttc gtgaccgccg ccgggatcac tctcggcatg     360
gacgagctgt acaagggcgg taccggaggg agcatggtga gcaagggcga ggagctgttc     420
accggggtgg tgcccatcca ggtcgagctg gacggcgacg taaacggcca caagttcagc     480
gtgtccggcg agggtgaggg cgatgccacc tacggcaagc tgaccctgaa gttcatctgc     540
accaccggca agctgcccgt gccctggccc accctcgtga ccaccctgac ctacggcgtg     600
cagtgcttca gccgctaccc cgaccacatg aagcagcacg acttcttcaa gtccgccatg     660
cccgaaggct acatccagga gcgcaccatc ttcttcaagg acgacggcaa ctacaagacc     720
cgcgccgagg tgaagttcga gggcgacacc ctggtgaacc gcatcgagct gaagggcatc     780
gacttcaagg aggacggcaa catcctgggg cacaagctgg agtacaacac gcgtaagaac     840
catgagttta tcgccacctt ctttgggcaa cccaccttct gttctgtgtg caaagacttt     900
gtctggggcc tcaacaagca aggctacaaa tgcaggcaat gtaacgctgc catccacaag     960
aaatgcatcg acaagatcat cggcagatgc actggcaccg cggccaacag ccgggacact    1020
atattccaga aagaacgctt caacatcgac atgccgcacc gcttcaaggt tcacaactac    1080
atgagcccca ccttctgtga ccactgcggc agcctgctct ggggactggt gaagcaggga    1140
ttaaagtgtg aagactgcgg catgaatgtg caccataaat gccgggagaa ggtggccaac    1200
ctctgcggca tcaaccagaa gcttttggct gaggccttga accaagtcac ccagagagcc    1260
tcccggagat cagactcagc ctcctcagag cctgttggga tatatcaggg tttcgagaag    1320
aagaccggag ttgctgggga ggacatgcaa gacaacagtg ggacctacgg caagatctgg    1380
gagggcagca gcaagtgcaa catcaacaac ttcatcttcc acaaggtcct gggcaaaggc    1440
agcttcggga aggtgctgct ggagagctg aagggcagag gagagtactt tgccatcaag    1500
gccctcaaga aggatgtggt cctgatcgac gacgacgtgg agtgcaccat ggttgagaag    1560
cgggtgctga cacttgccgc agagaatccc tttctcaccc acctcatctg caccttccag    1620
accaaggacc acctgttctt tgtgatggag ttcctcaacg gggggaccct gatgtaccac    1680
atccaggaca aaggccgctt tgaactctac cgtgccacgt tttatgccgc tgagataatg    1740
tgtggactgc agtttctaca cagcaagggc atcatttaca gggacctcaa actggacaat    1800
gtgctgttgg accgggatgg ccacatcaag attgccgact tgggatgtg caaagagaac    1860
atattcgggg agagccgggc cagcaccttc tgcggcaccc ctgactatat cgcccctgag    1920
atcctacagg gcctgaagta cacattctct gtggactggt ggtctttcgg ggtccttctg    1980
tacgagatgc tcattggcca gtccccctc catggtgatg atgaggatga actcttcgag    2040
tccatccgtg tggacacgcc acattatccc cgctggatca ccaaggagtc caaggacatc    2100
ctggagaagc tctttgaaag gaaccaacc aagaggctgg gagtgacggg aaacatcaaa    2160
atccacccct tcttcaagac cataaactgg actctgctgg aaaagcggag gttggagcca    2220
cccttcaggc ccaaagtgaa gtcacccaga gactacagta actttgacca ggagttcctg    2280
aacgagaagg cgcgcctctc ctacagcgac aagaacctca tcgactccat ggaccagtct    2340
gcattcgctg gcttctcctt tgtgaacccc aaattcgagc acctcctgga agattag       2397
```

<210> SEQ ID NO 48
<211> LENGTH: 2400
<212> TYPE: DNA
<213> ORGANISM: Artificial Sequence
<220> FEATURE:
<223> OTHER INFORMATION: Synthetic sequence, nt sequence of sensor 12
      [G21-20]

<400> SEQUENCE: 48

```
atggaggacg tggattgcaa acagtctatg cgcagtgagg acgaggccaa gttcccaacg      60
atgaaccgcc gcggagccat caaacaggcc aaaatccacc tcgagaacgt ctatatcaag     120
gccgacaagc agaagaacgg catcaaggcg aacttcaaga tccgccacaa catcgaggac     180
ggcggcgtgc agctcgccta ccactaccag cagaacaccc ccatcggcga cggcccgtg      240
ctgctgcccg acaaccacta cctgagcgtg cagtccatac tttcgaaaga ccccaacgag     300
aagcgcgatc acatggtcct gctggagttc gtgaccgccg ccgggatcac tctcggcatg     360
gacgagctgt acaagggcgg taccggaggg agcatggtga gcaagggcga ggagctgttc     420
accggggtgg tgcccatcca ggtcgagctg acggcgacg taaacggcca caagttcagc     480
gtgtccggcg agggtgaggg cgatgccacc tacggcaagc tgaccctgaa gttcatctgc     540
accaccggca gctgcccgt gccctggccc accctcgtga ccaccctgac ctacggcgtg     600
cagtgcttca gccgctaccc cgaccacatg aagcagcacg acttcttcaa gtccgccatg     660
cccgaaggct acatccagga gcgcaccatc ttcttcaagg acgacggcaa ctacaagacc     720
cgcgccgagg tgaagttcga gggcgacacc ctggtgaacc gcatcgagct gaagggcatc     780
gacttcaagg aggacggcaa catcctgggg cacaagctgg agtacaacac gcgtatcaag     840
aaccatgagt ttatcgccac cttctttggg caacccacct tctgttctgt gtgcaaagac     900
tttgtctggg gcctcaacaa gcaaggctac aaatgcaggc aatgtaacgc tgccatccac     960
aagaaatgca tcgacaagat catcggcaga tgcactggca ccgcggccaa cagccggac     1020
actatattcc agaaagaacg cttcaacatc gacatgccgc accgcttcaa ggttcacaac    1080
tacatgagcc ccaccttctg tgaccactgc ggcagcctgc tctggggact ggtgaagcag    1140
ggattaaagt gtgaagactg cggcatgaat gtgcaccata aatgccggga aaggtggcc    1200
aacctctgcg gcatcaacca gaagcttttg gctgaggcct tgaaccaagt cacccagaga    1260
gcctcccgga gatcagactc agcctcctca gagcctgttg gatatatca gggtttcgag    1320
aagaagaccg gagttgctgg ggaggacatg caagacaaca gtgggaccta cggcaagatc    1380
tgggagggca gcagcaagtg caacatcaac aacttcatct tccacaaggt cctgggcaaa    1440
ggcagcttcg ggaaggtgct gcttggagag ctgaagggca gagggagta ctttgccatc    1500
aaggccctca gaaggatgt ggtcctgatc gacgacgacg tggagtgcac catggttgag    1560
aagcgggtgc tgacacttgc cgcagagaat ccctttctca cccacctcat ctgcaccttc    1620
cagaccaagg accacctgtt ctttgtgatg gagttcctca cgggggggga cctgatgtac    1680
cacatccagg acaaaggccg ctttgaactc taccgtgcca cgtttatgc cgctgagata    1740
atgtgtggac tgcagtttct acacagcaag ggcatcattt acagggacct caaactggac    1800
aatgtgctgt ggaccggga tggccacatc aagattgccg actttgggat gtgcaaagag    1860
aacatattcg gggagagccg ggccagcacc ttctgcggca ccctgactat atcgcccct    1920
gagatcctac agggcctgaa gtacacattc tctgtggact ggtggtcttt cggggtcctt    1980
ctgtacgaga tgctcattgg ccagtccccc ttccatggtg atgatgagga tgaactcttc    2040
```

```
gagtccatcc gtgtggacac gccacattat ccccgctgga tcaccaagga gtccaaggac    2100
atcctggaga agctctttga aagggaacca accaagaggc tgggagtgac gggaaacatc    2160
aaaatccacc ccttcttcaa gaccataaac tggactctgc tggaaaagcg gaggttggag    2220
ccacccttca ggcccaaagt gaagtcaccc agagactaca gtaactttga ccaggagttc    2280
ctgaacgaga aggcgcgcct ctcctacagc gacaagaacc tcatcgactc catggaccag    2340
tctgcattcg ctggcttctc ctttgtgaac cccaaattcg agcacctcct ggaagattag    2400
```

<210> SEQ ID NO 49
<211> LENGTH: 2409
<212> TYPE: DNA
<213> ORGANISM: Artificial Sequence
<220> FEATURE:
<223> OTHER INFORMATION: Synthetic sequence, nt sequence of sensor 13
      [G21-23]

<400> SEQUENCE: 49

```
atggaggacg tggattgcaa acagtctatg cgcagtgagg acgaggccaa gttcccaacg      60
atgaaccgcc gcggagccat caaacaggcc aaaatccacc tcgagaacgt ctatatcaag     120
gccgacaagc agaagaacgg catcaaggcg aacttcaaga tccgccacaa catcgaggac     180
ggcggcgtgc agctcgccta ccactaccag cagaacaccc ccatcggcga cggccccgtg     240
ctgctgcccg acaaccacta cctgagcgtg cagtccatac tttcgaaaga ccccaacgag     300
aagcgcgatc acatggtcct gctggagttc gtgaccgccg ccgggatcac tctcggcatg     360
gacgagctgt acaagggcgg taccggaggg agcatggtga gcaagggcga ggagctgttc     420
accggggtgg tgcccatcca ggtcgagctg gacggcgacg taaacggcca agttcagc      480 gtgtccggcg agggtgaggg cgatgccacc tacggcaagc tgaccctgaa gttcatctgc     540
accaccggca agctgcccgt gccctggccc accctcgtga ccaccctgac ctacggcgtg     600
cagtgcttca ccgctacccc cgaccacatg aagcagcacg acttcttcaa gtccgccatg     660
cccgaaggct acatccagga gcgcaccatc ttcttcaagg acgacggcaa ctacaagacc     720
cgcgccgagg tgaagttcga gggcgacacc ctggtgaacc gcatcgagct gaagggcatc     780
gacttcaagg aggacggcaa catcctgggg cacaagctgg agtacaacac gcgtatccac     840
tacatcaaga accatgagtt tatcgccacc ttctttgggc aacccacctt ctgttctgtg     900
tgcaaagact ttgtctgggg cctcaacaag caaggctaca atgcaggca atgtaacgct     960 gccatccaca gaaatgcat cgacaagatc atcggcagat gcactggcac cgcggccaac    1020
agccgggaca ctatattcca gaaagaacgc ttcaacatcg acatgccgca ccgcttcaag    1080
gttcacaact acatgagccc caccttctgt gaccactgcg gcagcctgct ctggggactg    1140
gtgaagcagg gattaaagtg tgaagactgc ggcatgaatg tgcaccataa atgccgggag    1200
aaggtggcca acctctgcgg catcaaccag aagcttttgg ctgaggcctt gaaccaagtc    1260
acccagagag cctcccggag atcagactca gcctcctcag agcctgttgg gatatatcag    1320
ggtttcgaga agaagaccgg agttgctggg gaggacatgc aagacaacag tgggacctac    1380
ggcaagatct gggagggcag cagcaagtgc aacatcaaca acttcatctt ccacaaggtc    1440
ctgggcaaag gcagcttcgg aaaggtgctg cttggagagc tgaagggcag aggagagtac    1500
tttgccatca aggcccctcaa gaaggatgtg gtcctgatcg acgacgacgt ggagtgcacc    1560
atggttgaga agcgggtgct gacacttgcc gcagagaatc cctttctcac ccacctcatc    1620
tgcaccttcc agaccaagga ccacctgttc tttgtgatgg agttcctcaa cggggggac    1680
```

```
ctgatgtacc acatccagga caaaggccgc tttgaactct accgtgccac gttttatgcc    1740
gctgagataa tgtgtggact gcagtttcta cacagcaagg gcatcattta cagggacctc    1800
aaactggaca atgtgctgtt ggaccgggat ggccacatca agattgccga ctttgggatg    1860
tgcaaagaga acatattcgg ggagagccgg gccagcacct tctgcggcac ccctgactat    1920 atcgccctg agatcctaca gggcctgaag tacacattct ctgtggactg gtggtctttc    1980
ggggtccttc tgtacgagat gctcattggc cagtccccct tccatggtga tgatgaggat    2040
gaactcttcg agtccatccg tgtggacacg ccacattatc cccgctggat caccaaggag    2100
tccaaggaca tcctggagaa gctctttgaa agggaaccaa ccaagaggct gggagtgacg    2160
ggaaacatca aaatccaccc cttcttcaag accataaact ggactctgct ggaaaagcgg    2220
aggttggagc cacccttcag gcccaaagtg aagtcaccca gagactacag taactttgac    2280
caggagttcc tgaacgagaa ggcgcgcctc tcctacagcg acaagaacct catcgactcc    2340
atggaccagt ctgcattcgc tggcttctcc tttgtgaacc ccaaattcga gcacctcctg    2400
gaagattag                                                            2409

<210> SEQ ID NO 50
<211> LENGTH: 2403
<212> TYPE: DNA
<213> ORGANISM: Artificial Sequence
<220> FEATURE:
<223> OTHER INFORMATION: Synthetic sequence, nt sequence of sensor 14
      [G23]

<400> SEQUENCE: 50
atggaggacg tggattgcaa acagtctatg cgcagtgagg acgaggccaa gttcccaacg      60
atgaaccgcc gcggagccat caaacaggcc aaactcgaga acgtctatat caaggccgac    120
aagcagaaga acggcatcaa ggcgaacttc aagatccgcc acaacatcga ggacggcggc    180
gtgcagctcg cctaccacta ccagcagaac acccccatcg gcgacggccc cgtgctgctg    240
cccgacaacc actacctgag cgtgcagtcc atactttcga agaccccaa cgagaagcgc    300 gatcacatgg tcctgctgga gttcgtgacc gccgccggga tcactctcgg catggacgag    360
ctgtacaagg gcggtaccgg agggagcatg gtgagcaagg gcgaggagct gttcaccggg    420
gtggtgccca tccaggtcga gctggacggc gacgtaaacg gccacaagtt cagcgtgtcc    480
ggcgagggtg agggcgatgc cacctacggc aagctgaccc tgaagttcat ctgcaccacc    540
ggcaagctgc ccgtgccctg gcccaccctc gtgaccaccc tgacctacgg cgtgcagtgc    600
ttcagccgct acccgacca catgaagcag cacgacttct tcaagtccgc catgcccgaa    660
ggctacatcc aggagcgcac catcttcttc aaggacgacg gcaactacaa gacccgcgcc    720
gaggtgaagt tcgagggcga cacctggtg aaccgcatcg agctgaaggg catcgacttc    780
aaggaggacg gcaacatcct ggggcacaag ctggagtaca cacgcgtat ccactacatc    840 aagaaccatg agtttatcgc caccttcttt gggcaaccca ccttctgttc tgtgtgcaaa    900
gactttgtct ggggcctcaa caagcaaggc tacaaatgca ggcaatgtaa cgctgccatc    960
cacaagaaat gcatcgacaa gatcatcggc agatgcactg gcaccgcggc caacagccgg   1020
gacactatat tccagaaaga acgcttcaac atcgacatgc cgcaccgctt caaggttcac   1080
aactacatga gccccacctt ctgtgaccac tgcggcagcc tgctctgggg actggtgaag   1140
cagggattaa agtgtgaaga ctgcggcatg aatgtgcacc ataaatgccg ggagaaggtg   1200
gccaacctct gcggcatcaa ccagaagctt ttggctgagg ccttgaacca agtcaccag   1260
```

```
agagcctccc ggagatcaga ctcagcctcc tcagagcctg ttgggatata tcagggtttc    1320
gagaagaaga ccggagttgc tggggaggac atgcaagaca acagtgggac ctacggcaag    1380
atctgggagg gcagcagcaa gtgcaacatc aacaacttca tcttccacaa ggtcctgggc    1440
aaaggcagct tcgggaaggt gctgcttgga gagctgaagg gcagaggaga gtactttgcc    1500
atcaaggccc tcaagaagga tgtggtcctg atcgacgacg acgtggagtg caccatggtt    1560
gagaagcggg tgctgacact tgccgcagag aatccctttc tcacccacct catctgcacc    1620
ttccagacca aggaccacct gttctttgtg atggagttcc tcaacggggg ggacctgatg    1680
taccacatcc aggacaaagg ccgctttgaa ctctaccgtg ccacgtttta tgccgctgag    1740
ataatgtgtg gactgcagtt tctacacagc aagggcatca tttacaggga cctcaaactg    1800
gacaatgtgc tgttggaccg ggatggccac atcaagattg ccgactttgg gatgtgcaaa    1860
gagaacatat tcggggagag ccgggccagc accttctgcg gcaccnctga ctatatcgcc    1920
cctgagatcc tacagggcct gaagtacaca ttctctgtgg actggtggtc tttcggggtc    1980
cttctgtacg agatgctcat tggccagtcc cccttccatg gtgatgatga ggatgaactc    2040
ttcgagtcca tccgtgtgga cacgccacat tatccccgct ggatcaccaa ggagtccaag    2100
gacatcctgg agaagctctt tgaaagggaa ccaaccaaga ggctgggagt gacgggaaac    2160
atcaaaatcc acccttctt caagaccata aactggactc tgctggaaaa gcggaggttg    2220
gagccaccct tcaggcccaa agtgaagtca cccagagact acagtaactt tgaccaggag    2280
ttcctgaacg agaaggcgcg cctctcctac agcgacaaga acctcatcga ctccatggac    2340
cagtctgcat tcgctggctt ctcctttgtg aaccccaaat tcgagcacct cctggaagat    2400
tag                                                                  2403
```

<210> SEQ ID NO 51
<211> LENGTH: 2388
<212> TYPE: DNA
<213> ORGANISM: Artificial Sequence
<220> FEATURE:
<223> OTHER INFORMATION: Synthetic sequence, nt sequence of sensor 15
      [G23-18]

<400> SEQUENCE: 51

```
atggaggacg tggattgcaa acagtctatg cgcagtgagg acgaggccaa gttcccaacg      60
atgaaccgcc gcggagccat caaacaggcc aaactcgaga acgtctatat caaggccgac    120
aagcagaaga acggcatcaa ggcgaacttc aagatccgcc acaacatcga ggacggcggc    180
gtgcagctcg cctaccacta ccagcagaac acccccatcg gcgacggccc cgtgctgctg    240
cccgacaacc actacctgag cgtgcagtcc atactttcga agacccccaa cgagaagcgc    300
gatcacatgg tcctgctgga gttcgtgacc gccgcggga tcactctcgg catggacgag    360
ctgtacaagg gcgtaccgg agggagcatg gtgagcaagg gcgaggagct gttcaccggg    420
gtggtgccca tccaggtcga gctggacggc gacgtaaacg gccacaagtt cagcgtgtcc    480
ggcgagggtg agggcgatgc cacctacggc aagctgaccc tgaagttcat ctgcaccacc    540
ggcaagctgc ccgtgccctg gcccaccctc gtgaccaccc tgacctacgg cgtgcagtgc    600
ttcagccgct accccgacca catgaagcag cacgacttct tcaagtccgc catgcccgaa    660
ggctacatcc aggagcgcac catcttcttc aaggacgacg gcaactacaa gacccgcgcc    720
gaggtgaagt tcgagggcga cacgctggtg aaccgcatcg agctgaaggg catcgacttc    780
aaggaggacg gcaacatcct ggggcacaag ctggagtaca acacgcgtaa ccatgagttt    840
```

```
atcgccacct tctttgggca acccaccttc tgttctgtgt gcaaagactt tgtctggggc    900
ctcaacaagc aaggctacaa atgcaggcaa tgtaacgctg ccatccacaa gaaatgcatc    960
gacaagatca tcggcagatg cactggcacc gcggccaaca gccgggacac tatattccag   1020
aaagaacgct tcaacatcga catgccgcac cgcttcaagg ttcacaacta catgagcccc   1080
accttctgtg accactgcgg cagcctgctc tggggactgg tgaagcaggg attaaagtgt   1140
gaagactgcg gcatgaatgt gcaccataaa tgccgggaga aggtggccaa cctctgcggc   1200
atcaaccaga agcttttggc tgaggccttg aaccaagtca cccagagagc ctcccggaga   1260
tcagactcag cctcctcaga gcctgttggg atatatcagg gtttcgagaa gaagaccgga   1320
gttgctgggg aggacatgca agacaacagt gggacctacg gcaagatctg ggagggcagc   1380
agcaagtgca acatcaacaa cttcatcttc cacaaggtcc tgggcaaagg cagcttcggg   1440
aaggtgctgc ttggagagct gaagggcaga ggagagtact ttgccatcaa ggccctcaag   1500
aaggatgtgg tcctgatcga cgacgacgtg gagtgcacca tggttgagaa gcgggtgctg   1560
acacttgccg cagagaatcc ctttctcacc cacctcatct gcaccttcca gaccaaggac   1620
cacctgttct ttgtgatgga gttcctcaac gggggggacc tgatgtacca catccaggac   1680
aaaggccgct ttgaactcta ccgtgccacg ttttatgccg ctgagataat gtgtggactg   1740
cagtttctac acagcaaggg catcatttac agggacctca aactggacaa tgtgctgttg   1800
gaccgggatg gccacatcaa gattgccgac tttgggatgt gcaaagagaa catattcggg   1860
gagagccggg ccagcacctt ctgcggcacc cctgactata tcgcccctga gatcctacag   1920
ggcctgaagt acacattctc tgtggactgg tggtctttcg gggtccttct gtacgagatg   1980
ctcattggcc agtcccccct tccatggtgat gatgaggatg aactcttcga gtccatccgt   2040
gtggacacgc cacattatcc ccgctggatc accaaggagt ccaaggacat cctggagaag   2100
ctctttgaaa gggaaccaac caagaggctg ggagtgacgg gaaacatcaa aatccacccc   2160
ttcttcaaga ccataaactg gactctgctg gaaaagcgga ggttggagcc acccttcagg   2220
cccaaagtga agtcacccag agactacagt aactttgacc aggagttcct gaacgagaag   2280
gcgcgcctct cctacagcga caagaacctc atcgactcca tggaccagtc tgcattcgct   2340
ggcttctcct tgtgaacccc caaattcgag cacctcctgg aagattag              2388
```

<210> SEQ ID NO 52
<211> LENGTH: 2391
<212> TYPE: DNA
<213> ORGANISM: Artificial Sequence
<220> FEATURE:
<223> OTHER INFORMATION: Synthetic sequence, nt sequence of sensor 16
      [G23-19]

<400> SEQUENCE: 52

```
atggaggacg tggattgcaa acagtctatg cgcagtgagg acgaggccaa gttcccaacg    60
atgaaccgcc gcggagccat caaacaggcc aaactcgaga acgtctatat caaggccgac   120
aagcagaaga acggcatcaa ggcgaacttc aagatccgcc acaacatcga ggacggcggc   180
gtgcagctcg cctaccacta ccagcagaac accccccatcg gcgacggccc cgtgctgctg   240
cccgacaacc actacctgag cgtgcagtcc atactttcga agaccccaa cgagaagcgc   300 gatcacatgg tcctgctgga gttcgtgacc gccgccggga tcactctcgg catggacgag   360
ctgtacaagg gcgtaccggg agggagcatg gtgagcaagg gcgaggagct gttcaccggg   420
gtggtgccca tccaggtcga gctggacggc gacgtaaacg gccacaagtt cagcgtgtcc   480
```

```
ggcgagggtg agggcgatgc cacctacggc aagctgaccc tgaagttcat ctgcaccacc      540
ggcaagctgc ccgtgccctg gcccaccctc gtgaccaccc tgacctacgg cgtgcagtgc      600
ttcagccgct accccgacca catgaagcag cacgacttct tcaagtccgc catgcccgaa      660
ggctacatcc aggagcgcac catcttcttc aaggacgacg gcaactacaa gacccgcgcc      720
gaggtgaagt tcgagggcga caccctggtg aaccgcatcg agctgaaggg catcgacttc      780
aaggaggacg gcaacatcct ggggcacaag ctggagtaca cacgcgtaa gaaccatgag      840 tttatcgcca ccttctttgg gcaacccacc ttctgttctg tgtgcaaaga ctttgtctgg      900
ggcctcaaca gcaaggcta caaatgcagg caatgtaacg ctgccatcca agaaatgc       960 atcgacaaga tcatcggcag atgcactggc accgcggcca acagccggga cactatattc     1020
cagaaagaac gcttcaacat cgacatgccg caccgcttca aggttcacaa ctacatgagc    1080
cccaccttct gtgaccactg cggcagcctg ctctggggac tggtgaagca gggattaaag     1140
tgtgaagact gcggcatgaa tgtgcaccat aaatgccggg agaaggtggc caacctctgc     1200
ggcatcaacc agaagctttt ggctgaggcc ttgaaccaag tcacccagag agcctcccgg    1260
agatcagact cagcctcctc agagcctgtt gggatatatc agggtttcga agaagacc       1320 ggagttgctg gggaggacat gcaagacaac agtgggacct acggcaagat ctgggagggc    1380
agcagcaagt gcaacatcaa caacttcatc ttccacaagg tcctgggcaa aggcagcttc    1440
gggaaggtgc tgcttggaga gctgaagggc agaggagagt actttgccat caaggccctc    1500
aagaaggatg tggtcctgat cgacgacgac gtggagtgca ccatggttga aagcgggtg     1560 ctgacacttg ccgcagagaa tccctttctc acccacctca tctgcacctt ccagaccaag   1620
gaccacctgt tctttgtgat ggagttcctc aacgggggg acctgatgta ccacatccag     1680
gacaaaggcc gctttgaact ctaccgtgcc acgtttatg ccgctgagat aatgtgtgga     1740
ctgcagtttc tacacagcaa gggcatcatt tacaggaccc tcaaactgga caatgtgctg     1800
ttggaccggg atggccacat caagattgcc gactttggga tgtgcaaaga gaacatattc    1860
ggggagagcc gggccagcac cttctgcggc acccctgact atatcgcccc tgagatccta   1920
cagggcctga agtacacatt tctctgtgga ctggtggtctt tcgggtcct tctgtacgag    1980 atgctcattg ccagtccccc cttccatggt gatgatgagg atgaactctt cgagtccatc    2040
cgtgtggaca cgccacatta tccccgctgg atcaccaagg agtccaagga catcctggag    2100
aagctctttg aaagggaacc aaccaagagg ctgggagtga cgggaaacat caaaatccac    2160 ccttcttca agaccataaa ctggactctg ctggaaaagc ggaggttgga gccacccttc      2220 aggccaaag tgaagtcacc cagagactac agtaactttg accaggagtt cctgaacgag     2280
aaggcgcgcc tctcctacag cgacaagaac ctcatcgact ccatggacca gtctgcattc    2340
gctggcttct cctttgtgaa ccccaaattc gagcacctcc tggaagatta g             2391

<210> SEQ ID NO 53
<211> LENGTH: 2421
<212> TYPE: DNA
<213> ORGANISM: Artificial Sequence
<220> FEATURE:
<223> OTHER INFORMATION: Synthetic sequence, nt sequence of sensor 17
      [G27-19]

<400> SEQUENCE: 53
atggaggacg tggattgcaa acagtctatg cgcagtgagg acgaggccaa gttcccaacg      60
atgaaccgcc gcggagccat caaacaggcc aaaatccact acatcaagaa ccatgagttt     120
```

```
atcctcgaga acgtctatat caaggccgac aagcagaaga acggcatcaa ggcgaacttc      180
aagatccgcc acaacatcga ggacggcggc gtgcagctcg cctaccacta ccagcagaac      240 accccatcg gcgacggccc cgtgctgctg cccgacaacc actacctgag cgtgcagtcc      300
atactttcga aagaccccaa cgagaagcgc gatcacatgg tcctgctgga gttcgtgacc      360
gccgccggga tcactctcgg catggacgag ctgtacaagg cggtaccgg agggagcatg      420 gtgagcaagg gcgaggagct gttcaccggg gtggtgccca tccaggtcga gctgacggc       480 gacgtaaacg gccacaagtt cagcgtgtcc ggcgagggtg agggcgatgc cacctacggc      540
aagctgaccc tgaagttcat ctgcaccacc ggcaagctgc ccgtgccctg cccaccctc       600 gtgaccaccc tgacctacgg cgtgcagtgc ttcagccgct accccgacca catgaagcag      660
cacgacttct tcaagtccgc catgcccgaa ggctacatcc aggagcgcac catcttcttc      720
aaggacgacg gcaactacaa gacccgcgcc gaggtgaagt tcgagggcga caccctggtg      780
aaccgcatcg agctgaaggg catcgacttc aaggaggacg gcaacatcct ggggcacaag      840
ctggagtaca acacgcgtaa gaaccatgag tttatcgcca ccttctttgg caacccacc       900 ttctgttctg tgtgcaaaga cttgtctgg ggcctcaaca gcaaggcta caaatgcagg        960 caatgtaacg ctgccatcca caagaaatgc atcgacaaga tcatcggcag atgcactggc     1020
accgcggcca acagccggga cactatattc cagaaagaac gcttcaacat cgacatgccg     1080
caccgcttca aggttcacaa ctacatgagc cccaccttct gtgaccactg cggcagcctg     1140
ctctggggac tggtgaagca gggattaaag tgtgaagact gcggcatgaa tgtgcaccat     1200
aaatgccggg agaaggtggc caacctctgc ggcatcaacc agaagctttt ggctgaggcc     1260
ttgaaccaag tcacccagag agcctcccgg agatcagact cagcctcctc agagcctgtt     1320
gggatatatc agggtttcga agaagacc ggagttgctg ggaggacat gcaagacaac        1380 agtgggacct acggcaagat ctgggagggc agcagcaagt gcaacatcaa caacttcatc     1440
ttccacaagg tcctgggcaa aggcagcttc gggaaggtgc tgcttggaga gctgaagggc     1500
agaggagagt actttgccat caaggccctc aagaaggatg tggtcctgat cgacgacgac     1560
gtggagtgca ccatggttga gaagcgggtg ctgacacttg ccgcagagaa tccctttctc     1620
acccacctca tctgcacctt ccagaccaag gaccacctgt tctttgtgat ggagttcctc     1680 aacgggggg acctgatgta ccacatccag gacaaaggcc gctttgaact ctaccgtgcc     1740
acgttttatg ccgctgagat aatgtgtgga ctgcagtttc tacacagcaa gggcatcatt     1800
tacagggacc tcaaactgga caatgtgctg ttggaccggg atggccacat caagattgcc     1860
gactttggga tgtgcaaaga gaacatattc ggggagagcc gggccagcac cttctgcggc     1920 accccctgact atatcgcccc tgagatccta cagggcctga gtacacatt tctctgtggac     1980 tggtggtctt tcggggtcct tctgtacgag atgctcattg ccagtccccc cttccatggt    2040
gatgatgagg atgaactctt cgagtccatc cgtgtggaca cgccacatta tccccgctgg    2100
atcaccaagg agtccaagga catcctggag aagctctttg aaagggaacc aaccaagagg    2160 ctggagtga cggaaacat caaaatccac cccttcttca agaccataaa ctggactctg       2220
ctggaaaagc ggaggttgga gccacccttc aggcccaaag tgaagtcacc cagagactac    2280
agtaactttg accaggagtt cctgaacgag aaggcgcgcc tctcctacag cgacaagaac    2340
ctcatcgact ccatggacca gtctgcattc gctggcttct ccttgtgaa ccccaaattc      2400 gagcacctcc tggaagatta g                                               2421
```

<210> SEQ ID NO 54
<211> LENGTH: 2430
<212> TYPE: DNA
<213> ORGANISM: Artificial Sequence
<220> FEATURE:
<223> OTHER INFORMATION: Synthetic sequence, nt sequence of sensor 18
      [G27-22]

<400> SEQUENCE: 54

| | | | | |
|---|---|---|---|---|
| atggaggacg | tggattgcaa | acagtctatg | cgcagtgagg | acgaggccaa   gttcccaacg      60 |
| atgaaccgcc | gcggagccat | caaacaggcc | aaaatccact | acatcaagaa   ccatgagttt     120 |
| atcctcgaga | acgtctatat | caaggccgac | aagcagaaga | acggcatcaa   ggcgaacttc     180 |
| aagatccgcc | acaacatcga | ggacggcggc | gtgcagctcg | cctaccacta   ccagcagaac     240 |
| accccccatcg | gcgacggccc | cgtgctgctg | cccgacaacc | actacctgag   cgtgcagtcc     300 |
| atactttcga | aagaccccaa | cgagaagcgc | gatcacatgg | tcctgctgga   gttcgtgacc     360 |
| gccgccggga | tcactctcgg | catggacgag | ctgtacaagg | gcggtaccgg   agggagcatg     420 |
| gtgagcaagg | gcgaggagct | gttcaccggg | gtggtgccca | tccaggtcga   gctggacggc     480 |
| gacgtaaacg | gccacaagtt | cagcgtgtcc | ggcgagggtg | agggcgatgc   cacctacggc     540 |
| aagctgaccc | tgaagttcat | ctgcaccacc | ggcaagctgc | ccgtgccctg   gcccacctc      600 |
| gtgaccaccc | tgacctacgg | cgtgcagtgc | ttcagccgct | accccgacca   catgaagcag     660 |
| cacgacttct | tcaagtccgc | catgcccgaa | ggctacatcc | aggagcgcac   catcttcttc     720 |
| aaggacgacg | gcaactacaa | gacccgcgcc | gaggtgaagt | tcgagggcga   cacccctggtg    780 |
| aaccgcatcg | agctgaaggg | catcgacttc | aaggaggacg | gcaacatcct   ggggcacaag     840 |
| ctggagtaca | acacgcgtca | ctacatcaag | aaccatgagt | ttatcgccac   cttctttggg     900 |
| caacccacct | tctgttctgt | gtgcaaagac | tttgtctggg | gcctcaacaa   gcaaggctac     960 |
| aaatgcaggc | aatgtaacgc | tgccatccac | aagaaatgca | tcgacaagat   catcggcaga    1020 |
| tgcactggca | ccgcggccaa | cagccgggac | actatattcc | agaaagaacg   cttcaacatc    1080 |
| gacatgccgc | accgcttcaa | ggttcacaac | tacatgagcc | ccaccttctg   tgaccactgc    1140 |
| ggcagcctgc | tctggggact | ggtgaagcag | ggattaaagt | gtgaagactg   cggcatgaat    1200 |
| gtgcaccata | atgccgggga | aaggtggcc  | aacctctgcg | gcatcaacca   gaagcttttg    1260 |
| gctgaggcct | tgaaccaagt | cacccagaga | gcctcccgga | gatcagactc   agcctcctca    1320 |
| gagcctgttg | ggatatatca | gggtttcgag | aagaagaccg | gagttgctgg   ggaggacatg    1380 |
| caagacaaca | gtgggaccta | cggcaagatc | tgggagggca | gcagcaagtg   caacatcaac    1440 |
| aacttcatct | tccacaaggt | cctgggcaaa | ggcagcttcg | ggaaggtgct   gcttggagag    1500 |
| ctgaagggca | gaggagagta | ctttgccatc | aaggcccctca | agaaggatgt   ggtcctgatc    1560 |
| gacgacgacg | tggagtgcac | catggttgag | aagcgggtgc | tgacacttgc   cgcagagaat    1620 |
| cccttctca | cccacctcat | ctgcaccttc | cagaccaagg | accacctgtt   ctttgtgatg    1680 |
| gagttcctca | acgggggga  | cctgatgtac | cacatccagg | acaaaggccg   ctttgaactc    1740 |
| taccgtgcca | cgttttatgc | cgctgagata | atgtgtggac | tgcagtttct   acacagcaag    1800 |
| ggcatcattt | acagggacct | caaactggac | aatgtgctgt | tggaccggga   tggccacatc    1860 |
| aagattgccg | actttgggat | gtgcaaagag | aacatattcg | gggagagccg   ggccagcacc    1920 |
| ttctgcggca | cccctgacta | tatcgcccct | gagatcctac | agggcctgaa   gtacacattc    1980 |
| tctgtggact | ggtggtcttt | cggggtcctt | ctgtacgaga | tgctcattgg   ccagtccccc    2040 |

```
ttccatggtg atgatgagga tgaactcttc gagtccatcc gtgtggacac gccacattat    2100
ccccgctgga tcaccaagga gtccaaggac atcctggaga agctctttga aagggaacca    2160
accaagaggc tgggagtgac gggaaacatc aaaatccacc ccttcttcaa gaccataaac    2220
tggactctgc tggaaaagcg gaggttggag ccacccttca ggcccaaagt gaagtcaccc    2280
agagactaca gtaactttga ccaggagttc ctgaacgaga aggcgcgcct ctcctacagc    2340
gacaagaacc tcatcgactc catggaccag tctgcattcg ctggcttctc ctttgtgaac    2400
cccaaattcg agcacctcct ggaagattag                                      2430
```

<210> SEQ ID NO 55
<211> LENGTH: 2421
<212> TYPE: DNA
<213> ORGANISM: Artificial Sequence
<220> FEATURE:
<223> OTHER INFORMATION: Synthetic sequence, nt sequence of sensor 19
      [G28-18]

<400> SEQUENCE: 55

```
atggaggacg tggattgcaa acagtctatg cgcagtgagg acgaggccaa gttcccaacg      60
atgaaccgcc gcggagccat caaacaggcc aaaatccact acatcaagaa ccatgagttt    120
atcgccctcg agaacgtcta tatcaaggcc gacaagcaga gaacggcat caaggcgaac    180 ttcaagatcc gccacaacat cgaggacggc ggcgtgcagc tcgcctacca ctaccagcag    240 aacacccca tcggcgacgg ccccgtgctg ctgcccgaca ccactacct gagcgtgcag    300 tccatacttt cgaaagaccc caacgagaag cgcgatcaca tggtcctgct ggagttcgtg    360
accgccgccg ggatcactct cggcatggac gagctgtaca agggcggtac cggagggagc    420
atggtgagca agggcgagga gctgttcacc ggggtggtgc ccatccaggt cgagctggac    480
ggcgacgtaa acggccacaa gttcagcgtg tccggcgagg gtgagggcga tgccacctac    540
ggcaagctga ccctgaagtt catctgcacc accggcaagc tgcccgtgcc ctggcccacc    600
ctcgtgacca cccttgaccta cggcgtgcag tgcttcagcc gctaccccga ccacatgaag    660
cagcacgact tcttcaagtc cgccatgccc gaaggctaca tccaggagcg caccatcttc    720
ttcaaggacg acggcaacta caagacccgc gccgaggtga agttcgaggg cgacaccctg    780
gtgaaccgca tcgagctgaa gggcatcgac ttcaaggagg acggcaacat cctggggcac    840
aagctggagt acaacacgcg taaccatgag tttatcgcca ccttctttgg gcaacccacc    900
ttctgttctg tgtgcaaaga ctttgtctgg ggcctcaaca gcaaggcta caaatgcagg    960 caatgtaacg ctgccatcca agaaatgc atcgacaaga tcatcggcag atgcactggc   1020
accgcggcca acagccggga cactatattc cagaaagaac gcttcaacat cgacatgccg   1080
caccgcttca aggttcacaa ctacatgagc cccaccttct gtgaccactg cggcagcctg   1140
ctctggggac tggtgaagca gggattaaag tgtgaagact gcggcatgaa tgtgcaccat   1200
aaatgccggg agaaggtggc caacctctgc ggcatcaacc agaagctttt ggctgaggcc   1260
ttgaaccaag tcacccagag agcctcccgg agatcagact cagcctcctc agagcctgtt   1320
gggatatatc agggtttcga gaagaagacc ggagttgctg gggaggacat gcaagacaac   1380
agtgggacct acggcaagat ctgggagggc agcagcaagt gcaacatcaa caacttcatc   1440
ttccacaagg tcctgggcaa aggcagcttc gggaaggtgc tgcttggaga gctgaagggc   1500
agaggagagt actttgccat caaggcctc aagaaggatg tggtcctgat cgacgacgac   1560
gtggagtgca ccatggttga aagcgggtg ctgacacttg ccgcagagaa tcccttctctc   1620
```

| | |
|---|---|
| acccacctca tctgcaccttt ccagaccaag gaccacctgt tctttgtgat ggagttcctc | 1680 |
| aacgggggggg acctgatgta ccacatccag gacaaaggcc gctttgaact ctaccgtgcc | 1740 |
| acgttttatg ccgctgagat aatgtgtgga ctgcagtttc tacacagcaa gggcatcatt | 1800 |
| tacagggacc tcaaactgga caatgtgctg ttggaccggg atggccacat caagattgcc | 1860 |
| gactttggga tgtgcaaaga gaacatattc ggggagagcc gggccagcac cttctgcggc | 1920 |
| acccctgact atatcgcccc tgagatccta cagggcctga agtacacatt ctctgtggac | 1980 |
| tggtggtctt tcggggtcct tctgtacgag atgctcattg ccagtccccc cttccatggt | 2040 |
| gatgatgagg atgaactctt cgagtccatc cgtgtggaca cgccacatta tccccgctgg | 2100 |
| atcaccaagg agtccaagga catcctggag aagctctttg aaagggaacc aaccaagagg | 2160 |
| ctgggagtga cggaaacat caaaatccac cccttcttca agaccataaa ctggactctg | 2220 |
| ctggaaaagc ggaggttgga gccacccttc aggcccaaag tgaagtcacc cagagactac | 2280 |
| agtaactttg accaggagtt cctgaacgag aaggcgcgcc tctcctacag cgacaagaac | 2340 |
| ctcatcgact ccatggacca gtctgcattc gctggcttct cctttgtgaa ccccaaattc | 2400 |
| gagcacctcc tggaagatta g | 2421 |

<210> SEQ ID NO 56
<211> LENGTH: 2406
<212> TYPE: DNA
<213> ORGANISM: Artificial Sequence
<220> FEATURE:
<223> OTHER INFORMATION: Synthetic sequence, nt sequence of sensor 20 [G28-27]

<400> SEQUENCE: 56

| | |
|---|---|
| atggaggacg tggattgcaa acagtctatg cgcagtgagg acgaggccaa gttcccaacg | 60 |
| atgaaccgcc gcggagccat caaacaggcc aaaatccact acatcaagaa ccatgagttt | 120 |
| atcgccctcg agaacgtcta tatcaaggcc gacaagcaga gaacggcat caaggcgaac | 180 |
| ttcaagatcc gccacaacat cgaggacggc ggcgtgcagc tcgcctacca ctaccagcag | 240 |
| aacaccccca tcggcgacgg ccccgtgctg ctgcccgaca ccactacct gagcgtgcag | 300 |
| tccatacttt cgaaagaccc caacgagaag cgcgatcaca tggtcctgct ggagttcgtg | 360 |
| accgccgccg ggatcactct cggcatggac gagctgtaca agggcggtac cggagggagc | 420 |
| atggtgagca agggcgagga gctgttcacc ggggtggtgc ccatccaggt cgagctggac | 480 |
| ggcgacgtaa acggccacaa gttcagcgtg tccggcgagg gtgagggcga tgccacctac | 540 |
| ggcaagctga ccctgaagtt catctgcacc accggcaagc tgcccgtgcc ctggcccacc | 600 |
| ctcgtgacca ccctgaccta cggcgtgcag tgcttcagcc gctaccccga ccacatgaag | 660 |
| cagcacgact tcttcaagtc cgccatgccc gaaggctaca tccaggagcg caccatcttc | 720 |
| ttcaaggacg acggcaacta caagaccgc gccgaggtga agttcgaggg cgacaccctg | 780 |
| gtgaaccgca tcgagctgaa gggcatcgac ttcaaggagg acggcaacat cctggggcac | 840 |
| aagctggagt acaacacgcg tgccaccttc tttgggcaac ccaccttctg ttctgtgtgc | 900 |
| aaagactttg tctggggcct caacaagcaa ggctacaaat gcaggcaatg taacgctgcc | 960 |
| atccacaaga aatgcatcga caagatcatc ggcagatgca ctggcaccgc ggccaacagc | 1020 |
| cgggacacta tattccagaa agaacgcttc aacatcgaca tgccgcaccg cttcaaggtt | 1080 |
| cacaactaca tgagcccac cttctgtgac cactgcggca gcctgctctg gggactggtg | 1140 |
| aagcagggat taaagtgtga agactgcggc atgaatgtgc accataaatg ccgggagaag | 1200 |

| | |
|---|---|
| gtggccaacc tctgcggcat caaccagaag cttttggctg aggccttgaa ccaagtcacc | 1260 |
| cagagagcct cccggagatc agactcagcc tcctcagagc ctgttgggat atatcagggt | 1320 |
| ttcgagaaga agaccggagt tgctggggag gacatgcaag acaacagtgg gacctacggc | 1380 |
| aagatctggg agggcagcag caagtgcaac atcaacaact tcatcttcca caaggtcctg | 1440 |
| ggcaaaggca gcttcgggaa ggtgctgctt ggagagctga agggcagagg agagtacttt | 1500 |
| gccatcaagg ccctcaagaa ggatgtggtc ctgatcgacg acgacgtgga gtgcaccatg | 1560 |
| gttgagaagc gggtgctgac acttgccgca gagaatccct ttctcaccca cctcatctgc | 1620 |
| accttccaga ccaaggacca cctgttcttt gtgatggagt tcctcaacgg gggggacctg | 1680 |
| atgtaccaca tccaggacaa aggccgcttt gaactctacc gtgccacgtt ttatgccgct | 1740 |
| gagataatgt gtggactgca gtttctacac agcaagggca tcatttacag ggacctcaaa | 1800 |
| ctggacaatg tgctgttgga ccgggatggc cacatcaaga ttgccgactt tgggatgtgc | 1860 |
| aaagagaaca tattcgggga gagccgggcc agcaccttct gcggcacccc tgactatatc | 1920 |
| gcccctgaga tcctacaggg cctgaagtac acattctctg tggactggtg gtctttcggg | 1980 |
| gtccttctgt acgagatgct cattggccag tccccccttcc atggtgatga tgaggatgaa | 2040 |
| ctcttcgagt ccatccgtgt ggacacgcca cattatcccc gctggatcac caaggagtcc | 2100 |
| aaggacatcc tggagaagct ctttgaaagg gaaccaacca gaggctggg agtgacggga | 2160 |
| aacatcaaaa tccacccctt cttcaagacc ataaactgga ctctgctgga aaagcggagg | 2220 |
| ttggagccac ccttcaggcc caaagtgaag tcacccagag actacagtaa ctttgaccag | 2280 |
| gagttcctga cgagaaggc gcgcctctcc tacagcgaca gaacctcat cgactccatg | 2340 |
| gaccagtctg cattcgctgg cttctccttt gtgaaccca aattcgagca cctcctggaa | 2400 |
| gattag | 2406 |

<210> SEQ ID NO 57
<211> LENGTH: 2424
<212> TYPE: DNA
<213> ORGANISM: Artificial Sequence
<220> FEATURE:
<223> OTHER INFORMATION: Synthetic sequence, nt sequence of sensor 21
      [G29-18]

<400> SEQUENCE: 57

| | |
|---|---|
| atggaggacg tggattgcaa acagtctatg cgcagtgagg acgaggccaa gttcccaacg | 60 |
| atgaaccgcc gcggagccat caaacaggcc aaaatccact acatcaagaa ccatgagttt | 120 |
| atcgccaccc tcgagaacgt ctatatcaag gccgacaagc agaagaacgg catcaaggcg | 180 |
| aacttcaaga tccgccacaa catcgaggac ggcggcgtgc agctcgccta ccactaccag | 240 |
| cagaacaccc ccatcggcga cggccccgtg ctgctgcccg acaaccacta cctgagcgtg | 300 |
| cagtccatac tttcgaaaga ccccaacgag aagcgcgatc acatggtcct gctggagttc | 360 |
| gtgaccgccg ccgggatcac tctcggcatg gacgagctgt acaagggcgg taccggaggg | 420 |
| agcatggtga gcaagggcga ggagctgttc accggggtgg tgcccatcca ggtcgagctg | 480 |
| gacggcgacg taaacggcca caagttcagc gtgtccggcg agggtgaggg cgatgccacc | 540 |
| tacggcaagc tgaccctgaa gttcatctgc accaccggca agctgcccgt gccctggccc | 600 |
| accctcgtga ccaccctgac ctacggcgtg cagtgcttca gccgctaccc cgaccacatg | 660 |
| aagcagcacg acttcttcaa gtccgccatg cccgaaggct acatccagga gcgcaccatc | 720 |
| ttcttcaagg acgacggcaa ctacaagacc cgcgccgagg tgaagttcga gggcgacacc | 780 |

| | |
|---|---|
| ctggtgaacc gcatcgagct gaagggcatc gacttcaagg aggacggcaa catcctgggg | 840 |
| cacaagctgg agtacaacac gcgtaaccat gagtttatcg ccaccttctt tgggcaaccc | 900 |
| accttctgtt ctgtgtgcaa agactttgtc tggggcctca acaagcaagg ctacaaatgc | 960 |
| aggcaatgta acgctgccat ccacaagaaa tgcatcgaca agatcatcgg cagatgcact | 1020 |
| ggcaccgcgg ccaacagccg ggacactata ttccagaaag aacgcttcaa catcgacatg | 1080 |
| ccgcaccgct tcaaggttca caactacatg agccccacct tctgtgacca ctgcggcagc | 1140 |
| ctgctctggg gactggtgaa gcagggatta agtgtgaag actgcggcat gaatgtgcac | 1200 |
| cataaatgcc gggagaaggt ggccaacctc tgcggcatca accagaagct tttggctgag | 1260 |
| gccttgaacc aagtcaccca gagagcctcc cggagatcag actcagcctc ctcagagcct | 1320 |
| gttgggatat atcagggttt cgagaagaag accggagttg ctggggagga catgcaagac | 1380 |
| aacagtggga cctacggcaa gatctgggag ggcagcagca agtgcaacat caacaacttc | 1440 |
| atcttccaca aggtcctggg caaaggcagc ttcgggaagg tgctgcttgg agagctgaag | 1500 |
| ggcagaggag agtactttgc catcaaggcc ctcaagaagg atgtggtcct gatcgacgac | 1560 |
| gacgtggagt gcaccatggt tgagaagcgg gtgctgacac ttgccgcaga gaatcccttt | 1620 |
| ctcacccacc tcatctgcac cttccagacc aaggaccacc tgttctttgt gatggagttc | 1680 |
| ctcaacgggg gggacctgat gtaccacatc caggacaaag ccgctttga actctaccgt | 1740 |
| gccacgtttt atgccgctga gataatgtgt ggactgcagt ttctacacag caagggcatc | 1800 |
| atttacaggg acctcaaact ggacaatgtg ctgttggacc gggatggcca tcaagatt | 1860 |
| gccgactttg ggatgtgcaa agagaacata ttcggggaga gccgggccag caccttctgc | 1920 |
| ggcaccctg actatatcgc ccctgagatc ctacagggcc tgaagtacac attctctgtg | 1980 |
| gactggtggt ctttcggggt ccttctgtac gagatgctca ttggccagtc cccttccat | 2040 |
| ggtgatgatg aggatgaact cttcgagtcc atccgtgtgg acacgccaca ttatccccgc | 2100 |
| tggatcacca aggagtccaa ggacatcctg gagaagctct ttgaaaggga accaaccaag | 2160 |
| aggctgggag tgacgggaaa catcaaaatc cacccttct tcaagaccat aaactggact | 2220 |
| ctgctggaaa gcggaggtt ggagccaccc ttcaggccca agtgaagtc acccagagac | 2280 |
| tacagtaact ttgaccagga gttcctgaac gagaaggcgc gcctctccta cagcgacaag | 2340 |
| aacctcatcg actccatgga ccagtctgca ttcgctggct tctccttgt gaaccccaaa | 2400 |
| ttcgagcacc tcctggaaga ttag | 2424 |

<210> SEQ ID NO 58
<211> LENGTH: 2439
<212> TYPE: DNA
<213> ORGANISM: Artificial Sequence
<220> FEATURE:
<223> OTHER INFORMATION: Synthetic sequence, nt sequence of sensor 22
      [G29-23]

<400> SEQUENCE: 58

| | |
|---|---|
| atggaggacg tggattgcaa acagtctatg cgcagtgagg acgaggccaa gttcccaacg | 60 |
| atgaaccgcc gcggagccat caaacaggcc aaaatccact acatcaagaa ccatgagttt | 120 |
| atcgccaccc tcgagaacgt ctatatcaag gccgacaagc agaagaacgg catcaaggcg | 180 |
| aacttcaaga tccgccacaa catcgaggac ggcggcgtgc agctcgccta ccactaccag | 240 |
| cagaacaccc ccatcggcga cggccccgtg ctgctgcccg acaaccacta cctgagcgtg | 300 |
| cagtccatac tttcgaaaga ccccaacgag aagcgcgatc acatggtcct gctggagttc | 360 |

```
gtgaccgccg ccgggatcac tctcggcatg acgagctgt acaagggcgg taccggaggg    420
agcatggtga gcaagggcga ggagctgttc accggggtgg tgcccatcca ggtcgagctg    480
gacggcgacg taaacggcca caagttcagc gtgtccggcg agggtgaggg cgatgccacc    540
tacggcaagc tgaccctgaa gttcatctgc accaccggca agctgcccgt gccctggccc    600
accctcgtga ccaccctgac ctacggcgtg cagtgcttca gccgctaccc cgaccacatg    660
aagcagcacg acttcttcaa gtccgccatg cccgaaggct acatccagga gcgcaccatc    720
ttcttcaagg acgacggcaa ctacaagacc cgcgccgagg tgaagttcga gggcgacacc    780
ctggtgaacc gcatcgagct gaagggcatc gacttcaagg aggacggcaa catcctgggg    840
cacaagctgg agtacaacac gcgtatccac tacatcaaga accatgagtt tatcgccacc    900
ttctttgggc aacccacctt ctgttctgtg tgcaaagact ttgtctgggg cctcaacaag    960
caaggctaca aatgcaggca atgtaacgct gccatccaca agaaatgcat cgacaagatc   1020
atcggcagat gcactggcac cgcggccaac agccgggaca ctatattcca gaaagaacgc   1080
ttcaacatcg acatgccgca ccgcttcaag gttcacaact acatgagccc caccttctgt   1140
gaccactgcg gcagcctgct ctggggactg tgaagcagg gattaaagtg tgaagactgc   1200
ggcatgaatg tgcaccataa atgccgggag aaggtggcca acctctgcgg catcaaccag   1260
aagcttttgg ctgaggcctt gaaccaagtc acccagagag cctcccggag atcagactca   1320
gcctcctcag agcctgttgg gatatatcag ggtttcgaga agaagaccgg agttgctggg   1380
gaggacatgc aagacaacag tgggacctac ggcaagatct gggagggcag cagcaagtgc   1440
aacatcaaca acttcatctt ccacaaggtc ctgggcaaag gcagcttcgg gaaggtgctg   1500
cttggagagc tgaagggcag aggagagtac tttgccatca aggccctcaa gaaggatgtg   1560
gtcctgatcg acgacgacgt ggagtgcacc atggttgaga agcgggtgct gacacttgcc   1620
gcagagaatc cctttctcac ccacctcatc tgcaccttcc agaccaagga ccacctgttc   1680
tttgtgatga gttcctcaa cgggggggac ctgatgtacc acatccagga caaaggccgc   1740
tttgaactct accgtgccac gttttatgcc gctgagataa tgtgtggact gcagtttcta   1800
cacagcaagg gcatcattta cagggacctc aaactggaca atgtgctgtt ggaccgggat   1860
ggccacatca agattgccga cttt gggatg tgcaaagaga acatattcgg ggagagccgg   1920
gccagcacct tctgcggcac ccctgactat atcgccctg agatcctaca gggcctgaag   1980
tacacattct ctgtggactg gtggtctttc ggggtccttc tgtacgagat gctcattggc   2040
cagtccccct tccatggtga tgatgaggat gaactcttcg agtccatccg tgtggacacg   2100
ccacattatc cccgctggat caccaaggag tccaaggaca tcctggagaa gctctttgaa   2160
agggaaccaa ccaagaggct gggagtgacg ggaaacatca aaatccaccc cttcttcaag   2220
accataaact ggactctgct ggaaaagcgg aggttggagc cacccttcag gcccaaagtg   2280
aagtcaccca gagactacag taactttgac caggagttcc tgaacgagaa ggcgcgcctc   2340
tcctacagcg acaagaacct catcgactcc atgaccagt ctgcattcgc tggcttctcc   2400
tttgtgaacc ccaaattcga gcacctcctg gaagattag                          2439
```

<210> SEQ ID NO 59
<211> LENGTH: 2418
<212> TYPE: DNA
<213> ORGANISM: Artificial Sequence
<220> FEATURE:
<223> OTHER INFORMATION: Synthetic sequence, nt sequence of sensor 23
      [G29-24]

```
<400> SEQUENCE: 59
atggaggacg tggattgcaa acagtctatg cgcagtgagg acgaggccaa gttcccaacg      60
atgaaccgcc gcggagccat caaacaggcc aaaatccact acatcaagaa ccatgagttt     120
atcgccaccc tcgagaacgt ctatatcaag gccgacaagc agaagaacgg catcaaggcg     180
aacttcaaga tccgccacaa catcgaggac ggcggcgtgc agctcgccta ccactaccag     240
cagaacaccc ccatcggcga cggcccgtg ctgctgcccg acaaccacta cctgagcgtg      300
cagtccatac tttcgaaaga ccccaacgag aagcgcgatc acatggtcct gctggagttc     360
gtgaccgccg ccgggatcac tctcggcatg gacgagctgt acaagggcgg taccggaggg     420
agcatggtga gcaagggcga ggagctgttc accggggtgg tgcccatcca ggtcgagctg     480
gacggcgacg taaacggcca caagttcagc gtgtccggcg agggtgaggg cgatgccacc     540
tacggcaagc tgaccctgaa gttcatctgc accaccggca agctgccgt gccctggccc      600
accctcgtga ccaccctgac ctacggcgtg cagtgcttca gccgctaccc cgaccacatg     660
aagcagcacg acttcttcaa gtccgccatg cccgaaggct acatccagga gcgcaccatc     720
ttcttcaagg acgacggcaa ctacaagacc cgcgccgagg tgaagttcga gggcgacacc     780
ctggtgaacc gcatcgagct gaagggcatc gacttcaagg aggacggcaa catcctgggg     840
cacaagctgg agtacaacac gcgtgagttt atcgccacct ctttgggca acccaccttc      900
tgttctgtgt gcaaagactt tgtctggggc ctcaacaagc aaggctacaa atgcaggcaa     960
tgtaacgctg ccatccacaa gaaatgcatc gacaagatca tcggcagatg cactggcacc    1020
gcggccaaca gccgggacac tatattccag aaagaacgct tcaacatcga catgccgcac    1080
cgcttcaagg ttcacaacta catgagcccc accttctgtg accactgcgg cagcctgctc    1140
tggggactgt gaagcaggg attaaagtgt gaagactgcg gcatgaatgt gcaccataaa     1200
tgccgggaga aggtggccaa cctctgcggc atcaaccaga gcttttggc tgaggccttg     1260
aaccaagtca cccagagagc ctcccggaga tcagactcag cctcctcaga gcctgttggg    1320
atatatcagg gtttcgagaa gagaccggga gttgctgggg aggacatgca agacaacagt    1380
gggacctacg gcaagatctg ggagggcagc agcaagtgca acatcaacaa cttcatcttc    1440
cacaaggtcc tgggcaaagg cagcttcggg aaggtgctgc ttggagagct gaagggcaga    1500
ggagagtact tgccatcaa ggccctcaag aaggatgtgg tcctgatcga cgacgtg       1560
gagtgcacca tggttgagaa gcgggtgctg acacttgccg cagagaatcc ctttctcacc    1620
cacctcatct gcaccttcca gaccaaggac cacctgttct tgtgatgga gttcctcaac    1680
gggggggacc tgatgtacca catccaggac aaaggccgct tgaactcta ccgtgccacg    1740
tttatgccg ctgagataat gtgtggactg cagtttctac acagcaaggg catcattac     1800
agggacctca aactggacaa tgtgctgttg gaccgggatg ccacatcaa gattgccgac    1860
tttgggatgt gcaaagagaa catattcggg gagagccggg ccagcacctt ctgcggcacc    1920
cctgactata tcgcccctga gatcctacag ggcctgaagt acacattctc tgtggactgg    1980
tggtctttcg gggtccttct gtacgagatg ctcattggcc agtcccctt ccatggtgat    2040
gatgaggatg aactcttcga gtccatccgt gtggacacgc acattatcc ccgctggatc     2100
accaaggagt ccaaggacat cctggagaag ctctttgaaa gggaaccaac caagaggctg    2160
ggagtgacgg gaaacatcaa aatccaccc ttcttcaaga ccataaactg gactctgctg    2220
gaaaagcgga ggttggagcc accccttcagg cccaaagtga gtcacccag agactacagt    2280
aactttgacc aggagttcct gaacgagaag gcgcgcctct cctacagcga caagaacctc    2340
```

| | |
|---|---:|
| atcgactcca tggaccagtc tgcattcgct ggcttctcct ttgtgaaccc caaattcgag | 2400 |
| cacctcctgg aagattag | 2418 |

<210> SEQ ID NO 60
<211> LENGTH: 2343
<212> TYPE: DNA
<213> ORGANISM: Artificial Sequence
<220> FEATURE:
<223> OTHER INFORMATION: Synthetic sequence, nt sequence of sensor 24
      [G30-21]

<400> SEQUENCE: 60

| | |
|---|---:|
| atggaggacg tggattgcaa acagtctatg cgcagtgagc tcgagaacgt ctatatcaag | 60 |
| gccgacaagc agaagaacgg catcaaggcg aacttcaaga tccgccacaa catcgaggac | 120 |
| ggcggcgtgc agctcgccta ccactaccag cagaacaccc ccatcggcga cggccccgtg | 180 |
| ctgctgcccg acaaccacta cctgagcgtg cagtccatac tttcgaaaga ccccaacgag | 240 |
| aagcgcgatc acatggtcct gctggagttc gtgaccgccg ccgggatcac tctcggcatg | 300 |
| gacgagctgt acaagggcgg taccggaggg agcatggtga gcaagggcga ggagctgttc | 360 |
| accggggtgg tgcccatcca ggtcgagctg acggcgacg taaacggcca caagttcagc | 420 |
| gtgtccggcg agggtgaggg cgatgccacc tacggcaagc tgaccctgaa gttcatctgc | 480 |
| accaccggca agctgcccgt gccctggccc accctcgtga ccaccctgac ctacggcgtg | 540 |
| cagtgcttca gccgctaccc cgaccacatg aagcagcacg acttcttcaa gtccgccatg | 600 |
| cccgaaggct acatccagga gcgcaccatc ttcttcaagg acgacggcaa ctacaagacc | 660 |
| cgcgccgagg tgaagttcga gggcgacacc ctggtgaacc gcatcgagct gaagggcatc | 720 |
| gacttcaagg aggacggcaa catcctgggg cacaagctgg agtacaacac gcgttacatc | 780 |
| aagaaccatg agtttatcgc caccttcttt gggcaaccca ccttctgttc tgtgtgcaaa | 840 |
| gactttgtct ggggcctcaa caagcaaggc tacaaatgca ggcaatgtaa cgctgccatc | 900 |
| cacaagaaat gcatcgacaa gatcatcggc agatgcactg gcaccgcggc caacagccgg | 960 |
| gacactatat tccagaaaga acgcttcaac atcgacatgc cgcaccgctt caaggttcac | 1020 |
| aactacatga gccccaccct ctgtgaccac tgcggcagcc tgctctgggg actggtgaag | 1080 |
| cagggattaa agtgtgaaga ctgcggcatg aatgtgcacc ataaatgccg ggagaaggtg | 1140 |
| gccaacctct gcggcatcaa ccagaagctt ttggctgagg ccttgaacca agtcacccag | 1200 |
| agagcctccc ggagatcaga ctcagcctcc tcagagcctg ttgggatata tcagggtttc | 1260 |
| gagaagaaga ccggagttgc tggggaggac atgcaagaca acagtgggac ctacggcaag | 1320 |
| atctgggagg gcagcagcaa gtgcaacatc aacaacttca tcttccacaa ggtcctgggc | 1380 |
| aaaggcagct tcgggaaggt gctgcttgga gagctgaagg gcagaggaga gtactttgcc | 1440 |
| atcaaggccc tcaagaagga tgtggtcctg atcgacgacg acgtggagtg caccatggtt | 1500 |
| gagaagcggg tgctgacact gccgcagag aatccctttc tcacccacct catctgcacc | 1560 |
| ttccagacca aggaccacct gttctttgtg atggagttcc tcaacggggg ggacctgatg | 1620 |
| taccacatcc aggacaaagg ccgctttgaa ctctaccgtg ccacgtttta tgccgctgag | 1680 |
| ataatgtgtg gactgcagtt tctacacagc aagggcatca tttacaggga cctcaaactg | 1740 |
| gacaatgtgc tgttggaccg ggatggccac atcaagattg ccgactttgg gatgtgcaaa | 1800 |
| gagaacatat tcggggagag ccgggccagc acctctgcg gcaccccga ctatatcgcc | 1860 |
| cctgagatcc tacagggcct gaagtacaca ttctctgtgg actggtggtc tttcggggtc | 1920 |

```
cttctgtacg agatgctcat tggccagtcc cccttccatg gtgatgatga ggatgaactc    1980
ttcgagtcca tccgtgtgga cacgccacat tatccccgct ggatcaccaa ggagtccaag    2040
gacatcctgg agaagctctt tgaaagggaa ccaaccaaga ggctgggagt gacgggaaac    2100
atcaaaatcc acccttctt caagaccata aactggactc tgctggaaaa gcggaggttg     2160
gagccaccct tcaggcccaa agtgaagtca cccagagact acagtaactt tgaccaggag    2220
ttcctgaacg agaaggcgcg cctctcctac agcgacaaga acctcatcga ctccatggac    2280
cagtctgcat tcgctggctt ctcctttgtg aaccccaaat tcgagcacct cctggaagat    2340
tag                                                                  2343

<210> SEQ ID NO 61
<211> LENGTH: 2469
<212> TYPE: DNA
<213> ORGANISM: Artificial Sequence
<220> FEATURE:
<223> OTHER INFORMATION: Synthetic sequence, nt sequence of sensor 25
      [G19-30]

<400> SEQUENCE: 61
atggaggacg tggattgcaa acagtctatg cgcagtgagg acgaggccaa gttcccaacg    60
atgaaccgcc gcggagccat caaacaggcc aaaatccact acatcctcga gaacgtctat    120
atcaaggccg acaagcagaa gaacggcatc aaggcgaact tcaagatccg ccacaacatc    180
gaggacggcg gcgtgcagct cgcctaccac taccagcaga cacccccat cggcgacggc     240 cccgtgctgc tgcccgacaa ccactacctg agcgtgcagt ccatactttc gaaagacccc    300
aacgagaagc gcgatcacat ggtcctgctg gagttcgtga ccgccgccgg gatcactctc    360
ggcatggacg agctgtacaa gggcggtacc ggagggagca tggtgagcaa gggcgaggag    420
ctgttcaccg gggtggtgcc catccaggtc gagctggacg gcgacgtaaa cggccacaag    480
ttcagcgtgt ccggcgaggg tgagggcgat gccacctacg gcaagctgac cctgaagttc    540
atctgcacca ccggcaagct gcccgtgccc tggcccaccc tcgtgaccac cctgacctac    600
ggcgtgcagt gcttcagccg ctaccccgac cacatgaagc agcacgactt cttcaagtcc    660
gccatgcccg aaggctacat ccaggagcgc accatcttct tcaaggacga cggcaactac    720
aagacccgcg ccgaggtgaa gttcgagggc gacaccctgg tgaaccgcat cgagctgaag    780
ggcatcgact tcaaggagga cggcaacatc ctggggcaca gctggagta caacacgcgt     840 gacgaggcca gttcccaac gatgaaccgc gcggagcca tcaaacaggc caaaatccac      900
tacatcaaga accatgagtt tatcgccacc ttctttgggc aacccacctt ctgttctgtg    960
tgcaaagact ttgtctgggg cctcaacaag caaggctaca atgcaggca atgtaacgct     1020 gccatccaca gaaatgcat cgacaagatc atcggcagat gcactggcac cgcggccaac     1080
agccgggaca ctatattcca gaaagaacgc ttcaacatcg acatgccgca ccgcttcaag    1140
gttcacaact acatgagccc cacccttctgt gaccactgcg gcagcctgct ctggggactg    1200
gtgaagcagg gattaaagtg tgaagactgc ggcatgaatg tgcaccataa atgccgggag    1260
aaggtggcca acctctgcgg catcaaccag aagctttggg ctgaggcctt gaaccaagtc    1320
acccagagag cctcccggag atcagactca gcctcctcag agcctgttgg gatatatcag    1380
ggtttcgaga agaagaccgg agttgctggg gaggacatgc aagacaacag tgggacctac    1440
ggcaagatct gggagggcag cagcaagtgc aacatcaaca acttcatctt ccacaaggtc    1500
ctgggcaaag gcagcttcgg gaaggtgctg cttggagagc tgaagggcag aggagagtac    1560
```

```
tttgccatca aggccctcaa gaaggatgtg gtcctgatcg acgacgacgt ggagtgcacc      1620
atggttgaga agcgggtgct gacacttgcc gcagagaatc cctttctcac ccacctcatc      1680
tgcaccttcc agaccaagga ccacctgttc tttgtgatgg agttcctcaa cggggggggac      1740 ctgatgtacc acatccagga caaaggccgc tttgaactct accgtgccac gttttatgcc      1800
gctgagataa tgtgtggact gcagtttcta cacagcaagg gcatcattta cagggacctc      1860
aaactggaca atgtgctgtt ggaccgggat ggccacatca agattgccga ctttgggatg      1920
tgcaaagaga acatattcgg ggagagccgg gccagcacct tctgcggcac ccctgactat      1980
atcgcccctg agatcctaca gggcctgaag tacacattct ctgtggactg gtggtctttc      2040
ggggtccttc tgtacgagat gctcattggc cagtccccct ccatggtga tgatgaggat      2100 gaactcttcg agtccatccg tgtggacacg ccacattatc cccgctggat caccaaggag      2160
tccaaggaca tcctggagaa gctctttgaa agggaaccaa ccaagaggct gggagtgacg      2220
ggaaacatca aaatccaccc cttcttcaag accataaact ggactctgct ggaaaagcgg      2280
aggttggagc caccttcag gcccaaagtg aagtcaccca gagactacag taactttgac      2340
caggagttcc tgaacgagaa ggcgcgcctc tcctacagcg acaagaacct catcgactcc      2400
atggaccagt ctgcattcgc tggcttctcc tttgtgaacc ccaaattcga gcacctcctg      2460
gaagattag                                                             2469

<210> SEQ ID NO 62
<211> LENGTH: 2463
<212> TYPE: DNA
<213> ORGANISM: Artificial Sequence
<220> FEATURE:
<223> OTHER INFORMATION: Synthetic sequence, nt sequence of sensor 26
      [G21-30]

<400> SEQUENCE: 62
atggaggacg tggattgcaa acagtctatg cgcagtgagg acgaggccaa gttcccaacg        60
atgaaccgcc gcggagccat caaacaggcc aaaatccacc tcgagaacgt ctatatcaag      120
gccgacaagc agaagaacgg catcaaggcg aacttcaaga tccgccacaa catcgaggac      180
ggcggcgtgc agctcgccta ccactaccag cagaacaccc ccatcggcga cggccccgtg      240
ctgctgcccg acaaccacta cctgagcgtg cagtccatac tttcgaaaga ccccaacgag      300
aagcgcgatc acatggtcct gctggagttc gtgaccgccg ccgggatcac tctcggcatg      360
gacgagctgt acaagggcgg taccggaggg agcatggtga gcaagggcga ggagctgttc      420
accggggtgg tgcccatcca ggtcgagctg gacggcgacg taaacggcca aagttcagc      480 gtgtccggcg agggtgaggg cgatgccacc tacggcaagc tgaccctgaa gttcatctgc      540
accaccggca agctgcccgt gccctggccc accctcgtga ccaccctgac ctacggcgtg      600
cagtgcttca gccgctaccc cgaccacatg aagcagcacg acttcttcaa gtccgccatg      660
cccgaaggct acatccagga gcgcaccatc ttcttcaagg acgacggcaa ctacaagacc      720
cgcgccgagg tgaagttcga gggcgacacc ctggtgaacc gcatcgagct gaagggcatc      780
gacttcaagg aggacggcaa catcctgggg cacaagctgg agtacaacac gcgtgacgag      840
gccaagttcc aacgatgaa ccgccgcgga gccatcaaac aggccaaaat ccactacatc      900
aagaaccatg agtttatcgc caccttcttt gggcaaccca ccttctgttc tgtgtgcaaa      960
gactttgtct ggggcctcaa caagcaaggc tacaaatgca ggcaatgtaa cgctgccatc     1020
cacaagaaat gcatcgacaa gatcatcggc agatgcactg gcaccgcggc caacagccgg     1080
```

```
gacactatat tccagaaaga acgcttcaac atcgacatgc cgcaccgctt caaggttcac    1140
aactacatga gccccacctt ctgtgaccac tgcggcagcc tgctctgggg actggtgaag    1200
cagggattaa agtgtgaaga ctgcggcatg aatgtgcacc ataaatgccg ggagaaggtg    1260
gccaacctct gcggcatcaa ccagaagctt ttggctgagg ccttgaacca agtcacccag    1320
agagcctccc ggagatcaga ctcagcctcc tcagagcctg ttgggatata tcagggtttc    1380
gagaagaaga ccggagttgc tggggaggac atgcaagaca acagtgggac ctacggcaag    1440
atctgggagg gcagcagcaa gtgcaacatc aacaacttca tcttccacaa ggtcctgggc    1500
aaaggcagct tcgggaaggt gctgcttgga gagctgaagg gcagaggaga gtactttgcc    1560
atcaaggccc tcaagaagga tgtggtcctg atcgacgacg acgtggagtg caccatggtt    1620
gagaagcggg tgctgacact tgccgcagag aatccctttc tcacccacct catctgcacc    1680
ttccagacca aggaccacct gttctttgtg atggagttcc tcaacggggg ggacctgatg    1740
taccacatcc aggacaaagg ccgctttgaa ctctaccgtg ccacgtttta tgccgctgag    1800
ataatgtgtg gactgcagtt tctacacagc aagggcatca tttacaggga cctcaaactg    1860
gacaatgtgc tgttggaccg ggatggccac atcaagattg ccgactttgg gatgtgcaaa    1920
gagaacatat tcggggagag ccgggccagc accttctgcg gcaccccctga ctatatcgcc    1980 cctgagatcc tacagggcct gaagtacaca ttctctgtgg actggtggtc tttcggggtc    2040
cttctgtacg agatgctcat tggccagtcc cccttccatg tgatgatgaa ggatgaactc    2100
ttcgagtcca tccgtgtgga cacgccacat tatccccgct ggatcaccaa ggagtccaag    2160
gacatcctgg agaagctctt tgaaagggaa ccaaccaaga ggctgggagt gacgggaaac    2220
atcaaaatcc accccttctt caagaccata aactggactc tgctggaaaa gcggaggttg    2280
gagccacccc tcaggcccaa agtgaagtca cccagagact acagtaactt tgaccaggag    2340
ttcctgaacg agaaggcgcg cctctcctac agcgacaaga acctcatcga ctccatggac    2400
cagtctgcat tcgctggctt ctccttttgtg aacccccaaat tcgagcacct cctggaagat    2460
tag                                                                  2463
```

<210> SEQ ID NO 63
<211> LENGTH: 2457
<212> TYPE: DNA
<213> ORGANISM: Artificial Sequence
<220> FEATURE:
<223> OTHER INFORMATION: Synthetic sequence, nt sequence of sensor 27
[G23-30]

<400> SEQUENCE: 63

```
atggaggacg tggattgcaa acagtctatg cgcagtgagg acgaggccaa gttcccaacg    60
atgaaccgcc gcggagccat caaacaggcc aaactcgaga acgtctatat caaggccgac    120
aagcagaaga acggcatcaa ggcgaacttc aagatccgcc acaacatcga ggacggcggc    180
gtgcagctcg cctaccacta ccagcagaac accccccatcg cgacggcccc cgtgctgctg    240
cccgacaacc actacctgag cgtgcagtcc atactttcga agaccccaa cgagaagcgc    300 gatcacatgg tcctgctgga gttcgtgacc gccgccggga tcactctcgg catggacgag    360
ctgtacaagg gcggtaccgg agggagcatg gtgagcaagg gcgaggagct gttcaccggg    420
gtggtgccca tccaggtcga gctggacggc gacgtaaacg gccacaagtt cagcgtgtcc    480
ggcgagggtg agggcgatgc cacctacggc aagctgaccc tgaagttcat ctgcaccacc    540
ggcaagctgc ccgtgccctg gcccaccctc gtgaccaccc tgacctacgg cgtgcagtgc    600
```

```
ttcagccgct accccgacca catgaagcag cacgacttct tcaagtccgc catgcccgaa      660
ggctacatcc aggagcgcac catcttcttc aaggacgacg gcaactacaa gacccgcgcc      720
gaggtgaagt tcgagggcga caccctggtg aaccgcatcg agctgaaggg catcgacttc      780
aaggaggacg gcaacatcct ggggcacaag ctggagtaca cacgcgtga cgaggccaag       840 ttcccaacga tgaaccgccg cggagccatc aaacaggcca aaatccacta catcaagaac      900
catgagttta tcgccaccct ctttgggcaa cccaccttct gttctgtgtg caaagacttt      960
gtctggggcc tcaacaagca aggctacaaa tgcaggcaat gtaacgctgc atccacaag      1020 aaatgcatcg acaagatcat cggcagatgc actggcaccg cggccaacag ccgggacact     1080
atattccaga agaacgctt caacatcgac atgccgcacc gcttcaaggt tcacaactac      1140
atgagcccca ccttctgtga ccactgcggc agcctgctct ggggactggt gaagcaggga     1200
ttaaagtgtg aagactgcgg catgaatgtg caccataaat gccgggagaa ggtggccaac     1260
ctctgcggca tcaaccagaa gcttttggct gaggccttga accaagtcac ccagagagcc     1320
tcccggagat cagactcagc tcctcagag cctgttggga tatatcaggg tttcgagaag      1380
aagaccggag ttgctgggga ggacatgcaa gacaacagtg ggacctacgg caagatctgg     1440
gagggcagca gcaagtgcaa catcaacaac ttcatcttcc acaaggtcct gggcaaaggc     1500
agcttcggga aggtgctgct ggagagctg aagggcagag gagagtactt tgccatcaag     1560
gccctcaaga aggatgtggt cctgatcgac gacgacgtgg agtgcaccat ggttgagaag     1620
cgggtgctga cacttgccgc agagaatccc tttctcaccc acctcatctg cacccttccag    1680 accaaggacc acctgttctt tgtgatggag ttcctcaacg gggggaccct gatgtaccac     1740
atccaggaca aaggccgctt tgaactctac cgtgccacgt tttatgccgc tgagataatg     1800
tgtggactgc agtttctaca cagcaagggc atcatttaca gggacctcaa actggacaat     1860
gtgctgttgg accgggatgg ccacatcaag attgccgact tgggatgtg caaagagaac      1920 atattcgggg agagccgggc cagcaccttc tgcggcaccc ctgactatat cgcccctgag     1980
atcctacagg gcctgaagta cacattctct gtggactggt ggtctttcgg ggtccttctg     2040
tacgagatgc tcattggcca gtcccccttc catggtgatg atgaggatga actcttcgag     2100
tccatccgtg tggacacgcc acattatccc cgctggatca ccaaggagtc caaggacatc     2160
ctggagaagc tctttgaaag ggaaccaacc aagaggctgg gagtgacggg aaacatcaaa     2220 atccaccccct tcttcaagac cataaactgg actctgctgg aaaagcggag gttggagcca     2280
cccttcaggc ccaaagtgaa gtcacccaga gactacagta actttgacca ggagttcctg     2340
aacgagaagg cgcgcctctc ctacagcgac aagaacctca tcgactccat ggaccagtct     2400
gcattcgctg gcttctcctt tgtgaacccc aaattcgagc acctcctgga agattag       2457
```

<210> SEQ ID NO 64
<211> LENGTH: 2478
<212> TYPE: DNA
<213> ORGANISM: Artificial Sequence
<220> FEATURE:
<223> OTHER INFORMATION: Synthetic sequence, nt sequence of sensor 28
     [G24-30]

<400> SEQUENCE: 64

```
atggaggacg tggattgcaa acagtctatg cgcagtgagg acgaggccaa gttcccaacg       60
atgaaccgcc gcggagccat caacaggcca aaatccact acatcaagaa ccatctcgag       120
aacgtctata tcaaggccga caagcagaag aacggcatca aggcgaactt caagatccgc      180
```

```
cacaacatcg aggacggcgg cgtgcagctc gcctaccact accagcagaa cacccccatc    240
ggcgacggcc ccgtgctgct gcccgacaac cactacctga gcgtgcagtc catactttcg    300
aaagacccca acgagaagcg cgatcacatg gtcctgctgg agttcgtgac cgccgccggg    360
atcactctcg gcatggacga gctgtacaag ggcggtaccg agggagcat ggtgagcaag     420 ggcgaggagc tgttcaccgg ggtggtgccc atccaggtcg agctggacgg cgacgtaaac    480
ggccacaagt tcagcgtgtc cggcgagggt gagggcgatg ccacctacgg caagctgacc    540
ctgaagttca tctgcaccac cggcaagctg cccgtgccct ggcccaccct cgtgaccacc    600
ctgacctacg gcgtgcagtg cttcagccgc taccccgacc acatgaagca gcacgacttc    660
ttcaagtccg ccatgcccga aggctacatc caggagcgca ccatcttctt caaggacgac    720
ggcaactaca agacccgcgc cgaggtgaag ttcgagggcg acacccctggt gaaccgcatc    780 gagctgaagg gcatcgactt caaggaggac ggcaacatcc tggggcacaa gctggagtac    840
aacacgcgtg acgaggccaa gttcccaacg atgaaccgcc gcgagccat caaacaggcc     900 aaaatccact acatcaagaa ccatgagttt atcgccacct ctttgggca acccaccttc     960 tgttctgtgt gcaaagactt tgtctggggc ctcaacaagc aaggctacaa atgcaggcaa   1020
tgtaacgctg ccatccacaa gaaatgcatc gacaagatca tcggcagatg cactggcacc   1080
gcggccaaca gccgggacac tatattccag aaagaacgct tcaacatcga catgccgcac   1140
cgcttcaagg ttcacaacta catgagcccc accttctgtg accactgcgg cagcctgctc   1200
tggggactgg tgaagcaggg attaaagtgt gaagactgcg gcatgaatgt gcaccataaa   1260
tgccgggaga aggtggccaa cctctgcggc atcaaccaga gcttttggc tgaggccttg    1320 aaccaagtca cccagagagc ctcccggaga tcagactcag cctcctcaga gcctgttggg   1380
atatatcagg gtttcgagaa gaagaccgga gttgctgggg aggacatgca agacaacagt   1440
gggacctacg gcaagatctg ggagggcagc agcaagtgca acatcaacaa cttcatcttc   1500
cacaaggtcc tgggcaaagg cagcttcggg aaggtgctgc ttggagagct gaagggcaga   1560
ggagagtact ttgccatcaa ggccctcaag aaggatgtgg tcctgatcga cgacgtg     1620 gagtgcacca tggttgagaa gcgggtgctg acacttgccg cagagaatcc ctttctcacc   1680
cacctcatct gcaccttcca gaccaaggac cacctgttct ttgtgatgga gttcctcaac   1740
gggggggacc tgatgtacca catccaggac aaaggccgct tgaactcta ccgtgccacg    1800 ttttatgccg ctgagataat gtgtggactg cagtttctac acagcaaggg catcatttac   1860
agggacctca aactgacaa tgtgctgttg accgggatg ccacatcaa gattgccgac     1920 tttgggatgt gcaaagagaa catattcggg gagagccggg ccagcacctt ctgcggcacc   1980
cctgactata tcgcccctga gatcctacag gcctgaagt acacattctc tgtggactgg   2040
tggtctttcg gggtccttct gtacgagatg ctcattggcc agtcccct ccatggtgat    2100 gatgaggatg aactcttcga gtccatccgt gtggacacgc cacattatcc ccgctggatc   2160
accaaggagt ccaaggacat cctggagaag ctctttgaaa gggaaccaac caagaggctg   2220
ggagtgacgg gaaacatcaa aatccacccc ttcttcaaga ccataaactg gactctgctg   2280
gaaaagcgga ggttggagcc acccttcagg cccaaagtga agtcacccag agactacagt   2340
aactttgacc aggagttcct gaacgagaag gcgcgcctct cctacagcga caagaacctc   2400
atcgactcca tggaccagtc tgcattcgct ggcttctcct tgtgaaccc caaattcgag   2460 cacctcctgg aagattag                                                 2478
```

<210> SEQ ID NO 65
<211> LENGTH: 2490
<212> TYPE: DNA
<213> ORGANISM: Artificial Sequence
<220> FEATURE:
<223> OTHER INFORMATION: Synthetic sequence, nt sequence of sensor 29 [G28-30]

<400> SEQUENCE: 65

| | | | | | |
|---|---|---|---|---|---|
| atggaggacg | tggattgcaa | acagtctatg | cgcagtgagg | acgaggccaa | gttcccaacg | 60 |
| atgaaccgcc | gcggagccat | caaacaggcc | aaaatccact | acatcaagaa | ccatgagttt | 120 |
| atcgccctcg | agaacgtcta | tatcaaggcc | gacaagcaga | agaacggcat | caaggcgaac | 180 |
| ttcaagatcc | gccacaacat | cgaggacggc | ggcgtgcagc | tcgcctacca | ctaccagcag | 240 |
| aacaccccca | tcggcgacgg | ccccgtgctg | ctgcccgaca | accactacct | gagcgtgcag | 300 |
| tccatacttt | cgaaagaccc | caacgagaag | cgcgatcaca | tggtcctgct | ggagttcgtg | 360 |
| accgccgccg | ggatcactct | cggcatggac | gagctgtaca | agggcggtac | cggagggagc | 420 |
| atggtgagca | agggcgagga | gctgttcacc | ggggtggtgc | ccatccaggt | cgagctggac | 480 |
| ggcgacgtaa | acggccacaa | gttcagcgtg | tccggcgagg | gtgagggcga | tgccacctac | 540 |
| ggcaagctga | ccctgaagtt | catctgcacc | accggcaagc | tgcccgtgcc | ctggcccacc | 600 |
| ctcgtgacca | ccctgaccta | cggcgtgcag | tgcttcagcc | gctacccga  | ccacatgaag | 660 |
| cagcacgact | tcttcaagtc | cgccatgccc | gaaggctaca | tccaggagcg | caccatcttc | 720 |
| ttcaaggacg | acggcaacta | caagacccgc | gccgaggtga | agttcgaggg | cgacaccctg | 780 |
| gtgaaccgca | tcgagctgaa | gggcatcgac | ttcaaggagg | acggcaacat | cctggggcac | 840 |
| aagctggagt | acaacacgcg | tgacgaggcc | aagttcccaa | cgatgaaccg | ccgcggagcc | 900 |
| atcaaacagg | ccaaaatcca | ctacatcaag | aaccatgagt | ttatcgccac | cttctttggg | 960 |
| caacccacct | tctgttctgt | gtgcaaagac | tttgtctggg | gcctcaacaa | gcaaggctac | 1020 |
| aaatgcaggc | aatgtaacgc | tgccatccac | aagaaatgca | tcgacaagat | catcggcaga | 1080 |
| tgcactggca | ccgcgccaa  | cagccgggac | actatattcc | agaaagaacg | cttcaacatc | 1140 |
| gacatgccgc | accgcttcaa | ggttcacaac | tacatgagcc | ccaccttctg | tgaccactgc | 1200 |
| ggcagcctgc | tctggggact | ggtgaagcag | ggattaaagt | gtgaagactg | cggcatgaat | 1260 |
| gtgcaccata | atgccgggga | aaggtggcc  | aacctctgcg | catcaaccag | aagcttttg  | 1320 |
| gctgaggcct | tgaaccaagt | cacccagaga | gcctcccgga | gatcagactc | agcctcctca | 1380 |
| gagcctgttg | ggatatatca | gggtttcgag | aagaagaccg | gagttgctgg | ggaggacatg | 1440 |
| caagacaaca | gtgggaccta | cggcaagatc | tgggagggca | gcagcaagtg | caacatcaac | 1500 |
| aacttcatct | tccacaaggt | cctgggcaaa | ggcagcttcg | gaaggtgct  | gcttggagag | 1560 |
| ctgaagggca | gaggagagta | ctttgccatc | aaggcccctca | agaaggatgt | ggtcctgatc | 1620 |
| gacgacgacg | tggagtgcac | catggttgag | aagcgggtgc | tgacacttgc | cgcagagaat | 1680 |
| ccctttctca | cccacctcat | ctgcaccttc | cagaccaagg | accacctgtt | ctttgtgatg | 1740 |
| gagttcctca | acgggggga  | cctgatgtac | cacatccagg | acaaaggccg | ctttgaactc | 1800 |
| taccgtgcca | cgtttatgc  | cgctgagata | atgtgtggac | tgcagtttct | acacagcaag | 1860 |
| ggcatcattt | acagggacct | caaactggac | aatgtgctgt | tggaccggga | tggccacatc | 1920 |
| aagattgccg | actttgggat | gtgcaaagag | aacatattcg | gggagagccg | ggccagcacc | 1980 |
| ttctgcggca | cccctgacta | tatcgcccct | gagatcctac | agggcctgaa | gtacacattc | 2040 |

-continued

```
tctgtggact ggtggtcttt cggggtcctt ctgtacgaga tgctcattgg ccagtccccc     2100
ttccatggtg atgatgagga tgaactcttc gagtccatcc gtgtggacac gccacattat     2160
ccccgctgga tcaccaagga gtccaaggac atcctggaga agctctttga aagggaacca     2220
accaagaggc tgggagtgac gggaaacatc aaaatccacc ccttcttcaa gaccataaac     2280
tggactctgc tggaaaagcg gaggttggag ccacccttca ggcccaaagt gaagtcaccc     2340
agagactaca gtaactttga ccaggagttc ctgaacgaga aggcgcgcct ctcctacagc     2400
gacaagaacc tcatcgactc catggaccag tctgcattcg ctggcttctc ctttgtgaac     2460
cccaaattcg agcacctcct ggaagattag                                      2490
```

<210> SEQ ID NO 66
<211> LENGTH: 2493
<212> TYPE: DNA
<213> ORGANISM: Artificial Sequence
<220> FEATURE:
<223> OTHER INFORMATION: Synthetic sequence, nt sequence of sensor 30
      [G29-30]

<400> SEQUENCE: 66

```
atggaggacg tggattgcaa acagtctatg cgcagtgagg acgaggccaa gttcccaacg       60
atgaaccgcc gcggagccat caaacaggcc aaaatccact acatcaagaa ccatgagttt      120
atcgccaccc tcgagaacgt ctatatcaag gccgacaagc agaagaacgg catcaaggcg      180
aacttcaaga tccgccacaa catcgaggac ggcggcgtgc agctcgccta ccactaccag      240
cagaacaccc ccatcggcga cggccccgtg ctgctgcccg acaaccacta cctgagcgtg      300
cagtccatac tttcgaaaga ccccaacgag aagcgcgatc acatggtcct gctggagttc      360
gtgaccgccg ccgggatcac tctcggcatg gacgagctgt acaagggcgg taccggaggg      420
agcatggtga gcaagggcga ggagctgttc accggggtgg tgcccatcca ggtcgagctg      480
gacggcgacg taaacggcca caagttcagc gtgtccggcg agggtgaggg cgatgccacc      540
tacggcaagc tgaccctgaa gttcatctgc accaccggca agctgcccgt gccctggccc      600
accctcgtga ccaccctgac ctacggcgtg cagtgcttca gccgctaccc cgaccacatg      660
aagcagcacg acttcttcaa gtccgccatg cccgaaggct acatccagga gcgcaccatc      720
ttcttcaagg acgacggcaa ctacaagacc cgcgccgagg tgaagttcga gggcgacacc      780
ctggtgaacc gcatcgagct gaagggcatc gacttcaagg aggacggcaa catcctgggg      840
cacaagctgg agtacaacac gcgtgacgag gccaagttcc caacgatgaa ccgccgcgga      900
gccatcaaac aggccaaaat ccactacatc aagaaccatg agtttatcgc caccttcttt      960
gggcaaccca ccttctgttc tgtgtgcaaa gactttgtct ggggcctcaa caagcaaggc     1020
tacaaatgca ggcaatgtaa cgctgccatc cacaagaaat gcatcgacaa gatcatcggc     1080
agatgcactg gcaccgcggc caacagccgg gacactatat tccagaaaga acgcttcaac     1140
atcgacatgc gcaccgcctt caaggttcac aactacatga gccccacctt ctgtgaccac     1200
tgcggcagcc tgctctgggg actggtgaag cagggattaa agtgtgaaga ctgcggcatg     1260
aatgtgcacc ataaatgccg ggagaaggtg ccaacctctg cggcatcaa ccagaagctt     1320 ttggctgagg ccttgaacca agtcacccag agagcctccc ggagatcaga ctcagcctcc     1380
tcagagcctg ttgggatata tcagggtttc gagaagaaga ccggagttgc tggggaggac     1440
atgcaagaca cagtgggac ctacggcaag atctgggagg gcagcagcaa gtgcaacatc     1500
aacaacttca tcttccacaa ggtcctgggc aaaggcagct tcgggaaggt gctgcttgga     1560
```

-continued

```
gagctgaagg gcagaggaga gtactttgcc atcaaggccc tcaagaagga tgtggtcctg      1620
atcgacgacg acgtggagtg caccatggtt gagaagcggg tgctgacact tgccgcagag      1680
aatccctttc tcacccacct catctgcacc ttccagacca aggaccacct gttctttgtg      1740
atggagttcc tcaacggggg ggacctgatg taccacatcc aggacaaagg ccgcttttgaa     1800 ctctaccgtg ccacgtttta tgccgctgag ataatgtgtg gactgcagtt tctacacagc      1860
aagggcatca tttacaggga cctcaaactg gacaatgtgc tgttggaccg ggatggccac      1920
atcaagattg ccgactttgg gatgtgcaaa gagaacatat tcggggagag ccgggccagc      1980
accttctgcg gcacccctga ctatatcgcc cctgagatcc tacagggcct gaagtacaca      2040
ttctctgtgg actggtggtc tttcggggtc cttctgtacg agatgctcat tggccagtcc      2100 ccctccatg tgatgatga ggatgaactc ttcgagtcca tccgtgtgga cacgccacat        2160
tatccccgct ggatcaccaa ggagtccaag gacatcctgg agaagctctt tgaaagggaa      2220
ccaaccaaga ggctgggagt gacgggaaac atcaaaatcc accccttctt caagaccata      2280
aactggactc tgctggaaaa gcggaggttg gagccaccct tcaggcccaa agtgaagtca      2340
cccagagact acagtaactt tgaccaggag ttcctgaacg agaaggcgcg cctctcctac      2400
agcgacaaga acctcatcga ctccatggac cagtctgcat tcgctggctt ctcctttgtg      2460
aaccccaaat tcgagcacct cctggaagat tag                                   2493
```

<210> SEQ ID NO 67
<211> LENGTH: 2406
<212> TYPE: DNA
<213> ORGANISM: Artificial Sequence
<220> FEATURE:
<223> OTHER INFORMATION: Synthetic sequence, nt sequence of sensor 31
      [R17.2b]

<400> SEQUENCE: 67

```
atggaggacg tggattgcaa acagtctatg cgcagtgagg acgaggccaa gttcccaacg        60
atgaaccgcc gcggagccat caaacaggcc aaaatccact acatcaagaa ccccgtggtt       120
tccgagcgga tgtaccccga ggacggcgcc ctgaagagcg atcaagaa ggggctgagg         180 ctgaaggacg gcgccacta cgccgccgag gtcaagacca cctacaaggc caagaagccc        240
gtgcagctgc ccggcgccta catcgtcgac atcaagttgg acatcgtgtc ccacaacgag       300
gactacacca tcgtggaaca gtgcgaacgc gccgagggcc gccactccac cggcggcatg       360
gacgagctgt acaagggagg tacaggcggg agtctggtga gcaagggcga ggaggataac       420
atggccatca tcaaggagtt catgcgcttc aaggtgcaca tggagggctc cgtgaacggc       480
cacgagttcg agatcgaggg cgagggcgag ggccgcccct acgaggcctt tcagaccgct       540
aagctgaagg tgaccaaggg tggccccctg cccttcgcct gggacatcct gtcccctcag       600
ttcatgtacg gctccaaggc ctacattaag cacccagccg acatccccga ctacttcaag       660
ctgtccttcc ccgagggctt caggtgggag gcgtgatga acttcgagga cggcggcatt       720
attcacgtta accaggactc ctccctgcag gacggcgtat tcatctacaa ggtgaagctg       780
cgcggcacca acttcccccc cgacggcccc gtaatgcaga agaagaccat gggctgggag       840
gctacgcgtc atgagtttat cgccaccttc tttgggcaac ccaccttctg ttctgtgtgc       900
aaagactttg tctggggcct caacaagcaa ggctacaaat gcaggcaatg taacgctgcc       960
atccacaaga aatgcatcga caagatcatc ggcagatgca ctggcaccgc ggccaacagc      1020
cgggacacta tattccagaa agaacgcttc aacatcgaca tgccgcaccg cttcaaggtt      1080
```

```
cacaactaca tgagccccac cttctgtgac cactgcggca gcctgctctg gggactggtg      1140
aagcagggat taaagtgtga agactgcggc atgaatgtgc accataaatg ccgggagaag      1200
gtggccaacc tctgcggcat caaccagaag cttttggctg aggccttgaa ccaagtcacc      1260
cagagagcct cccggagatc agactcagcc tcctcagagc ctgttgggat atatcagggt      1320
ttcgagaaga agaccggagt tgctggggag gacatgcaag acaacagtgg gacctacggc      1380
aagatctggg agggcagcag caagtgcaac atcaacaact tcatcttcca caaggtcctg      1440
ggcaaaggca gcttcgggaa ggtgctgctt ggagagctga agggcagagg agagtacttt      1500
gccatcaagg ccctcaagaa ggatgtggtc ctgatcgacg acgacgtgga gtgcaccatg      1560
gttgagaagc gggtgctgac acttgccgca gagaatccct ttctcaccca cctcatctgc      1620
accttccaga ccaaggacca cctgttcttt gtgatggagt tcctcaacgg ggggacctg      1680 atgtaccaca tccaggacaa aggccgcttt gaactctacc gtgccacgtt ttatgccgct      1740
gagataatgt gtggactgca gtttctacac agcaagggca tcatttacag ggacctcaaa      1800
ctggacaatg tgctgttgga ccgggatggc cacatcaaga ttgccgactt tgggatgtgc      1860
aaagagaaca tattcgggga gagccgggcc agcaccttct gcggcacccc tgactatatc      1920
gcccctgaga tcctacaggg cctgaagtac acattctctg tggactggtg gtctttcggg      1980
gtccttctgt acgagatgct cattggccag tccccttcc atggtgatga tgaggatgaa      2040
ctcttcgagt ccatccgtgt ggacacgcca cattatcccc gctggatcac caaggagtcc      2100
aaggacatcc tggagaagct ctttgaaagg gaaccaacca gaggctggga agtgacggga      2160
aacatcaaaa tccaccctt cttcaagacc ataaactgga ctctgctgga aaagcggagg      2220
ttggagccac ccttcaggcc caaagtgaag tcacccagag actacagtaa ctttgaccag      2280
gagttcctga cgagaaggc gcgcctctcc tacagcgaca agaacctcat cgactccatg      2340
gaccagtctg cattcgctgg cttctccttt gtgaaccccc aattcgagca cctcctggaa      2400
gattag                                                               2406
```

<210> SEQ ID NO 68
<211> LENGTH: 2406
<212> TYPE: DNA
<213> ORGANISM: Artificial Sequence
<220> FEATURE:
<223> OTHER INFORMATION: Synthetic sequence, nt sequence of sensor 32 [R19]

<400> SEQUENCE: 68

```
atggaggacg tggattgcaa acagtctatg cgcagtgagg acgaggccaa gttcccaacg       60
atgaaccgcc gcggagccat caaacaggcc aaaatccact acatcccgt ggtttccgag      120 cggatgtacc ccgaggacgg cgccctgaag agcgagatca agaaggggct gaggctgaag      180
gacggcggcc actacgccgc cgaggtcaag accacctaca aggccaagaa gcccgtgcag      240
ctgcccggcg cctacatcgt cgacatcaag ttggacatcg tgtcccacaa cgaggactac      300
accatcgtgg aacagtgcga acgcgccgag ggccgccact ccaccggcgg catggacgag      360
ctgtacaagg gaggtacagg cgggagtctg gtgagcaagg gcgaggagga taacatggcc      420
atcatcaagg agttcatgcg cttcaaggtg cacatggagg gctccgtgaa cggccacgag      480
ttcgagatcg agggcgaggg cgagggccgc ccctacgagg cctttcagac cgctaagctg      540
aaggtgacca agggtggccc cctgcccttc gcctgggaca cctgtccccc tcagttcatg      600
tacggctcca aggcctacat taagcaccca gccgacatcc ccgactactt caagctgtcc      660
```

```
ttccccgagg gcttcaggtg ggagcgcgtg atgaacttcg aggacggcgg cattattcac      720
gttaaccagg actcctccct gcaggacggc gtattcatct acaaggtgaa gctgcgcggc      780
accaacttcc cccccgacgg ccccgtaatg cagaagaaga ccatgggctg ggaggctacg      840
cgtaagaacc atgagtttat cgccaccttc tttgggcaac ccaccttctg ttctgtgtgc      900
aaagactttg tctggggcct caacaagcaa ggctacaaat gcaggcaatg taacgctgcc      960
atccacaaga aatgcatcga caagatcatc ggcagatgca ctggcaccgc ggccaacagc     1020
cgggacacta tattccagaa agaacgcttc aacatcgaca tgccgcaccg cttcaaggtt     1080
cacaactaca tgagccccac cttctgtgac cactgcggca gcctgctctg ggactggtg      1140 aagcagggat taaagtgtga agactgcggc atgaatgtgc accataaatg ccgggagaag     1200
gtggccaacc tctgcggcat caaccagaag cttttggctg aggccttgaa ccaagtcacc     1260
cagagagcct cccggagatc agactcagcc tcctcagagc ctgttgggat atatcagggt     1320
ttcgagaaga agaccggagt tgctggggag gacatgcaag acaacagtgg gacctacggc     1380
aagatctggg agggcagcag caagtgcaac atcaacaact tcatcttcca caaggtcctg     1440
ggcaaaggca gcttcgggaa ggtgctgctt ggagagctga agggcagagg agagtacttt     1500
gccatcaagg ccctcaagaa ggatgtggtc ctgatcgacg acgacgtgga gtgcaccatg     1560
gttgagaagc gggtgctgac acttgccgca gagaatccct ttctcaccca cctcatctgc     1620
accttccaga ccaaggacca cctgttcttt gtgatggagt cctcaacgg ggggacctg      1680 atgtaccaca tccaggacaa aggccgcttt gaactctacc gtgccacgtt ttatgccgct     1740
gagataatgt gtggactgca gtttctacac agcaagggca tcatttacag ggacctcaaa     1800
ctggacaatg tgctgttgga ccgggatggc cacatcaaga ttgccgactt tgggatgtgc     1860
aaagagaaca tattcgggga gagccgggcc agcaccttct gcggcacccc tgactatatc     1920
gcccctgaga tcctacaggg cctgaagtac acattctctg tggactggtg gtctttcggg     1980
gtccttctgt acgagatgct cattggccag tccccccttcc atggtgatga tgaggatgaa     2040
ctcttcgagt ccatccgtgt ggacacgcca cattatcccc gctggatcac caaggagtcc     2100
aaggacatcc tggagaagct ctttgaaagg gaaccaacca agaggctggg agtgacggga     2160
aacatcaaaa tccacccctt cttcaagacc ataaactgga ctctgctgga aaagcggagg     2220
ttggagccac ccttcaggcc caaagtgaag tcacccagag actacagtaa ctttgaccag     2280
gagttcctga acgagaaggc gcgcctctcc tacagcgaca agaacctcat cgactccatg     2340
gaccagtctg cattcgctgg cttctccttt gtgaacccca aattcgagca cctcctggaa     2400
gattag                                                                 2406
```

<210> SEQ ID NO 69
<211> LENGTH: 2406
<212> TYPE: DNA
<213> ORGANISM: Artificial Sequence
<220> FEATURE:
<223> OTHER INFORMATION: Synthetic sequence, nt sequence of sensor 33
      [R20]

<400> SEQUENCE: 69

```
atggaggacg tggattgcaa acagtctatg cgcagtgagg acgaggccaa gttcccaacg       60
atgaaccgcc gcggagccat caaacaggcc aaaatccact accccgtggt ttccgagcgg      120
atgtaccccg aggacggcgc cctgaagagc gagatcaaga aggggctgag gctgaaggac      180
ggcggccact acgccgccga ggtcaagacc acctacaagg ccaagaagcc cgtgcagctg      240
```

```
cccggcgcct acatcgtcga catcaagttg gacatcgtgt cccacaacga ggactacacc    300
atcgtggaac agtgcgaacg cgccgagggc cgccactcca ccggcggcat ggacgagctg    360
tacaaggag  gtacaggcgg gagtctggtg agcaagggcg aggaggataa catggccatc    420
atcaaggagt tcatgcgctt caaggtgcac atggagggcc ccgtgaacgg ccacgagttc    480
gagatcgagg gcgagggcga gggccgcccc tacgaggcct tcagaccgc  taagctgaag    540
gtgaccaagg gtggcccct  gcccttcgcc tgggacatcc tgtccctca  gttcatgtac    600
ggctccaagg cctacattaa gcacccagcc gacatcccg  actacttcaa gctgtccttc    660
cccgagggct tcaggtggga gcgcgtgatg aacttcgagg acggcggcat tattcacgtt    720
aaccaggact cctccctgca ggacggcgta ttcatctaca aggtgaagct gcgcggcacc    780
aacttccccc ccgacggccc cgtaatgcag aagaagacca tgggctggga ggctacgcgt    840
atcaagaacc atgagtttat cgccaccttc tttgggcaac ccaccttctg ttctgtgtgc    900
aaagactttg tctggggcct caacaagcaa ggctacaaat gcaggcaatg taacgctgcc    960
atccacaaga aatgcatcga caagatcatc ggcagatgca ctggcaccgc ggccaacagc   1020
cgggacacta tattccagaa agaacgcttc aacatcgaca tgccgcaccg cttcaaggtt   1080
cacaactaca tgagccccac cttctgtgac cactgcggca gcctgctctg gggactggtg   1140
aagcagggat taaagtgtga agactgcggc atgaatgtgc accataaatg ccgggagaag   1200
gtggccaacc tctgcggcat caaccagaag cttttggctg aggccttgaa ccaagtcacc   1260
cagagagcct cccggagatc agactcagcc tcctcagagc ctgttgggat atatcagggt   1320
ttcgagaaga agaccggagt tgctggggag gacatgcaag acaacagtgg gacctacggc   1380
aagatctggg agggcagcag caagtgcaac atcaacaact tcatcttcca caaggtcctg   1440
ggcaaaggca gcttcgggaa ggtgctgctt ggagagctga agggcagagg agagtacttt   1500
gccatcaagg ccctcaagaa ggatgtggtc ctgatcgacg acgacgtgga gtgcaccatg   1560
gttgagaagc gggtgctgac acttgccgca gagaatccct ttctcaccca cctcatctgc   1620
accttccaga ccaaggacca cctgttcttt gtgatggagt tcctcaacgg gggggacctg   1680
atgtaccaca tccaggacaa aggccgcttt gaactctacc gtgccacgtt ttatgccgct   1740
gagataatgt gtggactgca gtttctacac agcaagggca tcatttacag ggacctcaaa   1800
ctggacaatg tgctgttgga ccgggatggc cacatcaaga ttgccgactt tgggatgtgc   1860
aaagagaaca tattcgggga gagccgggcc agcaccttct gcggcacccc tgactatatc   1920
gccctgaga  tcctacaggg cctgaagtac acattctctg tggactggtg gtctttcggg   1980
gtccttctgt acgagatgct cattggccag tccccttcc  atggtgatga tgaggatgaa   2040
ctcttcgagt ccatccgtgt ggacacgcca cattatcccc gctggatcac caaggagtcc   2100
aaggacatcc tggagaagct ctttgaaagg gaaccaacca gaggctggga agtgacggga   2160
aacatcaaaa tccaccccct cttcaagacc ataaactgga ctctgctgga aaagcggagg   2220
ttggagccac ccttcaggcc caaagtgaag tcacccagag actacagtaa ctttgaccag   2280
gagttcctga acgagaaggc gcgcctctcc tacagcgaca agaacctcat cgactccatg   2340
gaccagtctg cattcgctgg cttctccttt gtgaacccca aattcgagca cctcctggaa   2400
gattag                                                               2406

<210> SEQ ID NO 70
<211> LENGTH: 425
<212> TYPE: PRT
<213> ORGANISM: Artificial Sequence
```

```
<220> FEATURE:
<223> OTHER INFORMATION: Synthetic sequence, a.a. sequence of PIP2
      sensor fragment [PIP2-A1]

<400> SEQUENCE: 70

Met Val Ser Lys Ser Glu Glu Val Ile Lys Glu Phe Met Arg Phe Lys
1               5                   10                  15

Val Arg Leu Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
50                  55                  60

Gln Ile Met Tyr Gly Ser Lys Ala Tyr Val Lys His Pro Ala Asp Val
65                  70                  75                  80

Pro Asp Tyr Met Lys Leu Ser Phe Pro Glu Gly Phe Lys Trp Glu Arg
                85                  90                  95

Val Met His Phe Glu Asp Gly Gly Leu Val Thr Val Thr Gln Asp Thr
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Leu Gly Trp
130                 135                 140

Asp Tyr Ala Thr Glu Arg Leu Tyr Pro Glu Asp Gly Val Leu Lys Gly
145                 150                 155                 160

Glu Leu Leu Gly Arg Leu Lys Leu Lys Asp Gly Gly Leu Asn Leu Val
                165                 170                 175

Glu Phe Lys Thr Ile Tyr Met Ala Lys Lys Pro Val Gln Leu Pro Gly
            180                 185                 190

Tyr Tyr Phe Val Asp Thr Lys Leu Gly Ile Thr Ser His Asn Glu Asp
        195                 200                 205

Tyr Thr Ile Val Glu Gln Tyr Glu Arg Ser Glu Gly Arg His His Leu
210                 215                 220

Gly Met Asp Glu Leu Tyr Lys Arg Ser Arg Ala Gln Ala Ser Asn Ser
225                 230                 235                 240

Ala Val Asp Gly Thr Ala Gly Pro Gly Ser Met Asp Ser Gly Arg Asp
                245                 250                 255

Phe Leu Thr Leu His Gly Leu Gln Asp Asp Glu Asp Leu Gln Ala Leu
            260                 265                 270

Leu Lys Gly Ser Gln Leu Leu Lys Val Lys Ser Ser Ser Trp Arg Arg
        275                 280                 285

Glu Arg Phe Tyr Lys Leu Gln Glu Asp Cys Lys Thr Ile Trp Gln Glu
290                 295                 300

Ser Arg Lys Val Met Arg Thr Pro Glu Ser Gln Leu Phe Ser Ile Glu
305                 310                 315                 320

Asp Ile Gln Glu Val Arg Met Gly His Arg Thr Glu Gly Leu Glu Lys
                325                 330                 335

Phe Ala Arg Asp Val Pro Glu Asp Arg Cys Phe Ser Ile Val Phe Lys
            340                 345                 350

Asp Gln Arg Asn Thr Leu Asp Leu Ile Ala Pro Ser Pro Ala Asp Ala
        355                 360                 365

Gln His Trp Val Leu Gly Leu His Lys Ile Ile His His Ser Gly Ser
370                 375                 380

Met Asp Gln Arg Gln Lys Leu Gln His Trp Ile His Ser Cys Leu Arg
```

Lys Ala Asp Lys Asn Lys Asp Asn Lys Met Ser Phe Lys Glu Leu Gln
              405                 410                 415

Asn Phe Leu Lys Glu Leu Asn Ile Gln
              420                 425

<210> SEQ ID NO 71
<211> LENGTH: 425
<212> TYPE: PRT
<213> ORGANISM: Artificial Sequence
<220> FEATURE:
<223> OTHER INFORMATION: Synthetic sequence, a.a. sequence of PIP2
      sensor fragment [PIP2-B1]

<400> SEQUENCE: 71

Met Val Ser Lys Gly Glu Glu Thr Ile Lys Glu Phe Met Arg Phe Lys
1               5                   10                  15

Val Arg Met Glu Gly Ser Met Asn Gly His Glu Phe Glu Ile Glu Gly
                20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
    50                  55                  60

Gln Phe Met Tyr Gly Ser Glu Ala Tyr Val Arg His Pro Ala Asp Ile
65                  70                  75                  80

Pro Asp Tyr Lys Lys Leu Pro Phe Pro Glu Gly Phe Lys Trp Glu Arg
                85                  90                  95

Val Met Asn Phe Glu Asp Gly Gly Leu Val Thr Val Thr Gln Asp Ser
                100                 105                 110

Ser Leu Gln Asp Gly Thr Leu Ile Cys Lys Val Lys Met Arg Gly Thr
            115                 120                 125

Asn Phe Pro Pro Asp Gly Pro Val Met Gln Lys Lys Thr Met Gly Trp
    130                 135                 140

Glu Ala Ser Thr Glu Met Leu Tyr Pro Glu Asp Gly Val Leu Lys Gly
145                 150                 155                 160

His Ser Tyr Gln Ala Leu Lys Leu Lys Asp Gly Gly His Tyr Leu Val
                165                 170                 175

Glu Phe Glu Thr Ile Tyr Met Ala Lys Lys Pro Val Gln Leu Pro Gly
            180                 185                 190

Asp Tyr Cys Val Asp Thr Lys Leu Asp Ile Thr Ser His Asn Glu Asp
        195                 200                 205

Tyr Thr Ile Val Glu Gln Tyr Gly Arg Ser Glu Gly Arg His Arg Leu
    210                 215                 220

Gly Met Asp Glu Arg Tyr Lys Arg Ser Arg Ala Gln Ala Ser Asn Ser
225                 230                 235                 240

Ala Val Asp Gly Thr Ala Gly Pro Gly Ser Met Asp Ser Gly Arg Asp
                245                 250                 255

Phe Leu Thr Leu His Gly Leu Gln Asp Glu Asp Leu Gln Ala Leu
            260                 265                 270

Leu Lys Gly Ser Gln Leu Leu Lys Val Lys Ser Ser Trp Arg Arg
        275                 280                 285

Glu Arg Phe Tyr Lys Leu Gln Glu Asp Cys Lys Thr Ile Trp Gln Glu
    290                 295                 300

Ser Arg Lys Val Met Arg Thr Pro Glu Ser Gln Leu Phe Ser Ile Glu
305                 310                 315                 320

| | | | | | | | | | | | |
|---|---|---|---|---|---|---|---|---|---|---|---|
|Asp|Ile|Gln|Glu|Val|Arg|Met|Gly|His|Arg|Thr|Glu Gly Leu Glu Lys|
| | |325| | | |330| | | |335| |

Phe Ala Arg Asp Val Pro Glu Asp Arg Cys Phe Ser Ile Val Phe Lys
            340                  345              350

Asp Gln Arg Asn Thr Leu Asp Leu Ile Ala Pro Ser Pro Ala Asp Ala
            355                  360              365

Gln His Trp Val Leu Gly Leu His Lys Ile Ile His His Ser Gly Ser
     370                  375              380

Met Asp Gln Arg Gln Lys Leu Gln His Trp Ile His Ser Cys Leu Arg
385                  390              395            400

Lys Ala Asp Lys Asn Lys Asp Asn Lys Met Ser Phe Lys Glu Leu Gln
            405                  410              415

Asn Phe Leu Lys Glu Leu Asn Ile Gln
            420                  425

<210> SEQ ID NO 72
<211> LENGTH: 1278
<212> TYPE: DNA
<213> ORGANISM: Artificial Sequence
<220> FEATURE:
<223> OTHER INFORMATION: Synthetic sequence, nt sequence of PIP2 sensor
     fragment [PIP2-A1]

<400> SEQUENCE: 72

```
atggtgagca agagcgagga ggtcatcaaa gagttcatgc gcttcaaggt gcgcttggag      60
ggctccatga acggccacga gttcgagatc gagggcgagg gcgagggccg ccctacgag     120 ggcacccaga ccgccaagct gaaggtgacc aagggcggcc cctgcccttc gcctgggac     180 atcctgtccc cccagatcat gtacggctcc aaggcgtacg tgaagcaccc cgccgacgtc     240
cccgattaca tgaagctgtc cttccccgag ggcttcaagt gggagcgcgt gatgcacttc     300
gaggacggcg gtctggtgac cgtgactcag gacacctccc tgcaggacgg cacgctgatc     360
tacaaggtga agatgcgcgg caccaacttc ccccccgacg gccccgtaat gcagaagaag     420
accttgggct gggattatgc caccgagcgc ctgtaccccg aagacggcgt gctgaagggc     480
gagcttctgg ggcgcctgaa gctgaaggac ggcggcctca acctggtgga gttcaagacc     540
atctacatgg ccaagaagcc cgtgcaactg cccggctact acttcgtgga ccaccaagctg    600 ggcatcacct cccacaacga ggactacacc atcgtggaac agtacgagcg ctccgagggc    660
cgccaccacc tgggcatgga cgagctgtac aagagatctc gagctcaagc ttcgaattct    720
gcagtcgacg gtaccgcggg cccgggatcc atggactcgg ccgggacttc ctgaccctg     780 cacggcctac aggatgatga ggatctacag gcgctgctga agggcagcca gctcctgaag     840
gtgaagtcca gctcatggag gagagagcgc ttctacaagt gcaggagga ctgcaagacc     900 atctggcagg agtcccgcaa ggtcatgcgg accccggagt cccagctgtt ctccatcgag    960
gacattcagg aggtgcgaat ggggcaccgc acggagggtc tggagaagtt cgcccgtgat    1020
gtgcccgagg accgctgctt ctccattgtc ttcaaggacc agcgcaatac actagacctc    1080
atcgccccat cgccagctga tgcccagcac tgggtgctgg ggctgcacaa gatcatccac    1140
cactcaggct ccatggacca gcgtcagaag ctacagcact ggattcactc ctgcttgcga    1200
aaagctgaca aaaacaagga caacaagatg agcttcaagg agctgcagaa cttcctgaag    1260
gagctcaaca tccagtag                                                 1278
```

```
<210> SEQ ID NO 73
<211> LENGTH: 1278
<212> TYPE: DNA
<213> ORGANISM: Artificial Sequence
<220> FEATURE:
<223> OTHER INFORMATION: Synthetic sequence, nt sequence of PIP2 sensor
      fragment [PIP2-B1]

<400> SEQUENCE: 73
atggtgagca agggcgagga gaccatcaaa gagttcatgc gcttcaaggt gcgcatggag      60
ggctccatga acgccacga gttcgagatc gagggcgagg gcgagggccg cccctacgag     120
ggcacccaga ccgccaagct gaaggtgacc aagggcggcc cctgcccctt cgcctgggac     180
atcctgtccc cccagttcat gtacggctcc gaggcgtacg tgaggcaccc cgccgacatc     240
cccgattaca agaagctgcc cttccccgag ggcttcaagt gggagcgcgt gatgaacttc     300
gaagacggcg gtctggtgac cgttaccag gactcctccc tgcaggacgg cacgctgatc     360
tgcaaggtga agatgcgcgg caccaacttc ccccccgacg gccccgtaat gcagaagaag     420
accatgggct gggaggcctc caccgagatg ctgtaccccg aagacggcgt gctgaagggc     480
catagctatc aggccctgaa gctgaaggac ggcggccact acctggtgga gttcgagacc     540
atctacatgg ccaagaagcc cgtgcaactg cccgcgatt actgtgtgga caccaagctg     600
gacatcacct cccacaacga ggactacacc atcgtggaac agtacgggcg ctccgagggc     660
cgccaccgtc tgggcatgga cgagcggtac aagagatctc gagctcaagc ttcgaattct     720
gcagtcgacg gtaccgcggg cccgggatcc atggactcgg gccgggactt cctgaccctg     780
cacggcctac aggatgatga ggatctacag gcgctgctga agggcagcca gctcctgaag     840
gtgaagtcca gctcatggag gagagagcgc ttctacaagt tgcaggagga ctgcaagacc     900
atctggcagg agtcccgcaa ggtcatgcgg accccggagt cccagctgtt ctccatcgag     960
gacattcagg aggtgcgaat ggggcaccgc acggagggtc tggagaagtt cgcccgtgat    1020
gtgcccgagg accgctgctt ctccattgtc ttcaaggacc agcgcaatac actagacctc    1080
atcgccccat cgccagctga tgcccagcac tgggtgctgg ggctgcacaa gatcatccac    1140
cactcaggct ccatggacca gcgtcagaag ctacagcact ggattcactc ctgcttgcga    1200
aaagctgaca aaaacaagga caacaagatg agcttcaagg agctgcagaa cttcctgaag    1260
gagctcaaca tccagtag                                                    1278
```